US007384638B2

(12) United States Patent
Bhatia et al.

(10) Patent No.: US 7,384,638 B2
(45) Date of Patent: Jun. 10, 2008

(54) COMPOUNDS AND METHODS FOR TREATMENT AND DIAGNOSIS OF CHLAMYDIAL INFECTION

(75) Inventors: Ajay Bhatia, Seattle, WA (US); Peter Probst, Seattle, WA (US); Erika Jean Stromberg, Seattle, WA (US)

(73) Assignee: Corixa Corporation, Hamilton, MT (US)

( * ) Notice: Subject to any disclaimer, the term of this patent is extended or adjusted under 35 U.S.C. 154(b) by 335 days.

(21) Appl. No.: 10/762,058

(22) Filed: Jan. 15, 2004

(65) Prior Publication Data

US 2004/0137007 A1 Jul. 15, 2004

Related U.S. Application Data

(62) Division of application No. 09/841,260, filed on Apr. 23, 2001, now abandoned.

(60) Provisional application No. 60/219,752, filed on Jul. 20, 2000, provisional application No. 60/198,853, filed on Apr. 21, 2000.

(51) Int. Cl.

| | |
|---|---|
| ***A61K 39/00*** | (2006.01) |
| ***A61K 39/02*** | (2006.01) |
| ***C07K 14/00*** | (2006.01) |
| ***C12N 21/04*** | (2006.01) |

(52) U.S. Cl. .............................. 424/192.1; 424/234.1; 424/263.1; 435/69.1; 435/69.7; 536/23.1; 536/23.4; 530/350

(58) Field of Classification Search ............ 424/234.1, 424/263.1, 190.1, 192.1, 192; 435/69.7, 435/69.1; 536/23.4, 23.1; 530/350

See application file for complete search history.

(56) References Cited

U.S. PATENT DOCUMENTS

| | | | | |
|---|---|---|---|---|
| 4,118,469 | A | 10/1978 | Caldwell et al. | 424/1 |
| 4,497,899 | A | 2/1985 | Armstrong et al. | 436/510 |
| 5,166,053 | A | 11/1992 | Huguenel et al. | 435/7.36 |
| 5,318,892 | A | 6/1994 | Watanabe et al. | 435/7.36 |
| 5,725,863 | A | 3/1998 | Daniels et al. | 424/263.1 |
| 5,869,608 | A | 2/1999 | Caldwell et al. | 530/350 |
| 6,166,177 | A | 12/2000 | Probst et al. | 530/300 |
| 6,432,916 | B1 * | 8/2002 | Probst et al. | 514/2 |
| 6,448,234 | B1 | 9/2002 | Fling | 514/44 |

FOREIGN PATENT DOCUMENTS

| | | |
|---|---|---|
| EP | 348725 A2 | 1/1990 |
| EP | 784059 A1 | 7/1997 |
| WO | WO 94/06827 | 3/1994 |
| WO | WO 97/06263 | 2/1997 |
| WO | WO 98/02546 | 1/1998 |
| WO | WO 98/10789 | 3/1998 |
| WO | WO 99/17741 | 4/1999 |
| WO | WO 99/27105 | 6/1999 |
| WO | WO 99/28475 | 6/1999 |
| WO | WO 99/51748 | 10/1999 |
| WO | WO 00/34483 | 6/2000 |
| WO | WO 01/40474 | 6/2001 |

OTHER PUBLICATIONS

Baldridge et al J.Endotoxin Research 2002; 8(6); 453-8 (at present the examiner is sending the abstract only).*

Greenspan et al (Nature Biotechnology, 1999, 7:936-937).*

Holmes (Exp. Opin.Invest. Drugs, 2001, 10(3):511-519).*

Roitt et al (Immunology, 1993, Mosby, St. Louis, p. 7.7-7.8).*

Herbert et al (The Dictionary of Immunology, Academic Press, 3rd Edition, London, 1985, pp. 58-59).*

Bowie et al (Science, 1990, 257:1306-1310.*

Rudinger et al, in "Peptide Hormones", edited by Parsons, J.A., University Park Press, Jun. 1976.*

Allen and Stephens, "An intermolecular mechanism of T cell help for the production of antibodies to the bacterial pathogen, *Chlamydia trachomatis," European Journal of Immunology 23*: 1169-1172, 1993.

Baehr et al., "Mapping antigenic domains expressed by *Chlamydia trachomatis* major outer membrane protein genes," *Proc Natl Acad Sci 85*(1):4000-4004, Jun. 1, 1998.

Brunham et al., "*Chlamydia trachomatis* antigens: role in immunity and pathogenesis," *Infectious Agents and Disease 3*(5):218-233, Oct. 1994.

Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology 111*: 2129-2138, 1990.

Chakrabarti et al., "Vaccinia virus expression vector: coexpression of β-galactosidase provides visual screening of recombinant virus plaques," *Molecular and Cellular Biology 5*(12):3403-3409, Dec. 1985.

Conlan, J.W. et al., "Isolation of recombinant fragments of the major outer-membrane protein of *Chlamydia trachomatis*: their potential as subunit vaccines," *Journal of General Microbiology 136*: 2013-2020, 1990.

Earl et al., "Biological and immunological properties of human immunodeficiency virus type 1 envelope glycoprotein: analysis of proteins and truncations and deletions expressed by recombinant vaccinia viruses," *Journal of Virology 65*(1):31-41, Jan. 1991.

(Continued)

*Primary Examiner*—Shanon Foley
*Assistant Examiner*—Padma Baskar
(74) *Attorney, Agent, or Firm*—Seed IP Law Group PLLC

(57) ABSTRACT

Compounds and methods for the diagnosis and treatment of Chlamydial infection are disclosed. The compounds provided include polypeptides that contain at least one antigenic portion of a *Chlamydia* antigen and DNA sequences encoding such polypeptides. Pharmaceutical compositions and vaccines comprising such polypeptides or DNA sequences are also provided, together with antibodies directed against such polypeptides. Diagnostic kits containing such polypeptides or DNA sequences and a suitable detection reagent may be used for the detection of Chlamydial infection in patients and in biological samples.

8 Claims, No Drawings

OTHER PUBLICATIONS

GenBank Accession No. AE001273, "Genome sequence of an obligate intracellular pathogen of humans: *Chlamydia trachomatis*," Jun. 2, 2004.
Genbank Database, Accession No. AE001316, Jun. 1, 2004.
Genbank Database, Accession No. AE001320, Jun. 1, 2004.
GenBank Database, Accession No. AE001323, "Genome sequence of an obligate intracellular pathogen of humans: *Chlamydia trachomatis*," Jun. 1, 2004.
GenBank Database, Accession No. AE001324, "Genome sequence of an obligate intracellular pathogen of humans: *Chlamydia trachomatis*," Jun. 1, 2004.
Genbank Database, Accession No. AE001326, Jun. 1, 2004.
GenBank Database, Accession No. AE001335, "Genome sequence of an obligate intracellular pathogen of humans: *Chlamydia trachomatis*," Jun. 1, 2004.
Genbank Database, Accession No. AE001361, Jun. 1, 2004.
GenBank Database, Accession No. E71500, "Genome sequence of an obligate intracellular pathogen of humans: *Chlamydia trachomatis*," Nov. 3, 2000.
GenBank Database, Accession No. H71501, "Genome sequence of an obligate intracellular pathogen of humans: *Chlamydia trachomatis*," Jul. 28, 2000.
GenBankDatabase, Accession No. H71510, "Genome sequence of an obligate intracellular pathogen of humans: *Chlamydia trachomatis*," Oct. 8, 1999.
GenBank Database, Accession No. AAC68408, Jun. 1, 2004.
GenBank Database, Accession No. AAF39070, Mar. 26, 2003.
GenBank Database, Accession No. AE001333, Jun. 1, 2004.
GenBank Database, Accession No. AE001353, Oct. 30, 2000.
GenBank Database, Accession No. AE002286, Mar. 26, 2003.
GenBank Database, Accession No. AE002343, Mar. 26, 2003.
GenBank Database, Accession No. H71468, Oct. 8, 1999.
EMBL Database, Accession No. O84466, Jun. 1, 2003.
GenBank Database, Accession No. NC_000117, Sep. 14, 2004.
Grimwood, J. et al., "Expression of *Chlamydia pneumoniae* Polymorphic Membrane Protein Family Genes," *Infection and Immunity 69*(4): 2383-2389, Apr. 2001.
Hayes, L.J. et al., "*Chlamydia trachomatis* major outer membrane protein epitopes expressed as fusions with LamB in an attenuated *aroA* strain of *Salmonella typhimurium*; their application as potential immunogens," *Journal of General Microbiology 137*: 1557-1564, 1991.
Hayes, L.J. et al., "The major outer-membrane proteins of *Chlamydia trachomatis* serovars A and B: intra-serovar amino acid changes do not alter specificites of serovar- and C subspecies-reactive antibody-binding domains," *Journal of General Microbiology 136*: 1559-1566, 1990.
Janeway et al. (eds.), *Immunobiology: The Immune System in Health and Disease*, Garland Pub., New York, NY, 1997, pp. 7:6-7:10.
Jensen et al., "Infection of human and simian tissue cultures with rous sarcoma virus," *Proc. Natl. Acad. Sci. USA 52*:53-59, Jul. 1964.
Jobling, M.G. et al., "Analysis of structure and function of the B subunit of cholera toxin by the use of site-directed mutagenesis," *Molecular Microbiology 5*(7): 1755-1767, 1991.
Kalman, S. et al., "Comparative genomes of *Chlamydia pneumoniae* and *C. trachomatis," Nature Genetics 21*: 385-389, Apr. 1999.
Kim, S.-K. et al., "Induction of HLA Class I-Restricted CD8$^+$CTLs Specific for the Major Outer Membrane Protein of *Chlamydia trachomatis* in Human Genital Tract Infections," *The Journal of Immunology 162*: 6855-6866, 1999.
Knudsen, K. et al., "Identification of Two Novel Genes Encoding 97- to 99- Kilodalton Outer Membrane Proteins of *Chlamydia pneumoniae," Infection and Immunity 67*(1): 375-383, Jan. 1999.
Kuon, W. et al., "Recognition of Chlamydial Antigen By HLA-B27-Restricted Cytotoxic T Cells in HLA-B2705 Transgenic CBA(H-2$^k$ ) Mice," *Arthritis & Rheumatism 40*(5): 945-954, May 1997.
Lalvani et al., "Rapid effector function in CD8$^+$memory T cells," *J. Exp. Med. 186*(6):859-865, Sep. 15, 1997.
Lazar, E. et al., "Transforming Growth Factor α: Mutation of Aspartic Acid 47 and Leucine 48 Results in Different Biological Activities," *Molecular and Cellular Biology 8*(3): 1247-1252, Mar. 1988.
Levinson and Jawetz, *Medical Microbiology & Immunology*, 3d ed., Appleton & Lange, 1994, pp. 292-293.
Lu and Zhong, "Interleukin-12 Production IS Required for *Chlamydial* Antigen-Pulsed Dendritic Cells To Induce Protection against Live *Chlamydia trachomatis* Infection," *Infection and Immunity 67*(4): 1763-1769, Apr. 1999.
Maclean, I.W. et al., "Characterization of *Chlamydia trachomatis* antigens with monoclonal and polyclonal antibodies," *Can. J. Microbiol. 34*: 141-147, 1988.
Murdin, A.D. et al., "A Poliovirus Hybrid Expressing a Neutralization Epitope from the Major Outer Membrane Protein of *Chlamydia trachomatis* Is Highly Immunogenic," *Infection and Immunity 61*(10): 4406-4414, Oct. 1993.
Mygind, P.H. et al., "Membrane proteins PmpG and PmpH are major constituents of *Chlamydia trachomatis* L2 outer membrane complex," *FEMS Microbiol. Lett. 186*(2): 163-169, May 15, 2000.
Pal, S. et al., "Immunization with an Acellular Vaccine Consisting of the Outer Membrane Complex of *Chlamydia trachomatis* Induces Protection against a Genital Challenge," *Infection and Immunity 65*(8): 3361-3369, Aug. 1997.
Pawlikowska and Deptula, "Adherence and ingesting capacity of peripheral blood granulocytes in rabbits immunized with various antigens of *Chlamydia sp., " Central European Journal of Immunology 24*: 293-298, 1999.
Peterson, E.M. et al., "The Effect of Orientation Within a Chimeric Peptide on the Immunogenicity of *Chlamydia trachomatis* Epitopes," *Molecular Immunology 33*(4/5): 335-339, 1996.
Rank et al., "Immunization against *Chlamydial* Genital Infection in Guinea Pigs with UV-Inactivated and Viable *Chlamydiae* Administered by Different Routes," *Infection and Immunity, 58*(8):2599-2605, Aug. 1990.
Read et al., "Genome sequences of *Chlamydia trachomatis* MoPn and *Chlamydia pneumoniae* AR39," *Nucleic Acids Research 28*(6):1397-1406, 2000.
Rudinger, J., "Characteristics of the amino acids as components of a peptide hormone sequence," in *Peptide Hormones*, Parsons, J.A. (ed.), University Park Press, Baltimore, MD, Jun. 1976, pp. 1-5.
Sanderson et al., "Identification of a CD4$^+$T Cell-stimulating Antigen of Pathogenic Bacteria by Expression Cloning," *J. Exp. Med. 182*(6):1751-1757, 1995.
Scudiero et al., "Evaluation of a soluble tetrazolium/formazan assay for cell growth and drug sensitivity in culture using human and other tumor cell lines," *Cancer Research 48*:4827-4833, Sep. 1, 1988.
Shirai, M. et al., "Comparison of whole genome sequences of *Chlamydia pneumoniae* J138 from Japan and CWL029 from USA," *Nucleic Acid Research 28*(12): 2311-2314, 2000.
Stagg, A.J., "Vaccines against *Chlamydia*: approaches and progress," *Molecular Medicine Today 4*(4): 166-173, Apr. 1998.
Starnbach et al., "Protective cytotoxic T lymphocytes are induced during murine infection with *Chlamydia trachomatis*," *The Journal of Immunology 153*(11):5183-5189, Dec. 1, 1994.
Stephens et al., "Genome Sequence of an Obligate Intracellular Pathogen of Humans: *Chlamydia trachomatis*," *Science 282*:754-759, Oct. 23, 1998.
Su and Caldwell, "Immunogenicity of a synthetic oligopeptide corresponding to antigenically common T-helper and B-cell neutralizing epitopes of the major outer membrane protein of *Chlamydia trachomatis," Vaccine 11*(11): 1159-1166, 1993.
Su, H. et al., "Protective efficacy of a parenterally administered MOMP-derived synthetic oligopeptide vaccine in a murine model of *Chlamydia trachomatis* genital tract infection: serum neutralizing IgG antibodies do not protect against chlamydial genital tract infection," *Vaccine 13*(11): 1023-1032, 1995.
Unanue, E.R., "Chemical Features of Peptide Selection by the Class II Histocompatibility Molecules," *American Journal of Pathology 154*(3): 651-664, Mar. 1999.

Webb et al., "Molecular cloning of a novel protein antigen of Leishmania major that elicits a potent immune response in experimental murine leishmaniasis," *The Journal of Immunology 157*:5034-5041, 1996.

Yasuda, K. et al., "Serine 6 of Lck Tyrosine Kinase: A Critical Site for Lck Myristoylation, Membrane Localization, and Function in T Lymphocytes," *The Journal of Immunology 165*: 3226-3231, 2000.

Zhang, D. et al., "DNA vaccination with the major outer-membrane protein gene induces acquired immunity to *Chlamydia trachomatis* (mouse pneumonitis) infection," *J. Infect. Dis. 176*(4): 1035-1040, Oct. 1997.

Zhong, G. et al., "Immunogenicity Evaluation of a Lipidic Amino Acid-Based Synthetic Peptide Vaccine for *Chlamydia trachomatis," The Journal of Immunology 151*(7): 3728-3736, Oct. 1, 1993.

Zhong, G. et al., "Mapping epitopes of neutralizing monoclonal antibodies using phage random peptide libraries," *Journal of Industrial Microbiology & Biotechnology 19*: 71-76, 1997.

Zhong, G. et al., "Conformational Mimicry of a Chlamydial Neutralization Epitope on Filamentous Phage," *Journal of Biological Chemistry 269*(39): 24183-24188, Sep. 30, 1994.

* cited by examiner

SEQUENCE LISTING

```
<160> NUMBER OF SEQ ID NOS: 140

<210> SEQ ID NO 1
<211> LENGTH: 1311
<212> TYPE: DNA
<213> ORGANISM: Chlamydia trachomatis

<400> SEQUENCE: 1

taattcgctt ttacctctct tcttgctgaa gacttggcta tgttttttat tttgacgata     60

aacctagtta aggcataaaa gagttgcgaa ggaagagccc taaacttttc ttatcatctt    120

ctttaactag gagtcatcca tgagtcaaaa taagaactct gctttcatgc agcctgtgaa    180

cgtatccgct gatttagctg ccatcgttgg tgcaggacct atgcctcgca cagagatcat    240

taagaaaatg tgggattaca ttaagaagaa tagccttcaa gatcctacaa acaaacgtaa    300

tatcaatccc gatgataaat tggctaaagt ttttggaact gaaaaaccta tcgatatgtt    360

ccaaatgaca aaaatggttt ctcaacacat cattaaataa aatagaaatt gactcacgtg    420

ttcctcgtct ttaagatgag gaactagttc attctttttg ttcgtttctg tgggtattac    480

tgtatcttta acaactatct tagcagcacc tgttttgaca tgggtttggg ccaatcactt    540

agagcctaac ctattgagag taacgcgttt aaattggaat ctgcctaaaa aatttgctca    600

tcttcatggg cttcgcatta tacagatttc ggatttacac ctaaaccact cgacgcctga    660

tgcctttcta aaaaaagtat ctcgtaagat ctcttctctt tctccagata ttcttgtatt    720

tacaggagac tttgtctgtc gcgctaaagt agaaactcct gaaagattaa aacatttcct    780

atgttctctg catgcgccct taggctgttt tgcttgccta ggaaatcatg attacgccac    840

ctacgtatcc cgtgatattc acgggaaaat taataccatc tcagcaatga atagccgtcc    900

tttaaaaaga gcttttacct ctgtttatca aagtctattc gcctcttctc gcaatgaatt    960

tgcagatact ctgaatccac aaattcctaa tccacaccta gtcagtatat tacgcaatac   1020

tccatttcaa ttattgcata atcaaagcgc gacactttcc gatacaatca acatcgtggg   1080

attaggcgat ttttttgcca aacaattcga tcccaaaaaa gcttttactg actataatcc   1140
```

-continued

```
cacgttacct ggtattatcc tttctcataa tcccgatacg attcaccatc tccaagatta   1200

cccaggtgat gttgtttttt ccgggcactc gcatggccct caaatctctc ttccctggcc   1260

taagtttgcc aatacgataa ccaataaact ttcagggtta gaaaacccag a            1311
```

<210> SEQ ID NO 2
<211> LENGTH: 1516
<212> TYPE: DNA
<213> ORGANISM: Chlamydia trachomatis

<400> SEQUENCE: 2

```
tttgagctcg tgccgctcgt gccggtgcgt gtgaaccgct tcttcaaaag cttgtcttaa     60

aagatattgt ctcgcttccg gattagttac atgtttaaaa attgctagaa caatattatt    120

cccaaccaag ctctctgcgg tgctgaaaaa acctaaattc aaaagaatga ctcgccgctc    180

atcttcagaa agacgatccg acttccataa ttcgatgtct ttccccatgg ggatctctgt    240

agggagccag ttatttgcgc agccattcaa ataatgttcc caagcccatt tgtacttaat    300

aggaacaagt tggttgacat cgacctggtt gcagttcact agacgcttgc tatttagatt    360

aacgcgtttc tgttttccat ctaaaatatc tgcttgcata agaaccgtta attttattgt    420

taatttatat gattaattac tgacatgctt cacacccttc ttccaaagaa cagacaggtg    480

ctttcttcgc tctttcaaca ataattcctg ccgaagcaga cttattcttc atccaacgag    540

gctgaattcc tctcttatta atatctacaa aagatttttc aacggtcgtt gctgatgaag    600

atctcagata atacgtagtt ttcaaacctt ttttccaagc cgttaaatac atattcgaca    660

gtttttttccc gtctggctgg gcaagataaa ggttgaggga ttgccccata tcaatccatt    720

tttgtcttcg agacgcgcat tcgataatcc attctggttc aatctcaaaa gctgtcaaga    780

aaatatgttt taagtgatct ggtatacgct cgatttccaa taaagaccca tcaaaatatt    840

tcaggtcatc taacatatca gcatcccaga tacctaattt cttcaacttc tcaattaaat    900

acacatttgg aatcgtgaat tctccggaca aattagactt cacaaacaaa tgtttgtacg    960

ttggctcaat agattgagtt actcctataa tgttggagat cgtcgctgtc ggagctatag   1020

ccataagctg acaatgtcgc ataccatgct ctttaaccaa actacggata ggttcccaat   1080

cttttcttga tgacgtatcc atctggagat ttgcttctcc tcgatagttc gctaacaact   1140

gaatcgtatc aatagggagc aaacctctat cccatttcga tcctttataa gagctgtaag   1200

tgcctcgttc tttagcgagc agacaagaag cttgaatcgc atagtaagaa atcaactctg   1260

aactgtagtc agcaaattct acagcttctt gcgaagcata gcttatatct agcttataca   1320

aggcatcttg gaatcccatc acccctaatc caatagcgcg gtgagcaaag ttcgcctctt   1380

tagcttcctt tgttggataa aagttaatat caatcacgtt atccaacata cggactgcta   1440

tagagatcgt ctcagagagt tttcctcat caaacccatc ccctacgata tgttgaacta   1500

agttaatcga tcctaa                                                   1516
```

<210> SEQ ID NO 3
<211> LENGTH: 2397
<212> TYPE: DNA
<213> ORGANISM: Chlamydia trachomatis

<400> SEQUENCE: 3

```
agagtgtgct ggaggagcta tttttgcaaa acgggttcgt attgtagata accaagaggc     60

cgttgtattc tcgaacaact tctctgatat ttatggcggc gccattttta caggttctct    120

tcgagaagag gataagttag atgggcaaat ccctgaagtc ttgatctcag gcaatgcagg    180
```

-continued

```
ggatgttgtt ttttccggaa attcctcgaa gcgtgatgag catcttcctc atacaggtgg    240
gggagccatt tgtactcaaa atttgacgat ttctcagaat acagggaatg ttctgtttta    300
taacaacgtg gcctgttcgg gaggagctgt tcgtatagag gatcatggta atgttctttt    360
agaagctttt ggaggagata ttgtttttaa aggaaattct tctttcagag cacaaggatc    420
cgatgccatc tattttgcag gtaaagaatc gcatattaca gccctgaatg ctacggaagg    480
acatgctatt gttttccacg acgcattagt ttttgaaaat ctagaagaaa ggaaatctgc    540
tgaagtattg ttaatcaata gtcgagaaaa tccaggttca aaatttctca agtttgatgc    600
aattgtgcta ttcgctacct ttagttttct atgtccacgg taaagggatc ggaaagatac    660
gcatttattt tcatagtctt tagcttcgat ccctagtgct tccgcatgga ctcgtctgcc    720
aagacttttg gttacgaaaa caacaggctc tcgttgagaa atgatttgga gtagctctag    780
cgtgaggtgt tttttctgtt tctcgtggtt tgaaagattg actagaggag agacttcaat    840
acataactcg ctgccgtttt ttaataaaat ttgaccagag gagggtcttt ccgactgctc    900
tagtaataga cgaatattgc ccaatgctct ggaagcattt ttccctgatt catctcgaaa    960
ctttgcgcag gattccaatt cttcgattac tgtaaaaggg ataatgatgc gagtgttaga   1020
aaaagaggaa agggccttag gatcgtaaat caaaacgctg gtatcaataa cagaggtttt   1080
tttcattaca aattcctaaa tgactcaagt gtaaggggga gatagtactt tgattgtgta   1140
tcatatccag aaaaattaaa acatgtcttt gttagagaga agtcgggaga gagggttttt   1200
agcaatcaac ctccgcgtgt gctaatctgt ttgtcaaaaa tgtacccctt aactacaatg   1260
ccgaggaaag cgagtccttc tgttggaggt tgttatgaaa gtcaaaatta atgatcagtt   1320
catttgtatt tccccataca tttctgctcg atggaatcag atagctttca tagagtcttg   1380
tgatggaggg acggaagggg gtattacttt gaaactccat ttaattgatg gagagacagt   1440
ctctataccc aatctaggac aagcgattgt tgatgaggtg ttccaagagc acttgctata   1500
tttagagtcc acagctcctc agaaaaacaa ggaagaggaa aaaattagct ctttgttagg   1560
agctgttcaa caaatggcta aaggatgcga agtacaggtt ttttctcaaa agggcttggt   1620
ttctatgtta ctaggaggag ctggttcgat taatatgttg ttgcaacatt ctccagaaca   1680
taaggatcat cctgatcttc ctaccgattt actggagagg atagcgcaaa tgatgcgttc   1740
attatctata ggaccaactt ctattttagc taagccagag cctcattgca actgtttgca   1800
ttgtcaaatt ggacgagcta cagtggaaga agaggatgcc ggagtatcgg atgaggatct   1860
cacttttcgt tcatgggata tctctcaaag tggagaaaag atgtacactg ttacagatcc   1920
tttgaatcca gaagtatacc ttttgttttt tttatacgag ccagcactcc aatttctgac   1980
tgtgagaata tatcataaat agaccggcct ctagcgctgc gaatagaaaa agtctttgct   2040
atagcactat caagccttcc ctttatacgc tcaagcaata gaaacggaga tctacgcaat   2100
ggattttcat tgtactcatt aaacgagcgg aaaatgaaat tactcaaatt ttcttcagcg   2160
ctacacacgc tcaaatcatc gaggaaaacc gtatgagaaa cggatctact cgtgccgaat   2220
tcggcacgag gtctctaatc ttgcagaagg agcacaaatt tttgctgtcc aagggttaaa   2280
tactgctgga gaaataggat actgccctcc ttgccctcca gatgcgaagc atcgctatta   2340
cttttatgct tatgcgctcg atgttgtgct ttccgatgaa gaaggagtga ccaaaga      2397
```

<210> SEQ ID NO 4
<211> LENGTH: 1094
<212> TYPE: DNA

<213> ORGANISM: Chlamydia trachomatis

<400> SEQUENCE: 4

```
tgatgcagaa gacactgtta agaagttaca agaagccggt gctaaggctg ttgctaaagg     60
gctgtaattg ttatgggaaa gagaatgctt tgggggttgc ttgcaagctt ctcttttcgt    120
ttagctgcac agtagctggg cacagagggg ttcccggtac gtcttaacag atttgtctgg    180
acttaacttt tagtgtttgg catcgcaaac agaatatttc tgttgcaatg gtttttttctt   240
aatggaatca aggtgatagt atttgtcgga tggacaagtg tatagagagt atccagtgtc    300
tctgtattgg atagactctg ttttgtccta gctggaaagc atctgtcgta ttcctgttta    360
gagatcacag agggactaaa tagggaaatg gtatcgccaa aagtcttaaa gtcttaggag    420
agctcgcatg ttcaagtgcc cggagcgggt cagcgtcaaa aagaaagaag atattttaga    480
tcttcctaat cttgtcgaag ttcaaatcaa gtcgtataag cagtttcttc aaatcgggaa    540
gcttgctgaa gagcgagaaa acattggttt agaagaagtc ttcagagaaa ttttccctat    600
caagtcttat aatgaagcta cgattttaga gtacctctct tataacttag gagtgcccaa    660
atactcccca gaagagtgta ttcgtcgggg aatcacctat agtgttactt taaaggttcg    720
tttccgttta actgatgaaa cggggattaa agaagaagaa gtctatatgg gaaccatccc    780
catcatgact cataagggaa cctttattat taatggggca gagagagtcg ttgtttctca    840
agtccaccgt tctccaggaa tcaattttga acaagaaaaa cattctaaag ggaatgtttt    900
atttctttt agaattattc cttatcgagg aagttggtta gaagctgtct tcgacattaa     960
tgaccttatc tatatccata ttgataggaa aaaacgtcgc agaaagattt tagctattga   1020
cgtttatccg agctttagga tattcaacag atgcagatat tattgaagag ttcttttctg   1080
tagaggagcg ttcc                                                      1094
```

<210> SEQ ID NO 5
<211> LENGTH: 2129
<212> TYPE: DNA
<213> ORGANISM: Chlamydia trachomatis

<400> SEQUENCE: 5

```
gcttctttaa gagataagca acaaccgagg aatccactcc tccagacata gcaacaatga     60
tagttttacg cacaatgagc ccagaaaacg ctttcgttta ttgaagtttg cacattacaa    120
agggccatca tgttagcaaa aaaacaggat caaaaaaacc tatttctcaa gccgcctctt    180
ttaaatctta attacaaaaa taaaaatcaa ttcaactttt caaaaaaaga atttaaacat    240
taattgttat aaaaacaata tttattataa aataataacc atagttgcgg ggaaatctct    300
ttcatggttt attttagagc tcatcaacct aggcatacgc ctaaaacatt tcctttggaa    360
gttcaccatt cgttctccga taagcatcct caaattgcta aagctatgcg gattacgggg    420
ataaccctcg cagctctatc tctgctcgct gtagtcgcct gcgttattgc cgtctctgcg    480
ggaggagctg ccattcctct tgctgtcatt ggtggaattg ctgcaatgtc tggcctctta    540
tccgctgcca ccattatctg ttctgcaaaa aaggctctgg ctcaacgaaa acaaaaacaa    600
ctagaagagt tgcttccgtt agataatgcg accgagcatg tgaattacct gacctcagac    660
acctcttatt ttaatcaatg ggaatcctta gatgctctaa ataagcagtt gtctcagatt    720
gacttaacta ttcaagctcc cgaaaaaaaa ctattaaaag aagttcttgg ttccagatac    780
gattccatta atcactccat cgaagagatc tccgatcgct ttacgaaaat gctctctctt    840
cttcgattaa gagaacattt ttgtcgagga gaagagcgtt atgcccccta tttaagccct    900
```

-continued

```
cctctactta acaagaatcg tttgctgacc caaatcacat ccaatatgat taggatgcta    960

ccaaaatccg gtggtgtttt ttccctcaaa gccaatacac taagtcatgc cagccgcaca   1020

ctatatacag tattgaaagt cgctttatcc ttaggagttc tcgctggagt cgctgctctt   1080

atcatctttc ttccccctag cctgcctttt atcgctgtta taggagtatc ttccttagca   1140

ttggggatgg catctttcct tatgattcgg ggcattaagt atttgctcga acattctcct   1200

ctgaatagaa agcaattagc taaagatatt caaaaaacca ttatcccaga tgtcttggcc   1260

tctatggttc attaccagca tcaattacta tcacatctac atgaaactct attagatgaa   1320

gccatcacag ctagatggag cgagcccttc tttattgaac acgctaatct taaggcaaaa   1380

attgaagatt tgacaaaaca atatgatata ttgaacgcag cctttaataa atctttacaa   1440

caagatgagg cgctccgttc tcaattagag aaacgagctt acttattccc aattcctaat   1500

aacgacgaaa atgctaaaac taaagaatcg cagcttctag actcagaaaa tgattcaaat   1560

tctgaatttc aggagattat aaataaagga ctagaagctg ccaataaacg acgagctgac   1620

gctaagtcaa aattctatac ggaagacgaa acctctgaca aaagattctc tatatggaaa   1680

cccacaaaga acttggcatt agaagatttg tggagagtgc atgaagcttg caatgaagag   1740

caacaagctc tcctcttaga agattatatg agttataaaa cctcagaatg tcaagctgca   1800

ctccaaaaag tgagtcaaga actgaaggcg gcacaaaaat cattcgcagt cctagaaaag   1860

catgctctag acagatctta tgaatccagt gtagccatga tggatttagc tagagcgaat   1920

caagaaacac accggcttct gaacatcctc tctgaattac aacaactagc acaatacctg   1980

ttagataatc actaacggtt cttcataaat gacaaaaaga aaaaggagag ctgttgctgt   2040

gctctccttt ttctctaaat attcctgaaa gactaacctt tttatggttg cgttgagcct   2100

cctcctcctg ttcccgagga gcccgcaac                                     2129
```

<210> SEQ ID NO 6
<211> LENGTH: 1828
<212> TYPE: DNA
<213> ORGANISM: Chlamydia trachomatis

<400> SEQUENCE: 6

```
gagggagcag cctaactctc ccctctcttc ttaaaaaaga ggggagcctt ttttccttac     60

aaagatacgc tagctttttc ctgaagaatc tcatcaagag atatttgcat tttcccacgg    120

ataaaggcat cccaaggaag ccctggaatc acttcatatt ctcccgttgc tagcattcga    180

caagggaaac caaagattaa atcttccggt aatccatagg gattgtggtc cgaacacact    240

ccggaagaaa accattctcc ttcttttggc tgatatattg atcgagcagc ctctgctaaa    300

gctcgtgctg cagaagctgc cgaagacttc cctcgtgctt cgattactgc actaccacga    360

ctctgtacag aaggcaccat aatattctct aaccaatcac gatccgctat cgtctctgcg    420

ataggacggt cattaatcag agcttgcgta aaatcaggca cttgtttggc ggagtgattt    480

ccccaaacca caacttgtga tacagccgat aaaggtactt ctgctctatg cgataacatg    540

ctatgcatac gattctggtc caatcgtagc atcgcatgaa agttctttct caataatctg    600

ggagcatgat tcattgctat ccagcaattg gtattcacag ggttcccaac aacaaaaatc    660

tttgcatccc gcttggctgt tgtgttcaaa gcttttcctt gcgtagcaaa aatctcccca    720

tttttcttta gaagatccct tctctccatt cctgggcctc taggaactga ccctataagg    780

aatgccgcat caatgccatc aaaagcatca tgcaatgatg tcgttacctg cacacgctgt    840
```

-continued

```
aataaaggga aagcaccatc atctagctcc atgcgcacac cagataaagc cctttctgtt     900

ccaggaatat cgtagatacg cagatcgatg ccacaatcaa ggccaaaaac atctccatga     960

gccagagaaa atagaaagct ataggctatt tgccctgttc ctcctgttac tgctacactc    1020

actgtttgag aaaccataag ccaccctctc tttactttta caaaacgcac atactctcaa    1080

cactacgttt gcaactaact aattttggtc ccaacatacg tttggatgat aaaagaatca    1140

agtacctaga ttccttagta aaagcttttg gcaaaaaaaa gctcatctat ttttcaatag    1200

atgagccgac tttaactgaa taagaactta gaaaacttta taaaaaatag gcccgtgtga    1260

tcctacccat atacttgatc ccgaccgcat aacttgttgt cccttttag cagccaaata     1320

accgtggaca tctaaaaaac caataaaccg tgcgcgaata aagaacataa agcccctaaa    1380

aaaacgattt taagagagaa gtaatagaca gattgtaaca tatttaaaat aaaaactctg    1440

caaacaaaaa aactttgcct ggccgtctcc gtagaaagca ctttatgtta aaacgttaaa    1500

aagtcttaac atacctcgag cttcgggaaa ctctacagga gcattccccg acatgatgcc    1560

tataatttgc gttgccaatt ctttccctaa tgaaacccct tcttgatcaa aagaattgat    1620

tccccagcaa aacccttgaa atgcaaattt atgctcataa aaagccaata aactaccagc    1680

aatacgagga gaaagctgtt gcgctaccaa tatcgaagaa ggtctgttcc ctttaaacct    1740

cttattcggg ttcgcattat ctctaccctg agctaaagct aaagattgag caacaaggtt    1800

tgcaaagagc ttttgagatc tcgtgccg                                       1828
```

<210> SEQ ID NO 7
<211> LENGTH: 861
<212> TYPE: DNA
<213> ORGANISM: Chlamydia trachomatis

<400> SEQUENCE: 7

```
gggcgcacta ctttaaagat tcgtcgtcct tttggtacta cgagagaagt tcgtgtgaaa      60

tggcgttatg ttcctgaagg tgtaggagat ttggctacca tagctccttc tatcagggct     120

ccacagttac agaaatcgat gagaagcttt ttccctaaga aagatgatgc gtttcatcgg     180

tctagttcgc tattctactc tccaatggtt ccgcattttt gggcagagct tcgcaatcat     240

tatgcaacga gtggtttgaa aagcgggtac aatattggga gtaccgatgg gtttctccct     300

gtcattgggc ctgttatatg ggagtcggag ggtcttttcc gcgcttatat ttcttcggtg     360

actgatgggg atggtaagag ccataaagta ggatttctaa gaattcctac atatagttgg     420

caggacatgg aagattttga tccttcagga ccgcctcctt gggaagaatt tgctaagatt     480

attcaagtat tttcttctaa tacagaagct ttgattatcg accaaacgaa caacccaggt     540

ggtagtgtcc tttatcttta tgcactgctt tccatgttga cagaccgtcc tttagaactt     600

cctaaacata gaatgattct gactcaggat gaagtggttg atgctttaga ttggttaacc     660

ctgttggaaa acgtagacac aaacgtggag tctcgccttg ctctgggaga caacatggaa     720

ggatatactg tggatctaca ggttgccgag tatttaaaaa gctttggacg tcaagtattg     780

aattgttgga gtaaagggga tatcgagtta tcaacgccta ttcctctttt tggttttgag     840

aagattcatc cacatcctcg a                                              861
```

<210> SEQ ID NO 8
<211> LENGTH: 763
<212> TYPE: DNA
<213> ORGANISM: Chlamydia trachomatis

<400> SEQUENCE: 8

-continued

```
ataacaaaaa catcttgatt atttttgtta aaagaaatac ttaatgagtt ttatttaatt     60

aacgaaacga aaagcttgct aatgaaaatt attcacacag ctatcgaatt tgctccggta    120

atcaaagccg gaggcctggg agacgcgcta tacggactag caaaagcttt agccgctaat    180

cacacaacgg aagtggtaat ccctttatac cctaaattat ttactttgcc caaagaacaa    240

gatctttgct cgatccaaaa attatcttat ttttttgctg gagagcaaga agcaactgct    300

ttctcctact tttatgaagg aattaaagta actctattca aactcgacac acagccagag    360

ttattcgaga atgcggaaac aatctacaca agcgatgatg ccttccgttt ttgcgctttt    420

tctgctgctg cggcctccta catccaaaaa gaaggagcca atatcgttca tttacacgat    480

tggcatacag gattagttgc tggactactc aaacaacagc cctgctctca attacaaaag    540

attgttctta ccctacataa ttttggttat cgaggctata caacacgaga aatattagaa    600

gcctcctctt tgaatgaatt ttatatcagc cagtaccaac tatttcgcga tccacaaact    660

tgtgtgttgc taaaaggagc tttatactgt tcagatttcg tgactacggt ttctcctaca    720

tacgccaaag aaattcttga agattattcc gattacgaaa ttc                     763
```

<210> SEQ ID NO 9
<211> LENGTH: 665
<212> TYPE: DNA
<213> ORGANISM: Chlamydia trachomatis

<400> SEQUENCE: 9

```
ttgaaactaa aaacctaatt tatttaaagc tcaaaataaa aaagagtttt aaaatgggaa     60

attctggttt ttatttgtat aacactgaaa actgcgtctt tgctgataat atcaaagttg    120

ggcaaatgac agagccgctc aaggaccagc aaataatcct tgggacaaca tcaacacctg    180

tcgcagccaa aatgacagct tctgatggaa tatctttaac agtctccaat aattcatcaa    240

ccaatgcttc tattacaatt ggtttggatg cggaaaaagc ttaccagctt attctagaaa    300

agttgggaga tcaaattctt gatggaattg ctgatactat tgttgatagt acagtccaag    360

atattttaga caaaatcaaa acagaccctt ctctaggttt gttgaaagct tttaacaact    420

ttccaatcac taataaaatt caatgcaacg ggttattcac tcccagtaac attgaaactt    480

tattaggagg aactgaaata ggaaaattca cagtcacacc caaaagctct gggagcatgt    540

tcttagtctc agcagatatt attgcatcaa gaatggaagg cggcgttgtt ctagctttgg    600

tacgagaagg tgattctaag ccctgcgcga ttagttatgg atactcatca ggcattccta    660

attta                                                                665
```

<210> SEQ ID NO 10
<211> LENGTH: 843
<212> TYPE: DNA
<213> ORGANISM: Chlamydia trachomatis

<400> SEQUENCE: 10

```
tgggaatgtc gaagaatacg attacgttct cgtatctata ggacgccgtt tgaatacaga     60

aaatattggc ttggataaag ctggtgttat ttgtgatgaa cgcggagtca tccctaccga    120

tgccacaatg cgcacaaacg tacctaacat ttatgctatt ggagatatca caggaaaatg    180

gcaacttgcc catgtagctt ctcatcaagg aatcattgca gcacggaata tagctggcca    240

taaagaggaa atcgattact ctgccgtccc ttctgtgatc tttaccttcc ctgaagtcgc    300

ttcagtaggc ctctccccaa cagcagctca acaacaaaaa atccccgtca aagtaacaaa    360
```

-continued

```
attcccattt cgagctattg gaaaagcggt cgcaatgggc gaggccgatg gatttgcagc    420

cattatcagc catgagacta ctcagcagat cctaggagct tatgtgattg gccctcatgc    480

ctcatcactg atttccgaaa ttaccctagc agttcgtaat gaactgactc ttccttgtat    540

ttacgaaact atccacgcac atccaacctt agcagaagtt tgggctgaaa gtgcgttgtt    600

agctgctgat accccattac atatgccccc tgctaaaaaa tgaccgattc agaatctcct    660

actcctaaaa aatctatacc cgccagattc cctaagtggc tacgccagaa actcccttta    720

gggcgggtat ttgctcaaac tgataatact atcaaaaata aagggcttcc tacagtctgt    780

gaggaagcct cttgtccgaa tcgcacccat tgttggtcta gacatacagc gtacctatct    840

agc                                                                  843
```

<210> SEQ ID NO 11
<211> LENGTH: 1474
<212> TYPE: DNA
<213> ORGANISM: Chlamydia trachomatis

<400> SEQUENCE: 11

```
acagaaggga cggcagagta atcgatttcc tctttatggc cagctatatt ccgtgctgca     60

atgattcctt gatgagaagc tacatgggca agttgccatt ttcctgtgat atctccaata    120

gcataaatgt taggtacgtt tgtgcgcatt gtggcatcgg tagggatgac tccgcgttca    180

tcacaaataa caccagcttt atccaagcca atattttctg tattcaaacg gcgtcctata    240

gatacgagaa cgtaatcgta ttcttcgaca ttcccattga tagttaaccg aacgcgatct    300

cctatatcct caatatttga tacagaggct tctagtacga aacggagtcc ttgtcgggtg    360

aatttatcga acatggtttt tgaaatatct ggattattca aagcaaggat ttgagagctt    420

gcttcgatca cagaaacttc ggagcctaac gtatggaata aggaagcgaa ttcgcaaccg    480

atcacaccac cgccaataat ggccattttt tgagggattt ctttgaggtt tagcacgcct    540

gttgagcata aaatccgagg agattctgcg gaaaaaggaa tcccggggaa agctcgtggt    600

tcagagccgg tggctaggat aatggagtgc gctttgatta cagaagggtt ttctcctaag    660

atttttactt ctgttgaaga gatcaaagag cctcttccag agaagacagt gatcttattg    720

ctgcgaatga gaccattaag tccatcgcgg atgctacgga ctacggaatc cttcctttgt    780

accatagcgg gatagttgat gctgaatcct tctacatgaa tcccaaactg gtcagcatgg    840

cgtatttggg taacgacttc agctcctgct aagagggctt tagaaggaat acaccctcgg    900

tttaaacagg ttccgccagc ctctcgcttt tcgattagcg cagttttgag tcctgcttga    960

gcggcagtga ttgctgcaac atagcctcct ggccccgctc cgataactac acagtcgaaa   1020

gcttcattca taacatttcc tcttcaatga gtgtttagga ttgcaacgat ccatatgaga   1080

tgattatctg aaggaagagg attctccttc caagcctttc taggaaaggg aaagagaggt   1140

ccttcagaca aatacatttc ccggattgta catctgggtg gataaaatct caatgaggag   1200

aagtggtagc aggagagaaa aaataggaac gtaagagtgt tatttcgaat gctcagggag   1260

agagcggtac ccacgataag caagcagaat cccgactagt gcatagatgt atgagcgatt   1320

ctttggccag gagagaacga gtccagagcc tgtcgaaaac aagagaatca tgagcgaaaa   1380

ggtaaggaaa ccgcaaccca agaagagagc tgcagtcggc caatattgta gccagtccca   1440

ctgggagggg gcaggctctt gaacaggctc ctca                               1474
```

<210> SEQ ID NO 12
<211> LENGTH: 2017

-continued

<212> TYPE: DNA
<213> ORGANISM: Chlamydia trachomatis

<400> SEQUENCE: 12

```
ataagcattc tcatctaccc agaagtagaa gtcaaaacct tcataagtat ctaaaaagac     60
tcgcatataa tcttcgatac catccggagg cgctcctgcg atccatattc catggatgat    120
tttctcaaca ggtacacgat ggcctttaaa ttctgttttg atggtttcaa gaacaccttc    180
aatcggagtc gtcttaggtt tttcttcggc tttctgttcc ttagcttttg cctgtttagg    240
ctgagcctgc gatgatgctg gaagcttctt ctgaatggca tcgacgtatt ttccttgttg    300
aatcaaggaa ttctgtcccg cttccgaatt tttatctggc atagagttgt aagcactaat    360
gaccttttc agtttattta ataggtcttt aacagtagat ttctgttcag gagtaattcc    420
tagtttttct tctatgttct tgggagtaag atcgtatttg ctagcatcaa gattttctat    480
ctttccagaa gaagcttcct ccttcttctc ttctatagca cgcttttttc tcgataaaac    540
agctgctgta ggaggaactg cactagcaga aatcgttttt acccccccc ctctgaacag    600
agtacgtacg aacgttcact ggctgtgtaa taaacttcgt ctttctctta cgaggagagg    660
ttttgtcgtt acttcctgtt ctttagagat tgtagtgacc ttattctctg aagtagaagt    720
ctctgccgtc tcgtgccgaa ttcggcacga gaagccatgt tatctttgct tagatcaatg    780
ccttcttgtt ttttgaattc atcaagcatc cagttgatga tgactccgtc gaagtcgtct    840
cctcccaagt gagtatcccc gttggttgag agaacttcaa aaactccgtc accgatttcc    900
aagatagaaa tatcgaaagt tcctcctcct aagtcgaaga cggcgatttt tttatctcct    960
tccttatcaa taccataagc aagagcggcc gctgttggtt caggaataat gcgtttaaca   1020
tctaatcctg cgatacgtcc agcatctttt gtagaagctc tttgagaatc gttaaagtaa   1080
gctggtacgg taatgactgc ttccgttact gtttctccga gataagcctc agcagtttcc   1140
ttcatcttca tgaggatctg agcgccgatt tcttctggag tgtacagttt ttgttccaca   1200
tcaaagaccg catctccttt cgagttagga gcaactttgt aggggactgt tttaatttca   1260
gattcgactt cagagaattt tctaccgatg aatcgcttag tagaagccaa tgttttttca   1320
ggattggtta ctgcctgacg ttttgcagga attccaacaa gagtttcgcc acctttaaaa   1380
gcaacgatag aaggagtagt acgagttcct tcagaagagg caataacttt aggttggcca   1440
ccttccataa cagagacgca agagttggtc gtccctaggt cgataccaat aattttgtta   1500
gactttcttt tttcgctcat attgaacacc taatttctag gataattatt ctttttcttc   1560
gttaccgtct gagtttcctt tagcaggaag ttttgctact ttcactttgg ctacgcgaat   1620
aggacgatct cctatcttat aacctttagt aaattcctcc aagatagtcc cttctggaat   1680
tgttgtggtt tcttcgattt ctacagcttc atgcaggtac ggattaaata gttctccttt   1740
cgaggaatat tcaaccacac ctttctcttc gaagatttgc ttaaattgtt gaaggatcat   1800
ttggaatcct atagcccaat tttttacttc ttcagaggtt tgagaagcga atcccaaagc   1860
cttttccata ctttcgatag aaggaaggaa atccataaga gcattttcta cagcatactg   1920
catcatttct gtgcgttctt tctgtagtcg ttttcttgag ttttctgctt cagcgagagc   1980
catcagatat cgatcattct gttcttgcct cgtgccg                            2017
```

<210> SEQ ID NO 13
<211> LENGTH: 1171
<212> TYPE: DNA
<213> ORGANISM: Chlamydia trachomatis -continued

<400> SEQUENCE: 13

```
ggtaaacgag ttaaaacaag agcatacagg gctaacggac tcgcctttag tgaaaaaagc     60

tgaggagcag attagtcaag cacaaaaaga tattcaagag atcaaaccta gtggttcgga    120

tattcctatc gttggtccga gtgggtcagc tgcttccgca ggaagtgcgg caggagcgtt    180

gaaatcctct aacaattcag gaagaatttc cttgttgctt gatgatgtag acaatgaaat    240

ggcagcgatt gcactgcaag gttttcgatc tatgatcgaa caatttaatg taaacaatcc    300

tgcaacagct aaagagctac aagctatgga ggctcagctg actgcgatgt cagatcaact    360

ggttggtgcg gatggcgagc tcccagccga aatacaagca atcaaagatg ctcttgcgca    420

agctttgaaa caaccatcag cagatggttt ggctacagct atgggacaag tggcttttgc    480

agctgccaag gttggaggag gctccgcagg aacagctggc actgtccaga tgaatgtaaa    540

acagctttac aagacagcgt ttttcttcgac ttcttccagc tcttatgcag cagcactttc    600

cgatggatat tctgcttaca aaacactgaa ctctttatat tccgaaagca gaagcggcgt    660

gcagtcagct attagtcaaa ctgcaaatcc cgcgctttcc agaagcgttt ctcgttctgg    720

catagaaagt caaggacgca gtgcagatgc tagccaaaga gcagcagaaa ctattgtcag    780

agatagccaa acgttaggtg atgtatatag ccgcttacag gttctggatt ctttgatgtc    840

tacgattgtg agcaatccgc aagcaaatca agaagagatt atgcagaagc tcacggcatc    900

tattagcaaa gctccacaat ttgggtatcc tgctgttcag aattctgcgg atagcttgca    960

gaagtttgct gcgcaattgg aaagagagtt tgttgatggg gaacgtagtc tcgcagaatc   1020

tcaagagaat gcgtttagaa aacagcccgc tttcattcaa caggtgttgg taaacattgc   1080

ttctctattc tctggttatc tttcttaacg tgtgattgaa gtttgtgaat gagggggagc   1140

caaaaaagaa tttctttttt ggctcttttt t                                  1171
```

<210> SEQ ID NO 14
<211> LENGTH: 877
<212> TYPE: DNA
<213> ORGANISM: Chlamydia trachomatis

<400> SEQUENCE: 14

```
cagagaattc tcgacatact atctaatcgg atatgtaaag ctgctttaca tcccttgaac     60

tagaaataaa atggaaataa aaagcccaga acaagagaag ttgttctggg ctgacagaag    120

ctgtcagatc attttaataa gattgatgac aactacgaca agttcctgga tccaaaaaag    180

aatctaaaaa gccatacaaa gattgcgtta cttcttgcga tgcctctaac actttatcag    240

cgtcatcttt gagaagcatc tcaatgagcg ctttttcttc tctagcatgc cgcacatccg    300

cttcttcatg ttctgtgaaa tatgcatagt cttcaggatt ggaaaatcca aagtactcag    360

tcaatccacg aattttctct ctagcgatac gtggaatttg actctcataa gaatacaaag    420

cagccactcc tgcagctaaa gaatctcctg tacaccaccg cacgaaagta gctactttcg    480

cttttgctgc ttcactaggc tcatgagcct ctaactcttc tggagtaact cctagagcaa    540

acacaaactg cttccacaaa tcaatatgat tagggtaacc gttctcttca tccatcaagt    600

tatctaacaa taacttacgc gcctctaaat catcgcaacg actatgaatc gcagataaat    660

atttaggaaa ggctttgata tgtaaataat agtctttggc atacgcctgt aattgctctt    720

tagtaagctc ccccttcgac catttcacat aaaacgtgtg ttctagcata tgcttatttt    780

gaataattaa atctaactga tctaaaaaat tcataaacac ctccatcatt tcttttcttg    840

actccacgta accgcttgca aaaaaggtcc gtataag                            877
```

<210> SEQ ID NO 15
<211> LENGTH: 396
<212> TYPE: DNA
<213> ORGANISM: Chlamydia trachomatis serovar E

<400> SEQUENCE: 15
tgtaccaaat atgagcttag atcaatctgt tgttgaactt tacacagata ctgccttctc 60
ttggagcgtg ggcgctcgag cagctttgtg ggagtgcgga tgtgcgactt taggggcttc 120
tttccaatac gctcaatcta aacctaaagt cgaagaatta aacgttctct gtaacgcagc 180
tgagtttact atcaataagc ctaaaggata tgtagggcaa gaattccctc ttgcactcat 240
agcaggaact gatgcagcga cgggcactaa agatgcctct attgattacc atgagtggca 300
agcaagttta gctctctctt acagattgaa tatgttcact ccctacattg gagttaaatg 360
gtctcgagca agttttgatg ccgatacgat tcgtat 396

<210> SEQ ID NO 16
<211> LENGTH: 516
<212> TYPE: DNA
<213> ORGANISM: Chlamydia trachomatis serovar E

<400> SEQUENCE: 16
ctcaaaattt gacgatttct cagaatacag ggaatgttct gttttataac aacgtggcct 60
gttcgggagg agctgttcgt atagaggatc atggtaatgt tcttttagaa gcttttggag 120
gagatattgt ttttaaagga aattcttctt tcagagcaca aggatccgat gccatctatt 180
ttgcaggtaa agaatcgcat attacagccc tgaatgctac ggaaggacat gctattgttt 240
tccacgacgc attagttttt gaaaatctag aagaaaggaa atctgctgaa gtattgttaa 300
tcaatagtcg agaaaatcca ggttacactg gatctattcg atttttagaa gcagaaagta 360
aagttcctca atgtattcat gtacaacaag gaagccttga gttgctaaat ggagctacat 420
tatgtagtta tggttttaaa caagatgctg gagctaagtt ggtattggct tctggatcta 480
aactgaagat tttagattca ggaactcctg tacaag 516

<210> SEQ ID NO 17
<211> LENGTH: 723
<212> TYPE: DNA
<213> ORGANISM: Chlamydia trachomatis serovar E

<400> SEQUENCE: 17
ctccttttaa gggggacgat gtttacttga atggagactg cgcttttgtc aatgtctatg 60
caggggcaga gaacggctca attatctcag ctaatggcga caatttaacg attaccggac 120
aaaaccatac attatcattt acagattctc aagggccagt tcttcaaaat tatgccttca 180
tttcagcagg agagacactt actctgaaag atttttcgag tttgatgttc tcgaaaaatg 240
tttcttgcgg agaaaaggga atgatctcag ggaaaaccgt gagtatttcc ggagcaggcg 300
aagtgatttt ttgggataac tctgtggggt attctccttt gtctattgtg ccagcatcga 360
ctccaactcc tccagcacca gcaccagctc ctgctgcttc aagctcttta tctccaacag 420
ttagtgatgc tcggaaaggg tctatttttt ctgtagagac tagtttggag atctcaggcg 480
tcaaaaaagg ggtcatgttc gataataatg ccgggaattt tggaacagtt tttcgaggta 540
atagtaataa taatgctggt agtgggggta gtgggtctgc tacaacacca agttttacag 600
ttaaaaactg taaagggaaa gtttctttca cagataacgt agcctcctgt ggaggcggag 660

-continued

```
tagtctacaa aggaactgtg cttttcaaag acaatgaagg aggcatattc ttccgaggga    720

aca                                                                    723
```

<210> SEQ ID NO 18
<211> LENGTH: 1377
<212> TYPE: DNA
<213> ORGANISM: Chlamydia trachomatis serovar E

<400> SEQUENCE: 18

```
aaacagctaa tcgtcactac gctcacgtgg actgccctgg tcacgctgac tatgttaaaa     60

acatgatcac cggtgcggct caaatggacg gggctattct agtagtttct gcaacagacg    120

gagctatgcc tcaaactaaa gagcatattc ttttggcaag acaagttggg gttccttaca    180

tcgttgtttt tctcaataaa attgacatga tttccgaaga agacgctgaa ttggtcgact    240

tggttgagat ggagttggct gagcttcttg aagagaaagg atacaaaggg tgtccaatca    300

tcagaggttc tgctctgaaa gctttggaag ggatgctgc atacatagag aaagttcgag     360

agctaatgca agccgtcgat gataatatcc ctactccaga aagagaaatt gacaagcctt    420

tcttaatgcc tattgaggac gtgttctcta tctccggacg aggaactgta gtaactggac    480

gtattgagcg tggaattgtt aaagtttccg ataaagttca gttggtcggt cttagagata    540

ctaaagaaac gattgttact ggggttgaaa tgttcagaaa agaactccca gaaggtcgtg    600

caggagagaa cgttggattg ctcctcagag gtattggtaa gaacgatgtg gaaagaggaa    660

tggttgtttg cttgccaaac agtgttaaac ctcatacaca gtttaagtgt gctgtttacg    720

ttctgcaaaa agaagaaggt ggacgacata agcctttctt cacaggatat agacctcaat    780

tcttcttccg tacaacagac gttacaggtg tggtaactct gcctgaggga gttgagatgg    840

tcatgcctgg ggataacgtt gagtttgaag tgcaattgat tagccctgtg gctttagaag    900

aaggtatgag atttgcgatt cgtgaaggtg gtcgtacaat cggtgctgga actatttcta    960

agatcattgc ataaattaag tgatgtgttg gcgaggctga aaagccttgc ctttgggtgt   1020

gtagcttaga tggtagagca gtggcctcca aagccgccgg tcgggggttc gaatccctcc   1080

gcactcgtat taggtaactg aaagaagaat tcgcttatgg ggcaagatca ccgaagaaaa   1140

tttcttaaga aagtatcttt tgcaaaaaaa caagcagctt ttgcgggtaa ctttatcgaa   1200

gaaattaaga agattgagtg ggtaaataag cgaaatctta aaagatacgt caagattgtt   1260

ttgatgaata tttttggctt tggattttcc atctattgtg tggatttagc tcttcgaaag   1320

tccctttcat tgttcggtaa agtaacaagc tttttctttg gttgattcat gtttaag      1377
```

<210> SEQ ID NO 19
<211> LENGTH: 1736
<212> TYPE: DNA
<213> ORGANISM: Chlamydia trachomatis serovar E

<400> SEQUENCE: 19

```
gtagcggaac aaagccggac cacgaggcct catagaatat aaaaatacga ggagcttaaa     60

catgtcagat caagcaacga ccctcaagat taaacctttg ggagatagaa ttttagttaa    120

aagagaagaa gaagcttcca ctgcaagagg cggaatcatt cttcctgaca ctgccaagaa    180

aaagcaagat agagctgaag ttttagctct aggaacaggc aaaaaagatg ataaagggca    240

gcaacttcct tttgaagttc aggttggtga catcgtttta attgataaat attctggcca    300

agaactcact gtagaaggtg aagagtacgt catcgttcaa atgagcgaag ttatcgcagt    360

tctgcaataa aaactaagag agtgaagtaa gatttaaggg agcgcatcaa tggtcgctaa    420
```

```
aaacattaaa tacaacgaag aagccagaaa gaaaattcaa aaaggagtta agactttagc    480
tgaagctgta aaagtcactc tagggcctaa aggacgacat gttgtcatag ataaaagctt    540
cggatcccct caagtaacta aagatggtgt taccgttgcg aaagaagttg agcttgccga    600
caaacatgaa aatatgggcg ctcaaatggt caaagaagtc gccagcaaaa ctgctgacaa    660
agctggagac ggaactacaa cagctactgt tcttgctgaa gctatctata cagaaggatt    720
acgcaatgta acagctggag caaatccaat ggacctcaaa cgaggtattg ataaagctgt    780
taaggttgtt gttgatcaaa tcagaaaaat cagcaaacct gttcagcatc ataaagaaat    840
tgctcaagtt gcaacaattt ctgctaataa tgatgcagaa atcgggaatc tgattgctga    900
agcaatggag aaagttggta aaaacggctc tatcactgtt gaagaagcaa aaggatttga    960
aaccgttttg gatgttgttg aaggaatgaa tttcaataga ggttacctct ctagctactt   1020
cgcaacaaat ccagaaactc aagaatgtgt attagaagac gctttggttc taatctacga   1080
taagaaaatt tctgggatca aagatttcct tcctgtttta caacaagttg ctgaatccgg   1140
ccgtcctctt cttattatag cagaagacat tgaaggcgaa gctttagcta ctttggtcgt   1200
gaacagaatt cgtggaggat tccgggtttg cgcagttaaa gctccaggct ttggagatag   1260
aagaaaagct atgttggaag acatcgctat cttaactggc ggtcaactca ttagcgaaga   1320
gttgggcatg aaattagaaa acgctaactt agctatgtta ggtaaagcta aaaaagttat   1380
cgtttctaag gaagacacga ccatcgtcga aggaatgggt gaaaaagaag ctttagaagc   1440
tcgttgcgaa agcatcaaaa aacaaattga agacagctct tctgattacg ataaagaaaa   1500
actccaagag cgtcttgcta agctctctgg tggagtagca gtcattcgcg ttggagctgc   1560
aacagagatt gagatgaaag agaaaaaaga tcgtgtagac gatgctcaac atgctacaat   1620
cgctgctgtt gaagaaggaa ttcttcctgg tggaggaaca gcattaatcc gttgtatccc   1680
tactcttgag gccttcttgc caatgttgac taatgaagat gagcaaattg gagctc         1736
```

```
<210> SEQ ID NO 20
<211> LENGTH: 1135
<212> TYPE: DNA
<213> ORGANISM: Chlamydia trachomatis serovar E

<400> SEQUENCE: 20

ggctcttgat gaaaaagagc ggcaggttat ggctctttat tactatgatg acttggtatt     60
aaaagaaatt gggaagattt taggagtgag cgagtcccga gtttctcaga tacactccaa    120
agctttattg aagttacgag gtacattgtc cagtctgctt tagtaactgt ctccagaaga    180
tcctctttgt atttttccta tcaatattct attggagaag cgcgtcgttt ttttgacgag    240
gtgtctgcta tcgcttgcct tgctataaaa agaacaggat agataagatg ttgctagata    300
agtttatatg gatagatttt tatgcaacag ttaatcgata accttaagaa acggggtatt    360
ctagataatt cttctgcagg attagaaact cgtgccgaag tttgtggaga agagaaagaa    420
atctctctag cagactttcg tggtaagtat gtagtgctct tcttttatcc taaagatttc    480
acctatgtgt gtcctacaga attgcatgct tttcaagata gattggtaga ttttgaagag    540
cggggtgcag tcgtgcttgg ttgctccgtt gacgacattg agacacattc tcgttggctc    600
gctgtagcga gaaatgcagg aggaatagag ggaacagaat atcctctgtt agcagaccct    660
tcttttaaaa tatcagaagc ttttggtgtt ttgaatcctg aaggatcgct cgctttaaga    720
gcgactttcc ttatcgataa acatggggtt gttcgtcatg cggttatcaa tgatcttcct    780
```

-continued

```
ttagggcgtt ccattgacga ggaattgcgt attttagatt cattgatctt ctttgagaac    840

cacggaatgg tttgtccagc taactggcgt tctggagagc gtggaatggt gccttctgaa    900

gagggattaa aagaatattt ccagacgatg gattaagcat ctttgaaagt aagaaagtcg    960

tacagatctt gatctgaaaa gagaagaagg ctttttaatt ttctgcagag agccagcgag   1020

gcttcaataa tgttgaagtc tccgccacca ggcaatgcta aggcgatgat attagttagt   1080

gaaatctgag tgttaaggaa ataaaggcca aagaagtagc tatcaataaa gaagc        1135
```

<210> SEQ ID NO 21
<211> LENGTH: 731
<212> TYPE: DNA
<213> ORGANISM: Chlamydia trachomatis serovar E

<400> SEQUENCE: 21

```
ttgaagacac tctttctccc ggagtcacag ttcttgaagc tgcaggagct caaatttctt     60

gtaataaagt agtttggact gtgaaagaac tgaatcctgg agagtctcta cagtataaag    120

ttctagtaag agcacaaact cctggacaat tcacaaataa tgttgttgtg aagagctgct    180

ctgactgtgg tacttgtact tcttgcgcag aagcgacaac ttactggaaa ggagttgctg    240

ctactcatat gtgcgtagta gatacttgtg accctgtttg tgtaggagaa aatactgttt    300

accgtatttg tgtcaccaac agaggttctg cagaagatac aaatgtttct ttaatgctta    360

aattctctaa agaactgcaa cctgtatcct tctctggacc aactaaagga acgattacag    420

gcaatacagt agtattcgat tcgttaccta gattaggttc taaagaaact gtagagtttt    480

ctgtaacatt gaaagcagtt acagctggag atgctcgtgg ggaagcgatt ctttcttccg    540

atacattgac tgttccagtt tctgatacag agaatacaca catctattaa tctttgattt    600

tatcgatgtg taggtgccgt ccagggattc ctgggcggct ttttttgtt atctatatga    660

aaataaaaga gttcattttc ggtctcagag catattctag acgggttttt gaaaaaaata    720

agtgtttgtg t                                                         731
```

<210> SEQ ID NO 22
<211> LENGTH: 1181
<212> TYPE: DNA
<213> ORGANISM: Chlamydia trachomatis serovar E

<400> SEQUENCE: 22

```
ctatcgtctg aatgctgaac tgaaacatct ttttgattta gacgcgttag ccgatgctat     60

ggatctatct cgagatctac agttttctta catgggtatt caaaatctgt atgatcgtta    120

ttttaatcac cacgaagatt gccgtttaga aactccccaa attttttgga tgcgcgttgc    180

tatggggttg gcattgaatg agcaagacaa gacttcttgg gctattactt tttataattt    240

gctttcgaca ttccgatata caccagctac gccaaccttg ttcaattcag gtatgcggca    300

ttctcagtta agctcttgct atctttccac tgtacaagat aatttggtca atatctataa    360

ggtcattgct gataacgcta tgctatctaa gtgggcagga gggataggta atgattggac    420

ggcggttcgt gcaacagggg ctttaattaa aggaaccaat ggaagaagtc agggagtaat    480

tccttttatt aaggtgacaa atgatacagc agtcgcagtg aatcaaggtg gtaaacgcaa    540

gggagctgta tgcgtctatt tagaagtttg gcacctcgac tacgaagatt tccttgaatt    600

gagaaagaat acaggggatg agcgtcgacg ggctcatgat gtcaatatag ctagctggat    660

tccagatctt ttcttcaaac gtttacagca aaaagggaca tggactctat tcagcccaga    720

tgatgttccg ggattacacg atgcttatgg ggaagaattt gagcgtttgt acgaagaata    780
```

-continued

```
tgagcggaag gttgataccg gagagattcg gttattcaag aaggtagaag ctgaagatct    840

gtggagaaaa atgctcagca tgctttttga aacgggacac ccatggatga cttttaaaga    900

tccatccaac atccgttcgg ctcaagatca taaaggcgtg gtgcgttgtt ccaatctgtg    960

tacggagatt ttgttaaact gctcggagac agaaactgct gtttgtaatt taggatcgat   1020

taacttagtt caacatatcg taggggatgg gttagatgag gaaaaactct ctgagacgat   1080

ctctatagca gtccgtatgt tggataacgt gattgatatt aacttttatc caacaaagga   1140

agctaaagag gcgaactttg ctcaccgcgc tattggatta g                       1181
```

<210> SEQ ID NO 23
<211> LENGTH: 167
<212> TYPE: DNA
<213> ORGANISM: Chlamydia trachomatis serovar E

<400> SEQUENCE: 23

```
ttaaaaagat tttaaactaa aaagaagatt tttaattata gtttttcaaa atcattttga     60

tatttttaat gctgagataa acaagaaaag cggaaactcc ttgcgacaaa gattttctgc    120

tcgagccctc ttccctgagg attttttagg ggagatccat tcttcca                  167
```

<210> SEQ ID NO 24
<211> LENGTH: 1265
<212> TYPE: DNA
<213> ORGANISM: Chlamydia trachomatis serovar E

<400> SEQUENCE: 24

```
caggttcttt ctagacgaac aaagaataat cctatgttga taggggagcc cggagttggg     60

aaaacagcaa tcgctgaagg acttgctctt cgcatagtgc aaggggatgt tccagagagt    120

ttaaaggaaa agcatctgta tgtactggat atgggagctt tgattgcagg tgccaagtat    180

cgaggagagt ttgaagagcg gttaaaaagt gtattgaagg gtgtagaagc ttctgaaggc    240

gagtgtatcc tattcattga tgaagtgcat actttagtag gagcgggagc tacagatgga    300

gctatggatg cagcgaatct attaaagcct gctttagcac gaggcacttt gcattgtatt    360

ggcgctacga ctttgaatga ataccaaaaa tatatagaga aagacgcggc tttggaacgg    420

cgtttccagc ctatttttgt aacagaacct tctttggaag atgctgtatt cattctccgg    480

gggttaaggg aaaaatatga aatttttcat ggtgtgcgca ttacagaagg ggctttgaat    540

gcagctgtag ttctttctta tcgttacatc acagaccgat ttcttcctga taaggcgatt    600

gacctaattg atgaggctgc gagtttaatc cgtatgcaaa taggaagttt acctctgcct    660

attgatgaaa aggaaagaga attatcagct ttaatcgtga aacaagaagc tattaaacgc    720

gagcaagcac cagcttatca ggaagaggct gaagacatgc aaaaagcaat tgaccgggtt    780

aaggaagagc tggccgcttt acgcttgcgc tgggatgaag aaaaaggatt aattgcagga    840

ttaaaagaaa agaagaatgc tttagaaaat ttaaaatttg ccgaagagga agctgagcgt    900

actgccgatt acaatcgggt agcagaacta cgctatagtt tgattccttc tttggaggaa    960

gaaattcatt tagctgagga agctttaaat caaagagatg ggcgcctgct tcaagaggaa   1020

gttgatgagc ggttgattgc gcaagttgtt gcgaattgga ctggaatccc tgtgcaaaaa   1080

atgttggagg gagaatctga aaagttattg gtgttgagga gtctttagaa gaaagggttg   1140

tcggacagcc tttcgctatt gccgcagtca gtgattcgat tcgagctgct cgagtaggat   1200

tgagtgatcc gcagcgtctc cctcacaagg gaatattagc tggcgcggcg aaccgctggc   1260
```

-continued gaaac 1265

<210> SEQ ID NO 25
<211> LENGTH: 463
<212> TYPE: DNA
<213> ORGANISM: Chlamydia trachomatis serovar E

<400> SEQUENCE: 25
atgacgaaca accccatgtt tatcgataag gaaagtcgct cttaaagcga gcgatccttc 60
aggattcaaa acaccaaaag cttctgatat tttaaaagaa gggtctgcta acagaggata 120
ttctgttccc tctattcctc ctgcatttct cgctacagcg agccaacgag aatgtgtctc 180
aatgtcgtca acggagcaac caagcacgac tgcaccccgc tcttcaaaat ctaccaatct 240
atcttgaaaa gcatgcaatt ctgtaggaca cacataggtg aaatctttag gataaaagaa 300
gagcactaca tacttaccac gaaagtctgc tagagagatt tctttctctt ctccacaaac 360
aacggcttta ccagaaaaat ccggagcctg tcttccaatt agtgatccca taatactcct 420
cctagaaaga aacaacgcac cagagaggat ttgaacctct gac 463

<210> SEQ ID NO 26
<211> LENGTH: 636
<212> TYPE: DNA
<213> ORGANISM: Chlamydia trachomatis serovar E

<400> SEQUENCE: 26
ggtagaaaat tctctgaagt cgaatctgaa attaaaacag tcccctacaa agttgctcct 60
aactcgaaag gagatgcggt ctttgatgtg gaacaaaaac tgtacactcc agaagaaatc 120
ggcgctcaga tcctcatgaa gatgaaggaa actgctgagg cttatctcgg agaaacagta 180
acggaagcag tcattaccgt accagcttac tttaacgatt ctcaaagagc ttctacaaaa 240
gatgctggac gtatcgcagg attagatgtt aaacgcatta ttcctgaacc aacagcggcc 300
gctcttgctt atggtattga taaggaagga gataaaaaaa tcgccgtctt cgacttagga 360
ggaggaactt tcgatatttc tatcttggaa atcggtgacg gagtttttga agttctctca 420
accaacgggg atactcactt gggaggagac gacttcgacg gagtcatcat caactggatg 480
cttgatgaat tcaaaaaaca agaaggcatt gatctaagca aagataacat ggctttgcaa 540
agattgaaag atgctgctga aaaagcaaaa atagaattgt ctggtgtatc gtctactgaa 600
atcaatcagc cattcatcac tatcgacgct aatgga 636

<210> SEQ ID NO 27
<211> LENGTH: 1797
<212> TYPE: DNA
<213> ORGANISM: Chlamydia trachomatis serE

<400> SEQUENCE: 27
atgcatcacc atcaccatca catgagcatc aggggagtag gaggcaacgg gaatagtcga 60
atcccttctc ataatgggga tggatcgaat cgcagaagtc aaaatacgaa gggtaataat 120
aaagttgaag atcgagtttg ttctctatat tcatctcgta gtaacgaaaa tagagaatct 180
ccttatgcag tagtagacgt cagctctatg atcgagagca ccccaacgag tggagagacg 240
acaagagctt cgcgtggagt gctcagtcgt ttccaaagag gtttagtacg aatagctgac 300
aaagtaagac gagctgttca gtgtgcgtgg agttcagtct ctacaagcag atcgtctgca 360
acaagagccg cagaatccgg atcaagtagt cgtactgctc gtggtgcaag ttctgggtat 420
agggagtatt ctccttcagc agctagaggg ctgcgtctta tgttcacaga tttctggaga 480

```
actcgggttt tacgccagac ctctcctatg gctggagttt ttgggaatct tgatgtgaac    540
gaggctcgtt tgatggctgc gtacacaagt gagtgcgcgg atcatttaga agcgaaggag    600
ttggctggcc ctgacggggt agcggccgcc cgggaaattg ctaaaagatg ggagaaaaga    660
gttagagatc tacaagataa aggtgctgca cgaaaattat taaatgatcc tttaggccga    720
cgaacaccta attatcagag caaaaatcca ggtgagtata ctgtagggaa ttccatgttt    780
tacgatggtc ctcaggtagc gaatctccag aacgtcgaca ctggtttttg gctggacatg    840
agcaatctct cagacgttgt attatccaga gagattcaaa caggacttcg agcacgagct    900
actttggaag aatccatgcc gatgttagag aatttagaag agcgttttag acgtttgcaa    960
gaaacttgtg atgcggctcg tactgagata gaagaatcgg gatggactcg agagtccgca   1020
tcaagaatgg aaggcgatga ggcgcaagga ccttctagag tacaacaagc ttttcagagc   1080
tttgtaaatg aatgtaacag catcgagttc tcatttggga gctttggaga gcatgtgcga   1140
gttctctgcg ctagagtatc acgaggatta gctgccgcag gagaggcgat tcgccgttgc   1200
ttctcttgtt gtaaaggatc gacgcatcgc tacgctcctc gcgatgacct atctcctgaa   1260
ggtgcatcgt tagcagagac tttggctaga ttcgcagatg atatgggaat agagcgaggt   1320
gctgatggaa cctacgatat tcctttggta gatgattgga gaagaggggt tcctagtatt   1380
gaaggagaag gatctgactc gatctatgaa atcatgatgc ctatctatga agttatgaat   1440
atggatctag aaacacgaag atcttttgcg gtacagcaag ggcactatca ggacccaaga   1500
gcttcagatt atgacctccc acgtgctagc gactatgatt tgcctagaag cccatatcct   1560
actccacctt tgcctcctag atatcagcta cagaatatgg atgtagaagc agggttccgt   1620
gaggcagttt atgcttcttt tgtagcagga atgtacaatt atgtagtgac acagccgcaa   1680
gagcgtattc ccaatagtca gcaggtggaa gggattctgc gtgatatgct taccaacggg   1740
tcacagacat ttagagacct gatgaagcgt tggaatagag aagtcgatag ggaataa      1797
```

<210> SEQ ID NO 28
<211> LENGTH: 1983
<212> TYPE: DNA
<213> ORGANISM: Chlamydia trachomatis serE

<400> SEQUENCE: 28

```
atgcatcacc atcaccatca catggaatca ggaccagaat cagtttcttc taatcagagc     60
tcgatgaatc caattattaa tgggcaaatc gcttctaatt cggagaccaa agagtccacg    120
aaggcgtccg aagcgagtcc ttcagcatcg tcctctgtaa gcagctggag ttttttatcc    180
tcagcaaaga atgcattaat ctctcttcgt gatgccatct tgaataaaaa ttccagtcca    240
acagactctc tctctcaatt agaggcctct acttctacct ctacggttac acgtgtagcg    300
gcaaaagatt atgatgaggc taaatcgaat tttgatacgg cgaaaagtgg attagagaac    360
gctaagacac ttgctgaata cgaaacgaaa atggctgatt tgatggcagc tctccaagat    420
atggagcgtt tagctaattc agatcctagt aacaatcata ccgaagaagt aaataatatt    480
aagaaagcgc tcgaagcaca aaaagatact attgataagc tgaataaact cgttacgctg    540
caaaatcaga ataaatcttt aacagaagtg ttgaaaacaa ctgactctgc agatcagatt    600
ccagcgatta atagtcagtt agagatcaac aaaaattctg cagatcaaat tatcaaagat    660
ctggaaagac aaaacataag ttatgaagct gttctcacta acgcaggaga ggttatcaaa    720
gcttcttctg aagcgggaat taagttagga caagctttgc agtctattgt ggatgctggg    780
```

-continued

```
gaccaaagtc aggctgcagt tctgcaagca cagcaaaata atagcccaga taatattgca    840

gccacgaagg aattaattga tgctgctgaa acgaaggtaa acgagttaaa acaagagcat    900

acagggctaa cggactcgcc tttagtgaaa aaagctgagg agcagattag tcaagcacaa    960

aaagatattc aagagatcaa acctagtggt tcggatattc ctatcgttgg tccgagtggg   1020

tcagctgctt ccgcaggaag tgcggcagga gcgttgaaat cctctaacaa ttcaggaaga   1080

atttccttgt tgcttgatga tgtagacaat gaaatggcag cgattgcact gcaaggtttt   1140

cgatctatga tcgaacaatt taatgtaaac aatcctgcaa cagctaaaga gctacaagct   1200

atggaggctc agctgactgc gatgtcagat caactggttg gtgcggatgg cgagctccca   1260

gccgaaatac aagcaatcaa agatgctctt gcgcaagctt tgaaacaacc atcagcagat   1320

ggtttggcta cagctatggg acaagtggct tttgcagctg ccaaggttgg aggaggctcc   1380

gcaggaacag ctggcactgt ccagatgaat gtaaaacagc tttacaagac agcgttttct   1440

tcgacttctt ccagctctta tgcagcagca ctttccgatg gatattctgc ttacaaaaca   1500

ctgaactctt tatattccga aagcagaagc ggcgtgcagt cagctattag tcaaactgca   1560

aatcccgcgc tttccagaag cgtttctcgt tctggcatag aaagtcaagg acgcagtgca   1620

gatgctagcc aaagagcagc agaaactatt gtcagagata gccaaacgtt aggtgatgta   1680

tatagccgct tacaggttct ggattctttg atgtctacga ttgtgagcaa tccgcaagca   1740

aatcaagaag agattatgca gaagctcacg gcatctatta gcaaagctcc acaatttggg   1800

tatcctgctg ttcagaattc tgcggatagc ttgcagaagt ttgctgcgca attggaaaga   1860

gagtttgttg atggggaacg tagtctcgca gaatctcaag agaatgcgtt tagaaaacag   1920

cccgctttca ttcaacaggt gttggtaaac attgcttctc tattctctgg ttatcttttct   1980

taa                                                                 1983
```

<210> SEQ ID NO 29
<211> LENGTH: 1224
<212> TYPE: DNA
<213> ORGANISM: Chlamydia trachomatis serE

<400> SEQUENCE: 29

```
gtaactttc aacatttttc acaatgacaa gaataaaagc aaaaagaaag gctgccgata      60

aaataaaagt tttactgcga gaacagaaga ctaaaactat ctggacgaat aagccggatg    120

cgcaggataa ttgcgcataa aacactttaa tagagagtga tcttatgtct aaaacaccat    180

tatccatagc tcatccttgg catgggccag tattaacacg cgatgattat gaatctcttt    240

gttgctatat agaaatcact ccagccgact ccgttaaatt cgaactggat aaagaaactg    300

gtatcctaaa agtggatcgg ccacaaaagt tttctaactt ttgtccttgc ttatacgggc    360

tgttacctaa gacttattgt ggagatcttt ctggagaata cagtggtcaa caaagtaaca    420

gagagaatat caaaggcgat ggcgatcctc ttgatatctg tgtgttaacg gaaaaaaata    480

ttacacaagg gaacatcctc ttgcaagcgc gtcctatcgg agggattcgt attttagact    540

cggaagaagc cgatgataaa atcatcgctg ttctagaaga tgatttagtc tatggcaata    600

tagaagatat ttctgaatgc ccaggcacag ttttggacat gatccaacac tatttcttaa    660

cctataaagc tactccagaa agcttaattc aagcaaaacc agctaaaatt gaaattgtag    720

gtttatacgg caaaaaagaa gctcaaaaag tcattcgtct tgctcacgaa gactattgca    780

atctttttat gtaaatcgac agaaaaagaa aaggctgttg tgggagattc cacaacggcc    840

cctcctaacc aagttttttt catcctaggg gactttatga agcaaataga taactttgaa    900
```

-continued

```
caaattcatc tctcgtgccg aattcggcac gagattaaaa caaagctctc aaaaagagtt    960

ggtatcccga attcattcag cagttcccgg tgccaaagtt aaagagatac gctttttatt   1020

aggatagtta tggacgcaca agaaaagaaa tacgacgcat cagccatcac cgttttagaa   1080

ggattgcaag ctgttcgtga gcgtcctgga atgtacattg gtgatacagg agttaccgga   1140

ttgcatcact tggtttatga agtggtggat aacagtatcg atgaggcaat ggcgggtttt   1200

tgtaccgagg tcgttgttcg cata                                          1224
```

```
<210> SEQ ID NO 30
<211> LENGTH: 883
<212> TYPE: DNA
<213> ORGANISM: Chlamydia trachomatis serE

<400> SEQUENCE: 30

atgttgacta acatggcgac catcagaaac tctgtgaaga cattgaacag aattgaattg     60

gatcttgaag cttctaattc tggtcttacg aaaaaagaga tcgctttatt aacgaaaaga    120

catcgcaagt tgcttaacaa cctggaaggt gttcgtcata tgaactctct cccagggctt    180

ttaattgtaa ttgacccggg ctatgagcgc attgctgtcg cagaagctgg aaaactaggc    240

attcctgtaa tggccttagt tgatacaaac tgcgatccaa caccaatcaa ccacgttatt    300

ccttgcaacg atgattccat taagagtatc cgtctggttg tcaatgtact taaagacgct    360

gttattgatg cgaagaagcg ttcaggcatc gaaattttat ctccagtacg tcctgtagaa    420

agacctgcag aagaagctgt ggaagagttg cctcttccaa caggtgaagc tcaagatgaa    480

gcttcttcta aagaaggttt tttactttgg gcagatattg acaattgcgg ggcattgaaa    540

tgagcgactt ctccatggaa acattgaaaa atttaagaca gcagacaggt gtaggcctga    600

ctaaatgtaa agaggctcta gagcatgcta agggcaattt agaagatgct gttgtttatt    660

tacgtaagct tggtcttgcc tctgcaggca aaaaagaaca ccgagaaaca aaagaaggcg    720

taattgctgc actcgttgat gaacgtggtg cggcacttgt tgaagtcaac gttgaaactg    780

attttgttgc taacaacagt gttttccgag cattcgttac aggtttgtta tccgatcttc    840

ttgaccacaa gcttagcgat gttgaagctt tagctcgcgt aat                      883
```

```
<210> SEQ ID NO 31
<211> LENGTH: 393
<212> TYPE: DNA
<213> ORGANISM: Chlamydia trachomatis serE

<400> SEQUENCE: 31

agttgaaaaa ggctgtttct tgcattcaaa aaactatcga gcaagagaga tctattttgt     60

ttgttggaac aaaaaaacag gcaaaacaga tcattagaga agctgctatc gaatgtggcg    120

aattctttgc ttcagagaga tggttgggtg gcatgttgac taacatggcg accatcagaa    180

actctgtgaa gacattgaac agaattgaat tggatcttga agcttctaat tctggtctta    240

cgaaaaaaga gatcgcttta ttaacgaaaa gacatcgcaa gttgcttaac aacctggaag    300

gtgttcgtca tatgaactct ctcccagggc ttttaattgt aattgacccg ggctatgagc    360

gcattgctgt cgcagaagct ggaaaactag gca                                 393
```

```
<210> SEQ ID NO 32
<211> LENGTH: 2577
<212> TYPE: DNA
<213> ORGANISM: Chlamydia trachomatis serE
```

-continued

<400> SEQUENCE: 32

```
attacggagg ccatacggta tcttctcgag gaggatttca agggatatgc gtacgaatag     60
ccgatttatt ccgtaactgt ttctctcgta atagaggcac tactactacg ccatctcgaa    120
ctgttatcac tcaggcagat atttatcatc cgactatttc tggacaagga gctcaaccta    180
ttgtctctac aggagataag aaattagata gcgcaattat tcaagcagat ttgcgtgcgc    240
agaataaaca gactttggct acacatattc aaagtaagct aggttctatg gagggacaat    300
ctcctcaaga ttataaagct ggtgcgtata gtgcgctaag attgatgctg tttactccag    360
gcgaaactac tgtgagtagc gagcgggaac gtcaagcgtg cgttacgggt cgggatctct    420
gggaacaggc tgcaggagat cttgctacca atgggaatac agatgggctt atgttaatgg    480
ctaacctatc tgtgggaggg aagcatgtgc ctgcggggca tttaagagaa tacatggata    540
ctgtaaaggg tacgtttact gatgagaacg aggctacaga tcctacggta gatgccattt    600
tagatttagc agcaaaaatc gatgcgacgg aattctctag tcctggttca gggcaagtca    660
ttcttaatta tataggaaat tatggacaag tcgttttaga aaacgaggag atgaaccttc    720
ttgttttaga agatcaaaat gggcaagatc ctcaacgtgt tcaagataac tcaaaagagt    780
tacaaaaact gttagaaaat gctcgaaaaa cagatcctga gttatatttc caaacactaa    840
ctgtcataac ttcttctgtt ttcttagact aaagagaagg tatacggtgt tcggtccttt    900
caactattaa gaggaagtag tggtgagtag cataagccct atagggggga attctgggcc    960
agagggattt tctagtgcat ctcgaggcga tgagattgat gatgtaccag atagtgaaga   1020
gggagagcta gaagagcgcg tttcggatca tgcagagtct atcattaccg agagctcgga   1080
aacgctgttt cgtactactt cttcatcagg ggtcagtgaa gatcttcagc aacacgttag   1140
cttggaggaa tctccacgac aacgaggttt ccttggacgg atccgtgatg cagtagcttc   1200
tatttggaag cgtcgtgttg cacgaaggaa tgaaaactat gatgtgaaaa aagcagaaga   1260
gcagcaaggg attgtgcaat atctgcagga ttcgaaaatg cctgctttaa cgcgtgccta   1320
tcgccatctc cgtgctttca attctgcatg cttacgtacg attcgtgagt tttcgctac    1380
catttttcgt gctttaaggg atgcgtatta tcgacattgt acacgttctg ggatcaactt   1440
ttgtggagct gataaagact ctttagaagt tcttgttgcg gtgggtttgc ttttgcgtat   1500
ggctaccttta cgctcttttg aacatgtcgg tgggaattac gaagatcgat tagtaaataa   1560
tgatgctccg gtgacaggtg cggggagaac tcttgttgat gatgctgtag acgatattga   1620
atcgatttta aatacgagaa ccaactggcc tcaacatgtc atgatagggt tttctcgtgg   1680
tctcgttcaa ttatgtgcga ctccttataa tgcgacttct caagaatgtt tcaagtcgat   1740
tgttcgttta gaaaaagaag acccttcttc agattattct caagctttat tattagcagg   1800
gataatagat cgcttggcgg agaaagcccc tatggctgca aagtatgttt tggatgcatt   1860
gcgtgttcga acttcggagc tcataggaga actcattatt ctcgatttgc ttcctcctgt   1920
atggaaggtt ggccgcggag gcgtattccc tcctgtgaat gagcagctcg ttgtgcaaat   1980
tgttaatgca aacgtagaac gattgcattc cactttcgct catgagccac aagcttattt   2040
gcgtatgatc gaaggtttgg taaccaattt ctttttctta cctagcgagg aagatccttc   2100
ttcggttggg aatatctaag aacattttct aatagggaag aggataaata gcgtgaaata   2160
atactgatta tgtgaagaat aggcaaaaag acctaaatcc ttatatgcta ttagattctc   2220
gtttccctac agattattat ttacgtatcc tagaattagt catccgggat gcttcttgta   2280
aattggtata taaccgacgc ctgcatatgt tggaggcgat ccctcttgat caaaaacttt   2340
```

```
ctactgatca agagggggaa tcaagtattt tacgagaagt gattagcgag ctacttgcgc   2400

attctgggga aagttatgcg atttcagctc aattacttgc cgtaatcgat atttatttaa   2460

aacaagagca accgtcgaat tcatggttcg ctcgaatctt tcggaagaga gagcgggcta   2520

gaaaacgaca aacaattaat aagttgcttt tgttaaaaag tatcctattt tttgaac      2577
```

<210> SEQ ID NO 33
<211> LENGTH: 554
<212> TYPE: DNA
<213> ORGANISM: Chlamydia trachomatis serE

<400> SEQUENCE: 33

```
ttctttatta aaaaaaactt tctcttttct ctcagacttc ttatgagtca agaaactcaa     60

cgagtcttgg tgtatggaga aggatttttt agaaaatgtt tatcgtcatt tccgttaccg    120

tttttttaaa ttaagtgtac ttccagctct tctcggactc tggctatttt ttactcctaa    180

tattcttaac tatttggatt cttctgttat tttatcagat aaaatttgcg gcgtcctttt    240

aattttatta tcagctttat ccttttataa tcctgttatt ttgcaactag gcatttttat    300

tgggctctgg gtttctttct tttcttgttc ttccgaccta cttcctttag tatttgctca    360

tgattcgcta ctaggttttg ccacactagc tattattttt ctactcccta atcgtcctga    420

agatctagaa gttggtccta ctattccaga aacttgccat tataatcctt cttccggagg    480

gaaaagagct gcggttctta tttttgcttt tgtaggatgg ttacaaagtc gctacttaac    540

ttccgcggca cgag                                                      554
```

<210> SEQ ID NO 34
<211> LENGTH: 1433
<212> TYPE: DNA
<213> ORGANISM: Chlamydia trachomatis serE

<400> SEQUENCE: 34

```
ctgcacgaaa attattaaat gatcctttag gccgacgaac acctaattat cagagcaaaa     60

atccaggtga gtatactgta gggaattcca tgttttacga tggtcctcag gtagcgaatc    120

tccagaacgt cgacactggt tttggctgg acatgagcaa tctctcagac gttgtattat    180

ccagagagat tcaaacagga cttcgagcac gagctacttt ggaagaatcc atgccgatgt    240

tagagaattt agaagagcgt tttagacgtt tgcaagaaac ttgtgatgcg gctcgtactg    300

agatagaaga atcgggatgg actcgagagt ccgcatcaag aatggaaggc gatgaggcgc    360

aaggaccttc tagagcacaa caagcttttc agagctttgt aaatgaatgt aacagcatcg    420

agttctcatt tgggagcttt ggagagcatg tgcgagttct ctgcgctaga gtatcacgag    480

gattagctgc cgcaggagag gcgattcgcc gttgcttctc ttgttgtaaa ggatcgacgc    540

atcgctacgc tcctcgcgat gacctatctc ctgaaggtgc atcgttagca gagactttgg    600

ctagattcgc agatgatatg ggaatagagc gaggtgctga tggaacctac gatattcctt    660

tggtagatga ttggagaaga ggggttccta gtattgaagg agaaggatct gactcgatct    720

atgaaatcat gatgcctatc tatgaagtta tgaatatgga tctagaaaca cgaagatctt    780

ttgcggtaca gcaagggcac tatcaggacc caagagcttc agattatgac ctcccacgtg    840

ctagcgacta tgatttgcct agaagcccat atcctactcc acctttgcct cctagatatc    900

agctacagaa tatggatgta gaagcagggt tccgtgaggc agtttatgct tcttttgtag    960

caggaatgta caattatgta gtgacacagc cgcaagagcg tattcccaat agtcagcagg   1020
```

-continued

```
tggaagggat tctgcgtgat atgcttacca acgggtcaca gacatttaga gacctgatga   1080

agcgttggaa tagagaagtc gatagggaat aaactggtat ctaccatagg tttgtagcaa   1140

aaaactaagc ccaccaagaa gaaattctct ttggtgggct tcttttttta ttcaaaaaag   1200

aaagccctct tcaagattat accaagatgg gatgtataat ctgaaaggaa ggcgttttat   1260

tctctatcca tatgatggtg gtggtatcct cctttagagg agcagcagtc tccatgacgt   1320

tttttgaagc agcacttcaa gaagtttagg cagaccataa ccccagcgat tcccgttact   1380

acataagctg cttgtgtcca catggttcct tcaccaagca ggtgagtaag tag          1433
```

```
<210> SEQ ID NO 35
<211> LENGTH: 196
<212> TYPE: DNA
<213> ORGANISM: Chlamydia trachomatis

<400> SEQUENCE: 35

ctcgtgccga tgatacagca gtcgcagtga atcaaggtgg taaacgcaag ggagctgtat     60

gcgtctattt agaagtttgg cacctcgact acgaagattt ccttgaattg agaaagaata    120

caggggatga gcgtcgacgg gctcatgatg tcaatatagc tagctggatt ccagatcttt    180

tcttcaaacg tttaca                                                    196
```

```
<210> SEQ ID NO 36
<211> LENGTH: 1990
<212> TYPE: DNA
<213> ORGANISM: Chlamydia trachomatis

<400> SEQUENCE: 36

ttcactaggc tcatgagcct ctaactcttc tggagtaact cctagagcaa acacaaactg     60

cttccacaaa tcaatatgat tagggtaacc gttctcttca tccatcaagt tatctaacaa    120

taacttacgc gcctctaaat catcgcaacg actatgaatc gcagataaat atttaggaaa    180

ggctttgata tgtaaataat agtctttggc atacgcctgt aattgctctt tagtaagctc    240

ccccttcgac catttcacat aaaacgtgtg ttctagcata tgcttatttt gaataattaa    300

atctaactga tctaaaaaat tcataaacac ctccatcatt tcttttcttg actccacgta    360

accgcttgca aaaaaggtcc gtataagtcc tctgtttcat ctatgcgcaa agaacaatac    420

tcttctcgag aagtaggatg tgaatggtag accatattag gtgcctgctc tatcaccgct    480

aacggtgttt gctcattccc ctctcccata caaacaacag ccgcaactgc taaggcatct    540

acaagattac tttgcgtcat ctgtaagaga cgaccgaaac aatctagcga tcctatatag    600

ttgtgtaatg gagaaaatcc ataccaacac agcccgatac ccagtactcc acgccgcatt    660

ggagtagtat ggctatctgt aatgattacg cctagctctt tcactcgaaa ataatttctt    720

aaccattctc cgatgcgatt acacgatccc aaaatatctt taggatataa aacaaaaggc    780

tggtccgtat tcgattcatc aatccctgca gaaggaatca aaatacctte tttttttcgtt   840

agatatatcc cgcttttctc acaaaacaaa taagcatccg cttctttttt tatcagctct    900

gctttgcaca ttcttgcatc agcgacagcg ccttcacata aactcacaat ctttgaagag    960

acaactacca cactccgttc ttgcagaggc ggcaaagcct cttgcaagat ctcttgaagc   1020

gaatcatgtg caaatacttt acgtgttttg atcggagtta ttttcataat aataaatact   1080

gaaatcctct gtattacaaa tacattcctt cttccatcct gataatcgcg tgatagggaa   1140

gaaagtatcg ccccaatatt cctttttgat atgtgtgaca aaacaagctt tcagaaggtt   1200

ttgttggaaa aaactttcaa agagctccgc tcccccaatt aaaaacggat gattcaaaga   1260
```

```
tagtgtccca tactctgcaa aggaagaaac tcctatgcat tgtggtggat gcatcctgcg   1320

agaaaagaca acgatatccc gcccatgctt atacttgtct ggaagagact cccaagtctt   1380

tcgtcccata atgatgggat gatttcgaat ggtttctgca aaaaaacgta gatcttcggg   1440

ataactccaa gggagcttgc ctaaagctcc catcactcct ctgggatcaa tagcaacgat   1500

acctgttgct tggatcatac aaacatacca gcccaagcag cagcggctaa ggcacgtctg   1560

ttaccttcaa cctgatgcac gcgtagataa tcaactcctc gatcatgaag agatacagaa   1620

cagccgatcg tttcccaatc acgatcgtta ctattaaatc ggcccaacat actcaaacac   1680

gattttctag aatggcctat taatacagga cactctaaaa cacgtttaaa ctgctttact   1740

ccatccatca ataacatcga ctgaacggga gtcttcccaa atcctattcc tggatcgaaa   1800

acaacttgcc aacttgtatc taaacctact tgagcaaatt gttctaactg ggactctccc   1860

caacgcaaca tttgctcaat aggagattct tcataagaaa gtacacaatc tggtcttgga   1920

ggcagcgaac acgaatgatt tattaatagc cgtagcccaa actccttcgc caaatgagcc   1980

atttccaaag                                                          1990
```

<210> SEQ ID NO 37
<211> LENGTH: 2093
<212> TYPE: DNA
<213> ORGANISM: Chlamydia trachomatis

<400> SEQUENCE: 37

```
cagaaactct atccgcatac cttcttcggc aaattgatac caattttgcc tcttctcagg     60

aacgtactat agctcagtat attgtaggca acctctcccc agaaggactc tttttagaaa    120

atcctagtct tgtggctgca gatttaaacg tttccgaaca ccttttccac aaggtatggc    180

aacgtatcca acaattacat cctttaggag tcggagcgcc ttccctacag tcctactggg    240

tatcgctact acagacatct ccccataagg aggctttagc tattattcgc aaccatttcc    300

ctagattagc tcgttgtgat ttcactacta tcgctaggaa aatgcatgca accacaacag    360

agattcttac atttcttaga cacgcttttg cttccatccc ttggtgtcca gcagcaggct    420

tttccgagac actgcacccc cctgctccag cgcttcctga tgcctacctt tccttctcgc    480

gaaactctta ttgggatgtc tctattaata aagattgtct cccctctatt agactcaacg    540

acaccgtact agatatctat ccttctcttc ctcgtgaaga gaaagaccac ctatcgcaac    600

aaatccgagc agcaaaacaa ttgcttcgca atgtaaaaaa acgagaagaa acgttattgg    660

ctatccttcg agttctcatc ccctaccaag aagagttcct tcttaaaaaa cgcacctctc    720

ctaaagcttt ttctgtaaaa caaatagctc gcgaactctc tcttcatgaa gctaccgttt    780

gtcgcgccat tgataataaa acgttagcaa cccctgttgg attactccct atgcgatcgc    840

tatttccaca agcggttgga tcctgccccg atcaatctaa agcaactatt ttgcattgga    900

tccaccagtg gatttctaca gaaaaacatc ctctatctga tgcagctatt agccaaaaaa    960

ttattgagaa gggcatcccc tgcgcacgac gcacagtagc caaatatcgt tcgcaactga   1020

atatcccacc tgcgcaccaa cgcaaacacc tatgctctgt tttaacaaca acacgcacag   1080

agaattctcg acatactatc taatcggata tgtaaagctg ctttacatcc cttgaactag   1140

aaataaaatg gaaataaaaa gcccagaaca agagaagttg ttctgggctg acagaagctg   1200

tcagatcatt ttaataagat tgatgacaac tacgacaagt tcctggatcc aaaaaagaat   1260

ctaaaaagcc atacaaagat tgcgttactt cttgcgatgc ctctaacact ttatcagcgt   1320
```

-continued

```
catctttgag aagcatctca atgagcgctt tttcttctct agcatgccgc acatccgctt   1380
cttcatgttc tgtgaaatat gcatagtctt caggattgga aaatccaaag tactcagtca   1440
atccacgaat tttctctcta gcgatacgtg gaatttgact ctcataagaa tacaaagcag   1500
ccactcctgc agctaaagaa tctcctgtac accaccgcac gaaagtagct actttcgctt   1560
ttgctgcttc actaggctca tgagcctcta actcttctgg agtaactcct agagcaaaca   1620
caaactgctt ccacaaatca atatgattag ggtaaccgtt ctcttcatcc atcaagttat   1680
ctaacaataa cttacgcgcc tctaaatcat cgcaacgact atgaatcgca gataaatatt   1740
taggaaaggc tttgatatgt aaataatagt ctttggcata cgcctgtaat tgctctttag   1800
taagctcccc cttcgaccat ttcacataaa acgtgtgttc tagcatatgc ttattttgaa   1860
taattaaatc taactgatct aaaaaattca taaacacctc catcatttct tttcttgact   1920
ccacgtaacc gcttgcaaaa aaggtccgta taagtcctct gtttcatcta tgcgcaaaga   1980
acaatactct tctcgagaag taggatgtga atggtagacc atattaggtg cctgctctat   2040
caccgctaac ggtgtttgct cattcccctc tcccatacaa acaacagccg caa          2093
```

<210> SEQ ID NO 38
<211> LENGTH: 1834
<212> TYPE: DNA
<213> ORGANISM: Chlamydia trachomatis

<400> SEQUENCE: 38

```
ctctacttct acctctacgg ttacacgtgt agcggcaaaa gattatgatg aggctaaatc     60
gaattttgat acggcgaaaa gtggattaga gaacgctaag acacttgctg aatacgaaac    120
gaaaatggct gatttgatgg cagctctcca agatatggag cgtttagcta attcagatcc    180
tagtaacaat cataccgaag aagtaaataa tattaagaaa gcgctcgaag cacaaaaaga    240
tactattgat aagctgaata aactcgttac gctgcaaaat cagaataaat ctttaacaga    300
agtgttgaaa acaactgact ctgcagatca gattccagcg attaatagtc agttagagat    360
caacaaaaat tctgcagatc aaattatcaa agatctggaa agacaaaaca taagttatga    420
agctgttctc actaacgcag gagaggttat caaagcttct tctgaagcgg gaattaagtt    480
aggacaagct ttgcagtcta ttgtggatgc tggggaccaa agtcaggctg cagttctgca    540
agcacagcaa aataatagcc cagataatat tgcagccacg aaggaattaa ttgatgctgc    600
tgaaacgaag gtaaacgagt taaaacaaga gcatacaggg ctaacggact cgcctttagt    660
gaaaaaagct gaggagcaga ttagtcaagc acaaaaagat attcaagaga tcaaacctag    720
tggttcggat attcctatcg ttggtccgag tgggtcagct gcttccgcag gaagtgcggc    780
aggagcgttg aaatcctcta acaattcagg aagaatttcc ttgttgcttg atgatgtaga    840
caatgaaatg gcagcgattg cactgcaagg ttttcgatct atgatcgaac aatttaatgt    900
aaacaatcct gcaacagcta aagagctaca agctatggag gctcagctga ctgcgatgtc    960
agatcaactg gttggtgcgg atggcgagct cccagccgaa atacaagcaa tcaaagatgc   1020
tcttgcgcaa gctttgaaac aaccatcagc agatggtttg gctacagcta tgggacaagt   1080
ggcttttgca gctgccaagg ttggaggagg ctccgcagga acagctggca ctgtccagat   1140
gaatgtaaaa cagctttaca agacagcgtt ttcttcgact tcttccagct cttatgcagc   1200
agcactttcc gatggatatt ctgcttacaa aacactgaac tctttatatt ccgaaagcag   1260
aagcggcgtg cagtcagcta ttagtcaaac tgcaaatccc gcgctttcca gaagcgtttc   1320
tcgttctggc atagaaagtc aaggacgcag tgcagatgct agccaaagag cagcagaaac   1380
```

-continued

```
tattgtcaga gatagccaaa cgttaggtga tgtatatagc cgcttacagg ttctggattc   1440

tttgatgtct acgattgtga gcaatccgca agcaaatcaa gaagagatta tgcagaagct   1500

cacggcatct attagcaaag ctccacaatt tgggtatcct gctgttcaga attctgcgga   1560

tagcttgcag aagtttgctg cgcaattgga aagagagttt gttgatgggg aacgtagtct   1620

cgcagaatct caagagaatg cgtttagaaa acagcccgct ttcattcaac aggtgttggt   1680

aaacattgct tctctattct ctggttatct ttcttaacgt gtgattgaag tttgtgaatg   1740

agggggagcc aaaaaagaat ttcttttttg gctctttttt cttttcaaag gaatctcgtg   1800

tctacagaag tcttttcagc acgagcggca cgag                                1834
```

<210> SEQ ID NO 39
<211> LENGTH: 1180
<212> TYPE: DNA
<213> ORGANISM: Chlamydia trachomatis

<400> SEQUENCE: 39

```
agaaatttct caaaaatcaa agttttttac atttaagggg catcttacca ccacaacaac     60

cttctatgag cagaaactat ccattaaata aaagtaatta aatataacaa aaacatcttg    120

attatttttg ttaaaagaaa tacttaatga gttttattta attaacgaaa cgaaaagctt    180

gctaatgaaa attattcaca cagctatcga atttgctccg gtaatcaaag ccggaggcct    240

gggagacgcg ctatacggac tagcaaaagc tttagccgct aatcacacaa cggaagtggt    300

aatcccttta taccctaaat tatttacttt gcccaaagaa caagatcttt gctcgatcca    360

aaaattatct tatttttttg ctggagagca agaagcaact gctttctcct acttttatga    420

aggaattaaa gtaactctat tcaaactcga cacacagcca gagttattcg agaatgcgga    480

aacaatctac acaagcgatg atgccttccg tttttgcgct tttctgctg ctgcggcctc    540

ctacatccaa aaagaaggag ccaatatcgt tcatttacac gattggcata caggattagt    600

tgctggacta ctcaaacaac agccctgctc tcaattacaa aagattgttc ttaccctaca    660

taattttggt tatcgaggct atacaacacg agaaatatta gaagcctcct ctttgaatga    720

attttatatc agccagtacc aactatttcg cgatccacaa acttgtgtgt tgctaaaagg    780

agctttatac tgttcagatt tcgtgactac ggtttctcct acatacgcca aagaaattct    840

tgaagattat tccgattacg aaattcacga tgccattact gctagacaac atcatctccg    900

cgggatttta aatggaatcg acacgacaat ttgggggcct gaaacggatc ccaatttagc    960

gaaaaactac actaaagagc ttttcgagac cccttcaatt ttttttgaag ctaaagccga   1020

gaataaaaaa gccttgtacg aaagattagg cctctcttta gaacactctc cttgcgtgtg   1080

cattatttct agaattgctg agcagaaagg tcctcacttt atgaaacagg ccattctcca   1140

tgcactagaa aacgcttaca cgctcattat tataggtacc                          1180
```

<210> SEQ ID NO 40
<211> LENGTH: 1297
<212> TYPE: DNA
<213> ORGANISM: Chlamydia trachomatis

<400> SEQUENCE: 40

```
agaaacttct ataggagggg atgtgatcga cataggtacg tgtgagttat gggatatcga     60

tttgttgtat aatggataag aaattctctg aagataaaga ggctcctcca actaaaagac    120

cattaacatc agggcagagg gcaagtgagc gagcattatc ggctttcaca gatcctccgt    180
```

-continued

```
aaagaatggg ggtgcgttcc gcaatatctt tggaaaagag agaagcaatc gtttttctac    240

agaaagcatg ggtttcctga actagatcag gatgagctac ttttccggtg cctatagccc    300

agactggttc ataagctaga atgaaagagg cttgctcagg gagtttagat aatcctatag    360

tcagttgatt taaaagaata tcttgagttg ctccagattc ttgttcttct aaagtttctc    420

caatacacag aactggaatc attccactat ggatagctgc agcagctttt tcagcaagta    480

caggattttg ttcatgaaag atatgacgtc tttcggaatg tccgatgaga acaaaatcga    540

ctccgatatc tttgagcatt ggggctgaaa tctcaccagt aaaagctcct gagtcagctt    600

catgagtggt ttgggctcca agaaagatgg gggaatcgct tacagcttgt tgacaagctg    660

acagcagtgt gaaaggagga atgattcctg taatgatttg gggattagac agaatgtcac    720

tagagatgaa actttttaaa aaggtctgag cttcggtaag cgtcttgttc attttccaat    780

taccgaaaac aaattgcttt gatggctcag agtggagaag gtgggcccaa gttggaaatg    840

gttttctgtg agtttctttg tctgtaaaca tgagatttgc tgaataacct gtgcatgtat    900

tttgtttgta agatagatca aagcgtaata ctcgatttct tgcaaggaag gcttattttt    960

atatgattta ttttctattg ctttgatata aatctcttgg atatgctaat cttcctgtct   1020

tacttttttc tgtgaatttg cttaaatagt tggttttagc ccctttgtta tatgaaggtg   1080

aaaatttgtg gtattacgca tcctgatgat gctcgggaag ctgccaaagc gggagccgat   1140

tacattggca tgatttttgc taaagattct cgaagatgtg tgagtgaaga aaaagcaaag   1200

tatatcgtag aggctataca ggaagggaat tcggaacctg ttggagtatt cccagagcat   1260

tcagtagaag aaattttagc tattactgag acgacag                             1297
```

<210> SEQ ID NO 41
<211> LENGTH: 1141
<212> TYPE: DNA
<213> ORGANISM: Chlamydia trachomatis

<400> SEQUENCE: 41

```
ctttccataa gttctttctt tcaatgattc tagcttattc ttgctgctct ttaagtgggg     60

gggggtatgc agcagaaatc atgattcctc aaggaattta cgatggggag acgttaactg    120

tatcatttcc ctatactgtt ataggagatc cgagtgggac tactgttttt tctgcaggag    180

agttaacgtt aaaaaatctt gacaattcta ttgcagcttt gcctttaagt tgttttggga    240

acttattagg gagttttact gttttaggga gaggacactc gttgactttc gagaacatac    300

ggacttctac aaatggagct gcactaagtg acagcgctaa tagcgggtta tttactattg    360

agggttttaa agaattatct tttttccaatt gcaactcatt acttgccgta ctgcctgctg    420

caacgactaa taatggtagc cagactccga cgacaacatc tacaccgtct aatggtacta    480

tttattctaa aacagatctt ttgttactca ataatgagaa gttctcattc tatagtaatt    540

tagtctctgg agatgggggga gctatagatg ctaagagctt aacggttcaa ggaattagca    600

agctttgtgt cttccaagaa aatactgctc aagctgatgg gggagcttgt caagtagtca    660

ccagtttctc tgctatggct aacgaggctc ctattgcctt tatagcgaat gttgcaggag    720

taagaggggg agggattgct gctgttcagg atgggcagca gggagtgtca tcatctactt    780

caacagaaga tccagtagta agtttttcca gaaatactgc ggtagagttt gatgggaacg    840

tagcccgagt aggaggaggg atttactcct acgggaacgt tgctttcctg aataatggaa    900

aaaccttgtt tctcaacaat gttgcttctc ctgtttacat tgctgctgag caaccaacaa    960

atggacaggc ttctaatacg agtgataatt acggagatgg aggagctatc ttctgtaaga   1020
```

```
atggtgcgca agcagcagga tccaataact ctggatcagt ttcctttgat ggagagggag   1080

tagttttctt tagtagcaat gtagctgctg ggaaaggggg agctatttat gccaaaaagc   1140

t                                                                   1141
```

<210> SEQ ID NO 42
<211> LENGTH: 822
<212> TYPE: DNA
<213> ORGANISM: Chlamydia trachomatis

<400> SEQUENCE: 42

```
cggcacgagt gtatgctgaa caagcagaag ggcccactga gaacgagcct ctgagaaaaa     60

aagcttttat taaaaaatta aaaaaatact ttacaaaact tattctgtag gttgagaaag    120

agcttcaacg taagcattcc aaagctccgt acttacaata ttattgcgga tagagcgaat    180

taattctctt tttagtgatg gaagaggttt tttggggctg aagcgagcca aaagatcttt    240

atcgccaact tgacgagcta actctaacac ccgttcgata tcggtttttg tgaaattcac    300

aaagtctctg cgctttttag aacctcgagg agctcgtggt ttagggctaa tggatctggg    360

agtgatagaa tcgatcacaa acgtctttaa catttttaac agttgctcag gagcagagtt    420

cttcattttt tttaaagtaa aatgatgcat gtagccgcct gttggccctg ggagataacg    480

acaaagatca ttttctttac ttcctccgac tttgctaatc gctttagtta tgagctgctc    540

tatttcttct tggatagtaa tctgtgccgt agccatgaat agctccttag tgggtagtct    600

agttctacag atggtagttt ttgctttatt aattgtaata gtcaactaag tctgtttttt    660

tcgatttaat gttcagtcga aataaaaatc aattagtgtt tatcttttgg tgaattctat    720

agtggttttt gctttttcg caatctcatt ttagagattt ttttgatttg gacaaaagaa    780

aataaagtac ttcagattgt tttctaagtt tgtttgcata aa                       822
```

<210> SEQ ID NO 43
<211> LENGTH: 1634
<212> TYPE: DNA
<213> ORGANISM: Chlamydia trachomatis

<400> SEQUENCE: 43

```
ataaaaaatt aaattttggc tactccctgc tcctaataga atttcaccag aggagcttgc     60

tactgttatt gcatttcttc taggaggatt agctgacgta ctggtaccat ttgcattagt    120

tacattagtc acaatatttt cattaaaaat aatagcatgg cggtcggcag aaattttgga    180

gttactggtt ccgtctatat agatagcgcc ccccttatta ttggcgatat tgtttataaa    240

gtaggtaggg ccattatcca ctagggtaac tacaggagcg taaatagctc cgccataatt    300

ttttgtgata ttgtcactaa aaaagatcct accacgattg cctgtaacat ctaggcgagt    360

agttacttta attgctcctc catcagaagc ttctgaagaa gctgtttcta catttttaaa    420

gcagcgattg ttatagaaaa cgatgttacc acgatttcct gttagagaac agatagggga    480

gaagatcgct cctcctgcac aacaggcgtt attgatgaag aagagatcgc agttattact    540

ctcaaaagaa ttgctcgttc cagcatagat agcgccacct tttcctgctg tattagtttg    600

aatacagatg ttgtccataa agagaaaaca agactgattc tcgctcacaa caaaggtatt    660

agcggtacta atggctcctc cttggacata agaaaagttc ttcataaatc cgaccacatc    720

atgattatga tttatgtaaa gattttgagc atgaatggct ccgccttctc ttattttatc    780

agcagcataa ggatttctcc atgtaaatag tctgcaacaa gtattatttt caaagattac    840
```

-continued

```
aggacctatt gtatcacgaa tctccacggt aggagaattg ggactcgcat aaccaatcgc    900
accaccactt tcaggggtga gatttttttgc aaaataaata ccttcttttt gtgtatcaaa    960
aaagcttagg taatctgtta ttgtgacagc agctccttca ttgggagttt tttgtagaat   1020
agccagtatg tagcgtaggt tatcgagata gcagttagtg agattgtgag tgtctcctgt   1080
caaactaatt ttatttgata gcgactcttt cgtaggatct ggaactgagt tgggcataag   1140
aaagattcta gaaggaacct ctctagctag tcctgatagg gagtttccga taaggaaaaa   1200
gaaaaacgct tttttcataa ttaaaagacc agagctcctc ctgcattgat gtagtgtgag   1260
acagtggaag tagccacttc tgcttgatag ttagcaaata gtttcagatg agaaaatttg   1320
agggagtgag aacctctccc ataaaaggaa tgtttagcta atggggtatt tgtggtgacc   1380
caagaaccgt tattttggat taatagtgtg ttgagtagag gacgtttcca gtagagggtg   1440
ggttggtaag ctagttccat ttcccaagag agtgttggcc atgtatcaga agaataagct   1500
cctttgattc ctattggaga gacaacggca gtatgggctt gctctaatgt aaataatcta   1560
gctagatcac cgctttctcg gatagaagct ggttctgttc gagagaataa agcctgagca   1620
aatggggtga gcat                                                     1634
```

<210> SEQ ID NO 44
<211> LENGTH: 1862
<212> TYPE: DNA
<213> ORGANISM: Chlamydia trachomatis

<400> SEQUENCE: 44

```
gttagctttc cctccaggga tttgcaattt aatgatttta atgatttttt tattcgacat     60
attcaaccct ttcatttggc aagacatgga gtcatagtta gagggtctat gtatgcttct    120
ctaacaagca atatagaagt atatggccat ggaagatatg agtatcgaga tacttctcga    180
ggttatggtt tgagtgcagg aagtaaagtc cggttctaaa aatattggtt agatagttaa    240
gtgttagcga tgccttttttc tttgagatct acatcatttt gttttttagc ttgtttgtgt    300
tcctattcgt atggattcgc gagctctcct caagtgttaa cacctaatgt aaccactcct    360
tttaaggggg acgatgttta cttgaatgga gactgcgctt ttgtcaatgt ctatgcaggg    420
gcagagaacg gctcaattat ctcagctaat ggcgacaatt taacgattac cggacaaaac    480
catacattat catttacaga ttctcaaggg ccagttcttc aaaattatgc cttcatttca    540
gcaggagaga cacttactct gaaagatttt tcgagtttga tgttctcgaa aaatgtttct    600
tgcggagaaa agggaatgat ctcagggaaa accgtgagta tttccggagc aggcgaagtg    660
atttttttggg ataactctgt ggggtattct cctttgtcta ttgtgccagc atcgactcca    720
actcctccag caccagcacc agctcctgct gcttcaagct ctttatctcc aacagttagt    780
gatgctcgga aagggtctat tttttctgta gagactagtt tggagatctc aggcgtcaaa    840
aaaggggtca tgttcgataa taatgccggg aattttggaa cagtttttcg aggtaatagt    900
aataataatg ctggtagtgg gggtagtggg tctgctacaa caccaagttt tacagttaaa    960
aactgtaaag ggaaagtttc tttcacagat aacgtagcct cctgtggagg cggagtagtc   1020
tacaaaggaa ctgtgctttt caaagacaat gaaggaggca tattcttccg agggaacaca   1080
gcatacgatg atttagggat tcttgctgct actagtcggg atcagaatac ggagacagga   1140
ggcggtggag gagttatttg ctctccagat gattctgtaa agtttgaagg caataaaggt   1200
tctattgttt ttgattacaa ctttgcaaaa ggcagaggcg gaagcatcct aacgaaagaa   1260
ttctctcttg tagcagatga ttcggttgtc tttagtaaca atacagcaga aaaaggcggt   1320
```

-continued

```
ggagctattt atgctcctac tatcgatata agcacgaatg gaggatcgat tctgtttgaa   1380
agaaaccgag ctgcagaagg aggcgccatc tgcgtgagtg aagcaagctc tggttcaact   1440
ggaaatctta ctttaagcgc ttctgatggg gatattgttt tttctgggaa tatgacgagt   1500
gatcgtcctg gagagcgcag cgcagcaaga atcttaagtg atggaacgac tgtttcttta   1560
aatgcttccg gactatcgaa gctgatcttt tatgatcctg tagtacaaaa taattcagca   1620
gcgggtgcat cgacaccatc accatcttct tcttctatgc ctggtgctgt cacgattaat   1680
cagtccggta atggatctgt gatttttacc gccgagtcat tgactccttc agaaaaactt   1740
caagttctta actctacttc taacttccca ggagctctga ctgtgtcagg aggggagttg   1800
gttgtgacgg aaggagctac cttaactact gggaccatta cagccacctc tggctcgtgc   1860
cg                                                                 1862
```

<210> SEQ ID NO 45
<211> LENGTH: 1668
<212> TYPE: DNA
<213> ORGANISM: Chlamydia trachomatis

<400> SEQUENCE: 45

```
agaaaatccg atagcagaaa tagaagaatt cgatgtggtt gcgaacaaag ctcaagattg     60
ggatgtcgat gtagctatgt caaattcttt tggttttggc ggacacaatt caacgatatt    120
attttcgagg tatgaacctt cattatgatg aaaactaagc acgaatattc ttttggcgtt    180
attcctatca gatttttttgg tactccggat agaagtacct taaaggcttg ttttatctgc    240
catacagatg ggaaacattg ggtttccct aaggggcatg ctgaggaaaa agaaggccct    300
caggaagctg ctgagagaga acttgtagaa gaaactggtt tggggattgt taattttttc    360
ccaaaaatat ttgtggaaaa ttattccttt aatgacaaag aagaaatctt tgtacgtaaa    420
gaggtaactt attttcttgc agaggttaaa ggcgaagtac atgctgatcc tgatgagatc    480
tgtgatgtgc agtggctaag ctttcaagaa ggtttacgcc ttttaaattt cccagaaatt    540
cgtaatattg ttacggaagc agatgaattt gttcaaagtt atctatttgc ttcataaagt    600
cccctaggat gaaaaaaact tggttaggag gggccgttgt ggaatctccc acaacagcct    660
tttctttttc tgtcgattta cataaaaaga ttgcaatagt cttcgtgagc aagacgaatg    720
actttttgag cttctttttt gccgtataaa cctacaattt caattttagc tggttttgct    780
tgaattaagc tttctggagt agctttatag gttaagaaat agtgttggat catgtccaaa    840
actgtgcctg ggcattcaga aatatcttct atattgccat agactaaatc atcttctaga    900
acagcgatga ttttatcatc ggcttcttcc gagtctaaaa tacgaatccc tccgatagga    960
cgcgcttgca agaggatgtt cccttgtgta atattttttt ccgttaacac acagatatca   1020
agaggatcgc catcgccttt gatattctct ctgttacttt gttgaccact gtattctcca   1080
gaaagatctc cacaataagt cttaggtaac agcccgtata agcaaggaca aaagttagaa   1140
aacttttgtg gccgatccac ttttaggata ccagtttctt tatccagttc gaatttaacg   1200
gagtcggctg gagtgatttc tatatagcaa caaagagatt cataatcatc gcgtgttaat   1260
actggcccat gccaaggatg agctatggat aatggtgttt tagacataag atcactctct   1320
attaaagtgt tttatgcgca attatcctgc gcatccggct tattcgtcca gatagtttta   1380
gtcttctgtt ctcgcagtaa aacttttatt ttatcggcag cctttctttt tgcttttatt   1440
cttgtcattg tgaaaaatgt tgaaaagtta ctcgtggcaa cctttcagac aggtttttttg   1500
```

-continued

```
tacgaaagac gagagtgatt gtactgcaaa ataatatgag ccggacgtag gatatgaaat   1560

actctttgca aatagaagac ctacatattg aaggatatga acaggttttg aaagttactt   1620

gcgagtctgt acagttagtt gctgtaattg ctattcatca gacaaaag                 1668
```

<210> SEQ ID NO 46
<211> LENGTH: 2010
<212> TYPE: DNA
<213> ORGANISM: Chlamydia trachomatis

<400> SEQUENCE: 46

```
atatcaaagt tgggcaaatg acagagccgc tcaaggacca gcaaataatc cttgggacaa     60

catcaacacc tgtcgcagcc aaaatgacag cttctgatgg aatatcttta acagtctcca    120

ataattcatc aaccaatgct tctattacaa ttggtttgga tgcggaaaaa gcttaccagc    180

ttattctaga aaagttggga gatcaaattc ttgatggaat tgctgatact attgttgata    240

gtacagtcca agatatttta gacaaaatca aaacagaccc ttctctaggt ttgttgaaag    300

cttttaacaa ctttccaatc actaataaaa ttcaatgcaa cgggttattc actcccagta    360

acattgaaac tttattagga ggaactgaaa taggaaaatt cacagtcaca cccaaaagct    420

ctgggagcat gttcttagtc tcagcagata ttattgcatc aagaatggaa ggcggcgttg    480

ttctagcttt ggtacgagaa ggtgattcta agccctgcgc gattagttat ggatactcat    540

caggcattcc taatttatgt agtctaagaa ccagtattac taatacagga ttgactccga    600

caacgtattc attacgtgta ggcggtttag aaagcggtgt ggtatgggtt aatgcccttt    660

ctaatggcaa tgatatttta ggaataacaa atacttctaa tgtatctttt ttagaggtaa    720

tacctcaaac aaacgcttaa acaattttta ttggattttt cttataggtt ttatatttag    780

agaaaacagt tcgaattacg gggtttgtta tgcaaaataa aagaaaagtg agggacgatt    840

ttattaaaat tgttaaagat gtgaaaaaag atttccccga attagaccta aaaatacgag    900

taaacaagga aaaagtaact ttcttaaatt ctcccttaga actctaccat aaaagtgtct    960

cactaattct aggactgctt caacaaatag aaaactcttt aggattattc ccagactctc   1020

ctgttcttga aaaattagag gataacagtt taaagctaaa aaaggctttg attatgctta   1080

tcttgtctag aaaagacatg ttttccaagg ctgaatagac aacttactct aacgttggag   1140

ttgatttgca caccttagtt ttttgctctt ttaagggagg aactggaaaa acaacacttt   1200

ctctaaacgt gggatgcaac ttggcccaat ttttagggaa aaaagtgtta cttgctgacc   1260

tagacccgca atccaattta tcttctggat tgggggctag tgtcagaagt gaccaaaaag   1320

gcttgcacga catagtatac acatcaaacg atttaaaatc aatcatttgc gaaacaaaaa   1380

aagatagtgt ggacctaatt cctgcatcat tttcatccga acagtttaga gaattggata   1440

ttcatagagg acctagtaac aacttaaagt tatttctgaa tgagtactgc gctccttttt   1500

atgacatctg cataatagac actccaccta gcctaggagg gttaacgaaa gaagcttttg   1560

ttgcaggaga caaattaatt gcttgtttaa ctccagaacc tttttctatt ctagggttac   1620

aaaagatacg tgaattctta agttcggtcg gaaaacctga agaagaacac attcttggaa   1680

tagctttgtc tttttgggat gatcgtaact cgactaacca aatgtatata gacattatcg   1740

agtctattta caaaaacaag ctttttttcaa caaaaattcg tcgagatatt tctctcagcc   1800

gttctcttct taaagaagat tctgtagcta atgtctatcc aaattctagg gccgcagaag   1860

atattctgaa gttaacgcat gaaatagcaa atattttgca tatcgaatat gaacgagatt   1920

actctcagag gacaacgtga acaaactaaa aaaagaagcg gatgtctttt ttaaaaaaaa   1980
```

-continued

```
tcaaactgcc gcttctctag attttaagaa                                   2010


<210> SEQ ID NO 47
<211> LENGTH: 2044
<212> TYPE: DNA
<213> ORGANISM: Chlamydia trachomatis

<400> SEQUENCE: 47

gtcatcaaga aaagattggg aacctatccg tagtttggtt aaagagcatg gtatgcgaca     60

ttgtcagctt atggctatag ctccgacagc gacgatctcc aacattatag gagtaactca    120

atctattgag ccaacgtaca aacatttgtt tgtgaagtct aatttgtccg gagaattcac    180

gattccaaat gtgtatttaa ttgagaagtt gaagaaatta ggtatctggg atgctgatat    240

gttagatgac ctgaaatatt ttgatgggtc tttattggaa atcgagcgta taccagatca    300

cttaaaacat attttcttga cagcttttga gattgaacca gaatggatta tcgaatgcgc    360

gtctcgaaga caaaaatgga ttgatatggg gcaatccctc aacctttatc ttgcccagcc    420

agacgggaaa aaactgtcga atatgtattt aacggcttgg aaaaaaggtt tgaaaactac    480

gtattatctg agatcttcat cagcaacgac cgttgaaaaa tcttttgtag atattaataa    540

gagaggaatt cagcctcgtt ggatgaagaa taagtctgct tcggcaggaa ttattgttga    600

aagagcgaag aaagcacctg tctgttcttt ggaagaaggg tgtgaagcat gtcagtaatt    660

aatcatataa attaacaata aaattaacgg ttcttatgca agcagatatt ttagatggaa    720

aacagaaacg cgttaatcta aatagcaagc gtctagtgaa ctgcaaccag gtcgatgtca    780

accaacttgt tcctattaag tacaaatggg cttgggaaca ttatttgaat ggctgcgcaa    840

ataactggct ccctacagag atccccatgg ggaaagacat cgaattatgg aagtcggatc    900

gtctttctga agatgagcgg cgagtcattc ttttgaattt aggtttttttc agcaccgcag    960

agagcttggt tgggaataat attgttctag caatttttaa acatgtaact aatccggaag   1020

cgagacaata tcttttaaga caagcttttg aagaagcggt tcacacgcac acatttttgt   1080

atatttgtga gtcactcgga ttagacgaga aagaaatttt caatgcctat aacgagcgtg   1140

ctgcgattaa ggccaaagat gatttccaga tggaaatcac tggcaaggta ttggatccta   1200

attttcgcac ggactctgtt gagggtctac aggagtttgt taaaaactta gtaggatact   1260

acatcattat ggaagggatt ttcttctata gtgggtttgt gatgatcctt tccttccaca   1320

gacaaaataa gatgattggt attggagaac aatatcaata catcttaaga gatgagacaa   1380

tccacttgaa ctttggtatt gatttgatca acgggataaa agaagagaac ccggggattt   1440

ggactccaga gttacagcaa gaaattgtcg aattaattaa gcgagctgtc gatttagaaa   1500

ttgagtatgc gcaagactgt ctccctagag ggattttggg attgagagct tcgatgttca   1560

tcgattatgt gcagcatatt gcagaccgtc gtttggaaag aatcggatta aaacctattt   1620

atcatacgaa aaacccattc ccttggatga gcgaaacaat agaccttaat aaagagaaaa   1680

acttctttga aacaagggtt atagaatatc aacatgcagc aagcttaact tggtagtcct   1740

gatatcaaaa taggagaaag cctcaaccat agagttgagg cttttttttg tcatacggta   1800

acctgataag aatttttaga ttttcaggtt agaagtaaat gtatttaccc atgaattttt   1860

tttaattttc tcataatatc ttgtagccct tttattaaaa tggaaaaggc tagtcacctc   1920

tcctatgact actgttagag tggtgagatt tggggttgga gcaggtgtag cctttcgcat   1980

acgaagtatt ttcctgtgaa accacaagat ttgaaacttc cctatttttg ggaagaacgt   2040
```

-continued

```
tctc                                                                 2044

<210> SEQ ID NO 48
<211> LENGTH: 3734
<212> TYPE: DNA
<213> ORGANISM: Chlamydia trachomatis

<400> SEQUENCE: 48

gttattcgct tctactccat tagaagtccc taatgctaaa ctcaccattt ttcctccttt      60

ccgttaaaac aggaaagaaa ttgtacagaa acattttttt aaagaaatca aaaagccatt     120

tgcaggcaga tatcaggcca tttatatcaa aaacagaaag aatgattagg ataaaacttt     180

gtcttgccat cgttccagag agcattgaga agccgttttt attataaata cattgcacta     240

agaatcttaa aatcgaacag acaacacaat ggctcgaaca gactgatcca cacgcactaa     300

ttcaaatgca aaaaacttct aaaatgaaca cagcaagctt gataaaaaca tataaaagaa     360

ttggatcata gagctttacg agaaggggcg cactgcaatc tgtctcgacc aaatagcaat     420

gcaaacagat aaatacccct aatcattggg aaaaattgag tgtagaatag cctctttctc     480

ttcctctatt tgttgcttag ctaacgcgat ttcttcttta gagatatctg caagtctctg     540

cttatccaaa aagccttgtc tctcattttc caatacaaat ctgtccagag aaactttttt     600

tggctctcca ccatagctag aaattctagt aagaacagca cctagcatca cagatccaaa     660

aacaaccagg gtaaccacta cgtcaatcat aggaagcgta gtccaacctg ccccaataaa     720

taaggctgct cctgtaacta tgaataaaat actaagaata ccgagcgcaa gcacagcaat     780

acgttcgcta caacaagaaa ctctcgcttt agaagcgcta tccaccaaag gagcctctgg     840

catataactt ctaagaggta cactatctcc aacaaaactc atggcatccc ccttaaggta     900

aaagagaagc tttcctctaa atagaaaagc gtatcgtcaa ctcttttata gatctaaaaa     960

gtcttgcttt ccttaatccc acccatgaaa tttagcataa aaaccatcca acatattcac    1020

acgctcttct aaaaggccta tttccctatt tttctgagtc tctaaaaccc tataatggct    1080

ggaaattttc cgcgcacttt ccttggcttc ttgtaatagc tgatctgaat tgcgtatcac    1140

agataacagg taagaaacta atccaaaagc tcctatacaa gaaccaataa ttgcagctct    1200

cccactactc ctaaaactaa ggaagaatag actcccccaa gacaaagaaa aactcctcct    1260

aaagctgcaa gcaaacttgt tagaacaact acaaataact ggtatgtttt agaacggtga    1320

ataaaggagt tgttagccac attttcactg tacctcagtt tttgctgaac aacaattccc    1380

taaaaaattg gtaggacgcc aaacgttcat aattactcta cttggaaacc attaataatt    1440

atatcagact ttcttccaat acacatttca acccactttg aagctgttct atttttttct    1500

gagcaagctc taaatctttg ctcttttgag caagcaatcc ttcaacttct ttcaaatctt    1560

cttctgcttc atatagaagt tcttgataag ataacactaa tccaggagtc acggcctctg    1620

gagctaactc agatgactct gaagggagtc tcgtcggttt taaagaaaac ccatacatat    1680

aaactagact tcctcctata caggcagaac ccagtgtcat tgctaataag ctaagaatag    1740

gagcaaaaag agagaccaca cttcctgaaa aaagaagcag aagagcacca cctaaaactg    1800

ctagtacccc taataccaag gcacctattg ccaacaattg ctctttacgg cttgtagtag    1860

tctgagcacc gatagtttca gtatgatcgg cacgcaatgg tttgctggaa ttacaacaaa    1920

aagaaatatt aaacatggcg cctctatttc gcaaaaaaaa ggccaacatg ctacaggaaa    1980

gctaattaaa gtaaaaattt ttatatattt caatggtagt taaataccta atctacccaa    2040

ccaaaagatg tctaaatgac aaaaaaataa tcgtatttat attatcatga gacacttata    2100
```

-continued

```
gtcacgtctg cttcattcag ctcaaattct aatgaaaaat cggatttaga agaaaataga   2160
ctcgaagagt cagaactagc caaaatgttt gttctaattc tattttgcaa tccccgacta   2220
caagaccaat agagaaacgt taaccctact cctaaagcca cagaaccaat cataatcgct   2280
ccaataccta aaccggcaaa cacaagcgac gatcccccgc aaagcaaaca aagcaaggct   2340
acacaactta aaatagcaaa aattcctaag gaaacggcaa attctatatt tcctcttcgt   2400
ttgcaataaa tatgcgtctt atacagacac aactctgcgg ggctctccag agttggagcg   2460
caagaggaac aaaaaagata agacattgtc gactccggac caaaaaaagg cgagataata   2520
cgcgagatgg taaaaataca gaaatatttt tgacatagaa aaccctaacc ctcctttcat   2580
cgcgtgagac tagagtgtaa aacaagatgc gaaagcaagg ttcgctatgt ttggaaacaa   2640
acctccacac ggtcccggat tatcaaaaca agtcttccag ggatatgtta gagaacgtcc   2700
tatccatacc aaagcaacat atagacgtct tttgtgaaaa gactgaatag aggaatctaa   2760
gaagcttggt tagcgtctat agatgcttta agagcagctt tttccttttc agcactatcc   2820
aaccatcttg tgtagctaga taaaactaag cgcacatcgg acaataaagc ttgctcattt   2880
ttctctaatc tgtccaaaca atcaatctca acttctattg ccttagcttc caaagcttgg   2940
agatcgtccg taagacctcg cagaaacatc ttattaatga aagagacgga gaccaaagcg   3000
tccttctctt ctgaaagatt acgcaaacgt tgctcagcca aaacattttt tgcttctaag   3060
ctagcataag aggatcgaca cataagacga gatattcccg cacccacaca agcagatcca   3120
ataattaatg cagcaatacc tattgcagta aatatgacat tgctagcgca caaaaccaaa   3180
gctaataccc cagcgacaac aactaaagcg cctacgatag ctaaagctat atccaaaatt   3240
ttggaacaag tattcccttt tgttgaagac gaagtagatt ttatctctac gcaggaagct   3300
gttggcaatg gtaaagaaga agcgtctccg ctaatagtag tactcatttt tccacatttt   3360
tatttttaaa acggaaaaac tgtatcagaa cggcgcttta ttcgcaaatc attataaatc   3420
cgcaacatgc agaactaaag cgccgtaagc aaaaggaacc cctaactctc agatgcaata   3480
tctgaggagt ctttaattat tttttacgac gggatgcctg cacctgcagc cgctctgata   3540
atgtcttatt ctcagatctc aatttacaca actctgctgt taattgactg caagtgttct   3600
gactttgttg caaccgctgt ttaaaccctt ctgtctgatg acgaatttct tgttcagcat   3660
cctcctcaat ggagcaaact gtttcggcat aacgcttaca caaatctaat atttgttctt   3720
ccaactcttg gcaa                                                     3734
```

<210> SEQ ID NO 49
<211> LENGTH: 2937
<212> TYPE: DNA
<213> ORGANISM: Chlamydia pneumoniae

<400> SEQUENCE: 49

```
atgcctcttt ctttcaaatc ttcatctttt tgtctacttg cctgtttatg tagtgcaagt     60
tgcgcgtttg ctgagactag actcggaggg aactttgttc ctccaattac gaatcagggt    120
gaagagatct tactcacttc agattttgtt tgttcaaact tcttgggggc gagtttttca    180
agttccttta tcaatagttc cagcaatctc tccttattag ggaagggcct ttccttaacg    240
tttacctctt gtcaagctcc tacaaatagt aactatgcgc tactttctgc cgcagagact    300
ctgaccttca agaatttttc ttctataaac tttacaggga accaatcgac aggacttggc    360
ggcctcatct acggaaaaga tattgttttc caatctatca aagatttgat cttcactacg    420
```

-continued

```
aaccgtgttg cctattctcc agcatctgta actacgtcgg caactcccgc aatcactaca    480
gtaactacag gagcctctgc tctccaacct acagactcac tcactgtcga aaacatatcc    540
caatcgatca agtttttgg gaaccttgcc aacttcggct ctgcaattag cagttctccc     600
acggcagtcg ttaaattcat caataacacc gctaccatga gcttctccca taactttact    660
tcgtcaggag gcggcgtgat ttatggagga agctctctcc tttttgaaaa caattctgga    720
tgcatcatct tcaccgccaa ctcctgtgtg aacagcttaa aaggcgtcac cccttcatca    780
ggaacctatg ctttaggaag tggcggagcc atctgcatcc ctacgggaac tttcgaatta    840
aaaaacaatc aggggaagtg caccttctct tataatggta caccaaatga tgcgggtgcg    900
atctacgccg aaacctgcaa catcgtaggg aaccagggtg ccttgctcct agatagcaac    960
actgcagcga gaaatggcgg agccatctgt gctaaagtgc tcaatattca aggacgcggt   1020
cctattgaat tctctagaaa ccgcgcggag aagggtggag ctattttcat aggcccctct   1080
gttggagacc ctgcgaagca aacatcgaca cttacgattt tggcttccga aggtgatatt   1140
gcgttccaag gaaacatgct caatacaaaa cctggaatcc gcaatgccat cactgtagaa   1200
gcagggggag agattgtgtc tctatctgca caaggaggct cacgtcttgt attttatgat   1260
cccattacac atagcctccc aaccacaagt ccgtctaata aagacattac aatcaacgct   1320
aatggcgctt caggatctgt agtctttaca agtaagggac tctcctctac agaactcctg   1380
ttgcctgcca acacgacaac tatacttcta ggaacagtca agatcgctag tggagaactg   1440
aagattactg acaatgcggt tgtcaatgtt cttggcttcg ctactcaggg ctcaggtcag   1500
cttaccctgg gctctggagg aaccttaggg ctggcaacac ccacgggagc acctgccgct   1560
gtagacttta cgattggaaa gttagcattc gatccttttt ccttcctaaa aagagatttt   1620
gtttcagcat cagtaaatgc aggcacaaaa aacgtcactt taacaggagc tctggttctt   1680
gatgaacatg acgttacaga tctttatgat atggtgtcat tacaatctcc agtagcaatt   1740
cctatcgctg ttttcaaagg agcaaccgtt actaagacag gatttcctga tggggagatt   1800
gcgactccaa gccactacgg ctaccaagga aagtggtcct acacatggtc ccgtcccctg   1860
ttaattccag ctcctgatgg aggatttcct ggaggtccct ctcctagcgc aaatactctc   1920
tatgctgtat ggaattcaga cactctcgtg cgttctacct atatcttaga tcccgagcgt   1980
tacggagaaa ttgtcagcaa cagcttatgg atttccttct taggaaatca ggcattctct   2040
gatattctcc aagatgttct tttgatagat catcccgggt tgtccataac cgcgaaagct   2100
ttaggagcct atgtcgaaca cacaccaaga caaggacatg agggcttttc aggtcgctat   2160
ggaggctacc aagctgcgct atctatgaac tacacggacc acactacgtt aggacttttct  2220
ttcgggcagc tttatggaaa aactaacgcc aacccctacg attcacgttg ctcagaacaa   2280
atgtatttac tctcgttctt tggtcaattc cctatcgtga ctcaaaagag cgaggcctta   2340
atttcctgga aagcagctta tggttattcc aaaaatcacc taaataccac ctacctcaga   2400
cctgacaaag ctccaaaatc tcaagggcaa tggcataaca atagttacta tgttcttatt   2460
tctgcagaac atcctttcct aaactggtgt cttcttacaa gacctctggc tcaagcttgg   2520
gatctttcag gttttatttc cgcagaattc ctaggtggtt ggcaaagtaa gttcacagaa   2580
actggagatc tgcaacgtag ctttagtaga ggtaaagggt acaatgtttc cctaccgata   2640
ggatgttctt ctcaatggtt cacaccattt aagaaggctc cttctacact gaccatcaaa   2700
cttgcctaca agcctgatat ctatcgtgtc aaccctcaca atattgtgac tgtcgtctca   2760
aaccaagaga gcacttcgat ctcaggagca aatctacgcc gccacggttt gtttgtacaa   2820
```

-continued atccatgatg tagtagatct caccgaggac actcaggcct ttctaaacta tacctttgac 2880
gggaaaaatg gatttacaaa ccaccgagtg tctacaggac taaaatccac attttaa 2937

<210> SEQ ID NO 50
<211> LENGTH: 801
<212> TYPE: DNA
<213> ORGANISM: Chlamydia pneumoniae

<400> SEQUENCE: 50
atgcattcaa aatttctttc tcgaagaaaa aaaaatagtt ctcataagga ggaaacctct 60
tgggattgta tagcctcaag ttacaataag atagtccaag ataaagggca ctactatcat 120
agagaaacta tccttcccca actcctgcct tcactcacct taggttcaaa aagttctgta 180
ttggatattg gctgcggtca aggtttttta gaaagggccc ttcctaagga atgtcgttat 240
ctaggcatag atatctcttc tagattgatt gctctagcaa agaaaatgcg atcggtaaac 300
tctcatcagt ttaaggttgc agatcttagc aaacgcctag agttcgtaga accgacatta 360
ttctctcatg cagtagcaat cctctccctt caaaatatgg aattccccgg agaggctata 420
cgtaatacag ctacgctcct cgaaccactc gggcaatttt ttatagtttt aaaccatcct 480
tgttttcgta ttcctagggc atcatcctgg cactatgatg aaaataaaaa agctatctct 540
cgtcatatag atcgttatct ctccccaatg aaaatcccaa tcatggctca cccaggacaa 600
aaagattcgc cttctaccct ctcctttcac tttcctctaa gctattggtt taaagaactg 660
tcttctcatg gattcttagt ttcaggtctt gaggaatgga catcttcaaa aacctcaaca 720
ggaaaacgag ctaaggcaga aaacctttgt cgaaaggaat ttccattatt ccttatgatt 780
tcatgcatta agataaaata a 801

<210> SEQ ID NO 51
<211> LENGTH: 252
<212> TYPE: DNA
<213> ORGANISM: Chlamydia pneumoniae

<400> SEQUENCE: 51
atgaaacaac aacacaatcg taaggcttta tctcgcaaga ttggcacagt gaaaaaacaa 60
gccaaatttg caggaagctt tttagatgag attaaaaaaa ttgaatgggt aagcaagcac 120
gatcttaaga aatacataaa agtagttctt atcagtattt ttggttttgg atttgctatt 180
tatttcgtag atcttgtgtt gcgtaagtca atcacatgtt tagatggtat aacaaccttt 240
ttgttcggtt aa 252

<210> SEQ ID NO 52
<211> LENGTH: 1185
<212> TYPE: DNA
<213> ORGANISM: Chlamydia pneumoniae

<400> SEQUENCE: 52
atgtcaaaag aaacttttca acgtaataag ccccatatca atattgggac gatcgggcac 60
gttgaccatg gtaaaactac gctaacagcg gcaattacac gcgcgctatc aggggatgga 120
ttggcctctt tccgtgacta tagttcaatt gacaatactc cagaagaaaa ggctcgtgga 180
attactatca acgcttctca cgttgaatac gaaaccccaa atcgtcacta cgctcacgta 240
gactgccctg gtcacgctga ctatgttaaa aatatgatta caggcgccgc tcaaatggac 300
ggagctatcc tagtcgtttc agctacagac ggagctatgc cacaaactaa agaacatatc 360

-continued

```
ttgctagctc gccaggttgg agttccttat atcgttgttt tcttgaataa agtagatatg    420
atctctcaag aagatgctga acttattgac cttgttgaga tggaacttag tgagcttctt    480
gaagaaaaag gctacaaagg atgccctatt atccgtggtt ctgctttgaa agctcttgaa    540
ggtgatgcaa attatatcga aaaagttcga gaacttatgc aagctgtgga tgacaacatc    600
cctacaccag aaagagaaat tgataagcct ttcttaatgc ctatcgaaga cgtattctca    660
atctctggtc gtggtactgt ggttacagga agaatcgagc gtggaatcgt taaagtttct    720
gataaagttc agctcgtggg attaggagag actaaagaaa caatcgttac tggagtcgaa    780
atgttcagga aagaacttcc tgaaggtcgt gcaggagaaa acgttggttt actcctcaga    840
ggtattggaa agaacgatgt tgaaagaggt atggtggttt gtcagcctaa cagcgtgaag    900
cctcatacga aatttaagtc agctgtttac gttcttcaga aagaagaagg cggacgtcat    960
aagcctttct tcagcggata cagacctcag ttcttcttcc gtactacaga cgtgacagga   1020
gtcgtaactc ttcctgaagg aactgaaatg gtaatgcctg gagataacgt tgagcttgat   1080
gttgagctca ttggaacagt tgctcttgaa gaaggaatga gatttgcaat tcgtgaaggt   1140
ggtcgtacta tcggcgctgg aacgatttca aagatcaatg cttaa                   1185
```

<210> SEQ ID NO 53
<211> LENGTH: 1431
<212> TYPE: DNA
<213> ORGANISM: Chlamydia pneumoniae

<400> SEQUENCE: 53

```
atgagaatcg tacaagtcgc tgtagaattc actccaatcg ttaaagtagg cggtctaggc     60
gatgctgtag ctagtctatc taaggagtta gcgaaacaaa atgatgtgga agtacttctc    120
cctcattatc ctttaatttc caaattctct tcgtctcaag ttctttccga gcgttctttc    180
tattatgaat ttttaggcaa gcagcaagcc tctgcaattt cttattctta cgagggtctt    240
acgcttacta taattacgtt ggattcacaa atagagcttt tctcaaccac gtccgtgtac    300
tctgagaata atgttgtacg tttctctgct tttgcagctg cagctgcagc ttatcttcaa    360
gaagcggatc ctgctgacat tgtgcacttg catgactggc atgtaggttt acttgcgggt    420
ttattaaaaa accctttaaa ccctgtgcat tcgaagattg tctttactat ccataatttt    480
ggttatcgag ggtattgtag tacgcagcta ttagcagcgt cgcaaattga tgattttcat    540
ttgagtcact accaactatt tcgcgatccg caaacttctg ttctaatgaa gggagctctc    600
tattgttcgg attacattac gacagtgtct cttacttatg tgcaggaaat tataaacgac    660
tattctgatt acgaacttca tgatgcgatt ctagcaagaa attctgtatt ttctgggatc    720
atcaatggca ttgatgaaga cgtttggaac ccgaagacag atcctgcttt agctgtacag    780
tacgatgcaa gcctattaag cgaacctgac gttctcttta ctaaaaaaga agagaacaga    840
gcggtattat atgagaagtt ggggatcagt tcagactatt ttcctttgat ttgtgtgatc    900
tcacgcattg ttgaggaaaa gggtcctgaa tttatgaaag agattattct ccatgctatg    960
gagcacagtt atgcctttat cttgattggg acaagtcaaa atgaggttct tcttaatgag   1020
ttccgtaact tacaagattg tttagcgagc tcccccaaca ttcgtttgat cttggacttt   1080
aatgatcctt tagccaggct aacttatgct gctgccgata tgatctgcat cccttcacat   1140
agggaggctt gtggacttac ccagctgata gcgatgcgtt atggcacagt tcctttagtt   1200
cgtaaaactg gagggcttgc tgatacagtg attcctgggg taaatggttt cactttcttt   1260
gatacaaaca attttaatga atttcgggct atgcttagca acgctgtaac gacgtatcgt   1320
```

caggagcctg acgtttggtt gaatttgatt gagtcgggaa tgcttcgggc ctctggctta 1380
gatgccatgg ctaagcatta cgtaaatctt tatcaatctt tactctcatg a 1431

<210> SEQ ID NO 54
<211> LENGTH: 1041
<212> TYPE: DNA
<213> ORGANISM: Chlamydia pneumoniae

<400> SEQUENCE: 54
atggaagcag atattttaga tggaaagctc aaacgggttg aggtaagtaa aaaaggattg 60
gtgaattgta atcaagtaga tgtcaatcag ctagtcccta tcaagtataa atgggcttgg 120
gaacattacc tcaatggatg tgcaaacaac tggcttccta ctgaagttcc tatggcaaga 180
gatatcgagt tgtggaaatc agatgaactg tctgaagacg aacgcagggt cattttgtta 240
aacctaggat tttcagtac cgcggaaagc ctagtcggaa ataacatcgt tcttgctatc 300
ttcaaacata tcacaaaccc tgaagcaaga cagtatttac tgcgtcaagc ttttgaggaa 360
gccgtacata cacatacatt tctctatatt tgcgaatctt taggacttga tgaaggcgaa 420
gtattcaatg cctataatga aagagcctca attagggcta aagatgattt tcaaatgaca 480
ttaacagtcg atgtccttga tcctaatttt tctgtacagt cttcagaagg ccttgggcag 540
ttcattaaaa acttagtagg atactatatc attatggaag gaatcttctt ctatagtggt 600
tttgtaatga ttctctcttt ccatagacaa aataaaatga caggaattgg agaacagtac 660
caatacatcc tcagagatga aaccatacat ttaaattttg gaatcgatct tatcaatgga 720
attaaagaag aaaaccccga agtttggact acggaactac aagaagaaat cgtcgctctt 780
attgaaaaag ctgtagagct tgaaattgag tacgctaaag attgcttacc tcgaggaatc 840
ttgggattaa gatcttcgat gtttatagat tacgttcgtc atattgcaga tcgtcgttta 900
gagagaattg ggttgaagcc tatctatcac tccagaaatc ctttcccttg gatgagcgaa 960
accatggatc tgaataaaga aaagaatttc tttgaaaccc gggttaccga ataccaaacc 1020
gctggtaatt taagttggta a 1041

<210> SEQ ID NO 55
<211> LENGTH: 3135
<212> TYPE: DNA
<213> ORGANISM: Chlamydia pneumoniae

<400> SEQUENCE: 55
atggtcgaag ttgaagaaaa gcattacacc atcgtcaaac gtaatggaat gtttgtccca 60
tttaatcaag atcggatttt ccaggctttg gaggcagctt ttcgagatac gcgtagctta 120
gaaactagtt ctccactacc taaagactta gaagaatcta ttgcgcaaat tactcataaa 180
gtcgtgaagg aagtcctcgc taaaatttca gaaggtcagg tagtcactgt agagagaatc 240
caggatcttg tagaaagtca gctctatatt agcgggttgc aggatgtggc tcgcgattat 300
attgtttaca gggaccaacg caaggcagag cgcggtaact cttcgtccat aattgccatc 360
atacgtagag acgggggaag cgctaaattt aatcctatga agatctctgc agctctcgaa 420
aaagcattca gagcgacgct ccaaattaat gggatgactc ctcctgcaac actatccgaa 480
attaatgacc ttacccttag gatcgttgaa gatgtcctaa gccttcatgg tgaagaagct 540
attaatctgg aagagatcca agatattgtt gaaaagcaac ttatggttgc cggctattat 600
gatgtggcca agaattatat tttatataga gaagctcgtg cacgagcccg tgctaataaa 660

-continued

```
gatcaagatg gacaagaaga gtttgtcccc caagaggaaa cgtacgttgt tcaaaaagaa    720
gacggcacca cctaccttct gagaaaaaca gatttagaaa agaggttttc ttgggcatgc    780
aaacgctttc ctaaaactac agattctcaa ctgcttgcag atatggcatt tatgaatttg    840
tattcaggaa tcaaagaaga cgaggtcacc acagcatgca tcatggcggc acgtgccaat    900
atcgagagag aacctgatta cgcttttatc gcagcagaac tcctcacgag ttccttgtat    960
gaagagacct taggatgcag ctctcaagac cccaatttat cagaaataca taaaaaacat   1020
tttaaagaat acatcctcaa tggagaagag tatcgcttga atcctcaatt aaaggattat   1080
gatctcgatg ctcttagtga agtcctagac ctctctagag accaacagtt ttcctatatg   1140
ggagtccaaa atctctacga tcgctatttt aatctgcatg aaggacgacg tttagagact   1200
gcgcagatct tttggatgcg ggtttctatg ggcttagcct taaatgaagg agaacaaaag   1260
aatttttggg caatcacttt ctataatctg ttatccacat tccgctatac cccagcaact   1320
cctacattgt ttaactccgg aatgcgtcat tcccaactca gttcatgcta tctttccaca   1380
gtaaaagatg acctaagtca catttataag gtgatttctg ataatgcttt gctttctaaa   1440
tgggcagggg gaattggaaa tgattggaca gatgtccgtg ctacaggagc tgtaattaag   1500
ggaaccaatg gaaagagtca aggcgtcatt cccttcatta aggttgccaa tgatactgca   1560
attgcagtga atcagggggg caaacgtaaa ggtgctatgt gcgtatattt agaaaactgg   1620
cacttggatt acgaagactt tttagaattg cggaagaata caggagatga gcgtcgtaga   1680
actcacgata tcaatacagc aagctggatt cctgatctct tctttaagag actagaaaaa   1740
aaaggcatgt ggacactctt tagccccgat gatgtcccag gtttacacga agcctatggg   1800
ttagagtttg aaaagcttta tgaagaatat gaacgtaagg ttgaatctgg ggaaatccgt   1860
ctttataaaa aagtagaagc cgaagtgctg tggcgtaaaa tgttaagcat gctttacgaa   1920
acagggcatc cttggattac atttaaagat ccttcgaata ttcgctcaaa ccaagatcat   1980
gttggcgtcg tacgctgttc taatctatgt acagagattt tattgaactg ttcggaatca   2040
gagactgcag tttgtaattt aggttccata aacttggtag aacatatccg taatgacaag   2100
ttagatgaag aaaaattaaa agaaactatc tcaatagcca tccgtatttt ggataacgtt   2160
attgacctga acttctaccc tacaccagag gctaaacaag ccaacctaac tcacagagct   2220
gtggggttgg gggttatggg attccaggat gttctttacg agttgaacat tagctatgcc   2280
tcacaagaag ctgtcgaatt ttctgacgag tgctcggaga tcatcgcata ctacgctatt   2340
ctagcctcga gcttactcgc gaaagaacga ggtacatatg cttcttattc aggatctaag   2400
tgggatcgtg ggtatctacc cttagatact atcgagcttc tcaaagaaac tcgcggagag   2460
cataatgttc ttgtagacac atcaagtaaa aaagattgga ctccagttcg tgatactatc   2520
cagaaatacg gaatgagaaa tagccaggtc atggcaattg ctcctacagc aacgatctcg   2580
aatatcatag gggtcaccca atctatagag cccatgtata aacatctctt tgtaaagtcc   2640
aacctttccg gagagtttac gatccccaac acctacctga ttaaaaaact taaggaatta   2700
ggactttggg atgcagaaat gttagatgat ctaaaatatt ttgacggatc tctattggaa   2760
attgaaagga tccctaatca cttgaaaaag cttttcctta cggcatttga aatcgaaccc   2820
gagtggatta tagagtgtac ctctagaaga cagaaatgga ttgatatggg agtttctcta   2880
aatctgtatc ttgctgagcc agatggtaaa aaactctcca atatgtatct cacggcttgg   2940
aaaaaaggat taaagactac ctattattta agatctcaag ctgcaacatc agtagagaaa   3000
tcatttatag atatcaataa acgcggcatt cagcctcgtt ggatgaaaaa taaatcagcg   3060
```

```
tccacaagta ttgtggtcga aagaaaaaca acccccgttt gttcaatgga agaaggttgc   3120

gaatcttgtc aataa                                                    3135
```

<210> SEQ ID NO 56
<211> LENGTH: 1386
<212> TYPE: DNA
<213> ORGANISM: Chlamydia pneumoniae

<400> SEQUENCE: 56

```
atgatgagct ctaagcgtac ctcgaaaata gcggtgcttt caattttatt aacatttact     60

cactctatag ggttcgcaaa tgcgaattcg tccgtaggtc ttggcacggt ctacattaca    120

tccgaggttg taaagaagcc tcagaaagga tcagaaagga aacaagccaa aaaagaacct    180

cgtgctcgta aaggatactt agtcccttct tcaaggactc tttcagctcg agcccaaaag    240

atgaaaaact cctctcgtaa agagtcttca ggtggttgta acgaaatttc tgcaaattct    300

acacccagat ctgtaaaatt acgaagaaac aaacgtgcag aacaaaaggc agctaaacaa    360

ggattttcag ctttttctaa cctaactttg aaaagcctac ttcctaaact tccttcaaaa    420

caaaaaactt caattcacga gagagaaaaa gcaacctcaa gatttgttaa tgagtctcag    480

cttagttccg cacgaaaacg ctactgcaca ccatcttcag ccgctccttc cctattttta    540

gaaacagaaa tcgttcgagc tcctgtagaa agaactaaag aacttcaaga taatgaaatt    600

catattcctg tagtgcaagt ccaaacgaac cccaaagaac aaaatacaaa gacaactaaa    660

cagttggcat cccaagcctc gattcaacaa tctgaaggaa ccgagcaatc attgcgagag    720

ctcgcccaag gtgctagcct acctgtctta gtgcgctcta atcctgaagt gtctgtacaa    780

agacaaaaag aagagttatt aaaagaactc gtagctgaac gtagacaatg taaaagaaag    840

tctgtaagac aagctcttga agctcgttct ttaactaaga aagttgctag aggcggttct    900

gtgacctcga ctttacgata cgatccagaa aaagcggcgg aaatcaaaag tagacgcaat    960

tgcaaagtaa gtcctgaagc acgtgaacaa aaatattcat cttgcaaaag agatgctcgc   1020

gctaatggga aacaagacaa gacaactcct agtgaagatg cttctcaaga agaacaacaa   1080

actggggcag gactcgtacg caagactcct aaatctcagg ttgcaagtaa tgctcagaac   1140

ttctaccgaa attctaaaaa tacaaacata gatagctatc ttacagctaa ccaatacagc   1200

tgtagttctg aagaaacaga ttggccatgt tcttcctgcg tctctaaacg cagaactcac   1260

aacagtatat ctgtatgtac catggtagtt actgtcattg cgatgatcgt aggggctttg   1320

attatagcta atgctacaga atctcaaaca acatcagatc caactcctcc aactcctact   1380

ccatag                                                              1386
```

<210> SEQ ID NO 57
<211> LENGTH: 1731
<212> TYPE: DNA
<213> ORGANISM: Chlamydia pneumoniae

<400> SEQUENCE: 57

```
atgacagatt ttcctactca cttcaaagga cccaaactta accccattaa agtaaatcca     60

aactttttg agaggaatcc taaagtcgca agggtactgc aaattacagc cgtagtctta    120

ggaatcattg ccctcttatc cggtatagta ctcattatag gcacccctct cggagctcct    180

ataagtatga tcctcggcgg atgtctttta gcttctggag gcgccttatt tgttggtggt    240

acgattgcta cgatattgca agctagaaat agttataaga aggccgtgaa ccaaaagaaa    300
```

```
ctctcagagc ctttgatgga acgccccgaa ttgaaagcct tagattattc cctagatctg    360

aaagaggtat gggacctaca tcattctgtt gtcaaacatc ttaaaaaatt agacctgaat    420

ctttccaaaa cccaaaggga agttctaaat caaatcaaaa ttgatgatga gggaccctcc    480

ctaggggaat gcgccgctat gatttcagaa aactacgacg catgcttaaa gatgctcgcg    540

tatcgtgagg agctcctgaa agaacaaacc caataccaag agacacgatt caatcagaac    600

ctcactcata gaaataaagt tttgctctcc atcctctcaa ggatcacgga caatatttct    660

aaagcgggcg gggtcttttc tttgaaattt tccacgctaa gctcgcggat gtcacgaatt    720

cataccacca ccactgtgat tctggcttta agtgccgttg tttctgtcat ggtcgtagca    780

gctctaattc caggtggcat tttagcacta cctatacttt tggctgttgc tatttctgca    840

ggagtgattg tcaccggact ttcctatcta gttcgtcaga ttttaagtaa caccaagcgt    900

aatcgtcagg atttttataa agattttgta aaaaatgtag atatagagct tcttaaccaa    960

acggtaactt tacagcgatt cctctttgaa atgctcaaag gtgttctgaa agaagaagaa   1020

gaagtctcct tagaaggtca agattggtat acacaataca taaccaatgc acccatagaa   1080

aaaagattga tcgaagagat cagagttacc tacaaagaga tcgatgctca gaccaaaaaa   1140

atgaagacag acttggagtt cttagaaaat gaggtgcgtt ccgggagact gtctgtagcg   1200

tccccgtcgg aagatccaag tgaaactcct atttttactc aaggtaagga gtttgcaaag   1260

ttacgtcgcc aaacctctca gaatatatcc acgatttatg gtccggacaa tgaaaatatt   1320

gatcccgaat tttccttacc ctggatgcct aaaaaagaag aagaaataga ccatagctta   1380

gaacctgtta caaagttgga acccggttca agagaagagt tgttgttggt agagggggtc   1440

aacccaacct taagagaact caatatgaga attgcacttc tacaacaaca actatcaagt   1500

gtccgaaaat ggagacaccc tcgaggggaa cattacggga atgttatcta ttcagataca   1560

gaactcgatc gtattcagat gctagaaggc gcattttata atcacctcag ggaagctcaa   1620

gaggaaatca cccagtctct cggagacctt gttgacattc aaaaccgtat tttagggatc   1680

atagttgaag ggactcaga ttcaagaaca gaagaagagc ctcaggaata g             1731
```

<210> SEQ ID NO 58
<211> LENGTH: 1086
<212> TYPE: DNA
<213> ORGANISM: Chlamydia pneumoniae

<400> SEQUENCE: 58

```
atgcaacaaa ctgtaattgt agcaatgtca ggaggcgtgg attcttctgt cgttgcctat     60

ttattcaaaa aatttaccaa ttataaggtt attggcctct tcatgaagaa ttgggaagag    120

gatagcgaag gcggcctttg ctcgtctact aaagattatg aagatgtcga gagggtatgt    180

cttcagctcg atatccctta ttacaccgta tcttttgcta aagaatatag agaaagagtg    240

ttcgctcgtt tcctcaagga atactcttta ggctacactc ctaaccccga cattctttgt    300

aaccgagaaa tcaaatttga ccttctacaa aagaaagtcc aggaacttgg cggagattac    360

ctcgctacag ggcactactg ccgattaaat accgagctcc aagaaaccca actccttaga    420

ggttgcgatc ctcaaaaaga tcagagctat tttttatcag gaactcctaa aagtgctctt    480

cacaatgtgc tctttcctct tggggaaatg aataagactg aagttcgtgc gattgcagct    540

caagcagctc ttcccacagc agaaaaaaaa gatagtacag gcatttgctt tatagggaag    600

cgcccttta aagagttcct agagaagttt cttcccaata aaacaggcaa cgttatcgat     660

tgggatacca aggaaattgt agggcaacat cagggagctc actattatac tatagggcag    720
```

-continued cggcgaggac ttgatcttgg aggatccgag aaaccctgtt atgttgtggg aaaaaatata 780
gaggaaaata gcatttatat tgtgaggggg gaagaccatc cccagctcta cctacgggaa 840
ttaacagcta gagagctcaa ttggtttacc cctcctaaat ccggatgtca ctgtagcgct 900
aaagtccgct accgttctcc tgatgaagct tgcacgatag attatagctc aggtgacgag 960
gtcaaggtgc gattttcaca acccgtcaag gcggtaactc caggacaaac aatagcgttt 1020
tatcaaggag atacctgcct tggtagtgga gttatcgacg ttcctatgat tccaagtgag 1080
ggctag 1086

<210> SEQ ID NO 59
<211> LENGTH: 4830
<212> TYPE: DNA
<213> ORGANISM: Chlamydia pneumoniae

<400> SEQUENCE: 59
atggtagcga aaaaaacagt acgatcttat aggtcttcat ttctcattc cgtaatagta 60 gcaatattgt cagcaggcat tgcttttgaa gcacattcct tacacagctc agaactagat 120
ttaggtgtat tcaataaaca gtttgaggaa cattctgctc atgttgaaga ggctcaaaca 180
tctgttttaa agggatcaga tcctgtaaat ccctctcaga aagaatccga gaaggttttg 240
tacactcaag tgcctcttac ccaaggaagc tctggagaga gtttggatct cgccgatgct 300
aatttcttag agcattttca gcatcttttt gaagagacta cagtatttgg tatcgatcaa 360
aagctggttt ggtcagattt agatactagg aatttttccc aacccactca agaacctgat 420
acaagtaatg ctgtaagtga gaaaatctcc tcagatacca aagagaatag aaaagaccta 480
gagactgaag atccttcaaa aaaaagtggc cttaaagaag tttcatcaga tctccctaaa 540
agtcctgaaa ctgcagtagc agctatttct gaagatcttg aaatctcaga aaacatttca 600
gcaagagatc ctcttcaggg tttagcattt ttttataaaa atacatcttc tcagtctatc 660
tctgaaaagg attcttcatt tcaaggaatt atcttttctg gttcaggagc taattcaggg 720
ctaggttttg aaaatcttaa ggcgccgaaa tctggggctg cagtttattc tgatcgagat 780
attgtttttg aaaatcttgt taaaggattg agttttatat cttgtgaatc tttagaagat 840
ggctctgccg caggtgtaaa cattgttgtg acccattgtg gtgatgtaac tctcactgat 900
tgtgccactg gtttagacct tgaagcttta cgtctggtta aagatttttc tcgtggagga 960
gctgttttca ctgctcgcaa ccatgaagtg caaaataacc ttgcaggtgg aattctatcc 1020
gttgtaggca ataaaggagc tattgttgta gagaaaaata gtgctgagaa gtccaatgga 1080
ggagcttttg cttgcggaag ttttgtttac agtaacaacg aaaacaccgc cttgtggaaa 1140
gaaaatcaag cattatcagg aggagccata tcctcagcaa gtgatattga tattcaaggg 1200
aactgtagcg ctattgaatt ttcaggaaac cagtctctaa ttgctcttgg agagcatata 1260
gggcttacag attttgtagg tggaggagct ttagctgctc aagggacgct taccttaaga 1320
aataatgcag tagtgcaatg tgttaaaaac acttctaaaa cacatggtgg agctatttta 1380
gcaggtactg ttgatctcaa cgaaacaatt agcgaagttg cctttaagca gaatacagca 1440
gctctaactg gaggtgcttt aagtgcaaat gataaggtta taattgcaaa taactttgga 1500
gaaattcttt ttgagcaaaa cgaagtgagg aatcacggag gagccattta ttgtggatgt 1560
cgatctaatc ctaagttaga acaaaaggat tctggagaga acatcaatat tattggaaac 1620
tccggagcta tcactttttt aaaaaataag gcttctgttt tagaagtgat gacacaagct 1680

-continued

```
gaagattatg ctggtggagg cgctttatgg gggcataatg ttcttctaga ttccaatagt   1740

gggaatattc aatttatagg aaatataggt ggaagtacct tctggatagg agaatatgtc   1800

ggtggtggtg cgattctctc tactgataga gtgacaattt ctaataactc tggagatgtt   1860

gtttttaaag gaaacaaagg ccaatgtctt gctcaaaaat atgtagctcc tcaagaaaca   1920

gctcccgtgg aatcagatgc ttcatctaca aataaagacg agaagagcct taatgcttgt   1980

agtcatggag atcattatcc tcctaaaact gtagaagagg aagtgccacc ttcattgtta   2040

gaagaacatc ctgttgtttc ttcgacagat attcgtggtg gtggggccat tctagctcaa   2100

catatcttta ttacagataa tacaggaaat ctgagattct ctgggaacct tggtggtggt   2160

gaagagtctt ctactgtcgg tgatttagct atcgtaggag gaggtgcttt gctttctact   2220

aatgaagtta atgtttgcag taaccaaaat gttgtttttt ctgataacgt gacttcaaat   2280

ggttgtgatt caggggggagc tattttagct aaaaaagtag atatctccgc gaaccactcg   2340

gttgaatttg tctctaatgg ttcagggaaa ttcggtggtg ccgtttgcgc tttaaacgaa   2400

tcagtaaaca ttacggacaa tggctcggca gtatcattct ctaaaaatag aacacgtctt   2460

ggcggtgctg gagttgcagc tcctcaaggc tctgtaacga tttgtggaaa tcagggaaac   2520

atagcattta aagagaactt tgtttttggc tctgaaaatc aaagatcagg tggaggagct   2580

atcattgcta actcttctgt aaatattcag gataacgcag gagatatcct atttgtaagt   2640

aactctacgg gatcttatgg aggtgctatt tttgtaggat ctttggttgc ttctgaaggc   2700

agcaacccac gaacgcttac aattacaggc aacagtgggg atatcctatt tgctaaaaat   2760

agcacgcaaa cagccgcttc tttatcagaa aaagattcct ttggtggagg ggccatctat   2820

acacaaaacc tcaaaattgt aaagaatgca gggaacgttt ctttctatgg caacagagct   2880

cctagtggtg ctggtgtcca aattgcagac ggaggaactg tttgtttaga ggcttttgga   2940

ggagatatct tatttgaagg gaatatcaat tttgatggga gtttcaatgc gattcactta   3000

tgcgggaatg actcaaaaat cgtagagctt tctgctgttc aagataaaaa tattattttc   3060

caagatgcaa ttacttatga agagaacaca attcgtggct tgccagataa agatgtcagt   3120

cctttaagtg ccccttcatt aatttttaac tccaagccac aagatgacag cgctcaacat   3180

catgaaggga cgatacggtt ttctcgaggg gtatctaaaa ttcctcagat tgctgctata   3240

caagagggaa ccttagcttt atcacaaaac gcagagcttt ggttggcagg acttaaacag   3300

gaaacaggaa gttctatcgt attgtctgcg ggatctattc tccgtatttt tgattcccag   3360

gttgatagca gtgcgcctct tcctacagaa aataaagagg agactcttgt ttctgccgga   3420

gttcaaatta acatgagctc tcctacaccc aataaagata aagctgtaga tactccagta   3480

cttgcagata tcataagtat tactgtagat ttgtcttcat ttgttcctga gcaagacgga   3540

actcttcctc ttcctcctga aattatcatt cctaagggaa caaaattaca ttctaatgcc   3600

atagatctta agattataga tcctaccaat gtgggatatg aaaatcatgc tcttctaagt   3660

tctcataaag atattccatt aatttctctt aagacagcgg aaggaatgac agggacgcct   3720

acagcagatg cttctctatc taatataaaa atagatgtat ctttaccttc gatcacacca   3780

gcaacgtatg gtcacacagg agtttggtct gaaagtaaaa tggaagatgg aagacttgta   3840

gtcggttggc aacctacggg atataagtta aatcctgaga agcaaggggc tctagttttg   3900

aataatctct ggagtcatta tacagatctt agagctctta agcaggagat ctttgctcat   3960

catacgatag ctcaaagaat ggagttagat ttctcgacaa atgtctgggg atcaggatta   4020

ggtgttgttg aagattgtca gaacatcgga gagtttgatg ggttcaaaca tcatctcaca   4080
```

gggtatgccc taggcttgga tacacaacta gttgaagact tcttaattgg aggatgtttc 4140
tcacagttct ttggtaaaac tgaaagccaa tcctacaaag ctaagaacga tgtgaagagt 4200
tatatgggag ctgcttatgc ggggatttta gcaggtcctt ggttaataaa aggagctttt 4260
gtttacggta atataaacaa cgatttgact acagattacg gtactttagg tatttcaaca 4320
ggttcatgga taggaaaagg gtttatcgca ggcacaagca ttgattaccg ctatattgta 4380
aatcctcgac ggtttatatc ggcaatcgta tccacagtgg ttccttttgt agaagccgag 4440
tatgtccgta tagatcttcc agaaattagc gaacagggta aagaggttag aacgttccaa 4500
aaaactcgtt ttgagaatgt cgccattcct tttggatttg ctttagaaca tgcttattcg 4560
cgtggctcac gtgctgaagt gaacagtgta cagcttgctt acgtctttga tgtatatcgt 4620
aagggacctg tctctttgat tacactcaag gatgctgctt attcttggaa gagttatggg 4680
gtagatattc cttgtaaagc ttggaaggct cgcttgagca ataatacgga atggaattca 4740
tatttaagta cgtatttagc gtttaattat gaatggagag aagatctgat agcttatgac 4800
ttcaatggtg gtatccgtat tattttctag 4830

<210> SEQ ID NO 60
<211> LENGTH: 591
<212> TYPE: DNA
<213> ORGANISM: Chlamydia pneumoniae

<400> SEQUENCE: 60
atgacactct ccctagttgg aaaggaagcc cctgattttg ttgcgcaagc tgttgttaat 60
ggcgaaacgt gtaccgtatc tttaaaagat tatttaggaa agtatgttgt gcttttcttc 120
tatcctaaag attttactta cgtgtgtcct acggaattgc acgcatttca agatgcttta 180
ggagaattcc acacccgagg agctgaagtc ataggctgtt ccgtggatga cattgccacc 240
catcaacagt ggttagctac taagaaaaag caaggtggta tcgaaggtat tacctatcct 300
cttctctcag acgaagataa agtcatttca agaagttatc atgtgttaaa acccgaagaa 360
gaattatctt tcagaggagt tttcctgatt gataaaggtg gaatcatccg tcatcttgta 420
gtgaatgatc ttcctctagg ccgttctata gaagaagaac ttagaaccct agatgcttta 480
atcttctttg aaactaatgg cttagtctgt cctgcaaatt ggcatgaagg agagcgagcg 540
atggctccaa atgaagaagg actgcaaaat tatttcggga ctatagacta g 591

<210> SEQ ID NO 61
<211> LENGTH: 1983
<212> TYPE: DNA
<213> ORGANISM: Chlamydia pneumoniae

<400> SEQUENCE: 61
atgagtgaac acaaaaaatc aagcaaaatt ataggtatag acttaggcac aacaaactcc 60
tgcgtatctg ttatggaagg aggacaagct aaagtaatta catcatccga aggaacaaga 120
accacgccat cgatcgttgc cttcaaaggt aatgagaaat tagtggggat tccagcaaaa 180
cgtcaagcag tgacaaatcc agaaaaaact ctcggctcta caaaacgctt tattggccgt 240
aagtactctg aagtagcttc ggaaatccaa accgttcctt atacagtcac ctccggatct 300
aaaggtgatg ccgttttcga agttgatggc aaacaataca ctccagaaga aattggcgca 360
caaatcttaa tgaaaatgaa agagacagca gaagcttatc taggcgaaac tgtcacagaa 420
gcagtgatca ccgtccccgc atacttcaat gattctcaac gagcatccac aaaagatgct 480

-continued

```
ggacgcattg caggtctaga tgtaaaacgt atcattccag aacctaccgc agcagctctt    540
gcctacggaa tcgataaagt cggtgataaa aaaatcgctg tcttcgacct tggtggagga    600
acttttgata tctccatcct agaaatcggt gatggcgtct tcgaagttct atctacaaat    660
ggagatactc tcctcggtgg agacgacttt gatgaagtca ttatcaaatg gatgatcgaa    720
gaattcaaaa aacaagaagg cattgatctt agcaaagata atatggcctt acaaagactt    780
aaagatgctg ctgagaaagc aaaaatagaa ctttcaggag tctcttccac agaaatcaat    840
cagccattca tcacaatgga tgcacaagga cctaaacacc ttgcattgac actcacacgt    900
gcgcaattcg agaaactcgc agcctctcta atcgaaagaa caaaatctcc atgcatcaaa    960
gcactcagtg acgcaaaact ttccgctaag gatatcgatg atgttctctt agttggaggt   1020
atgtcaagaa tgcccgcagt gcaagaaact gtaaaagaac tcttcggcaa agagcctaat   1080
aaaggagtca accccgacga agttgttgct attggagccg caattcaagg tggtgttctt   1140
ggcggagaag ttaaggatgt tctacttcta gacgttatcc ccctatctct gggtatcgaa   1200
actctaggag gcgtcatgac gactctggta gagagaaata ctacaatccc tacacagaaa   1260
aaacaaatct tctccacagc tgctgataac cagcctgcgg ttaccatcgt agttctccaa   1320
ggagagcgtc ccatggccaa agataacaag gaaatcggaa gattcgatct tacagatatc   1380
cctccggctc ctcgaggcca tcctcaaatc gaagtctcct tcgatatcga tgcaaacgga   1440
attttccatg tctcagctaa agatgttgcc agcggtaaag aacagaaaat tcgtatcgaa   1500
gcaagctcag gacttcaaga agatgaaatc caaagaatgg ttcgagatgc cgaaattaat   1560
aaggaagaag ataaaaaacg tcgtgaagct tcagatgcta aaatgaagc cgatagcatg    1620
atcttcagag ccgaaaaagc tattaaagat tataaggagc aaattcctga aactttagtt   1680
aaagaaatcg aagagcgaat cgaaaacgtg cgcaacgcac tcaaagatga cgctcctatt   1740
gaaaaaatta aagaggttac tgaagaccta agcaagcata tgcaaaaaat tggagagtct   1800
atgcaatcgc agtctgcatc agcagcagca tcatcggcag ccaatgctaa aggtggacct   1860
aacatcaata cagaagattt gaaaaaacat agtttcagta cgaagcctcc ttcaaataac   1920
ggttcttcag aagaccatat cgaagaagct gatgtagaaa ttattgataa cgacgataag   1980
taa                                                                 1983
```

```
<210> SEQ ID NO 62
<211> LENGTH: 1860
<212> TYPE: DNA
<213> ORGANISM: Chlamydia pneumoniae
```

```
<400> SEQUENCE: 62
```

```
atgaaaaaag ggaaattagg agccatagtt tttggccttc tatttacaag tagtgttgct      60
ggtttttcta aggatttgac taaagacaac gcttatcaag atttaaatgt catagagcat    120
ttaatatcgt taaaatatgc tcctttacca tggaaggaac tattatttgg ttgggattta    180
tctcagcaaa cacagcaagc tcgcttgcaa ctggtcttag aagaaaaacc aacaaccaac    240
tactgccaga aggtactctc taactacgtg agatcattaa acgattatca tgcagggatt    300
acgttttatc gtactgaaag tgcgtatatc ccttacgtat tgaagttaag tgaagatggt    360
catgtctttg tagtcgacgt acagactagc caaggggata tttacttagg ggatgaaatc    420
cttgaagtag atggaatggg gattcgtgag gctatcgaaa gccttcgctt tggacgaggg    480
agtgccacag actattctgc tgcagttcgt tccttgacat cgcgttccgc cgcttttgga    540
gatgcggttc cttcaggaat tgccatgttg aaacttcgcc gacccagtgg tttgatccgt    600
```

-continued

```
tcgacaccgg tccgttggcg ttatactcca gagcatatcg gagatttttc tttagttgct    660
cctttgattc ctgaacataa acctcaatta cctacacaaa gttgtgtgct attccgttcc    720
ggggtaaatt cacagtcttc tagtagctct ttattcagtt cctacatggt gccttatttc    780
tgggaagaat tgcgggttca aaataagcag cgttttgaca gtaatcacca tatagggagc    840
cgtaatggat ttttacctac gtttggtcct attctttggg aacaagacaa ggggccctat    900
cgttcctata tctttaaagc aaaagattct cagggcaatc cccatcgcat aggattttta    960
agaatttctt cttatgtttg gactgattta gaaggacttg aagaggatca taaggatagt   1020
ccttgggagc tctttggaga gatcatcgat catttggaaa aagagactga tgctttgatt   1080
attgatcaga cccataatcc tggaggcagt gttttctatc tctattcgtt actatctatg   1140
ttaacagatc atcctttaga tactcctaaa catagaatga ttttcactca ggatgaagtc   1200
agctcggctt tgcactggca agatctacta gaagatgtct tcacagatga gcaggcagtt   1260
gccgtgctag ggaaactat ggaaggatat tgcatggata tgcatgctgt agcctctctt   1320
caaaacttct ctcagagtgt cctttcttcc tgggtttcag gtgatattaa cctttcaaaa   1380
cctatgcctt tgctaggatt tgcacaggtt cgacctcatc ctaaacatca atatactaaa   1440
cctttgttta tgttgataga cgaggatgac ttctcttgtg gagatttagc gcctgcaatt   1500
ttgaaggata atggccgcgc tactctcatt ggaaagccaa cagcaggagc tggaggtttt   1560
gtattccaag tcactttccc taaccgttct ggaattaaag gtctttcttt aacaggatct   1620
ttagctgtta ggaaagatgg tgagtttatt gaaaacttag gagtggctcc tcatattgat   1680
ttaggattta cctccaggga tttgcaaact tccaggttta ctgattacgt tgaggcagtg   1740
aaaactatag ttttaacttc tttgtctgag aacgctaaga agagtgaaga gcagacttct   1800
ccgcaagaga cgcctgaagt tattcgagtc tcttatccca caacgacttc tgcttcgtaa   1860
```

<210> SEQ ID NO 63
<211> LENGTH: 1956
<212> TYPE: DNA
<213> ORGANISM: Chlamydia pneumoniae

<400> SEQUENCE: 63

```
atggttaatc ctattggtcc aggtcctata gacgaaacag aacgcacacc tcccgcagat     60
ctttctgctc aaggattgga ggcgagtgca gcaaataaga gtgcggaagc tcaaagaata    120
gcaggtgcgg aagctaagcc taaagaatct aagaccgatt ctgtagagcg atggagcatc    180
ttgcgttctg cagtgaatgc tctcatgagt ctggcagata agctgggtat tgcttctagt    240
aacagctcgt cttctactag cagatctgca gacgtggact caacgacagc gaccgcacct    300
acgcctcctc cacccacgtt tgatgattat aagactcaag cgcaaacagc ttacgatact    360
atctttacct caacatcact agctgacata caggctgctt tggtgagcct ccaggatgct    420
gtcactaata taaaggatac agcggctact gatgaggaaa ccgcaatcgc tgcggagtgg    480
gaaactaaga atgccgatgc agttaaagtt ggcgcgcaaa ttacagaatt agcgaaatat    540
gcttcggata accaagcgat tcttgactct ttaggtaaac tgacttcctt cgacctctta    600
caggctgctc ttctccaatc tgtagcaaac aataacaaag cagctgagct tcttaaagag    660
atgcaagata acccagtagt cccagggaaa acgcctgcaa ttgctcaatc tttagttgat    720
cagacagatg ctacagcgac acagatagag aaagatggaa atgcgattag ggatgcatat    780
tttgcaggac agaacgctag tggagctgta gaaaatgcta aatctaataa cagtataagc    840
```

-continued

```
aacatagatt cagctaaagc agcaatcgct actgctaaga cacaaatagc tgaagctcag    900

aaaaagttcc ccgactctcc aattcttcaa gaagcggaac aaatggtaat acaggctgag    960

aaagatctta aaaatatcaa acctgcagat ggttctgatg ttccaaatcc aggaactaca   1020

gttggaggct ccaagcaaca aggaagtagt attggtagta ttcgtgtttc catgctgtta   1080

gatgatgctg aaaatgagac cgcttccatt ttgatgtctg ggtttcgtca gatgattcac   1140

atgttcaata cggaaaatcc tgattctcaa gctgcccaac aggagctcgc agcacaagct   1200

agagcagcga aagccgctgg agatgacagt gctgctgcag cgctggcaga tgctcagaaa   1260

gctttagaag cggctctagg taaagctggg caacaacagg gcatactcaa tgctttagga   1320

cagatcgctt ctgctgctgt tgtgagcgca ggagttcctc ccgctgcagc aagttctata   1380

gggtcatctg taaaacagct ttacaagacc tcaaaatcta caggttctga ttataaaaca   1440

cagatatcag caggttatga tgcttacaaa tccatcaatg atgcctatgg tagggcacga   1500

aatgatgcga ctcgtgatgt gataaacaat gtaagtaccc ccgctctcac acgatccgtt   1560

cctagagcac gaacagaagc tcgaggacca gaaaaaacag atcaagccct cgctagggtg   1620

atttctggca atagcagaac tcttggagat gtctatagtc aagtttcggc actacaatct   1680

gtaatgcaga tcatccagtc gaatcctcaa gcgaataatg aggagatcag acaaaagctt   1740

acatcggcag tgacaaagcc tccacagttt ggctatcctt atgtgcaact ttctaatgac   1800

tctacacaga agttcatagc taaattagaa agtttgtttg ctgaaggatc taggacagca   1860

gctgaaataa aagcactttc ctttgaaacg aactccttgt ttattcagca ggtgctggtc   1920

aatatcggct ctctatattc tggttatctc caataa                             1956
```

```
<210> SEQ ID NO 64
<211> LENGTH: 264
<212> TYPE: DNA
<213> ORGANISM: Chlamydia pneumoniae

<400> SEQUENCE: 64

atgagtcaaa aaaataaaaa ctctgctttt atgcatcccg tgaatatttc cacagattta     60

gcagttatag ttggcaaggg acctatgccc agaaccgaaa ttgtaaagaa agtttgggaa    120

tacattaaaa aacacaactg tcaggatcaa aaaaataaac gtaatatcct tcccgatgcg    180

aatcttgcca aagtctttgg ctctagtgat cctatcgaca tgttccaaat gaccaaagcc    240

ctttccaaac atattgtaaa ataa                                           264
```

```
<210> SEQ ID NO 65
<211> LENGTH: 978
<212> TYPE: PRT
<213> ORGANISM: Chlamydia pneumoniae

<400> SEQUENCE: 65

Met Pro Leu Ser Phe Lys Ser Ser Ser Phe Cys Leu Leu Ala Cys Leu
                5                   10                  15

Cys Ser Ala Ser Cys Ala Phe Ala Glu Thr Arg Leu Gly Gly Asn Phe
            20                  25                  30

Val Pro Pro Ile Thr Asn Gln Gly Glu Glu Ile Leu Leu Thr Ser Asp
        35                  40                  45

Phe Val Cys Ser Asn Phe Leu Gly Ala Ser Phe Ser Ser Ser Phe Ile
    50                  55                  60

Asn Ser Ser Ser Asn Leu Ser Leu Leu Gly Lys Gly Leu Ser Leu Thr
65                  70                  75                  80
```

-continued

```
Phe Thr Ser Cys Gln Ala Pro Thr Asn Ser Asn Tyr Ala Leu Leu Ser
                85                  90                  95

Ala Ala Glu Thr Leu Thr Phe Lys Asn Phe Ser Ser Ile Asn Phe Thr
            100                 105                 110

Gly Asn Gln Ser Thr Gly Leu Gly Gly Leu Ile Tyr Gly Lys Asp Ile
        115                 120                 125

Val Phe Gln Ser Ile Lys Asp Leu Ile Phe Thr Thr Asn Arg Val Ala
    130                 135                 140

Tyr Ser Pro Ala Ser Val Thr Thr Ser Ala Thr Pro Ala Ile Thr Thr
145                 150                 155                 160

Val Thr Thr Gly Ala Ser Ala Leu Gln Pro Thr Asp Ser Leu Thr Val
                165                 170                 175

Glu Asn Ile Ser Gln Ser Ile Lys Phe Phe Gly Asn Leu Ala Asn Phe
            180                 185                 190

Gly Ser Ala Ile Ser Ser Ser Pro Thr Ala Val Val Lys Phe Ile Asn
        195                 200                 205

Asn Thr Ala Thr Met Ser Phe Ser His Asn Phe Thr Ser Ser Gly Gly
    210                 215                 220

Gly Val Ile Tyr Gly Gly Ser Ser Leu Leu Phe Glu Asn Asn Ser Gly
225                 230                 235                 240

Cys Ile Ile Phe Thr Ala Asn Ser Cys Val Asn Ser Leu Lys Gly Val
                245                 250                 255

Thr Pro Ser Ser Gly Thr Tyr Ala Leu Gly Ser Gly Gly Ala Ile Cys
            260                 265                 270

Ile Pro Thr Gly Thr Phe Glu Leu Lys Asn Asn Gln Gly Lys Cys Thr
        275                 280                 285

Phe Ser Tyr Asn Gly Thr Pro Asn Asp Ala Gly Ala Ile Tyr Ala Glu
    290                 295                 300

Thr Cys Asn Ile Val Gly Asn Gln Gly Ala Leu Leu Leu Asp Ser Asn
305                 310                 315                 320

Thr Ala Ala Arg Asn Gly Gly Ala Ile Cys Ala Lys Val Leu Asn Ile
                325                 330                 335

Gln Gly Arg Gly Pro Ile Glu Phe Ser Arg Asn Arg Ala Glu Lys Gly
            340                 345                 350

Gly Ala Ile Phe Ile Gly Pro Ser Val Gly Asp Pro Ala Lys Gln Thr
        355                 360                 365

Ser Thr Leu Thr Ile Leu Ala Ser Glu Gly Asp Ile Ala Phe Gln Gly
    370                 375                 380

Asn Met Leu Asn Thr Lys Pro Gly Ile Arg Asn Ala Ile Thr Val Glu
385                 390                 395                 400

Ala Gly Gly Glu Ile Val Ser Leu Ser Ala Gln Gly Gly Ser Arg Leu
                405                 410                 415

Val Phe Tyr Asp Pro Ile Thr His Ser Leu Pro Thr Thr Ser Pro Ser
            420                 425                 430

Asn Lys Asp Ile Thr Ile Asn Ala Asn Gly Ala Ser Gly Ser Val Val
        435                 440                 445

Phe Thr Ser Lys Gly Leu Ser Ser Thr Glu Leu Leu Leu Pro Ala Asn
    450                 455                 460

Thr Thr Thr Ile Leu Leu Gly Thr Val Lys Ile Ala Ser Gly Glu Leu
465                 470                 475                 480

Lys Ile Thr Asp Asn Ala Val Val Asn Val Leu Gly Phe Ala Thr Gln
                485                 490                 495

Gly Ser Gly Gln Leu Thr Leu Gly Ser Gly Gly Thr Leu Gly Leu Ala
```

-continued

```
            500                 505                 510

Thr Pro Thr Gly Ala Pro Ala Ala Val Asp Phe Thr Ile Gly Lys Leu
        515                 520                 525

Ala Phe Asp Pro Phe Ser Phe Leu Lys Arg Asp Phe Val Ser Ala Ser
    530                 535                 540

Val Asn Ala Gly Thr Lys Asn Val Thr Leu Thr Gly Ala Leu Val Leu
545                 550                 555                 560

Asp Glu His Asp Val Thr Asp Leu Tyr Asp Met Val Ser Leu Gln Ser
                565                 570                 575

Pro Val Ala Ile Pro Ile Ala Val Phe Lys Gly Ala Thr Val Thr Lys
            580                 585                 590

Thr Gly Phe Pro Asp Gly Glu Ile Ala Thr Pro Ser His Tyr Gly Tyr
        595                 600                 605

Gln Gly Lys Trp Ser Tyr Thr Trp Ser Arg Pro Leu Leu Ile Pro Ala
    610                 615                 620

Pro Asp Gly Gly Phe Pro Gly Gly Pro Ser Pro Ser Ala Asn Thr Leu
625                 630                 635                 640

Tyr Ala Val Trp Asn Ser Asp Thr Leu Val Arg Ser Thr Tyr Ile Leu
                645                 650                 655

Asp Pro Glu Arg Tyr Gly Glu Ile Val Ser Asn Ser Leu Trp Ile Ser
            660                 665                 670

Phe Leu Gly Asn Gln Ala Phe Ser Asp Ile Leu Gln Asp Val Leu Leu
        675                 680                 685

Ile Asp His Pro Gly Leu Ser Ile Thr Ala Lys Ala Leu Gly Ala Tyr
    690                 695                 700

Val Glu His Thr Pro Arg Gln Gly His Glu Gly Phe Ser Gly Arg Tyr
705                 710                 715                 720

Gly Gly Tyr Gln Ala Ala Leu Ser Met Asn Tyr Thr Asp His Thr Thr
                725                 730                 735

Leu Gly Leu Ser Phe Gly Gln Leu Tyr Gly Lys Thr Asn Ala Asn Pro
            740                 745                 750

Tyr Asp Ser Arg Cys Ser Glu Gln Met Tyr Leu Leu Ser Phe Phe Gly
        755                 760                 765

Gln Phe Pro Ile Val Thr Gln Lys Ser Glu Ala Leu Ile Ser Trp Lys
    770                 775                 780

Ala Ala Tyr Gly Tyr Ser Lys Asn His Leu Asn Thr Thr Tyr Leu Arg
785                 790                 795                 800

Pro Asp Lys Ala Pro Lys Ser Gln Gly Gln Trp His Asn Asn Ser Tyr
                805                 810                 815

Tyr Val Leu Ile Ser Ala Glu His Pro Phe Leu Asn Trp Cys Leu Leu
            820                 825                 830

Thr Arg Pro Leu Ala Gln Ala Trp Asp Leu Ser Gly Phe Ile Ser Ala
        835                 840                 845

Glu Phe Leu Gly Gly Trp Gln Ser Lys Phe Thr Glu Thr Gly Asp Leu
    850                 855                 860

Gln Arg Ser Phe Ser Arg Gly Lys Gly Tyr Asn Val Ser Leu Pro Ile
865                 870                 875                 880

Gly Cys Ser Ser Gln Trp Phe Thr Pro Phe Lys Lys Ala Pro Ser Thr
                885                 890                 895

Leu Thr Ile Lys Leu Ala Tyr Lys Pro Asp Ile Tyr Arg Val Asn Pro
            900                 905                 910

His Asn Ile Val Thr Val Val Ser Asn Gln Glu Ser Thr Ser Ile Ser
        915                 920                 925
```

```
Gly Ala Asn Leu Arg Arg His Gly Leu Phe Val Gln Ile His Asp Val
    930                 935                 940

Val Asp Leu Thr Glu Asp Thr Gln Ala Phe Leu Asn Tyr Thr Phe Asp
945                 950                 955                 960

Gly Lys Asn Gly Phe Thr Asn His Arg Val Ser Thr Gly Leu Lys Ser
                965                 970                 975

Thr Phe


<210> SEQ ID NO 66
<211> LENGTH: 266
<212> TYPE: PRT
<213> ORGANISM: Chlamydia pneumoniae

<400> SEQUENCE: 66

Met His Ser Lys Phe Leu Ser Arg Arg Lys Lys Asn Ser Ser His Lys
                5                   10                  15

Glu Glu Thr Ser Trp Asp Cys Ile Ala Ser Ser Tyr Asn Lys Ile Val
            20                  25                  30

Gln Asp Lys Gly His Tyr Tyr His Arg Glu Thr Ile Leu Pro Gln Leu
        35                  40                  45

Leu Pro Ser Leu Thr Leu Gly Ser Lys Ser Ser Val Leu Asp Ile Gly
     50                  55                  60

Cys Gly Gln Gly Phe Leu Glu Arg Ala Leu Pro Lys Glu Cys Arg Tyr
 65                  70                  75                  80

Leu Gly Ile Asp Ile Ser Ser Arg Leu Ile Ala Leu Ala Lys Lys Met
                85                  90                  95

Arg Ser Val Asn Ser His Gln Phe Lys Val Ala Asp Leu Ser Lys Arg
            100                 105                 110

Leu Glu Phe Val Glu Pro Thr Leu Phe Ser His Ala Val Ala Ile Leu
        115                 120                 125

Ser Leu Gln Asn Met Glu Phe Pro Gly Glu Ala Ile Arg Asn Thr Ala
    130                 135                 140

Thr Leu Leu Glu Pro Leu Gly Gln Phe Phe Ile Val Leu Asn His Pro
145                 150                 155                 160

Cys Phe Arg Ile Pro Arg Ala Ser Ser Trp His Tyr Asp Glu Asn Lys
                165                 170                 175

Lys Ala Ile Ser Arg His Ile Asp Arg Tyr Leu Ser Pro Met Lys Ile
            180                 185                 190

Pro Ile Met Ala His Pro Gly Gln Lys Asp Ser Pro Ser Thr Leu Ser
        195                 200                 205

Phe His Phe Pro Leu Ser Tyr Trp Phe Lys Glu Leu Ser Ser His Gly
    210                 215                 220

Phe Leu Val Ser Gly Leu Glu Glu Trp Thr Ser Ser Lys Thr Ser Thr
225                 230                 235                 240

Gly Lys Arg Ala Lys Ala Glu Asn Leu Cys Arg Lys Glu Phe Pro Leu
                245                 250                 255

Phe Leu Met Ile Ser Cys Ile Lys Ile Lys
            260                 265


<210> SEQ ID NO 67
<211> LENGTH: 83
<212> TYPE: PRT
<213> ORGANISM: Chlamydia pneumoniae

<400> SEQUENCE: 67
```

-continued

Met Lys Gln Gln His Asn Arg Lys Ala Leu Ser Arg Lys Ile Gly Thr
1 5 10 15

Val Lys Lys Gln Ala Lys Phe Ala Gly Ser Phe Leu Asp Glu Ile Lys
20 25 30

Lys Ile Glu Trp Val Ser Lys His Asp Leu Lys Lys Tyr Ile Lys Val
35 40 45

Val Leu Ile Ser Ile Phe Gly Phe Gly Phe Ala Ile Tyr Phe Val Asp
50 55 60

Leu Val Leu Arg Lys Ser Ile Thr Cys Leu Asp Gly Ile Thr Thr Phe
65 70 75 80

Leu Phe Gly

<210> SEQ ID NO 68
<211> LENGTH: 394
<212> TYPE: PRT
<213> ORGANISM: Chlamydia pneumoniae

<400> SEQUENCE: 68

Met Ser Lys Glu Thr Phe Gln Arg Asn Lys Pro His Ile Asn Ile Gly
5 10 15

Thr Ile Gly His Val Asp His Gly Lys Thr Thr Leu Thr Ala Ala Ile
20 25 30

Thr Arg Ala Leu Ser Gly Asp Gly Leu Ala Ser Phe Arg Asp Tyr Ser
35 40 45

Ser Ile Asp Asn Thr Pro Glu Glu Lys Ala Arg Gly Ile Thr Ile Asn
50 55 60

Ala Ser His Val Glu Tyr Glu Thr Pro Asn Arg His Tyr Ala His Val
65 70 75 80

Asp Cys Pro Gly His Ala Asp Tyr Val Lys Asn Met Ile Thr Gly Ala
85 90 95

Ala Gln Met Asp Gly Ala Ile Leu Val Val Ser Ala Thr Asp Gly Ala
100 105 110

Met Pro Gln Thr Lys Glu His Ile Leu Leu Ala Arg Gln Val Gly Val
115 120 125

Pro Tyr Ile Val Val Phe Leu Asn Lys Val Asp Met Ile Ser Gln Glu
130 135 140

Asp Ala Glu Leu Ile Asp Leu Val Glu Met Glu Leu Ser Glu Leu Leu
145 150 155 160

Glu Glu Lys Gly Tyr Lys Gly Cys Pro Ile Ile Arg Gly Ser Ala Leu
165 170 175

Lys Ala Leu Glu Gly Asp Ala Asn Tyr Ile Glu Lys Val Arg Glu Leu
180 185 190

Met Gln Ala Val Asp Asp Asn Ile Pro Thr Pro Glu Arg Glu Ile Asp
195 200 205

Lys Pro Phe Leu Met Pro Ile Glu Asp Val Phe Ser Ile Ser Gly Arg
210 215 220

Gly Thr Val Val Thr Gly Arg Ile Glu Arg Gly Ile Val Lys Val Ser
225 230 235 240

Asp Lys Val Gln Leu Val Gly Leu Gly Glu Thr Lys Glu Thr Ile Val
245 250 255

Thr Gly Val Glu Met Phe Arg Lys Glu Leu Pro Glu Gly Arg Ala Gly
260 265 270

Glu Asn Val Gly Leu Leu Leu Arg Gly Ile Gly Lys Asn Asp Val Glu
275 280 285

```
Arg Gly Met Val Val Cys Gln Pro Asn Ser Val Lys Pro His Thr Lys
    290                 295                 300

Phe Lys Ser Ala Val Tyr Val Leu Gln Lys Glu Glu Gly Gly Arg His
305                 310                 315                 320

Lys Pro Phe Phe Ser Gly Tyr Arg Pro Gln Phe Phe Phe Arg Thr Thr
                325                 330                 335

Asp Val Thr Gly Val Val Thr Leu Pro Glu Gly Thr Glu Met Val Met
            340                 345                 350

Pro Gly Asp Asn Val Glu Leu Asp Val Glu Leu Ile Gly Thr Val Ala
        355                 360                 365

Leu Glu Glu Gly Met Arg Phe Ala Ile Arg Glu Gly Gly Arg Thr Ile
    370                 375                 380

Gly Ala Gly Thr Ile Ser Lys Ile Asn Ala
385                 390


<210> SEQ ID NO 69
<211> LENGTH: 476
<212> TYPE: PRT
<213> ORGANISM: Chlamydia pneumoniae

<400> SEQUENCE: 69

Met Arg Ile Val Gln Val Ala Val Glu Phe Thr Pro Ile Val Lys Val
1               5                   10                  15

Gly Gly Leu Gly Asp Ala Val Ala Ser Leu Ser Lys Glu Leu Ala Lys
            20                  25                  30

Gln Asn Asp Val Glu Val Leu Leu Pro His Tyr Pro Leu Ile Ser Lys
        35                  40                  45

Phe Ser Ser Ser Gln Val Leu Ser Glu Arg Ser Phe Tyr Tyr Glu Phe
    50                  55                  60

Leu Gly Lys Gln Gln Ala Ser Ala Ile Ser Tyr Ser Tyr Glu Gly Leu
65                  70                  75                  80

Thr Leu Thr Ile Ile Thr Leu Asp Ser Gln Ile Glu Leu Phe Ser Thr
                85                  90                  95

Thr Ser Val Tyr Ser Glu Asn Asn Val Val Arg Phe Ser Ala Phe Ala
            100                 105                 110

Ala Ala Ala Ala Ala Tyr Leu Gln Glu Ala Asp Pro Ala Asp Ile Val
        115                 120                 125

His Leu His Asp Trp His Val Gly Leu Leu Ala Gly Leu Leu Lys Asn
    130                 135                 140

Pro Leu Asn Pro Val His Ser Lys Ile Val Phe Thr Ile His Asn Phe
145                 150                 155                 160

Gly Tyr Arg Gly Tyr Cys Ser Thr Gln Leu Leu Ala Ala Ser Gln Ile
                165                 170                 175

Asp Asp Phe His Leu Ser His Tyr Gln Leu Phe Arg Asp Pro Gln Thr
            180                 185                 190

Ser Val Leu Met Lys Gly Ala Leu Tyr Cys Ser Asp Tyr Ile Thr Thr
        195                 200                 205

Val Ser Leu Thr Tyr Val Gln Glu Ile Ile Asn Asp Tyr Ser Asp Tyr
    210                 215                 220

Glu Leu His Asp Ala Ile Leu Ala Arg Asn Ser Val Phe Ser Gly Ile
225                 230                 235                 240

Ile Asn Gly Ile Asp Glu Asp Val Trp Asn Pro Lys Thr Asp Pro Ala
                245                 250                 255

Leu Ala Val Gln Tyr Asp Ala Ser Leu Leu Ser Glu Pro Asp Val Leu
            260                 265                 270
```

```
Phe Thr Lys Lys Glu Glu Asn Arg Ala Val Leu Tyr Glu Lys Leu Gly
        275                 280                 285

Ile Ser Ser Asp Tyr Phe Pro Leu Ile Cys Val Ile Ser Arg Ile Val
    290                 295                 300

Glu Glu Lys Gly Pro Glu Phe Met Lys Glu Ile Ile Leu His Ala Met
305                 310                 315                 320

Glu His Ser Tyr Ala Phe Ile Leu Ile Gly Thr Ser Gln Asn Glu Val
                325                 330                 335

Leu Leu Asn Glu Phe Arg Asn Leu Gln Asp Cys Leu Ala Ser Ser Pro
            340                 345                 350

Asn Ile Arg Leu Ile Leu Asp Phe Asn Asp Pro Leu Ala Arg Leu Thr
        355                 360                 365

Tyr Ala Ala Ala Asp Met Ile Cys Ile Pro Ser His Arg Glu Ala Cys
    370                 375                 380

Gly Leu Thr Gln Leu Ile Ala Met Arg Tyr Gly Thr Val Pro Leu Val
385                 390                 395                 400

Arg Lys Thr Gly Gly Leu Ala Asp Thr Val Ile Pro Gly Val Asn Gly
                405                 410                 415

Phe Thr Phe Phe Asp Thr Asn Asn Phe Asn Glu Phe Arg Ala Met Leu
            420                 425                 430

Ser Asn Ala Val Thr Thr Tyr Arg Gln Glu Pro Asp Val Trp Leu Asn
        435                 440                 445

Leu Ile Glu Ser Gly Met Leu Arg Ala Ser Gly Leu Asp Ala Met Ala
    450                 455                 460

Lys His Tyr Val Asn Leu Tyr Gln Ser Leu Leu Ser
465                 470                 475
```

<210> SEQ ID NO 70
<211> LENGTH: 346
<212> TYPE: PRT
<213> ORGANISM: Chlamydia pneumoniae

<400> SEQUENCE: 70

```
Met Glu Ala Asp Ile Leu Asp Gly Lys Leu Lys Arg Val Glu Val Ser
                  5                  10                  15

Lys Lys Gly Leu Val Asn Cys Asn Gln Val Asp Val Asn Gln Leu Val
             20                  25                  30

Pro Ile Lys Tyr Lys Trp Ala Trp Glu His Tyr Leu Asn Gly Cys Ala
         35                  40                  45

Asn Asn Trp Leu Pro Thr Glu Val Pro Met Ala Arg Asp Ile Glu Leu
     50                  55                  60

Trp Lys Ser Asp Glu Leu Ser Glu Asp Glu Arg Arg Val Ile Leu Leu
 65                  70                  75                  80

Asn Leu Gly Phe Phe Ser Thr Ala Glu Ser Leu Val Gly Asn Asn Ile
                 85                  90                  95

Val Leu Ala Ile Phe Lys His Ile Thr Asn Pro Glu Ala Arg Gln Tyr
            100                 105                 110

Leu Leu Arg Gln Ala Phe Glu Glu Ala Val His Thr His Thr Phe Leu
        115                 120                 125

Tyr Ile Cys Glu Ser Leu Gly Leu Asp Glu Gly Glu Val Phe Asn Ala
    130                 135                 140

Tyr Asn Glu Arg Ala Ser Ile Arg Ala Lys Asp Asp Phe Gln Met Thr
145                 150                 155                 160

Leu Thr Val Asp Val Leu Asp Pro Asn Phe Ser Val Gln Ser Ser Glu
```

-continued

```
                165                 170                 175

Gly Leu Gly Gln Phe Ile Lys Asn Leu Val Gly Tyr Tyr Ile Ile Met
            180                 185                 190

Glu Gly Ile Phe Phe Tyr Ser Gly Phe Val Met Ile Leu Ser Phe His
        195                 200                 205

Arg Gln Asn Lys Met Thr Gly Ile Gly Glu Gln Tyr Gln Tyr Ile Leu
    210                 215                 220

Arg Asp Glu Thr Ile His Leu Asn Phe Gly Ile Asp Leu Ile Asn Gly
225                 230                 235                 240

Ile Lys Glu Glu Asn Pro Glu Val Trp Thr Thr Glu Leu Gln Glu Glu
                245                 250                 255

Ile Val Ala Leu Ile Glu Lys Ala Val Glu Leu Glu Ile Glu Tyr Ala
            260                 265                 270

Lys Asp Cys Leu Pro Arg Gly Ile Leu Gly Leu Arg Ser Ser Met Phe
        275                 280                 285

Ile Asp Tyr Val Arg His Ile Ala Asp Arg Arg Leu Glu Arg Ile Gly
    290                 295                 300

Leu Lys Pro Ile Tyr His Ser Arg Asn Pro Phe Pro Trp Met Ser Glu
305                 310                 315                 320

Thr Met Asp Leu Asn Lys Glu Lys Asn Phe Phe Glu Thr Arg Val Thr
                325                 330                 335

Glu Tyr Gln Thr Ala Gly Asn Leu Ser Trp
            340                 345


<210> SEQ ID NO 71
<211> LENGTH: 1044
<212> TYPE: PRT
<213> ORGANISM: Chlamydia pneumoniae

<400> SEQUENCE: 71

Met Val Glu Val Glu Glu Lys His Tyr Thr Ile Val Lys Arg Asn Gly
                  5                  10                  15

Met Phe Val Pro Phe Asn Gln Asp Arg Ile Phe Gln Ala Leu Glu Ala
             20                  25                  30

Ala Phe Arg Asp Thr Arg Ser Leu Glu Thr Ser Ser Pro Leu Pro Lys
         35                  40                  45

Asp Leu Glu Glu Ser Ile Ala Gln Ile Thr His Lys Val Val Lys Glu
     50                  55                  60

Val Leu Ala Lys Ile Ser Glu Gly Gln Val Val Thr Val Glu Arg Ile
 65                  70                  75                  80

Gln Asp Leu Val Glu Ser Gln Leu Tyr Ile Ser Gly Leu Gln Asp Val
                 85                  90                  95

Ala Arg Asp Tyr Ile Val Tyr Arg Asp Gln Arg Lys Ala Glu Arg Gly
            100                 105                 110

Asn Ser Ser Ser Ile Ile Ala Ile Ile Arg Arg Asp Gly Gly Ser Ala
        115                 120                 125

Lys Phe Asn Pro Met Lys Ile Ser Ala Ala Leu Glu Lys Ala Phe Arg
    130                 135                 140

Ala Thr Leu Gln Ile Asn Gly Met Thr Pro Pro Ala Thr Leu Ser Glu
145                 150                 155                 160

Ile Asn Asp Leu Thr Leu Arg Ile Val Glu Asp Val Leu Ser Leu His
                165                 170                 175

Gly Glu Glu Ala Ile Asn Leu Glu Glu Ile Gln Asp Ile Val Glu Lys
            180                 185                 190
```

-continued

```
Gln Leu Met Val Ala Gly Tyr Tyr Asp Val Ala Lys Asn Tyr Ile Leu
        195                 200                 205

Tyr Arg Glu Ala Arg Ala Arg Ala Arg Ala Asn Lys Asp Gln Asp Gly
    210                 215                 220

Gln Glu Glu Phe Val Pro Gln Glu Glu Thr Tyr Val Val Gln Lys Glu
225                 230                 235                 240

Asp Gly Thr Thr Tyr Leu Leu Arg Lys Thr Asp Leu Glu Lys Arg Phe
                245                 250                 255

Ser Trp Ala Cys Lys Arg Phe Pro Lys Thr Thr Asp Ser Gln Leu Leu
            260                 265                 270

Ala Asp Met Ala Phe Met Asn Leu Tyr Ser Gly Ile Lys Glu Asp Glu
        275                 280                 285

Val Thr Thr Ala Cys Ile Met Ala Ala Arg Ala Asn Ile Glu Arg Glu
    290                 295                 300

Pro Asp Tyr Ala Phe Ile Ala Ala Glu Leu Leu Thr Ser Ser Leu Tyr
305                 310                 315                 320

Glu Glu Thr Leu Gly Cys Ser Ser Gln Asp Pro Asn Leu Ser Glu Ile
                325                 330                 335

His Lys Lys His Phe Lys Glu Tyr Ile Leu Asn Gly Glu Glu Tyr Arg
            340                 345                 350

Leu Asn Pro Gln Leu Lys Asp Tyr Asp Leu Asp Ala Leu Ser Glu Val
        355                 360                 365

Leu Asp Leu Ser Arg Asp Gln Gln Phe Ser Tyr Met Gly Val Gln Asn
    370                 375                 380

Leu Tyr Asp Arg Tyr Phe Asn Leu His Glu Gly Arg Arg Leu Glu Thr
385                 390                 395                 400

Ala Gln Ile Phe Trp Met Arg Val Ser Met Gly Leu Ala Leu Asn Glu
                405                 410                 415

Gly Glu Gln Lys Asn Phe Trp Ala Ile Thr Phe Tyr Asn Leu Leu Ser
            420                 425                 430

Thr Phe Arg Tyr Thr Pro Ala Thr Pro Thr Leu Phe Asn Ser Gly Met
        435                 440                 445

Arg His Ser Gln Leu Ser Ser Cys Tyr Leu Ser Thr Val Lys Asp Asp
    450                 455                 460

Leu Ser His Ile Tyr Lys Val Ile Ser Asp Asn Ala Leu Leu Ser Lys
465                 470                 475                 480

Trp Ala Gly Gly Ile Gly Asn Asp Trp Thr Asp Val Arg Ala Thr Gly
                485                 490                 495

Ala Val Ile Lys Gly Thr Asn Gly Lys Ser Gln Gly Val Ile Pro Phe
            500                 505                 510

Ile Lys Val Ala Asn Asp Thr Ala Ile Ala Val Asn Gln Gly Gly Lys
        515                 520                 525

Arg Lys Gly Ala Met Cys Val Tyr Leu Glu Asn Trp His Leu Asp Tyr
    530                 535                 540

Glu Asp Phe Leu Glu Leu Arg Lys Asn Thr Gly Asp Glu Arg Arg Arg
545                 550                 555                 560

Thr His Asp Ile Asn Thr Ala Ser Trp Ile Pro Asp Leu Phe Phe Lys
                565                 570                 575

Arg Leu Glu Lys Lys Gly Met Trp Thr Leu Phe Ser Pro Asp Asp Val
            580                 585                 590

Pro Gly Leu His Glu Ala Tyr Gly Leu Glu Phe Glu Lys Leu Tyr Glu
        595                 600                 605

Glu Tyr Glu Arg Lys Val Glu Ser Gly Glu Ile Arg Leu Tyr Lys Lys
```

-continued

```
    610                 615                 620

Val Glu Ala Glu Val Leu Trp Arg Lys Met Leu Ser Met Leu Tyr Glu
625                 630                 635                 640

Thr Gly His Pro Trp Ile Thr Phe Lys Asp Pro Ser Asn Ile Arg Ser
                645                 650                 655

Asn Gln Asp His Val Gly Val Val Arg Cys Ser Asn Leu Cys Thr Glu
            660                 665                 670

Ile Leu Leu Asn Cys Ser Glu Ser Glu Thr Ala Val Cys Asn Leu Gly
        675                 680                 685

Ser Ile Asn Leu Val Glu His Ile Arg Asn Asp Lys Leu Asp Glu Glu
    690                 695                 700

Lys Leu Lys Glu Thr Ile Ser Ile Ala Ile Arg Ile Leu Asp Asn Val
705                 710                 715                 720

Ile Asp Leu Asn Phe Tyr Pro Thr Pro Glu Ala Lys Gln Ala Asn Leu
                725                 730                 735

Thr His Arg Ala Val Gly Leu Gly Val Met Gly Phe Gln Asp Val Leu
            740                 745                 750

Tyr Glu Leu Asn Ile Ser Tyr Ala Ser Gln Glu Ala Val Glu Phe Ser
        755                 760                 765

Asp Glu Cys Ser Glu Ile Ile Ala Tyr Tyr Ala Ile Leu Ala Ser Ser
    770                 775                 780

Leu Leu Ala Lys Glu Arg Gly Thr Tyr Ala Ser Tyr Ser Gly Ser Lys
785                 790                 795                 800

Trp Asp Arg Gly Tyr Leu Pro Leu Asp Thr Ile Glu Leu Leu Lys Glu
                805                 810                 815

Thr Arg Gly Glu His Asn Val Leu Val Asp Thr Ser Ser Lys Lys Asp
            820                 825                 830

Trp Thr Pro Val Arg Asp Thr Ile Gln Lys Tyr Gly Met Arg Asn Ser
        835                 840                 845

Gln Val Met Ala Ile Ala Pro Thr Ala Thr Ile Ser Asn Ile Ile Gly
    850                 855                 860

Val Thr Gln Ser Ile Glu Pro Met Tyr Lys His Leu Phe Val Lys Ser
865                 870                 875                 880

Asn Leu Ser Gly Glu Phe Thr Ile Pro Asn Thr Tyr Leu Ile Lys Lys
                885                 890                 895

Leu Lys Glu Leu Gly Leu Trp Asp Ala Glu Met Leu Asp Asp Leu Lys
            900                 905                 910

Tyr Phe Asp Gly Ser Leu Leu Glu Ile Glu Arg Ile Pro Asn His Leu
        915                 920                 925

Lys Lys Leu Phe Leu Thr Ala Phe Glu Ile Glu Pro Glu Trp Ile Ile
    930                 935                 940

Glu Cys Thr Ser Arg Arg Gln Lys Trp Ile Asp Met Gly Val Ser Leu
945                 950                 955                 960

Asn Leu Tyr Leu Ala Glu Pro Asp Gly Lys Lys Leu Ser Asn Met Tyr
                965                 970                 975

Leu Thr Ala Trp Lys Lys Gly Leu Lys Thr Thr Tyr Tyr Leu Arg Ser
            980                 985                 990

Gln Ala Ala Thr Ser Val Glu Lys Ser Phe Ile Asp Ile Asn Lys Arg
        995                 1000                1005

Gly Ile Gln Pro Arg Trp Met Lys Asn Lys Ser Ala Ser Thr Ser Ile
    1010                1015                1020

Val Val Glu Arg Lys Thr Thr Pro Val Cys Ser Met Glu Glu Gly Cys
1025                1030                1035                1040
```

-continued

```
Glu Ser Cys Gln

<210> SEQ ID NO 72
<211> LENGTH: 461
<212> TYPE: PRT
<213> ORGANISM: Chlamydia pneumoniae

<400> SEQUENCE: 72

Met Met Ser Ser Lys Arg Thr Ser Lys Ile Ala Val Leu Ser Ile Leu
                5                   10                  15

Leu Thr Phe Thr His Ser Ile Gly Phe Ala Asn Ala Asn Ser Ser Val
            20                  25                  30

Gly Leu Gly Thr Val Tyr Ile Thr Ser Glu Val Val Lys Lys Pro Gln
        35                  40                  45

Lys Gly Ser Glu Arg Lys Gln Ala Lys Lys Glu Pro Arg Ala Arg Lys
    50                  55                  60

Gly Tyr Leu Val Pro Ser Ser Arg Thr Leu Ser Ala Arg Ala Gln Lys
65                  70                  75                  80

Met Lys Asn Ser Ser Arg Lys Glu Ser Ser Gly Gly Cys Asn Glu Ile
                85                  90                  95

Ser Ala Asn Ser Thr Pro Arg Ser Val Lys Leu Arg Arg Asn Lys Arg
            100                 105                 110

Ala Glu Gln Lys Ala Ala Lys Gln Gly Phe Ser Ala Phe Ser Asn Leu
        115                 120                 125

Thr Leu Lys Ser Leu Leu Pro Lys Leu Pro Ser Lys Gln Lys Thr Ser
    130                 135                 140

Ile His Glu Arg Glu Lys Ala Thr Ser Arg Phe Val Asn Glu Ser Gln
145                 150                 155                 160

Leu Ser Ser Ala Arg Lys Arg Tyr Cys Thr Pro Ser Ser Ala Ala Pro
                165                 170                 175

Ser Leu Phe Leu Glu Thr Glu Ile Val Arg Ala Pro Val Glu Arg Thr
            180                 185                 190

Lys Glu Leu Gln Asp Asn Glu Ile His Ile Pro Val Val Gln Val Gln
        195                 200                 205

Thr Asn Pro Lys Glu Gln Asn Thr Lys Thr Thr Lys Gln Leu Ala Ser
    210                 215                 220

Gln Ala Ser Ile Gln Gln Ser Glu Gly Thr Glu Gln Ser Leu Arg Glu
225                 230                 235                 240

Leu Ala Gln Gly Ala Ser Leu Pro Val Leu Val Arg Ser Asn Pro Glu
                245                 250                 255

Val Ser Val Gln Arg Gln Lys Glu Glu Leu Leu Lys Glu Leu Val Ala
            260                 265                 270

Glu Arg Arg Gln Cys Lys Arg Lys Ser Val Arg Gln Ala Leu Glu Ala
        275                 280                 285

Arg Ser Leu Thr Lys Lys Val Ala Arg Gly Gly Ser Val Thr Ser Thr
    290                 295                 300

Leu Arg Tyr Asp Pro Glu Lys Ala Ala Glu Ile Lys Ser Arg Arg Asn
305                 310                 315                 320

Cys Lys Val Ser Pro Glu Ala Arg Glu Gln Lys Tyr Ser Ser Cys Lys
                325                 330                 335

Arg Asp Ala Arg Ala Asn Gly Lys Gln Asp Lys Thr Thr Pro Ser Glu
            340                 345                 350

Asp Ala Ser Gln Glu Glu Gln Gln Thr Gly Ala Gly Leu Val Arg Lys
        355                 360                 365
```

```
Thr Pro Lys Ser Gln Val Ala Ser Asn Ala Gln Asn Phe Tyr Arg Asn
    370                 375                 380

Ser Lys Asn Thr Asn Ile Asp Ser Tyr Leu Thr Ala Asn Gln Tyr Ser
385                 390                 395                 400

Cys Ser Ser Glu Glu Thr Asp Trp Pro Cys Ser Ser Cys Val Ser Lys
                405                 410                 415

Arg Arg Thr His Asn Ser Ile Ser Val Cys Thr Met Val Val Thr Val
            420                 425                 430

Ile Ala Met Ile Val Gly Ala Leu Ile Ile Ala Asn Ala Thr Glu Ser
        435                 440                 445

Gln Thr Thr Ser Asp Pro Thr Pro Pro Thr Pro Thr Pro
    450                 455                 460


<210> SEQ ID NO 73
<211> LENGTH: 576
<212> TYPE: PRT
<213> ORGANISM: Chlamydia pneumoniae

<400> SEQUENCE: 73

Met Thr Asp Phe Pro Thr His Phe Lys Gly Pro Lys Leu Asn Pro Ile
1               5                   10                  15

Lys Val Asn Pro Asn Phe Phe Glu Arg Asn Pro Lys Val Ala Arg Val
            20                  25                  30

Leu Gln Ile Thr Ala Val Val Leu Gly Ile Ile Ala Leu Leu Ser Gly
        35                  40                  45

Ile Val Leu Ile Ile Gly Thr Pro Leu Gly Ala Pro Ile Ser Met Ile
    50                  55                  60

Leu Gly Gly Cys Leu Leu Ala Ser Gly Gly Ala Leu Phe Val Gly Gly
65                  70                  75                  80

Thr Ile Ala Thr Ile Leu Gln Ala Arg Asn Ser Tyr Lys Lys Ala Val
                85                  90                  95

Asn Gln Lys Lys Leu Ser Glu Pro Leu Met Glu Arg Pro Glu Leu Lys
            100                 105                 110

Ala Leu Asp Tyr Ser Leu Asp Leu Lys Glu Val Trp Asp Leu His His
        115                 120                 125

Ser Val Val Lys His Leu Lys Lys Leu Asp Leu Asn Leu Ser Lys Thr
    130                 135                 140

Gln Arg Glu Val Leu Asn Gln Ile Lys Ile Asp Asp Glu Gly Pro Ser
145                 150                 155                 160

Leu Gly Glu Cys Ala Ala Met Ile Ser Glu Asn Tyr Asp Ala Cys Leu
                165                 170                 175

Lys Met Leu Ala Tyr Arg Glu Glu Leu Leu Lys Glu Gln Thr Gln Tyr
            180                 185                 190

Gln Glu Thr Arg Phe Asn Gln Asn Leu Thr His Arg Asn Lys Val Leu
        195                 200                 205

Leu Ser Ile Leu Ser Arg Ile Thr Asp Asn Ile Ser Lys Ala Gly Gly
    210                 215                 220

Val Phe Ser Leu Lys Phe Ser Thr Leu Ser Ser Arg Met Ser Arg Ile
225                 230                 235                 240

His Thr Thr Thr Thr Val Ile Leu Ala Leu Ser Ala Val Val Ser Val
                245                 250                 255

Met Val Val Ala Ala Leu Ile Pro Gly Gly Ile Leu Ala Leu Pro Ile
            260                 265                 270

Leu Leu Ala Val Ala Ile Ser Ala Gly Val Ile Val Thr Gly Leu Ser
```

-continued

```
        275                 280                 285

Tyr Leu Val Arg Gln Ile Leu Ser Asn Thr Lys Arg Asn Arg Gln Asp
    290                 295                 300

Phe Tyr Lys Asp Phe Val Lys Asn Val Asp Ile Glu Leu Leu Asn Gln
305                 310                 315                 320

Thr Val Thr Leu Gln Arg Phe Leu Phe Glu Met Leu Lys Gly Val Leu
                325                 330                 335

Lys Glu Glu Glu Glu Val Ser Leu Glu Gly Gln Asp Trp Tyr Thr Gln
            340                 345                 350

Tyr Ile Thr Asn Ala Pro Ile Glu Lys Arg Leu Ile Glu Glu Ile Arg
        355                 360                 365

Val Thr Tyr Lys Glu Ile Asp Ala Gln Thr Lys Lys Met Lys Thr Asp
    370                 375                 380

Leu Glu Phe Leu Glu Asn Glu Val Arg Ser Gly Arg Leu Ser Val Ala
385                 390                 395                 400

Ser Pro Ser Glu Asp Pro Ser Glu Thr Pro Ile Phe Thr Gln Gly Lys
                405                 410                 415

Glu Phe Ala Lys Leu Arg Arg Gln Thr Ser Gln Asn Ile Ser Thr Ile
            420                 425                 430

Tyr Gly Pro Asp Asn Glu Asn Ile Asp Pro Glu Phe Ser Leu Pro Trp
        435                 440                 445

Met Pro Lys Lys Glu Glu Glu Ile Asp His Ser Leu Glu Pro Val Thr
    450                 455                 460

Lys Leu Glu Pro Gly Ser Arg Glu Glu Leu Leu Leu Val Glu Gly Val
465                 470                 475                 480

Asn Pro Thr Leu Arg Glu Leu Asn Met Arg Ile Ala Leu Leu Gln Gln
                485                 490                 495

Gln Leu Ser Ser Val Arg Lys Trp Arg His Pro Arg Gly Glu His Tyr
            500                 505                 510

Gly Asn Val Ile Tyr Ser Asp Thr Glu Leu Asp Arg Ile Gln Met Leu
        515                 520                 525

Glu Gly Ala Phe Tyr Asn His Leu Arg Glu Ala Gln Glu Glu Ile Thr
    530                 535                 540

Gln Ser Leu Gly Asp Leu Val Asp Ile Gln Asn Arg Ile Leu Gly Ile
545                 550                 555                 560

Ile Val Glu Gly Asp Ser Asp Ser Arg Thr Glu Glu Glu Pro Gln Glu
                565                 570                 575


<210> SEQ ID NO 74
<211> LENGTH: 361
<212> TYPE: PRT
<213> ORGANISM: Chlamydia pneumoniae

<400> SEQUENCE: 74

Met Gln Gln Thr Val Ile Val Ala Met Ser Gly Gly Val Asp Ser Ser
                  5                  10                  15

Val Val Ala Tyr Leu Phe Lys Lys Phe Thr Asn Tyr Lys Val Ile Gly
             20                  25                  30

Leu Phe Met Lys Asn Trp Glu Glu Asp Ser Glu Gly Gly Leu Cys Ser
         35                  40                  45

Ser Thr Lys Asp Tyr Glu Asp Val Glu Arg Val Cys Leu Gln Leu Asp
     50                  55                  60

Ile Pro Tyr Tyr Thr Val Ser Phe Ala Lys Glu Tyr Arg Glu Arg Val
 65                  70                  75                  80
```

-continued

```
Phe Ala Arg Phe Leu Lys Glu Tyr Ser Leu Gly Tyr Thr Pro Asn Pro
                 85                  90                  95

Asp Ile Leu Cys Asn Arg Glu Ile Lys Phe Asp Leu Leu Gln Lys Lys
            100                 105                 110

Val Gln Glu Leu Gly Gly Asp Tyr Leu Ala Thr Gly His Tyr Cys Arg
        115                 120                 125

Leu Asn Thr Glu Leu Gln Glu Thr Gln Leu Leu Arg Gly Cys Asp Pro
    130                 135                 140

Gln Lys Asp Gln Ser Tyr Phe Leu Ser Gly Thr Pro Lys Ser Ala Leu
145                 150                 155                 160

His Asn Val Leu Phe Pro Leu Gly Glu Met Asn Lys Thr Glu Val Arg
                165                 170                 175

Ala Ile Ala Ala Gln Ala Ala Leu Pro Thr Ala Glu Lys Lys Asp Ser
            180                 185                 190

Thr Gly Ile Cys Phe Ile Gly Lys Arg Pro Phe Lys Glu Phe Leu Glu
        195                 200                 205

Lys Phe Leu Pro Asn Lys Thr Gly Asn Val Ile Asp Trp Asp Thr Lys
    210                 215                 220

Glu Ile Val Gly Gln His Gln Gly Ala His Tyr Tyr Thr Ile Gly Gln
225                 230                 235                 240

Arg Arg Gly Leu Asp Leu Gly Gly Ser Glu Lys Pro Cys Tyr Val Val
                245                 250                 255

Gly Lys Asn Ile Glu Glu Asn Ser Ile Tyr Ile Val Arg Gly Glu Asp
            260                 265                 270

His Pro Gln Leu Tyr Leu Arg Glu Leu Thr Ala Arg Glu Leu Asn Trp
        275                 280                 285

Phe Thr Pro Pro Lys Ser Gly Cys His Cys Ser Ala Lys Val Arg Tyr
    290                 295                 300

Arg Ser Pro Asp Glu Ala Cys Thr Ile Asp Tyr Ser Ser Gly Asp Glu
305                 310                 315                 320

Val Lys Val Arg Phe Ser Gln Pro Val Lys Ala Val Thr Pro Gly Gln
                325                 330                 335

Thr Ile Ala Phe Tyr Gln Gly Asp Thr Cys Leu Gly Ser Gly Val Ile
            340                 345                 350

Asp Val Pro Met Ile Pro Ser Glu Gly
        355                 360
```

<210> SEQ ID NO 75
<211> LENGTH: 1609
<212> TYPE: PRT
<213> ORGANISM: Chlamydia pneumoniae

<400> SEQUENCE: 75

```
Met Val Ala Lys Lys Thr Val Arg Ser Tyr Arg Ser Ser Phe Ser His
                  5                  10                  15

Ser Val Ile Val Ala Ile Leu Ser Ala Gly Ile Ala Phe Glu Ala His
             20                  25                  30

Ser Leu His Ser Ser Glu Leu Asp Leu Gly Val Phe Asn Lys Gln Phe
         35                  40                  45

Glu Glu His Ser Ala His Val Glu Glu Ala Gln Thr Ser Val Leu Lys
     50                  55                  60

Gly Ser Asp Pro Val Asn Pro Ser Gln Lys Glu Ser Glu Lys Val Leu
 65                  70                  75                  80

Tyr Thr Gln Val Pro Leu Thr Gln Gly Ser Ser Gly Glu Ser Leu Asp
                 85                  90                  95
```

-continued

```
Leu Ala Asp Ala Asn Phe Leu Glu His Phe Gln His Leu Phe Glu Glu
            100                 105                 110

Thr Thr Val Phe Gly Ile Asp Gln Lys Leu Val Trp Ser Asp Leu Asp
        115                 120                 125

Thr Arg Asn Phe Ser Gln Pro Thr Gln Glu Pro Asp Thr Ser Asn Ala
    130                 135                 140

Val Ser Glu Lys Ile Ser Ser Asp Thr Lys Glu Asn Arg Lys Asp Leu
145                 150                 155                 160

Glu Thr Glu Asp Pro Ser Lys Lys Ser Gly Leu Lys Glu Val Ser Ser
                165                 170                 175

Asp Leu Pro Lys Ser Pro Glu Thr Ala Val Ala Ala Ile Ser Glu Asp
            180                 185                 190

Leu Glu Ile Ser Glu Asn Ile Ser Ala Arg Asp Pro Leu Gln Gly Leu
        195                 200                 205

Ala Phe Phe Tyr Lys Asn Thr Ser Ser Gln Ser Ile Ser Glu Lys Asp
    210                 215                 220

Ser Ser Phe Gln Gly Ile Ile Phe Ser Gly Ser Gly Ala Asn Ser Gly
225                 230                 235                 240

Leu Gly Phe Glu Asn Leu Lys Ala Pro Lys Ser Gly Ala Ala Val Tyr
                245                 250                 255

Ser Asp Arg Asp Ile Val Phe Glu Asn Leu Val Lys Gly Leu Ser Phe
            260                 265                 270

Ile Ser Cys Glu Ser Leu Glu Asp Gly Ser Ala Ala Gly Val Asn Ile
        275                 280                 285

Val Val Thr His Cys Gly Asp Val Thr Leu Thr Asp Cys Ala Thr Gly
    290                 295                 300

Leu Asp Leu Glu Ala Leu Arg Leu Val Lys Asp Phe Ser Arg Gly Gly
305                 310                 315                 320

Ala Val Phe Thr Ala Arg Asn His Glu Val Gln Asn Asn Leu Ala Gly
                325                 330                 335

Gly Ile Leu Ser Val Val Gly Asn Lys Gly Ala Ile Val Val Glu Lys
            340                 345                 350

Asn Ser Ala Glu Lys Ser Asn Gly Gly Ala Phe Ala Cys Gly Ser Phe
        355                 360                 365

Val Tyr Ser Asn Asn Glu Asn Thr Ala Leu Trp Lys Glu Asn Gln Ala
    370                 375                 380

Leu Ser Gly Gly Ala Ile Ser Ser Ala Ser Asp Ile Asp Ile Gln Gly
385                 390                 395                 400

Asn Cys Ser Ala Ile Glu Phe Ser Gly Asn Gln Ser Leu Ile Ala Leu
                405                 410                 415

Gly Glu His Ile Gly Leu Thr Asp Phe Val Gly Gly Gly Ala Leu Ala
            420                 425                 430

Ala Gln Gly Thr Leu Thr Leu Arg Asn Asn Ala Val Val Gln Cys Val
        435                 440                 445

Lys Asn Thr Ser Lys Thr His Gly Gly Ala Ile Leu Ala Gly Thr Val
    450                 455                 460

Asp Leu Asn Glu Thr Ile Ser Glu Val Ala Phe Lys Gln Asn Thr Ala
465                 470                 475                 480

Ala Leu Thr Gly Gly Ala Leu Ser Ala Asn Asp Lys Val Ile Ile Ala
                485                 490                 495

Asn Asn Phe Gly Glu Ile Leu Phe Glu Gln Asn Glu Val Arg Asn His
            500                 505                 510
```

-continued

```
Gly Gly Ala Ile Tyr Cys Gly Cys Arg Ser Asn Pro Lys Leu Glu Gln
        515                 520                 525

Lys Asp Ser Gly Glu Asn Ile Asn Ile Ile Gly Asn Ser Gly Ala Ile
    530                 535                 540

Thr Phe Leu Lys Asn Lys Ala Ser Val Leu Glu Val Met Thr Gln Ala
545                 550                 555                 560

Glu Asp Tyr Ala Gly Gly Gly Ala Leu Trp Gly His Asn Val Leu Leu
                565                 570                 575

Asp Ser Asn Ser Gly Asn Ile Gln Phe Ile Gly Asn Ile Gly Gly Ser
            580                 585                 590

Thr Phe Trp Ile Gly Glu Tyr Val Gly Gly Gly Ala Ile Leu Ser Thr
        595                 600                 605

Asp Arg Val Thr Ile Ser Asn Asn Ser Gly Asp Val Val Phe Lys Gly
    610                 615                 620

Asn Lys Gly Gln Cys Leu Ala Gln Lys Tyr Val Ala Pro Gln Glu Thr
625                 630                 635                 640

Ala Pro Val Glu Ser Asp Ala Ser Ser Thr Asn Lys Asp Glu Lys Ser
                645                 650                 655

Leu Asn Ala Cys Ser His Gly Asp His Tyr Pro Pro Lys Thr Val Glu
            660                 665                 670

Glu Glu Val Pro Pro Ser Leu Leu Glu Glu His Pro Val Val Ser Ser
        675                 680                 685

Thr Asp Ile Arg Gly Gly Gly Ala Ile Leu Ala Gln His Ile Phe Ile
    690                 695                 700

Thr Asp Asn Thr Gly Asn Leu Arg Phe Ser Gly Asn Leu Gly Gly Gly
705                 710                 715                 720

Glu Glu Ser Ser Thr Val Gly Asp Leu Ala Ile Val Gly Gly Gly Ala
                725                 730                 735

Leu Leu Ser Thr Asn Glu Val Asn Val Cys Ser Asn Gln Asn Val Val
            740                 745                 750

Phe Ser Asp Asn Val Thr Ser Asn Gly Cys Asp Ser Gly Gly Ala Ile
        755                 760                 765

Leu Ala Lys Lys Val Asp Ile Ser Ala Asn His Ser Val Glu Phe Val
    770                 775                 780

Ser Asn Gly Ser Gly Lys Phe Gly Gly Ala Val Cys Ala Leu Asn Glu
785                 790                 795                 800

Ser Val Asn Ile Thr Asp Asn Gly Ser Ala Val Ser Phe Ser Lys Asn
                805                 810                 815

Arg Thr Arg Leu Gly Gly Ala Gly Val Ala Ala Pro Gln Gly Ser Val
            820                 825                 830

Thr Ile Cys Gly Asn Gln Gly Asn Ile Ala Phe Lys Glu Asn Phe Val
        835                 840                 845

Phe Gly Ser Glu Asn Gln Arg Ser Gly Gly Gly Ala Ile Ile Ala Asn
    850                 855                 860

Ser Ser Val Asn Ile Gln Asp Asn Ala Gly Asp Ile Leu Phe Val Ser
865                 870                 875                 880

Asn Ser Thr Gly Ser Tyr Gly Gly Ala Ile Phe Val Gly Ser Leu Val
                885                 890                 895

Ala Ser Glu Gly Ser Asn Pro Arg Thr Leu Thr Ile Thr Gly Asn Ser
            900                 905                 910

Gly Asp Ile Leu Phe Ala Lys Asn Ser Thr Gln Thr Ala Ala Ser Leu
        915                 920                 925

Ser Glu Lys Asp Ser Phe Gly Gly Gly Ala Ile Tyr Thr Gln Asn Leu
```

-continued

```
    930                 935                 940

Lys Ile Val Lys Asn Ala Gly Asn Val Ser Phe Tyr Gly Asn Arg Ala
945                 950                 955                 960

Pro Ser Gly Ala Gly Val Gln Ile Ala Asp Gly Gly Thr Val Cys Leu
                965                 970                 975

Glu Ala Phe Gly Gly Asp Ile Leu Phe Glu Gly Asn Ile Asn Phe Asp
            980                 985                 990

Gly Ser Phe Asn Ala Ile His Leu Cys Gly Asn Asp Ser Lys Ile Val
        995                 1000                1005

Glu Leu Ser Ala Val Gln Asp Lys Asn Ile Ile Phe Gln Asp Ala Ile
    1010                1015                1020

Thr Tyr Glu Glu Asn Thr Ile Arg Gly Leu Pro Asp Lys Asp Val Ser
1025                1030                1035                1040

Pro Leu Ser Ala Pro Ser Leu Ile Phe Asn Ser Lys Pro Gln Asp Asp
                1045                1050                1055

Ser Ala Gln His His Glu Gly Thr Ile Arg Phe Ser Arg Gly Val Ser
            1060                1065                1070

Lys Ile Pro Gln Ile Ala Ala Ile Gln Glu Gly Thr Leu Ala Leu Ser
        1075                1080                1085

Gln Asn Ala Glu Leu Trp Leu Ala Gly Leu Lys Gln Glu Thr Gly Ser
    1090                1095                1100

Ser Ile Val Leu Ser Ala Gly Ser Ile Leu Arg Ile Phe Asp Ser Gln
1105                1110                1115                1120

Val Asp Ser Ser Ala Pro Leu Pro Thr Glu Asn Lys Glu Glu Thr Leu
                1125                1130                1135

Val Ser Ala Gly Val Gln Ile Asn Met Ser Ser Pro Thr Pro Asn Lys
            1140                1145                1150

Asp Lys Ala Val Asp Thr Pro Val Leu Ala Asp Ile Ile Ser Ile Thr
        1155                1160                1165

Val Asp Leu Ser Ser Phe Val Pro Glu Gln Asp Gly Thr Leu Pro Leu
    1170                1175                1180

Pro Pro Glu Ile Ile Ile Pro Lys Gly Thr Lys Leu His Ser Asn Ala
1185                1190                1195                1200

Ile Asp Leu Lys Ile Ile Asp Pro Thr Asn Val Gly Tyr Glu Asn His
                1205                1210                1215

Ala Leu Leu Ser Ser His Lys Asp Ile Pro Leu Ile Ser Leu Lys Thr
            1220                1225                1230

Ala Glu Gly Met Thr Gly Thr Pro Thr Ala Asp Ala Ser Leu Ser Asn
        1235                1240                1245

Ile Lys Ile Asp Val Ser Leu Pro Ser Ile Thr Pro Ala Thr Tyr Gly
    1250                1255                1260

His Thr Gly Val Trp Ser Glu Ser Lys Met Glu Asp Gly Arg Leu Val
1265                1270                1275                1280

Val Gly Trp Gln Pro Thr Gly Tyr Lys Leu Asn Pro Glu Lys Gln Gly
                1285                1290                1295

Ala Leu Val Leu Asn Asn Leu Trp Ser His Tyr Thr Asp Leu Arg Ala
            1300                1305                1310

Leu Lys Gln Glu Ile Phe Ala His His Thr Ile Ala Gln Arg Met Glu
        1315                1320                1325

Leu Asp Phe Ser Thr Asn Val Trp Gly Ser Gly Leu Gly Val Val Glu
    1330                1335                1340

Asp Cys Gln Asn Ile Gly Glu Phe Asp Gly Phe Lys His His Leu Thr
1345                1350                1355                1360
```

```
Gly Tyr Ala Leu Gly Leu Asp Thr Gln Leu Val Glu Asp Phe Leu Ile
                1365                1370                1375

Gly Gly Cys Phe Ser Gln Phe Phe Gly Lys Thr Glu Ser Gln Ser Tyr
            1380                1385                1390

Lys Ala Lys Asn Asp Val Lys Ser Tyr Met Gly Ala Ala Tyr Ala Gly
        1395                1400                1405

Ile Leu Ala Gly Pro Trp Leu Ile Lys Gly Ala Phe Val Tyr Gly Asn
    1410                1415                1420

Ile Asn Asn Asp Leu Thr Thr Asp Tyr Gly Thr Leu Gly Ile Ser Thr
1425                1430                1435                1440

Gly Ser Trp Ile Gly Lys Gly Phe Ile Ala Gly Thr Ser Ile Asp Tyr
                1445                1450                1455

Arg Tyr Ile Val Asn Pro Arg Arg Phe Ile Ser Ala Ile Val Ser Thr
            1460                1465                1470

Val Val Pro Phe Val Glu Ala Glu Tyr Val Arg Ile Asp Leu Pro Glu
        1475                1480                1485

Ile Ser Glu Gln Gly Lys Glu Val Arg Thr Phe Gln Lys Thr Arg Phe
    1490                1495                1500

Glu Asn Val Ala Ile Pro Phe Gly Phe Ala Leu Glu His Ala Tyr Ser
1505                1510                1515                1520

Arg Gly Ser Arg Ala Glu Val Asn Ser Val Gln Leu Ala Tyr Val Phe
                1525                1530                1535

Asp Val Tyr Arg Lys Gly Pro Val Ser Leu Ile Thr Leu Lys Asp Ala
            1540                1545                1550

Ala Tyr Ser Trp Lys Ser Tyr Gly Val Asp Ile Pro Cys Lys Ala Trp
        1555                1560                1565

Lys Ala Arg Leu Ser Asn Asn Thr Glu Trp Asn Ser Tyr Leu Ser Thr
    1570                1575                1580

Tyr Leu Ala Phe Asn Tyr Glu Trp Arg Glu Asp Leu Ile Ala Tyr Asp
1585                1590                1595                1600

Phe Asn Gly Gly Ile Arg Ile Ile Phe
                1605


<210> SEQ ID NO 76
<211> LENGTH: 196
<212> TYPE: PRT
<213> ORGANISM: Chlamydia pneumoniae

<400> SEQUENCE: 76

Met Thr Leu Ser Leu Val Gly Lys Glu Ala Pro Asp Phe Val Ala Gln
                  5                  10                  15

Ala Val Val Asn Gly Glu Thr Cys Thr Val Ser Leu Lys Asp Tyr Leu
             20                  25                  30

Gly Lys Tyr Val Val Leu Phe Phe Tyr Pro Lys Asp Phe Thr Tyr Val
         35                  40                  45

Cys Pro Thr Glu Leu His Ala Phe Gln Asp Ala Leu Gly Glu Phe His
     50                  55                  60

Thr Arg Gly Ala Glu Val Ile Gly Cys Ser Val Asp Asp Ile Ala Thr
 65                  70                  75                  80

His Gln Gln Trp Leu Ala Thr Lys Lys Lys Gln Gly Gly Ile Glu Gly
                 85                  90                  95

Ile Thr Tyr Pro Leu Leu Ser Asp Glu Asp Lys Val Ile Ser Arg Ser
            100                 105                 110

Tyr His Val Leu Lys Pro Glu Glu Glu Leu Ser Phe Arg Gly Val Phe
```

-continued

```
        115                 120                 125

Leu Ile Asp Lys Gly Gly Ile Ile Arg His Leu Val Val Asn Asp Leu
    130                 135                 140

Pro Leu Gly Arg Ser Ile Glu Glu Glu Leu Arg Thr Leu Asp Ala Leu
145                 150                 155                 160

Ile Phe Phe Glu Thr Asn Gly Leu Val Cys Pro Ala Asn Trp His Glu
                165                 170                 175

Gly Glu Arg Ala Met Ala Pro Asn Glu Glu Gly Leu Gln Asn Tyr Phe
            180                 185                 190

Gly Thr Ile Asp
        195


<210> SEQ ID NO 77
<211> LENGTH: 619
<212> TYPE: PRT
<213> ORGANISM: Chlamydia pneumoniae

<400> SEQUENCE: 77

Met Lys Lys Gly Lys Leu Gly Ala Ile Val Phe Gly Leu Leu Phe Thr
                  5                  10                  15

Ser Ser Val Ala Gly Phe Ser Lys Asp Leu Thr Lys Asp Asn Ala Tyr
             20                  25                  30

Gln Asp Leu Asn Val Ile Glu His Leu Ile Ser Leu Lys Tyr Ala Pro
         35                  40                  45

Leu Pro Trp Lys Glu Leu Leu Phe Gly Trp Asp Leu Ser Gln Gln Thr
     50                  55                  60

Gln Gln Ala Arg Leu Gln Leu Val Leu Glu Glu Lys Pro Thr Thr Asn
 65                  70                  75                  80

Tyr Cys Gln Lys Val Leu Ser Asn Tyr Val Arg Ser Leu Asn Asp Tyr
                 85                  90                  95

His Ala Gly Ile Thr Phe Tyr Arg Thr Glu Ser Ala Tyr Ile Pro Tyr
            100                 105                 110

Val Leu Lys Leu Ser Glu Asp Gly His Val Phe Val Val Asp Val Gln
        115                 120                 125

Thr Ser Gln Gly Asp Ile Tyr Leu Gly Asp Glu Ile Leu Glu Val Asp
    130                 135                 140

Gly Met Gly Ile Arg Glu Ala Ile Glu Ser Leu Arg Phe Gly Arg Gly
145                 150                 155                 160

Ser Ala Thr Asp Tyr Ser Ala Ala Val Arg Ser Leu Thr Ser Arg Ser
                165                 170                 175

Ala Ala Phe Gly Asp Ala Val Pro Ser Gly Ile Ala Met Leu Lys Leu
            180                 185                 190

Arg Arg Pro Ser Gly Leu Ile Arg Ser Thr Pro Val Arg Trp Arg Tyr
        195                 200                 205

Thr Pro Glu His Ile Gly Asp Phe Ser Leu Val Ala Pro Leu Ile Pro
    210                 215                 220

Glu His Lys Pro Gln Leu Pro Thr Gln Ser Cys Val Leu Phe Arg Ser
225                 230                 235                 240

Gly Val Asn Ser Gln Ser Ser Ser Ser Ser Leu Phe Ser Ser Tyr Met
                245                 250                 255

Val Pro Tyr Phe Trp Glu Glu Leu Arg Val Gln Asn Lys Gln Arg Phe
            260                 265                 270

Asp Ser Asn His His Ile Gly Ser Arg Asn Gly Phe Leu Pro Thr Phe
        275                 280                 285
```

-continued

```
Gly Pro Ile Leu Trp Glu Gln Asp Lys Gly Pro Tyr Arg Ser Tyr Ile
    290                 295                 300

Phe Lys Ala Lys Asp Ser Gln Gly Asn Pro His Arg Ile Gly Phe Leu
305                 310                 315                 320

Arg Ile Ser Ser Tyr Val Trp Thr Asp Leu Glu Gly Leu Glu Glu Asp
                325                 330                 335

His Lys Asp Ser Pro Trp Glu Leu Phe Gly Glu Ile Ile Asp His Leu
            340                 345                 350

Glu Lys Glu Thr Asp Ala Leu Ile Ile Asp Gln Thr His Asn Pro Gly
        355                 360                 365

Gly Ser Val Phe Tyr Leu Tyr Ser Leu Leu Ser Met Leu Thr Asp His
    370                 375                 380

Pro Leu Asp Thr Pro Lys His Arg Met Ile Phe Thr Gln Asp Glu Val
385                 390                 395                 400

Ser Ser Ala Leu His Trp Gln Asp Leu Leu Glu Asp Val Phe Thr Asp
                405                 410                 415

Glu Gln Ala Val Ala Val Leu Gly Glu Thr Met Glu Gly Tyr Cys Met
            420                 425                 430

Asp Met His Ala Val Ala Ser Leu Gln Asn Phe Ser Gln Ser Val Leu
        435                 440                 445

Ser Ser Trp Val Ser Gly Asp Ile Asn Leu Ser Lys Pro Met Pro Leu
    450                 455                 460

Leu Gly Phe Ala Gln Val Arg Pro His Pro Lys His Gln Tyr Thr Lys
465                 470                 475                 480

Pro Leu Phe Met Leu Ile Asp Glu Asp Asp Phe Ser Cys Gly Asp Leu
                485                 490                 495

Ala Pro Ala Ile Leu Lys Asp Asn Gly Arg Ala Thr Leu Ile Gly Lys
            500                 505                 510

Pro Thr Ala Gly Ala Gly Gly Phe Val Phe Gln Val Thr Phe Pro Asn
        515                 520                 525

Arg Ser Gly Ile Lys Gly Leu Ser Leu Thr Gly Ser Leu Ala Val Arg
    530                 535                 540

Lys Asp Gly Glu Phe Ile Glu Asn Leu Gly Val Ala Pro His Ile Asp
545                 550                 555                 560

Leu Gly Phe Thr Ser Arg Asp Leu Gln Thr Ser Arg Phe Thr Asp Tyr
                565                 570                 575

Val Glu Ala Val Lys Thr Ile Val Leu Thr Ser Leu Ser Glu Asn Ala
            580                 585                 590

Lys Lys Ser Glu Glu Gln Thr Ser Pro Gln Glu Thr Pro Glu Val Ile
        595                 600                 605

Arg Val Ser Tyr Pro Thr Thr Thr Ser Ala Ser
    610                 615
```

<210> SEQ ID NO 78
<211> LENGTH: 651
<212> TYPE: PRT
<213> ORGANISM: Chlamydia pneumoniae

<400> SEQUENCE: 78

```
Met Val Asn Pro Ile Gly Pro Gly Pro Ile Asp Glu Thr Glu Arg Thr
                  5                  10                  15

Pro Pro Ala Asp Leu Ser Ala Gln Gly Leu Glu Ala Ser Ala Ala Asn
             20                  25                  30

Lys Ser Ala Glu Ala Gln Arg Ile Ala Gly Ala Glu Ala Lys Pro Lys
         35                  40                  45
```

-continued

```
Glu Ser Lys Thr Asp Ser Val Glu Arg Trp Ser Ile Leu Arg Ser Ala
     50                  55                  60

Val Asn Ala Leu Met Ser Leu Ala Asp Lys Leu Gly Ile Ala Ser Ser
 65                  70                  75                  80

Asn Ser Ser Ser Ser Thr Ser Arg Ser Ala Asp Val Asp Ser Thr Thr
                 85                  90                  95

Ala Thr Ala Pro Thr Pro Pro Pro Pro Thr Phe Asp Asp Tyr Lys Thr
            100                 105                 110

Gln Ala Gln Thr Ala Tyr Asp Thr Ile Phe Thr Ser Thr Ser Leu Ala
        115                 120                 125

Asp Ile Gln Ala Ala Leu Val Ser Leu Gln Asp Ala Val Thr Asn Ile
    130                 135                 140

Lys Asp Thr Ala Ala Thr Asp Glu Glu Thr Ala Ile Ala Ala Glu Trp
145                 150                 155                 160

Glu Thr Lys Asn Ala Asp Ala Val Lys Val Gly Ala Gln Ile Thr Glu
                165                 170                 175

Leu Ala Lys Tyr Ala Ser Asp Asn Gln Ala Ile Leu Asp Ser Leu Gly
            180                 185                 190

Lys Leu Thr Ser Phe Asp Leu Leu Gln Ala Ala Leu Leu Gln Ser Val
        195                 200                 205

Ala Asn Asn Asn Lys Ala Ala Glu Leu Leu Lys Glu Met Gln Asp Asn
    210                 215                 220

Pro Val Val Pro Gly Lys Thr Pro Ala Ile Ala Gln Ser Leu Val Asp
225                 230                 235                 240

Gln Thr Asp Ala Thr Ala Thr Gln Ile Glu Lys Asp Gly Asn Ala Ile
                245                 250                 255

Arg Asp Ala Tyr Phe Ala Gly Gln Asn Ala Ser Gly Ala Val Glu Asn
            260                 265                 270

Ala Lys Ser Asn Asn Ser Ile Ser Asn Ile Asp Ser Ala Lys Ala Ala
        275                 280                 285

Ile Ala Thr Ala Lys Thr Gln Ile Ala Glu Ala Gln Lys Lys Phe Pro
    290                 295                 300

Asp Ser Pro Ile Leu Gln Glu Ala Glu Gln Met Val Ile Gln Ala Glu
305                 310                 315                 320

Lys Asp Leu Lys Asn Ile Lys Pro Ala Asp Gly Ser Asp Val Pro Asn
                325                 330                 335

Pro Gly Thr Thr Val Gly Gly Ser Lys Gln Gln Gly Ser Ser Ile Gly
            340                 345                 350

Ser Ile Arg Val Ser Met Leu Leu Asp Asp Ala Glu Asn Glu Thr Ala
        355                 360                 365

Ser Ile Leu Met Ser Gly Phe Arg Gln Met Ile His Met Phe Asn Thr
    370                 375                 380

Glu Asn Pro Asp Ser Gln Ala Ala Gln Gln Glu Leu Ala Ala Gln Ala
385                 390                 395                 400

Arg Ala Ala Lys Ala Ala Gly Asp Asp Ser Ala Ala Ala Ala Leu Ala
                405                 410                 415

Asp Ala Gln Lys Ala Leu Glu Ala Ala Leu Gly Lys Ala Gly Gln Gln
            420                 425                 430

Gln Gly Ile Leu Asn Ala Leu Gly Gln Ile Ala Ser Ala Ala Val Val
        435                 440                 445

Ser Ala Gly Val Pro Pro Ala Ala Ala Ser Ser Ile Gly Ser Ser Val
    450                 455                 460
```

```
Lys Gln Leu Tyr Lys Thr Ser Lys Ser Thr Gly Ser Asp Tyr Lys Thr
465                 470                 475                 480

Gln Ile Ser Ala Gly Tyr Asp Ala Tyr Lys Ser Ile Asn Asp Ala Tyr
                485                 490                 495

Gly Arg Ala Arg Asn Asp Ala Thr Arg Asp Val Ile Asn Asn Val Ser
            500                 505                 510

Thr Pro Ala Leu Thr Arg Ser Val Pro Arg Ala Arg Thr Glu Ala Arg
        515                 520                 525

Gly Pro Glu Lys Thr Asp Gln Ala Leu Ala Arg Val Ile Ser Gly Asn
    530                 535                 540

Ser Arg Thr Leu Gly Asp Val Tyr Ser Gln Val Ser Ala Leu Gln Ser
545                 550                 555                 560

Val Met Gln Ile Ile Gln Ser Asn Pro Gln Ala Asn Asn Glu Glu Ile
                565                 570                 575

Arg Gln Lys Leu Thr Ser Ala Val Thr Lys Pro Pro Gln Phe Gly Tyr
            580                 585                 590

Pro Tyr Val Gln Leu Ser Asn Asp Ser Thr Gln Lys Phe Ile Ala Lys
        595                 600                 605

Leu Glu Ser Leu Phe Ala Glu Gly Ser Arg Thr Ala Ala Glu Ile Lys
    610                 615                 620

Ala Leu Ser Phe Glu Thr Asn Ser Leu Phe Ile Gln Gln Val Leu Val
625                 630                 635                 640

Asn Ile Gly Ser Leu Tyr Ser Gly Tyr Leu Gln
                645                 650
```

<210> SEQ ID NO 79
<211> LENGTH: 87
<212> TYPE: PRT
<213> ORGANISM: Chlamydia pneumoniae

<400> SEQUENCE: 79

```
Met Ser Gln Lys Asn Lys Asn Ser Ala Phe Met His Pro Val Asn Ile
1               5                   10                  15

Ser Thr Asp Leu Ala Val Ile Val Gly Lys Gly Pro Met Pro Arg Thr
            20                  25                  30

Glu Ile Val Lys Lys Val Trp Glu Tyr Ile Lys Lys His Asn Cys Gln
        35                  40                  45

Asp Gln Lys Asn Lys Arg Asn Ile Leu Pro Asp Ala Asn Leu Ala Lys
    50                  55                  60

Val Phe Gly Ser Ser Asp Pro Ile Asp Met Phe Gln Met Thr Lys Ala
65                  70                  75                  80

Leu Ser Lys His Ile Val Lys
                85
```

<210> SEQ ID NO 80
<211> LENGTH: 3048
<212> TYPE: DNA
<213> ORGANISM: Chlamydia trachomatis serovar D

<400> SEQUENCE: 80

```
atgccttttt ctttgagatc tacatcattt tgttttttag cttgtttgtg ttcctattcg     60

tatggattcg cgagctctcc tcaagtgtta acacctaatg taaccactcc ttttaagggg    120

gacgatgttt acttgaatgg agactgcgct tttgtcaatg tctatgcagg ggcagagaac    180

ggctcaatta tctcagctaa tggcgacaat ttaacgatta ccggacaaaa ccatacatta    240

tcatttacag attctcaagg gccagttctt caaaattatg ccttcatttc agcaggagag    300
```

-continued

```
acacttactc tgaaagattt ttcgagtttg atgttctcga aaaatgtttc ttgcggagaa    360
aagggaatga tctcagggaa aaccgtgagt atttccggag caggcgaagt gatttttttgg    420
gataactctg tggggtattc tcctttgtct attgtgccag catcgactcc aactcctcca    480
gcaccagcac cagctcctgc tgcttcaagc tctttatctc caacagttag tgatgctcgg    540
aaagggtcta ttttttctgt agagactagt ttggagatct caggcgtcaa aaaaggggtc    600
atgttcgata ataatgccgg gaattttgga acagtttttc gaggtaatag taataataat    660
gctggtagtg gggtagtgg gtctgctaca acaccaagtt ttacagttaa aaactgtaaa    720
gggaaagttt ctttcacaga taacgtagcc tcctgtggag gcggagtagt ctacaaagga    780
actgtgcttt tcaaagacaa tgaaggaggc atattcttcc gagggaacac agcatacgat    840
gatttaggga ttcttgctgc tactagtcgg gatcagaata cggagacagg aggcggtgga    900
ggagttattt gctctccaga tgattctgta aagtttgaag gcaataaagg ttctattgtt    960
tttgattaca actttgcaaa aggcagaggc ggaagcatcc taacgaaaga attctctctt   1020
gtagcagatg attcggttgt ctttagtaac aatacagcag aaaaaggcgg tggagctatt   1080
tatgctccta ctatcgatat aagcacgaat ggaggatcga ttctatttga aagaaaccga   1140
gctgcagaag gaggcgccat ctgcgtgagt gaagcaagct ctggttcaac tggaaatctt   1200
actttaagcg cttctgatgg ggatattgtt ttttctggga atatgacgag tgatcgtcct   1260
ggagagcgca gcgcagcaag aatcttaagt gatggaacga ctgtttcttt aaatgcttcc   1320
ggactatcga agctgatctt ttatgatcct gtagtacaaa ataattcagc agcgggtgca   1380
tcgacaccat caccatcttc ttcttctatg cctggtgctg tcacgattaa tcagtccggt   1440
aatggatctg tgatttttac cgccgagtca ttgactcctt cagaaaaact tcaagttctt   1500
aactctactt ctaacttccc aggagctctg actgtgtcag gaggggagtt ggttgtgacg   1560
gaaggagcta ccttaactac tgggaccatt acagccacct ctggacgagt gactttagga   1620
tccggagctt cgttgtctgc cgttgcaggt gctgcaaata ataattatac ttgtacagta   1680
tctaagttgg ggattgattt agaatccttt ttaactccta actataagac ggccatactg   1740
ggtgcggatg gaacagttac tgttaacagc ggctctactt tagacctagt gatggagagt   1800
gaggcagagg tatatgataa tccgcttttt gtgggatcgc tgacaattcc ttttgttact   1860
ctatcttcta gtagtgctag taacggagtt acaaaaaatt ctgtcactat taatgatgca   1920
gacgctgcgc actatgggta tcaaggctct tggtctgcag attggacgaa accgcctctg   1980
gctcctgatg ctaaggggat ggtacctcct aataccaata acactctgta tctgacatgg   2040
agacctgctt cgaattacgg tgaatatcga ctggatcctc agagaaaggg agaactagta   2100
cccaactctc tttgggtagc gggatctgca ttaagaacct ttactaatgg tttgaaagaa   2160
cactatgttt ctagagatgt tggatttgta gcatctctgc atgctctcgg ggattatatt   2220
ttgaattata cgcaagatga tcgggatggc tttttagcta gatatggggg attccaggcg   2280
accgcagcct cccattatga aaatgggtca atatttggag tggcttttgg acaactctat   2340
ggtcagacaa agagcagaat gtattactct aaagatgctg ggaacatgac gatgttgtcc   2400
tgtttcggaa gaagttacgt agatattaaa ggaacagaaa ctgttatgta ttgggagacg   2460
gcttatggct attctgtgca cagaatgcat acgcagtatt ttaatgacaa aacgcagaag   2520
ttcgatcatt cgaaatgtca ttggcacaac aataactatt atgcgtttgt gggtgccgag   2580
cataatttct tagagtactg cattcctact cgtcagttcg ctagagatta tgagcttaca   2640
```

```
gggtttatgc gttttgaaat ggccggagga tggtccagtt ctacacgaga aactggctcc   2700

ctaactagat atttcgctcg cgggtcaggg cataatatgt cgcttccaat aggaattgta   2760

gctcatgcag tttctcatgt gcgaagatct cctccttcta aactgacact aaatatggga   2820

tatagaccag acatttggcg tgtcactcca cattgcaata tggaaattat tgctaacgga   2880

gtgaagacac ctatacaagg atctccgctg gcacggcatg ccttcttctt agaagtgcat   2940

gatactttgt atattcatca ttttggaaga gcctatatga actattcgct ggatgctcgt   3000

cgtcgacaaa cggcacattt tgtatccatg ggcttgaata gaatcttt                3048
```

<210> SEQ ID NO 81
<211> LENGTH: 1038
<212> TYPE: DNA
<213> ORGANISM: Chlamydia trachomatis serovar D

<400> SEQUENCE: 81

```
atgcaagcag atattttaga tggaaaacag aaacgcgtta atctaaatag caagcgtcta     60

gtgaactgca accaggtcga tgtcaaccaa cttgttccta ttaagtacaa atgggcttgg    120

gaacattatt tgaatggctg cgcaaataac tggctcccta cagagatccc catggggaaa    180

gacatcgaat tatggaagtc ggatcgtctt tctgaagatg agcggcgagt cattcttttg    240

aatttaggtt ttttcagcac cgcagagagc ttggttggga ataatattgt tctagcaatt    300

tttaaacatg taactaatcc ggaagcgaga caatatcttt taagacaagc ttttgaagaa    360

gcggttcaca cgcacacatt tttgtatatt tgtgagtcac tcggattaga cgagaaagaa    420

attttcaatg cctataacga gcgtgctgcg attaaggcca aagatgattt ccagatggaa    480

atcactggca aggtattaga tcctaatttt cgcacggact ctgttgaggg tctacaggag    540

tttgttaaaa acttagtagg atactacatc attatggaag ggatttttct ctatagtggg    600

tttgtgatga tcctttcctt ccacagacaa aataagatga ttggtattgg agaacaatat    660

caatacatct taagagatga gacaatccac ttgaactttg gtattgattt gatcaacggg    720

ataaaagaag agaacccgga gatttggact ccagagttac agcaagaaat tgtcgaatta    780

attaagcgag ctgtcgattt agaaattgag tatgcgcaag actgtctccc tagagggatt    840

ttgggattga gagcttcgat gttcatcgat tatgtgcagc atattgcaga ccgtcgtttg    900

gaaagaatcg gattaaaacc tatttatcat acgaaaaacc cattcccttg gatgagcgaa    960

acaatagacc ttaataaaga gaaaaacttc tttgaaacaa gggttataga atatcaacat   1020

gcagcaagct taacttgg                                                 1038
```

<210> SEQ ID NO 82
<211> LENGTH: 3159
<212> TYPE: DNA
<213> ORGANISM: Chlamydia trachomatis serovar D

<400> SEQUENCE: 82

```
atgtttacaa ggatagttat ggtcgatcta caagaaaagc aatgcacaat tgttaagcgc     60

aatggaatgt ttgttccttt cgatcggaac cgtatttttc aggctttaga agcagctttt    120

cgagacactc gcagaattga tgatcatatg cctttgcctg aagatctgga aagttccata    180

cgctcgataa cgcatcaggt agttaaagaa gttgtgcaaa agattacaga tggacaagtg    240

gttactgtag agcgtatcca agatatggtt gaaagccaac tatatgtgaa tggtttgcaa    300

gatgttgctc gcgattatat tgtctatcgc gatgaccgta aagcgcatcg gaaaaaatct    360

tggcaaagcc tatccgttgt tcgtcgttgt gggactgttg tacactttaa tcctatgaaa    420
```

-continued

```
atttccgccg ctttggaaaa agctttccga gctaccgata agactgaggg gatgactcca    480
agttctgtgc gagaggaaat caatgctttg acgcaaaaca ttgtcgcgga aatagaagaa    540
tgttgtcctc aacaggatag acgcattgat atcgagaaga ttcaagatat tgttgaacag    600
caactaatgg ttgttgggca ttatgctgtt gcaaagaact atattcttta tcgagaagct    660
cgcgctcgtg ttcgtgataa cagagaagag gacgggagta cagaaaagac tatagcagaa    720
gaagctgttg aggtgctcag taaagacggt tctacctata caatgacgca ttcgcagttg    780
ttggctcatt tagcgcgcgc ttgtagtcgt tttccagaaa cgacagatgc ggcgctgctt    840
accgatatgg ctttcgcaaa tttctattcc ggtatcaaag agtctgaagt agtactggcc    900
tgtattatgg cggctcgtgc caatattgaa aaggagcctg attatgcctt tgttgctgca    960
gagctcttac ttgacgttgt atataaggaa gcgttaggga aatcgaaata tgctgaggat   1020
ttagaacaag cacatcgcga tcatttcaaa cgctacatcg cagaagggga tacctatcgt   1080
ctgaatgctg aactgaaaca tctttttgat ttagacgcgt tagccgatgc tatggatcta   1140
tctcgagatc tacagttttc ttacatgggt attcaaaatc tgtatgatcg ttattttaat   1200
caccacgaag gttgccgttt agaaactccc caaatttttt ggatgcgcgt tgctatgggg   1260
ttggcattga atgagcaaga caagacttct tgggctatta ctttttataa tttgctttcg   1320
acattccgat atacaccagc tacgccaacc ttgttcaatt caggtatgcg gcattctcag   1380
ttaagctctt gctatctttc cactgtacaa gataatttgg tcaatatcta taaggtcatt   1440
gctgataacg ctatgctatc taagtgggca ggagggatag gtaatgattg gacggcgatt   1500
cgtgcaacag gggctttaat taaaggaacc aatggaagaa gtcagggagt aattcctttt   1560
attaaggtga caaatgatac agcagtcgca gtgaatcaag gtggtaaacg caagggagct   1620
gtatgcgtct atttagaagt ttggcacctc gactacgaag atttccttga attgagaaag   1680
aatacagggg atgagcgtcg acgggctcat gatgtcaata tagctagctg gattccagat   1740
cttttcttca aacgtttaca gcaaaaaggg acatggactc tattcagccc agatgatgtt   1800
ccgggattac acgatgctta tggggaagaa tttgagcgtt tgtacgaaga atatgagcgg   1860
aaggttgata ccggagagat tcggttattc aagaaggtag aagctgaaga tctgtggaga   1920
aaaatgctca gcatgctttt tgaaacggga cacccatgga tgacttttaa agatccatcc   1980
aacatccgtt cggctcaaga tcataaaggc gtggtgcgtt gttccaatct gtgtacggag   2040
attttgttaa actgctcgga gacagaaact gctgtttgta atttaggatc gattaactta   2100
gttcaacata tcgtagggga tgggttagat gaggaaaaac tctctgagac gatctctata   2160
gcagtccgta tgttggataa cgtgattgat attaactttt atccaacaaa ggaagctaaa   2220
gaggcgaact ttgctcaccg cgctattgga ttaggggtga tgggattcca agatgccttg   2280
tataagctag atataagcta tgcttcgcaa gaagctgtag aatttgctga ctacagttca   2340
gagttgattt cttactatgc gattcaagct tcttgtctgc tcgctaaaga acgaggcact   2400
tacagctctt ataaaggatc gaaatgggat agaggtttgc tccctattga tacgattcag   2460
ttgttagcga actatcgagg agaagcaaat ctccagatgg atacgtcatc aagaaaagat   2520
tgggaaccta tccgtagttt ggttaaagag catggtatgc gacattgtca gcttatggct   2580
atagctccga cagcgacgat ctccaacatt ataggagtaa ctcaatctat tgagccaacg   2640
tacaaacatt tgtttgtgaa gtctaatttg tccggagaat tcacgattcc aaatgtgtat   2700
ttaattgaga agttgaagaa attaggtatc tgggatgctg atatgttaga tgacctgaaa   2760
```

```
tattttgatg ggtctttatt ggaaatcgag cgtataccag atcacttaaa acatattttc   2820

ttgacagctt ttgagattga accagaatgg attatcgaat gcgcgtctcg aagacaaaaa   2880

tggattgata tggggcaatc cctcaacctt tatcttgccc agccagacgg gaaaaaactg   2940

tcgaatatgt atttaacggc ttggaaaaaa ggtttgaaaa ctacgtatta tctgagatct   3000

tcatcagcaa cgaccgttga aaaatctttt gtagatatta ataagagagg aattcagcct   3060

cgttggatga agaataagtc tgcttcggca ggaattattg ttgaaagagc gaagaaagca   3120

cctgtctgtt ctttggaaga agggtgtgaa gcatgtcag                           3159
```

<210> SEQ ID NO 83
<211> LENGTH: 4593
<212> TYPE: DNA
<213> ORGANISM: Chlamydia trachomatis serovar D

<400> SEQUENCE: 83

```
atgagttccg agaaagatat aaaaagcacc tgttctaagt ttctctttgtc tgtagtagca     60

gctatccttg cctctgttag cgggttagct agttgcgtag atcttcatgc tggaggacag    120

tctgtaaatg agctggtata tgtaggccct caagcggttt tattgttaga ccaaattcga    180

gatctattcg ttgggtctaa agatagtcag gctgaaggac agtataggtt aattgtagga    240

gatccaagtt ctttccaaga gaaagatgcg gatactcttc ccgggaaggt agagcaaagt    300

actttgttct cagtaaccaa tcccgtggtt ttccaaggtg tggaccaaca ggatcaagtc    360

tcttcccaag ggttaatttg tagttttacg agcagcaacc ttgattctcc tcgtgacgga    420

gaatcttttt taggtattgc ttttgttggg gatagtagta aggctggaat cacattaact    480

gacgtgaaag cttctttgtc tggagcggct ttatattcta cagaagatct tatctttgaa    540

aagattaagg gtggattgga atttgcatca tgttcttctc tagaacaggg gggagcttgt    600

gcagctcaaa gtattttgat tcatgattgt caaggattgc aggttaaaca ctgtactaca    660

gccgtgaatg ctgaggggtc tagtgcgaat gatcatcttg gatttggagg aggcgctttc    720

tttgttacgg gttctctttc tggagagaaa agtctctata tgcctgcagg agatatggta    780

gttgcgaatt gtgatggggc tatatctttt gaaggaaaca gcgcgaactt tgctaatgga    840

ggagcgattg ctgcctctgg gaaagtgctt tttgtcgcta atgataaaaa gacttctttt    900

atagagaacc gagctttgtc tggaggagcg attgcagcct cttctgatat tgcctttcaa    960

aactgcgcag aactagtttt caaaggcaat tgtgcaattg gaacagagga taaaggttct   1020

ttaggtggag ggctatatc ttctctaggc accgttcttt tgcaagggaa tcacgggata   1080

acttgtgata agaatgagtc tgcttcgcaa ggaggcgcca tttttggcaa aaattgtcag   1140

atttctgaca acgaggggcc agtggttttc agagatagta cagcttgctt aggaggaggc   1200

gctattgcag ctcaagaaat tgtttctatt cagaacaatc aggctgggat ttccttcgag   1260

ggaggtaagg ctagtttcgg aggaggtatt gcgtgtggat ctttttcttc cgcaggtggt   1320

gcttctgttt tagggaccat tgatatttcg aagaatttag gcgcgatttc gttctctcgt   1380

actttatgta cgacctcaga tttaggacaa atggagtacc agggaggagg agctctattt   1440

ggtgaaaata tttctctttc tgagaatgct ggtgtgctca cctttaaaga caacattgtg   1500

aagacttttg cttcgaatgg gaaaattctg ggaggaggag cgattttagc tactggtaag   1560

gtggaaatta ctaataattc cgaaggaatt tcttttacag gaaatgcgag agctccacaa   1620

gctcttccaa ctcaagagga gtttccttta ttcagcaaaa aagaagggcg accactctct   1680

tcaggatatt ctgggggagg agcgatttta ggaagagaag tagctattct ccacaacgct   1740
```

-continued

```
gcagtagtat ttgagcaaaa tcgtttgcag tgcagcgaag aagaagcgac attattaggt   1800
tgttgtggag gaggcgctgt tcatgggatg gatagcactt cgattgttgg caactcttca   1860
gtaagatttg gtaataatta cgcaatggga caaggagtct caggaggagc tcttttatct   1920
aaaacagtgc agttagctgg gaatggaagc gtcgattttt ctcgaaatat tgctagtttg   1980
ggaggaggag ctcttcaagc ttctgaagga aattgtgagc tagttgataa cggctatgtg   2040
ctattcagag ataatcgagg gagggtttat gggggtgcta tttcttgctt acgtggagat   2100
gtagtcattt ctggaaacaa gggtagagtt gaatttaaag acaacatagc aacacgtctt   2160
tatgtggaag aaactgtaga aaaggttgaa gaggtagagc cagctcctga gcaaaaagac   2220
aataatgagc tttctttctt agggagagca gaacagagtt ttattactgc agctaatcaa   2280
gctcttttcg catctgaaga tggggattta tcacctgagt catccatttc ttctgaagaa   2340
cttgcgaaaa gaagagagtg tgctggagga gctatttttg caaaacgggt tcgtattgta   2400
gataaccaag aggccgttgt attctcgaat aacttctctg atatttatgg cggcgccatt   2460
tttacaggtt ctcttcgaga agaggataag ttagatgggc aaatccctga agtcttgatc   2520
tcaggcaatg caggggatgt tgttttttcc ggaaattcct cgaagcgtga tgagcatctt   2580
cctcatacag gtgggggagc catttgtact caaaatttga cgatttctca gaatacaggg   2640
aatgttctgt tttataacaa cgtggcctgt tcgggaggag ctgttcgtat agaggatcat   2700
ggtaatgttc ttttagaagc ttttggagga gatattgttt ttaaaggaaa ttcttctttc   2760
agagcacaag gatccgatgc tatctatttt gcaggtaaag aatcgcatat tacagccctg   2820
aatgctacgg aaggacatgc tattgttttc cacgacgcat tagtttttga aaatctagaa   2880
gaaaggaaat ctgctgaagt attgttaatc aatagtcgag aaaatccagg ttacactgga   2940
tctattcgat tttagaagc agaaagtaaa gttcctcaat gtattcatgt acaacaagga    3000
agccttgagt tgctaaatgg agccacatta tgtagttatg gttttaaaca agatgctgga   3060
gctaagttgg tattggctgc tggagctaaa ctgaagattt tagattcagg aactcctgta   3120
caacaagggc atgctatcag taaacctgaa gcagaaatcg agtcatcttc tgaaccagag   3180
ggtgcacatt ctctttggat tgcgaagaat gctcaaacaa cagttcctat ggttgatatc   3240
catactattt ctgtagattt agcctccttc tcttctagtc aacaggaggg gacagtagaa   3300
gctcctcagg ttattgttcc tggaggaagt tatgttcgat ctggagagct taatttggag   3360
ttagttaaca caacaggtac tggttatgaa aatcatgctt tattgaagaa tgaggctaaa   3420
gttccattga tgtctttcgt tgcttctggt gatgaagctt cagccgaaat cagtaacttg   3480
tcggtttctg atttacagat tcatgtagta actccagaga ttgaagaaga cacatacggc   3540
catatgggag attggtctga ggctaaaatt caagatggaa ctcttgtcat tagttggaat   3600
cctactggat atcgattaga tcctcaaaaa gcaggggctt tagtatttaa tgcattatgg   3660
gaagaagggg ctgtcttgtc tgctctgaaa aatgcacgct ttgctcataa tctcactgct   3720
cagcgtatgg aattcgatta ttctacaaat gtgtggggat tcgcctttgg tggtttccga   3780
actctatctg cagagaatct ggttgctatt gatggataca aaggagctta tggtggtgct   3840
tctgctggag tcgatattca attgatggaa gattttgttc taggagttag tggagctgct   3900
ttcctaggta aaatggatag tcagaagttt gatgcggagg tttctcggaa gggagttgtt   3960
ggttctgtat atacaggatt tttagctgga tcctggttct tcaaaggaca atatagcctt   4020
ggagaaacac agaacgatat gaaaacgcgt tatggagtac taggagagtc gagtgcttct   4080
```

-continued

```
tggacatctc gaggagtact ggcagatgct ttagttgaat accgaagttt agttggtcct   4140

gtgagaccta ctttttatgc tttgcatttc aatccttatg tcgaagtatc ttatgcttct   4200

atgaaattcc ctggctttac agaacaagga agagaagcgc gttcttttga agacgcttcc   4260

cttaccaata tcaccattcc tttagggatg aagtttgaat tggcgttcat aaaaggacag   4320

ttttcagagg tgaactcttt gggaataagt tatgcatggg aagcttatcg aaaagtagaa   4380

ggaggcgcgg tgcagctttt agaagctggg tttgattggg agggagctcc aatggatctt   4440

cctagacagg agctgcgtgt cgctctggaa aataatacgg aatggagttc ttacttcagc   4500

acagtcttag gattaacagc tttttgtgga ggatttactt ctacagatag taaactagga   4560

tatgaggcga atactggatt gcgattgatc ttt                                4593
```

<210> SEQ ID NO 84
<211> LENGTH: 1422
<212> TYPE: DNA
<213> ORGANISM: Chlamydia trachomatis serovar D

<400> SEQUENCE: 84

```
atgaaaatta ttcacacagc tatcgaattt gctccggtaa tcaaagccgg aggcctggga     60

gacgcgctat acggactagc aaaagcttta gccgctaatc acacaacgga agtggtaatc    120

cctttatacc ctaaattatt tactttgccc aaagaacaag atctttgctc gatccaaaaa    180

ttatcttatt tttttgctgg agagcaagaa gcaactgctt tctcctactt ttatgaagga    240

attaaagtaa ctctattcaa actcgacaca cagccagagt tattcgagaa tgcggaaaca    300

atctacacaa gcgatgatgc cttccgtttt tgcgcttttt ctgctgctgc ggcctcctac    360

atccaaaaag aaggagccaa tatcgttcat ttacacgatt ggcatacagg attagttgct    420

ggactactca aacaacagcc ctgctctcaa ttacaaaaga ttgttcttac cctacataat    480

tttggttatc gaggctatac aacacgagaa atattagaag cctcctcttt gaatgaattt    540

tatatcagcc agtaccaact atttcgcgat ccacaaactt gtgtgttgct aaaaggagct    600

ttatactgtt cagatttcgt gactacggtt tctcctacat acgccaaaga aattcttgaa    660

gattattccg attacgaaat tcacgatgcc attactgcta gacaacatca tctccgcggg    720

attttaaatg gaatcgacac gacaatttgg gggcctgaaa cggatcccaa tttagcgaaa    780

aactacacta aagagctttt cgagacccct tcaatttttt ttgaagctaa agccgagaat    840

aaaaaagcct tgtacgaaag attaggcctc tctttagaac actctccttg cgtgtgcatt    900

atttctagaa ttgctgagca gaaaggtcct cactttatga aacaggccat tctccatgca    960

ctagaaaacg cttacacgct cattattata ggtacctgct acgggaatca attgcatgaa   1020

gaatttgcaa atcttcaaga atcattagcg aattcccctg atgtaaggat tcttttgact   1080

tatagtgatg tgctggcacg acaaattttc gccgctgcag atatgatctg cattccttct   1140

atgtttgaac catgtggact cacacaaatg attggaatgc gttacgggac tgtaccgtta   1200

gtaagagcta caggaggact agcagatact gtagcaaatg gaatcaatgg attttccttc   1260

tttaatccgc atgacttcta tgaattccga aacatgcttt cggaagcagt gacaacctac   1320

cgtaccaacc acgacaagtg gcaacatatt gtacgtgctt gtctagattt ttcttcagac   1380

ctagaaactg ccgccaataa atatttagaa atttataaac aa                      1422
```

<210> SEQ ID NO 85
<211> LENGTH: 1179
<212> TYPE: DNA
<213> ORGANISM: Chlamydia trachomatis serovar D

<400> SEQUENCE: 85

```
atgaaaaaac tcttgaaatc ggtattagta tttgccgctt tgagttctgc ttcctccttg     60
caagctctgc ctgtggggaa tcctgctgaa ccaagcctta tgatcgacgg aattctgtgg    120
gaaggtttcg gcggagatcc ttgcgatcct tgcgccactt ggtgtgacgc tatcagcatg    180
cgtgttggtt actacggaga ctttgttttc gaccgtgttt tgaaaactga tgtgaataaa    240
gaatttcaga tgggtgccaa gcctacaact gatacaggca atagtgcagc tccatccact    300
cttacagcaa gagagaatcc tgcttacggc cgacatatgc aggatgctga gatgtttaca    360
aatgccgctt gcatggcatt gaatatttgg gatcgttttg atgtattctg tacattagga    420
gccaccagtg gatatcttaa aggaaactct gcttctttca atttagttgg attgtttgga    480
gataatgaaa atcaaaaaac ggtcaaagcg gagtctgtac caaatatgag ctttgatcaa    540
tctgttgttg agttgtatac agatactact tttgcgtgga gcgtcggcgc tcgcgcagct    600
ttgtgggaat gtggatgtgc aactttagga gcttcattcc aatatgctca atctaaacct    660
aaagtagaag aattaaacgt tctctgcaat gcagcagagt ttactattaa taaacctaaa    720
gggtatgtag gtaaggagtt tcctcttgat cttacagcag gaacagatgc tgcgacagga    780
actaaggatg cctctattga ttaccatgaa tggcaagcaa gtttagctct ctcttacaga    840
ctgaatatgt tcactcccta cattggagtt aaatggtctc gagcaagctt tgatgccgat    900
acgattcgta tagcccagcc aaaatcagct acagctattt ttgatactac cacgcttaac    960
ccaactattg ctggagctgg cgatgtgaaa actggcgcag agggtcagct cggagacaca   1020
atgcaaatcg tttccttgca attgaacaag atgaaatcta gaaaatcttg cggtattgca   1080
gtaggaacaa ctattgtgga tgcagacaaa tacgcagtta cagttgagac tcgcttgatc   1140
gatgagagag cagctcacgt aaatgcacaa ttccgcttc                          1179
```

<210> SEQ ID NO 86
<211> LENGTH: 585
<212> TYPE: DNA
<213> ORGANISM: Chlamydia trachomatis serovar D

<400> SEQUENCE: 86

```
atgggatcac tagttggaag acaggctccg gatttttctg gtaaagccgt tgtttgtgga     60
gaagagaaag aaatctctct agcagacttt cgtggtaagt atgtagtgct cttcttttat    120
cctaaagatt ttacctatgt ttgtcctaca gaattgcatg cttttcaaga tagattggta    180
gattttgaag agcgaggtgc agtcgtgctt ggttgctccg ttgacgacat tgagacacat    240
tctcgttggc tcgctgtagc gagaaatgca ggaggaatag agggaacaga atatcctctg    300
ttagcagacc cttcttttaa aatatcagaa gcttttggtg ttttgaatcc tgaaggatcg    360
ctcgctttaa gagcgacttt ccttatcgat aaatatgggg ttgttcgtca tgcggttatc    420
aatgatcttc ctttagggcg ttccattgac gaggaattgc gtattttaga ttcattgatc    480
ttctttgaga accacggaat ggtttgtcca gctaactggc gttctggaga gcgtggaatg    540
gtgccttctg aagagggatt aaaagaatat ttccagacga tggat                    585
```

<210> SEQ ID NO 87
<211> LENGTH: 258
<212> TYPE: DNA
<213> ORGANISM: Chlamydia trachomatis serovar D

<400> SEQUENCE: 87

-continued

```
atgagtcaaa ataagaactc tgctttcatg cagcctgtga acgtatccgc tgatttagct     60

gccatcgttg gtgcaggacc tatgcctcgc acagagatca ttaagaaaat gtgggattac    120

attaagaaga atggccttca agatcctaca aacaaacgta atatcaatcc cgatgataaa    180

ttggctaaag tttttggaac tgaaaaacct atcgatatgt tccaaatgac aaaaatggtt    240

tctcaacaca tcattaaa                                                  258
```

<210> SEQ ID NO 88
<211> LENGTH: 1182
<212> TYPE: DNA
<213> ORGANISM: Chlamydia trachomatis serovar D

<400> SEQUENCE: 88

```
atgtcaaaag aaacttttca acgtaataag cctcatatca acatagggac cattggccac     60

gttgaccatg gtaagactac gttgacagct gctattacgc gtgcgttgtc tggagatggg    120

ttggctgatt ttcgtgatta tagctctatt gacaacactc ctgaagaaaa agctcgcggt    180

attacaatta acgcttccca cgttgagtac gaaacagcta atcgtcacta cgctcacgtg    240

gactgccctg gtcacgctga ctatgttaaa aacatgatca ccggtgcagc tcaaatggac    300

ggggctattc tagtagtttc tgcaacagac ggagctatgc ctcaaactaa agagcatatt    360

cttttggcaa gacaagttgg ggttccttac atcgttgttt ttctcaataa aattgacatg    420

atttccgaag aagacgctga attggtcgac ttagttgaga tggagttggt tgagcttctt    480

gaagagaaag gatacaaagg gtgtccaatc atcagaggtt ctgctctgaa agctttggaa    540

ggggatgctg catacataga gaaagttcga gagctaatgc aagccgtcga tgataacatc    600

cctactccag aaagagaaat tgacaagcct ttcttaatgc ctattgagga cgtattctct    660

atctccggac gaggaactgt agtaactgga cgtattgagc gtggaattgt taaagtttcc    720

gataaagttc agttggtcgg tcttagagat actaaagaaa cgattgttac tggggttgaa    780

atgttcagaa aagaactccc agaaggtcgt gcaggagaga acgttggatt gctcctcaga    840

ggtattggta agaacgatgt ggaaagagga atggttgttt gcttgccaaa cagtgttaaa    900

cctcatacac agttcaagtg tgctgtttac gttttgcaaa aagaagaagg tggacgacat    960

aagcctttct tcacaggata tagacctcaa ttcttcttcc gtacaacaga cgtcacaggt   1020

gtggtaactc tgcctgaggg aattgagatg gtcatgcctg gggataacgt tgagtttgaa   1080

gtgcaattga ttagccctgt ggctttagaa gaaggtatga gatttgcgat tcgtgaaggt   1140

ggtcgtacaa tcggtgctgg aactatttct aagatcattg ca                      1182
```

<210> SEQ ID NO 89
<211> LENGTH: 246
<212> TYPE: DNA
<213> ORGANISM: Chlamydia trachomatis serovar D

<400> SEQUENCE: 89

```
atggggcaag atcaccgaag aaaatttctt aagaaagtat cttttgtaaa aaaacaagca     60

gcttttgcgg gtaactttat cgaagaaatt aagaagattg agtgggtaaa taagcgagat    120

cttaaaagat acgtcaagat tgttttgatg aatatttttg gctttggatt ttccatctat    180

tgtgtggatt tagctcttcg aaagtccctt tcattgttcg gtaaagtaac aagcttttc    240

tttggt                                                               246
```

<210> SEQ ID NO 90
<211> LENGTH: 1137

<212> TYPE: DNA
<213> ORGANISM: Chlamydia trachomatis serovar D

<400> SEQUENCE: 90

```
atggtgatcc ctaaggtgga tctaggagaa agtgccgtca tgatgggtta caagcttact      60
tcgcaacttg ctatgctttc gatcttattg actttcaccc atactatggg tcatgcaagt     120
cagatgagcc aaactcttcc tactattata gaagcacaag cggaagaggc attgcaggct     180
gacaggggag ttgctggaca ggctcttaaa aacttcgta aaaaaagatg tgcttctaga     240
aaatctgcat gtaaggcttc ttttaagaaa aaggatttct tttcttgtat tacaaatgga     300
ttgttctctg gaaatcatga gcagcgttta actgcgaaaa aagagaacaa ggctcgaggt     360
aaagagcctc gagtagtggt tcaaacgact aaaaaacgac aaataactca gtctgagaaa     420
gaatttttcg attggctatg taatagtaaa agagaaagaa agcttctcaa gaaaaagcct     480
gtaaatactt ctcttgctaa gagtgaagaa ttgagtccta aagaagcagc aatagctgct     540
gctcgagctt ctctttctcc agaagaaaaa cgtcaattga ttcgtgagtg gttagcagaa     600
gaaaagactg ctcgtaaatc tgggcgtgcg gcttgtgcgg taagtgagaa tcttaaaaga     660
gacggaagta ttacttctac attgcgctat gatgcggaga aagctttgac tacacgtgta     720
aaacgcaatg aaaattctgt aaatgctaga gcaagacaac gagccgctct tcaaaaagcc     780
aagaaagcaa agacggagaa acctgaggct gatgagaaag ctgcagaagc tgttgccgca     840
gctccaacca aacaggcgca taaggagcca gagaattact tcgcagctac agcttctaca     900
aataatacta atgttatgtc ctatctaaat gctcatcaat accgttgtga ttcttcggag     960
acggactggc cttgctcttc ttgtgttacg aaacgccgag ctaacttcgg tatttctgtg    1020
tgtactatgg tggttaccgt cattgctatg atcgtaggag ctgttatcat ttctaatgct    1080
acagactcta ccgttgcggg ctcctcggga acaggaggag gaggctcaac gcaacca       1137
```

<210> SEQ ID NO 91
<211> LENGTH: 1689
<212> TYPE: DNA
<213> ORGANISM: Chlamydia trachomatis serovar D

<400> SEQUENCE: 91

```
atggtttatt ttagagctca tcaacctagg catacgccta aaacatttcc tttggaagtt      60
caccattcgt tctccgataa gcatcctcaa attgctaaag ctatgcggat tacggggata     120
gccctcgcag ctctatctct gctcgctgta gtcgcctgcg ttattgccgt ctctgcggga     180
ggagctgcca ttcctcttgc tgtcattagt ggaattgctg taatgtctgg cctcttatcc     240
gctgccacca ttatctgttc tgcaaaaaag gctttggctc aacgaaaaca aaaacaacta     300
gaagagtcgc ttccgttaga taatgcgacc gagcatgtga gttacctgac ctcagacacc     360
tcttatttta atcaatggga atccttaggt gctctaaata agcagttgtc tcagattgac     420
ttaactattc aagctcccga aaaaaaacta ttaaaagaag ttcttggttc cagatacgat     480
tccattaatc actccatcga agagatctcc gatcgcttta cgaaaatgct ctctcttctt     540
cgattaagag aacattttta tcgaggagaa gagcgttatg ccccctattt aagccctcct     600
ctacttaaca agaatcgttt gctgacccaa atcacatcca atatgattag gatgctacca     660
aaatccggtg gtgtttttttc cctcaaagcc aatacactaa gtcatgccag ccgcacacta     720
tatacagtat taaaagtcgc tttatcctta ggagttctcg ctggagtcgc tgctcttatc     780
atctttcttc cccctagcct gccttttatc gctgttatag gagtatcttc cttagcattg     840
```

-continued

```
gggatggcat ctttccttat gattcggggc attaagtatt tgctcgaaca ttctcctctg    900

aatagaaagc aactagctaa agatattcaa aaaaccattg gcccagatgt cttggcctct    960

atggttcatt accagcatca attactatca catctacatg aaactctatt agatgaagcc   1020

atcacagcta gatggagcga gcccttcttt attgaacacg ctaatcttaa ggcaaaaatt   1080

gaagatttga caaaacaata tgatatattg aacgcagcct ttaataaatc tttacaacaa   1140

gatgaggcgc tccgttctca attagagaaa cgagcttact tattcccaat tcctaataac   1200

gacgaaaatg ctaaaactaa agaatcgcag cttctagact cagaaaatga ttcaaattct   1260

gaatttcagg agattataaa taaaggacta gaagctgcca ataaacgacg agctgacgct   1320

aagtcaaaat tctatacgga agacgaaacc tctgacaaaa tattctctat atggaaaccc   1380

acaaagaact tggcattaga agatttgtgg agagtgcatg aagcttgcaa tgaagagcaa   1440

caagctctcc tcttagaaga ttatatgagt tataaaacct cagaatgtca agctgcactc   1500

caaaaagtga gtcaagaact gaaggcggca caaaaatcat tcgcagtcct agaaaagcat   1560

gctctagaca gatcttatga atccagtgta gccacgatgg atttagctag agcgaatcaa   1620

gaaacacacc ggcttctgaa catcctctct gaattacaac aactagcaca atacctgtta   1680

gataatcac                                                           1689
```

<210> SEQ ID NO 92
<211> LENGTH: 1074
<212> TYPE: DNA
<213> ORGANISM: Chlamydia trachomatis serovar D

<400> SEQUENCE: 92

```
gtgcgtaaaa ctgtcattgt tgctatgtct ggaggagtgg attcctcggt tgttgcttat     60

ctcttaaaga agcaaggga gtataatgtt gttgggctct tcatgaaaaa ttggggagag    120

caggacgaga atggtgagtg tactgcaacc aaagattttc gcgatgtaga gcggatcgca    180

gaacaattgt ccattccata ttacacagtt tccttttcta aggaatataa agagcgagtg    240

ttttctagat ttctaagaga atatgcgaac ggctacactc ccaatcctga tgtgttatgc    300

aatcgagaaa tcaaatttga tttattacag aagaaggtac gtgagctaaa aggtgatttt    360

ttagccacgg gacattattg tcgaggaggg gctgatggaa ctggtttgtc cagaggaata    420

gaccccaata aagaccaaag ttatttctta tgtggcactc ctaaggatgc tttatccaat    480

gtacttttcc ccctgggagg tatgtataaa acggaggtac gtcgaattgc tcaagaagct    540

ggtttagcta ccgccacaaa aaaagatagc acagggattt gcttcattgg taaacggcct    600

tttaagagtt tccttgagca gtttgtagca gactctcctg gagacattat tgattttgat    660

acacaacagg tagtcggccg acatgaagga gcccattatt atacgattgg acagcgtcga    720

gggttaaaca taggaggaat ggaaaagcct tgttatgttc ttagcaagaa tatggaaaag    780

aatattgttt acattgtaag gggtgaagat catcctttac tttatcgaca agagctttta    840

gctaaggaac ttaattggtt tgttcccttg caggagccta tgatctgtag tgctaaagtt    900

cggtacagat cccctgacga gaaatgttct gtatatcctt tggaagatgg aacggtaaaa    960

gtgattttcg atgtccctgt gaaagctgtc acccctggac agactgtagc tttctaccag   1020

ggggacattt gtttaggagg aggagtgatt gaagtgccta tgattcatca gctg         1074
```

<210> SEQ ID NO 93
<211> LENGTH: 801
<212> TYPE: DNA
<213> ORGANISM: Chlamydia trachomatis serovar D -continued

<400> SEQUENCE: 93

```
atgtccagaa aaccggcttc taactcatcc cggaacacca aacggtcctc agacacttcc     60
tgggaagtca ttgcccaaga ttataataaa gccgttgatc gcgatggaca tttctatcat    120
aaggaagtga ttctccctaa tctcctttct aagctacata tttcccgctc atcgtctctg    180
gttgatgtag gatgtggtca agggattttg gagaagcatt tacccaaaca tctcccttat    240
ctaggaatcg atctttcccc tagtctgctg cgttttgcaa agaaaagcgc ttcctcaaaa    300
tcacgtcgct ttcttcatca cgatatgacg caaccggtac cagcagatca tcatgagcag    360
ttttcccatg ctacagcaat cctttctctt cagaatatgg aatctccaga acaagctatc    420
gcacacacag cgaatctttt ggctcctcaa ggtaggttgt ttattgttct caaccatcca    480
tgctttcgca tccctaggct ttcttcatgg ctttatgatg agcctaaaaa actcttatct    540
agaaaaatag accgctatct ctctcctgtg gcggttccta tcgttgtgca tcctggagaa    600
aaacattctg agacgacata ttctttccat ttccccttaa gctattgggt acaagcttta    660
tctaatcaca atcttctgat tgatagtatg gaagaatgga tctcccctaa aaaatcctca    720
gggaagaggg ctcgagcaga aaatctttgt cgcaaggagt ttccgctttt cttgtttatc    780
tcagcattaa aaatatcaaa a                                              801
```

<210> SEQ ID NO 94
<211> LENGTH: 2601
<212> TYPE: DNA
<213> ORGANISM: Chlamydia trachomatis serovar D

<400> SEQUENCE: 94

```
atggagaaat tttcagatgc agtaagcgaa gccttagaaa aggcgtttga gttagctaaa     60
aactctaagc attcctacgt gacagaaaac catttgctga aaagtctttt gcaaaatcca    120
ggttccctat tttgtttggt cattaaggat gtgcacggta atcttggttt gcttacttct    180
gctgtggacg acgccttacg cagagaacca actgtagtcg agggaaccgc tgttgctagt    240
ccttctccaa gtttacagca gttgttgctc aatgcgcatc aagaagctag aagtatgggt    300
gacgaatatc tatcagggga tcatttgtta ctagcttttt ggcgatcgac taaagagcct    360
tttgcttctt ggagaaaaac tgtaaaaact acctctgaag cgttgaaaga attaattact    420
aaattaagac aaggaagtcg tatggactca cctagtgctg aagaaaatct gaaaggatta    480
gagaaatact gcaaaaattt gactgtactt gcaagagaag gcaagcttga tcctgtgatt    540
ggtcgagatg aagagattag acgtacgata caggttcttt ctagacgaac aaagaataat    600
cctatgttga taggggagcc cggagttggg aaaacagcaa tcgctgaagg acttgctctt    660
cgcatagtgc aaggggatgt tccagagagt ttaaaggaaa agcatctgta tgtactggat    720
atgggagctt tgattgcagg tgccaagtat cgaggagagt ttgaagagcg gttaaaaagt    780
gtattgaagg gtgtagaagc ttctgaaggc gagtgtatcc tattcattga tgaagtgcat    840
actttagtag gagcgggagc tacagatgga gctatggatg cagcgaatct attaaagcct    900
gctttagcac gaggcacttt gcattgtatt ggcgctacga ctttgaatga ataccaaaaa    960
tatatagaga aagacgcggc tttggaacgg cgtttccagc ctatttttgt aacagaacct   1020
tctttggaag atgctgtatt cattctccgg gggttaaggg aaaaatatga aatttttcat   1080
ggtgtgcgca ttacagaagg ggctttgaat gcagctgtag ttctttctta tcgttacatc   1140
acagaccgat ttcttcctga taaggcgatt gacctaattg atgaggctgc gagtttaatc   1200
```

-continued

```
cgtatgcaaa taggaagttt acctctgcct attgatgaaa aggaaagaga attatcagct   1260

ttaatcgtga aacaagaagc tattaaacgc gagcaagcac cagcttatca ggaagaggct   1320

gaagacatgc aaaaagcaat tgaccgggtt aaggaagagc tggccgcttt acgcttgcgc   1380

tgggatgaag aaaaaggatt aattacagga ttaaaagaaa agaagaatgc tttagaaaat   1440

ttaaaatttg ccgaagagga agctgagcgt actgccgatt acaatcgggt ggcagaacta   1500

cgctatagtt tgattccttc tttggaggaa gaaattcatt tagctgagga agctttaaat   1560

caaagagatg ggcgcctgct tcaagaggaa gttgatgagc ggttgattgc gcaagttgtt   1620

gcgaattgga ctggaatccc tgtgcaaaaa atgttggagg gagaatctga aaagttattg   1680

gtgttggagg agtctttaga agaaagggtt gttggacaac ctttcgctat tgccgcagtc   1740

agtgattcga ttcgagctgc tcgagtagga ttgagtgatc cgcagcgtcc tctaggagtg   1800

tttctatttc ttggacctac aggggtaggg aaaactgagc ttgctaaagc attagcagag   1860

cttttattta ataaggaaga agcgatgatt cggtttgaca tgaccgaata tatggaaaaa   1920

cattccgttt ccaaattgat aggatctcct ccagggtatg taggatatga agaaggaggg   1980

agtctctcag aagctttaag aagacgacct tattctgttg ttctttttga tgagatagaa   2040

aaagcagata aagaagtatt taatatttta ttgcagattt ttgatgatgg gattcttacg   2100

gatagcaaga agcgtaaggt aaattgtaag aatgctcttt tcattatgac atcaaatatt   2160

ggttcgcaag agcttgctga ttattgtact aagaaaggaa ctatcgtaga caaagaagct   2220

gtgctatctg ttgttgcccc tgcgcttaaa aattatttta gtccagaatt tatcaatcgt   2280

atcgatgaca ttctgccttt cgttcctttg actacggaag acattgtaaa aattgtcggt   2340

attcaaatga atcgggttgc tttacgtttg ctggaaagaa aaatttcgtt aacttgggat   2400

gattctttag tgctatttct cagtgagcaa ggttatgaca gcgcttttgg agctcgccct   2460

ctgaagcgtt tgatacagca aaaagtagtg actatgttgt ctaaagctct tttgaaagga   2520

gatatcaaac ctggaatggc ggtggagctt actatggcaa aagatgtagt tgtgtttaaa   2580

attaaaacaa atccagctgt g                                             2601
```

<210> SEQ ID NO 95
<211> LENGTH: 1016
<212> TYPE: PRT
<213> ORGANISM: Chlamydia trachomatis serovar D

<400> SEQUENCE: 95

```
Met Pro Phe Ser Leu Arg Ser Thr Ser Phe Cys Phe Leu Ala Cys Leu
                5                   10                  15

Cys Ser Tyr Ser Tyr Gly Phe Ala Ser Ser Pro Gln Val Leu Thr Pro
            20                  25                  30

Asn Val Thr Thr Pro Phe Lys Gly Asp Asp Val Tyr Leu Asn Gly Asp
        35                  40                  45

Cys Ala Phe Val Asn Val Tyr Ala Gly Ala Glu Asn Gly Ser Ile Ile
    50                  55                  60

Ser Ala Asn Gly Asp Asn Leu Thr Ile Thr Gly Gln Asn His Thr Leu
65                  70                  75                  80

Ser Phe Thr Asp Ser Gln Gly Pro Val Leu Gln Asn Tyr Ala Phe Ile
                85                  90                  95

Ser Ala Gly Glu Thr Leu Thr Leu Lys Asp Phe Ser Ser Leu Met Phe
            100                 105                 110

Ser Lys Asn Val Ser Cys Gly Glu Lys Gly Met Ile Ser Gly Lys Thr
        115                 120                 125
```

```
Val Ser Ile Ser Gly Ala Gly Glu Val Ile Phe Trp Asp Asn Ser Val
    130                 135                 140

Gly Tyr Ser Pro Leu Ser Ile Val Pro Ala Ser Thr Pro Thr Pro Pro
145                 150                 155                 160

Ala Pro Ala Pro Ala Pro Ala Ala Ser Ser Ser Leu Ser Pro Thr Val
                165                 170                 175

Ser Asp Ala Arg Lys Gly Ser Ile Phe Ser Val Glu Thr Ser Leu Glu
            180                 185                 190

Ile Ser Gly Val Lys Lys Gly Val Met Phe Asp Asn Asn Ala Gly Asn
        195                 200                 205

Phe Gly Thr Val Phe Arg Gly Asn Ser Asn Asn Asn Ala Gly Ser Gly
    210                 215                 220

Gly Ser Gly Ser Ala Thr Thr Pro Ser Phe Thr Val Lys Asn Cys Lys
225                 230                 235                 240

Gly Lys Val Ser Phe Thr Asp Asn Val Ala Ser Cys Gly Gly Gly Val
                245                 250                 255

Val Tyr Lys Gly Thr Val Leu Phe Lys Asp Asn Glu Gly Gly Ile Phe
            260                 265                 270

Phe Arg Gly Asn Thr Ala Tyr Asp Asp Leu Gly Ile Leu Ala Ala Thr
        275                 280                 285

Ser Arg Asp Gln Asn Thr Glu Thr Gly Gly Gly Gly Gly Val Ile Cys
    290                 295                 300

Ser Pro Asp Asp Ser Val Lys Phe Glu Gly Asn Lys Gly Ser Ile Val
305                 310                 315                 320

Phe Asp Tyr Asn Phe Ala Lys Gly Arg Gly Gly Ser Ile Leu Thr Lys
                325                 330                 335

Glu Phe Ser Leu Val Ala Asp Asp Ser Val Val Phe Ser Asn Asn Thr
            340                 345                 350

Ala Glu Lys Gly Gly Gly Ala Ile Tyr Ala Pro Thr Ile Asp Ile Ser
        355                 360                 365

Thr Asn Gly Gly Ser Ile Leu Phe Glu Arg Asn Arg Ala Ala Glu Gly
    370                 375                 380

Gly Ala Ile Cys Val Ser Glu Ala Ser Ser Gly Ser Thr Gly Asn Leu
385                 390                 395                 400

Thr Leu Ser Ala Ser Asp Gly Asp Ile Val Phe Ser Gly Asn Met Thr
                405                 410                 415

Ser Asp Arg Pro Gly Glu Arg Ser Ala Ala Arg Ile Leu Ser Asp Gly
            420                 425                 430

Thr Thr Val Ser Leu Asn Ala Ser Gly Leu Ser Lys Leu Ile Phe Tyr
        435                 440                 445

Asp Pro Val Val Gln Asn Asn Ser Ala Ala Gly Ala Ser Thr Pro Ser
    450                 455                 460

Pro Ser Ser Ser Ser Met Pro Gly Ala Val Thr Ile Asn Gln Ser Gly
465                 470                 475                 480

Asn Gly Ser Val Ile Phe Thr Ala Glu Ser Leu Thr Pro Ser Glu Lys
                485                 490                 495

Leu Gln Val Leu Asn Ser Thr Ser Asn Phe Pro Gly Ala Leu Thr Val
            500                 505                 510

Ser Gly Gly Glu Leu Val Val Thr Glu Gly Ala Thr Leu Thr Thr Gly
        515                 520                 525

Thr Ile Thr Ala Thr Ser Gly Arg Val Thr Leu Gly Ser Gly Ala Ser
    530                 535                 540
```

-continued

```
Leu Ser Ala Val Ala Gly Ala Ala Asn Asn Asn Tyr Thr Cys Thr Val
545                 550                 555                 560

Ser Lys Leu Gly Ile Asp Leu Glu Ser Phe Leu Thr Pro Asn Tyr Lys
                565                 570                 575

Thr Ala Ile Leu Gly Ala Asp Gly Thr Val Thr Val Asn Ser Gly Ser
            580                 585                 590

Thr Leu Asp Leu Val Met Glu Ser Glu Ala Glu Val Tyr Asp Asn Pro
        595                 600                 605

Leu Phe Val Gly Ser Leu Thr Ile Pro Phe Val Thr Leu Ser Ser Ser
    610                 615                 620

Ser Ala Ser Asn Gly Val Thr Lys Asn Ser Val Thr Ile Asn Asp Ala
625                 630                 635                 640

Asp Ala Ala His Tyr Gly Tyr Gln Gly Ser Trp Ser Ala Asp Trp Thr
                645                 650                 655

Lys Pro Pro Leu Ala Pro Asp Ala Lys Gly Met Val Pro Pro Asn Thr
            660                 665                 670

Asn Asn Thr Leu Tyr Leu Thr Trp Arg Pro Ala Ser Asn Tyr Gly Glu
        675                 680                 685

Tyr Arg Leu Asp Pro Gln Arg Lys Gly Glu Leu Val Pro Asn Ser Leu
    690                 695                 700

Trp Val Ala Gly Ser Ala Leu Arg Thr Phe Thr Asn Gly Leu Lys Glu
705                 710                 715                 720

His Tyr Val Ser Arg Asp Val Gly Phe Val Ala Ser Leu His Ala Leu
                725                 730                 735

Gly Asp Tyr Ile Leu Asn Tyr Thr Gln Asp Asp Arg Asp Gly Phe Leu
            740                 745                 750

Ala Arg Tyr Gly Gly Phe Gln Ala Thr Ala Ala Ser His Tyr Glu Asn
        755                 760                 765

Gly Ser Ile Phe Gly Val Ala Phe Gly Gln Leu Tyr Gly Gln Thr Lys
    770                 775                 780

Ser Arg Met Tyr Tyr Ser Lys Asp Ala Gly Asn Met Thr Met Leu Ser
785                 790                 795                 800

Cys Phe Gly Arg Ser Tyr Val Asp Ile Lys Gly Thr Glu Thr Val Met
                805                 810                 815

Tyr Trp Glu Thr Ala Tyr Gly Tyr Ser Val His Arg Met His Thr Gln
            820                 825                 830

Tyr Phe Asn Asp Lys Thr Gln Lys Phe Asp His Ser Lys Cys His Trp
        835                 840                 845

His Asn Asn Asn Tyr Tyr Ala Phe Val Gly Ala Glu His Asn Phe Leu
    850                 855                 860

Glu Tyr Cys Ile Pro Thr Arg Gln Phe Ala Arg Asp Tyr Glu Leu Thr
865                 870                 875                 880

Gly Phe Met Arg Phe Glu Met Ala Gly Gly Trp Ser Ser Ser Thr Arg
                885                 890                 895

Glu Thr Gly Ser Leu Thr Arg Tyr Phe Ala Arg Gly Ser Gly His Asn
            900                 905                 910

Met Ser Leu Pro Ile Gly Ile Val Ala His Ala Val Ser His Val Arg
        915                 920                 925

Arg Ser Pro Pro Ser Lys Leu Thr Leu Asn Met Gly Tyr Arg Pro Asp
    930                 935                 940

Ile Trp Arg Val Thr Pro His Cys Asn Met Glu Ile Ile Ala Asn Gly
945                 950                 955                 960

Val Lys Thr Pro Ile Gln Gly Ser Pro Leu Ala Arg His Ala Phe Phe
```

-continued

```
                965                 970                 975

Leu Glu Val His Asp Thr Leu Tyr Ile His His Phe Gly Arg Ala Tyr
            980                 985                 990

Met Asn Tyr Ser Leu Asp Ala Arg Arg Arg Gln Thr Ala His Phe Val
        995                 1000                1005

Ser Met Gly Leu Asn Arg Ile Phe
    1010                1015


<210> SEQ ID NO 96
<211> LENGTH: 346
<212> TYPE: PRT
<213> ORGANISM: Chlamydia trachomatis serovar D

<400> SEQUENCE: 96

Met Gln Ala Asp Ile Leu Asp Gly Lys Gln Lys Arg Val Asn Leu Asn
                  5                  10                  15

Ser Lys Arg Leu Val Asn Cys Asn Gln Val Asp Val Asn Gln Leu Val
             20                  25                  30

Pro Ile Lys Tyr Lys Trp Ala Trp Glu His Tyr Leu Asn Gly Cys Ala
         35                  40                  45

Asn Asn Trp Leu Pro Thr Glu Ile Pro Met Gly Lys Asp Ile Glu Leu
     50                  55                  60

Trp Lys Ser Asp Arg Leu Ser Glu Asp Glu Arg Arg Val Ile Leu Leu
 65                  70                  75                  80

Asn Leu Gly Phe Phe Ser Thr Ala Glu Ser Leu Val Gly Asn Asn Ile
                 85                  90                  95

Val Leu Ala Ile Phe Lys His Val Thr Asn Pro Glu Ala Arg Gln Tyr
            100                 105                 110

Leu Leu Arg Gln Ala Phe Glu Glu Ala Val His Thr His Thr Phe Leu
        115                 120                 125

Tyr Ile Cys Glu Ser Leu Gly Leu Asp Glu Lys Glu Ile Phe Asn Ala
    130                 135                 140

Tyr Asn Glu Arg Ala Ala Ile Lys Ala Lys Asp Asp Phe Gln Met Glu
145                 150                 155                 160

Ile Thr Gly Lys Val Leu Asp Pro Asn Phe Arg Thr Asp Ser Val Glu
                165                 170                 175

Gly Leu Gln Glu Phe Val Lys Asn Leu Val Gly Tyr Tyr Ile Ile Met
            180                 185                 190

Glu Gly Ile Phe Phe Tyr Ser Gly Phe Val Met Ile Leu Ser Phe His
        195                 200                 205

Arg Gln Asn Lys Met Ile Gly Ile Gly Glu Gln Tyr Gln Tyr Ile Leu
    210                 215                 220

Arg Asp Glu Thr Ile His Leu Asn Phe Gly Ile Asp Leu Ile Asn Gly
225                 230                 235                 240

Ile Lys Glu Glu Asn Pro Glu Ile Trp Thr Pro Glu Leu Gln Gln Glu
                245                 250                 255

Ile Val Glu Leu Ile Lys Arg Ala Val Asp Leu Glu Ile Glu Tyr Ala
            260                 265                 270

Gln Asp Cys Leu Pro Arg Gly Ile Leu Gly Leu Arg Ala Ser Met Phe
        275                 280                 285

Ile Asp Tyr Val Gln His Ile Ala Asp Arg Arg Leu Glu Arg Ile Gly
    290                 295                 300

Leu Lys Pro Ile Tyr His Thr Lys Asn Pro Phe Pro Trp Met Ser Glu
305                 310                 315                 320
```

-continued

```
Thr Ile Asp Leu Asn Lys Glu Lys Asn Phe Phe Glu Thr Arg Val Ile
                325                 330                 335

Glu Tyr Gln His Ala Ala Ser Leu Thr Trp
            340                 345


<210> SEQ ID NO 97
<211> LENGTH: 1053
<212> TYPE: PRT
<213> ORGANISM: Chlamydia trachomatis serovar D

<400> SEQUENCE: 97

Met Phe Thr Arg Ile Val Met Val Asp Leu Gln Glu Lys Gln Cys Thr
                  5                  10                  15

Ile Val Lys Arg Asn Gly Met Phe Val Pro Phe Asp Arg Asn Arg Ile
             20                  25                  30

Phe Gln Ala Leu Glu Ala Ala Phe Arg Asp Thr Arg Arg Ile Asp Asp
         35                  40                  45

His Met Pro Leu Pro Glu Asp Leu Glu Ser Ser Ile Arg Ser Ile Thr
     50                  55                  60

His Gln Val Val Lys Glu Val Val Gln Lys Ile Thr Asp Gly Gln Val
 65                  70                  75                  80

Val Thr Val Glu Arg Ile Gln Asp Met Val Glu Ser Gln Leu Tyr Val
                 85                  90                  95

Asn Gly Leu Gln Asp Val Ala Arg Asp Tyr Ile Val Tyr Arg Asp Asp
            100                 105                 110

Arg Lys Ala His Arg Lys Lys Ser Trp Gln Ser Leu Ser Val Val Arg
        115                 120                 125

Arg Cys Gly Thr Val Val His Phe Asn Pro Met Lys Ile Ser Ala Ala
    130                 135                 140

Leu Glu Lys Ala Phe Arg Ala Thr Asp Lys Thr Glu Gly Met Thr Pro
145                 150                 155                 160

Ser Ser Val Arg Glu Glu Ile Asn Ala Leu Thr Gln Asn Ile Val Ala
                165                 170                 175

Glu Ile Glu Glu Cys Cys Pro Gln Gln Asp Arg Arg Ile Asp Ile Glu
            180                 185                 190

Lys Ile Gln Asp Ile Val Glu Gln Gln Leu Met Val Val Gly His Tyr
        195                 200                 205

Ala Val Ala Lys Asn Tyr Ile Leu Tyr Arg Glu Ala Arg Ala Arg Val
    210                 215                 220

Arg Asp Asn Arg Glu Glu Asp Gly Ser Thr Glu Lys Thr Ile Ala Glu
225                 230                 235                 240

Glu Ala Val Glu Val Leu Ser Lys Asp Gly Ser Thr Tyr Thr Met Thr
                245                 250                 255

His Ser Gln Leu Leu Ala His Leu Ala Arg Ala Cys Ser Arg Phe Pro
            260                 265                 270

Glu Thr Thr Asp Ala Ala Leu Leu Thr Asp Met Ala Phe Ala Asn Phe
        275                 280                 285

Tyr Ser Gly Ile Lys Glu Ser Glu Val Val Leu Ala Cys Ile Met Ala
    290                 295                 300

Ala Arg Ala Asn Ile Glu Lys Glu Pro Asp Tyr Ala Phe Val Ala Ala
305                 310                 315                 320

Glu Leu Leu Leu Asp Val Val Tyr Lys Glu Ala Leu Gly Lys Ser Lys
                325                 330                 335

Tyr Ala Glu Asp Leu Glu Gln Ala His Arg Asp His Phe Lys Arg Tyr
            340                 345                 350
```

-continued

```
Ile Ala Glu Gly Asp Thr Tyr Arg Leu Asn Ala Glu Leu Lys His Leu
        355                 360                 365

Phe Asp Leu Asp Ala Leu Ala Asp Ala Met Asp Leu Ser Arg Asp Leu
    370                 375                 380

Gln Phe Ser Tyr Met Gly Ile Gln Asn Leu Tyr Asp Arg Tyr Phe Asn
385                 390                 395                 400

His His Glu Gly Cys Arg Leu Glu Thr Pro Gln Ile Phe Trp Met Arg
                405                 410                 415

Val Ala Met Gly Leu Ala Leu Asn Glu Gln Asp Lys Thr Ser Trp Ala
            420                 425                 430

Ile Thr Phe Tyr Asn Leu Leu Ser Thr Phe Arg Tyr Thr Pro Ala Thr
        435                 440                 445

Pro Thr Leu Phe Asn Ser Gly Met Arg His Ser Gln Leu Ser Ser Cys
    450                 455                 460

Tyr Leu Ser Thr Val Gln Asp Asn Leu Val Asn Ile Tyr Lys Val Ile
465                 470                 475                 480

Ala Asp Asn Ala Met Leu Ser Lys Trp Ala Gly Gly Ile Gly Asn Asp
                485                 490                 495

Trp Thr Ala Ile Arg Ala Thr Gly Ala Leu Ile Lys Gly Thr Asn Gly
            500                 505                 510

Arg Ser Gln Gly Val Ile Pro Phe Ile Lys Val Thr Asn Asp Thr Ala
        515                 520                 525

Val Ala Val Asn Gln Gly Gly Lys Arg Lys Gly Ala Val Cys Val Tyr
    530                 535                 540

Leu Glu Val Trp His Leu Asp Tyr Glu Asp Phe Leu Glu Leu Arg Lys
545                 550                 555                 560

Asn Thr Gly Asp Glu Arg Arg Arg Ala His Asp Val Asn Ile Ala Ser
                565                 570                 575

Trp Ile Pro Asp Leu Phe Phe Lys Arg Leu Gln Gln Lys Gly Thr Trp
            580                 585                 590

Thr Leu Phe Ser Pro Asp Asp Val Pro Gly Leu His Asp Ala Tyr Gly
        595                 600                 605

Glu Glu Phe Glu Arg Leu Tyr Glu Glu Tyr Glu Arg Lys Val Asp Thr
    610                 615                 620

Gly Glu Ile Arg Leu Phe Lys Lys Val Glu Ala Glu Asp Leu Trp Arg
625                 630                 635                 640

Lys Met Leu Ser Met Leu Phe Glu Thr Gly His Pro Trp Met Thr Phe
                645                 650                 655

Lys Asp Pro Ser Asn Ile Arg Ser Ala Gln Asp His Lys Gly Val Val
            660                 665                 670

Arg Cys Ser Asn Leu Cys Thr Glu Ile Leu Leu Asn Cys Ser Glu Thr
        675                 680                 685

Glu Thr Ala Val Cys Asn Leu Gly Ser Ile Asn Leu Val Gln His Ile
    690                 695                 700

Val Gly Asp Gly Leu Asp Glu Glu Lys Leu Ser Glu Thr Ile Ser Ile
705                 710                 715                 720

Ala Val Arg Met Leu Asp Asn Val Ile Asp Ile Asn Phe Tyr Pro Thr
                725                 730                 735

Lys Glu Ala Lys Glu Ala Asn Phe Ala His Arg Ala Ile Gly Leu Gly
            740                 745                 750

Val Met Gly Phe Gln Asp Ala Leu Tyr Lys Leu Asp Ile Ser Tyr Ala
        755                 760                 765
```

-continued

```
Ser Gln Glu Ala Val Glu Phe Ala Asp Tyr Ser Ser Glu Leu Ile Ser
    770                 775                 780

Tyr Tyr Ala Ile Gln Ala Ser Cys Leu Leu Ala Lys Glu Arg Gly Thr
785                 790                 795                 800

Tyr Ser Ser Tyr Lys Gly Ser Lys Trp Asp Arg Gly Leu Leu Pro Ile
                805                 810                 815

Asp Thr Ile Gln Leu Leu Ala Asn Tyr Arg Gly Glu Ala Asn Leu Gln
            820                 825                 830

Met Asp Thr Ser Ser Arg Lys Asp Trp Glu Pro Ile Arg Ser Leu Val
        835                 840                 845

Lys Glu His Gly Met Arg His Cys Gln Leu Met Ala Ile Ala Pro Thr
    850                 855                 860

Ala Thr Ile Ser Asn Ile Ile Gly Val Thr Gln Ser Ile Glu Pro Thr
865                 870                 875                 880

Tyr Lys His Leu Phe Val Lys Ser Asn Leu Ser Gly Glu Phe Thr Ile
                885                 890                 895

Pro Asn Val Tyr Leu Ile Glu Lys Leu Lys Lys Leu Gly Ile Trp Asp
            900                 905                 910

Ala Asp Met Leu Asp Asp Leu Lys Tyr Phe Asp Gly Ser Leu Leu Glu
        915                 920                 925

Ile Glu Arg Ile Pro Asp His Leu Lys His Ile Phe Leu Thr Ala Phe
    930                 935                 940

Glu Ile Glu Pro Glu Trp Ile Ile Glu Cys Ala Ser Arg Arg Gln Lys
945                 950                 955                 960

Trp Ile Asp Met Gly Gln Ser Leu Asn Leu Tyr Leu Ala Gln Pro Asp
                965                 970                 975

Gly Lys Lys Leu Ser Asn Met Tyr Leu Thr Ala Trp Lys Lys Gly Leu
            980                 985                 990

Lys Thr Thr Tyr Tyr Leu Arg Ser Ser Ser Ala Thr Thr Val Glu Lys
        995                 1000                1005

Ser Phe Val Asp Ile Asn Lys Arg Gly Ile Gln Pro Arg Trp Met Lys
    1010                1015                1020

Asn Lys Ser Ala Ser Ala Gly Ile Ile Val Glu Arg Ala Lys Lys Ala
1025                1030                1035                1040

Pro Val Cys Ser Leu Glu Glu Gly Cys Glu Ala Cys Gln
                1045                1050


<210> SEQ ID NO 98
<211> LENGTH: 1531
<212> TYPE: PRT
<213> ORGANISM: Chlamydia trachomatis serovar D

<400> SEQUENCE: 98

Met Ser Ser Glu Lys Asp Ile Lys Ser Thr Cys Ser Lys Phe Ser Leu
                5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45

Gly Pro Gln Ala Val Leu Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95
```

-continued

```
Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160

Asp Val Lys Ala Ser Leu Ser Gly Ala Ala Leu Tyr Ser Thr Glu Asp
                165                 170                 175

Leu Ile Phe Glu Lys Ile Lys Gly Gly Leu Glu Phe Ala Ser Cys Ser
            180                 185                 190

Ser Leu Glu Gln Gly Gly Ala Cys Ala Ala Gln Ser Ile Leu Ile His
        195                 200                 205

Asp Cys Gln Gly Leu Gln Val Lys His Cys Thr Thr Ala Val Asn Ala
    210                 215                 220

Glu Gly Ser Ser Ala Asn Asp His Leu Gly Phe Gly Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly Gly
385                 390                 395                 400

Ala Ile Ala Ala Gln Glu Ile Val Ser Ile Gln Asn Asn Gln Ala Gly
                405                 410                 415

Ile Ser Phe Glu Gly Gly Lys Ala Ser Phe Gly Gly Gly Ile Ala Cys
            420                 425                 430

Gly Ser Phe Ser Ser Ala Gly Gly Ala Ser Val Leu Gly Thr Ile Asp
        435                 440                 445

Ile Ser Lys Asn Leu Gly Ala Ile Ser Phe Ser Arg Thr Leu Cys Thr
    450                 455                 460

Thr Ser Asp Leu Gly Gln Met Glu Tyr Gln Gly Gly Gly Ala Leu Phe
465                 470                 475                 480

Gly Glu Asn Ile Ser Leu Ser Glu Asn Ala Gly Val Leu Thr Phe Lys
                485                 490                 495

Asp Asn Ile Val Lys Thr Phe Ala Ser Asn Gly Lys Ile Leu Gly Gly
            500                 505                 510
```

-continued

```
Gly Ala Ile Leu Ala Thr Gly Lys Val Glu Ile Thr Asn Asn Ser Glu
        515                 520                 525

Gly Ile Ser Phe Thr Gly Asn Ala Arg Ala Pro Gln Ala Leu Pro Thr
    530                 535                 540

Gln Glu Glu Phe Pro Leu Phe Ser Lys Lys Glu Gly Arg Pro Leu Ser
545                 550                 555                 560

Ser Gly Tyr Ser Gly Gly Gly Ala Ile Leu Gly Arg Glu Val Ala Ile
                565                 570                 575

Leu His Asn Ala Ala Val Val Phe Glu Gln Asn Arg Leu Gln Cys Ser
            580                 585                 590

Glu Glu Glu Ala Thr Leu Leu Gly Cys Cys Gly Gly Gly Ala Val His
        595                 600                 605

Gly Met Asp Ser Thr Ser Ile Val Gly Asn Ser Ser Val Arg Phe Gly
    610                 615                 620

Asn Asn Tyr Ala Met Gly Gln Gly Val Ser Gly Gly Ala Leu Leu Ser
625                 630                 635                 640

Lys Thr Val Gln Leu Ala Gly Asn Gly Ser Val Asp Phe Ser Arg Asn
                645                 650                 655

Ile Ala Ser Leu Gly Gly Gly Ala Leu Gln Ala Ser Glu Gly Asn Cys
            660                 665                 670

Glu Leu Val Asp Asn Gly Tyr Val Leu Phe Arg Asp Asn Arg Gly Arg
        675                 680                 685

Val Tyr Gly Gly Ala Ile Ser Cys Leu Arg Gly Asp Val Val Ile Ser
    690                 695                 700

Gly Asn Lys Gly Arg Val Glu Phe Lys Asp Asn Ile Ala Thr Arg Leu
705                 710                 715                 720

Tyr Val Glu Glu Thr Val Glu Lys Val Glu Glu Val Glu Pro Ala Pro
                725                 730                 735

Glu Gln Lys Asp Asn Asn Glu Leu Ser Phe Leu Gly Arg Ala Glu Gln
            740                 745                 750

Ser Phe Ile Thr Ala Ala Asn Gln Ala Leu Phe Ala Ser Glu Asp Gly
        755                 760                 765

Asp Leu Ser Pro Glu Ser Ser Ile Ser Ser Glu Glu Leu Ala Lys Arg
    770                 775                 780

Arg Glu Cys Ala Gly Gly Ala Ile Phe Ala Lys Arg Val Arg Ile Val
785                 790                 795                 800

Asp Asn Gln Glu Ala Val Val Phe Ser Asn Asn Phe Ser Asp Ile Tyr
                805                 810                 815

Gly Gly Ala Ile Phe Thr Gly Ser Leu Arg Glu Glu Asp Lys Leu Asp
            820                 825                 830

Gly Gln Ile Pro Glu Val Leu Ile Ser Gly Asn Ala Gly Asp Val Val
        835                 840                 845

Phe Ser Gly Asn Ser Ser Lys Arg Asp Glu His Leu Pro His Thr Gly
    850                 855                 860

Gly Gly Ala Ile Cys Thr Gln Asn Leu Thr Ile Ser Gln Asn Thr Gly
865                 870                 875                 880

Asn Val Leu Phe Tyr Asn Asn Val Ala Cys Ser Gly Gly Ala Val Arg
                885                 890                 895

Ile Glu Asp His Gly Asn Val Leu Leu Glu Ala Phe Gly Gly Asp Ile
            900                 905                 910

Val Phe Lys Gly Asn Ser Ser Phe Arg Ala Gln Gly Ser Asp Ala Ile
        915                 920                 925

Tyr Phe Ala Gly Lys Glu Ser His Ile Thr Ala Leu Asn Ala Thr Glu
```

```
    930                 935                 940

Gly His Ala Ile Val Phe His Asp Ala Leu Val Phe Glu Asn Leu Glu
945                 950                 955                 960

Glu Arg Lys Ser Ala Glu Val Leu Leu Ile Asn Ser Arg Glu Asn Pro
                965                 970                 975

Gly Tyr Thr Gly Ser Ile Arg Phe Leu Glu Ala Glu Ser Lys Val Pro
            980                 985                 990

Gln Cys Ile His Val Gln Gln Gly Ser Leu Glu Leu Leu Asn Gly Ala
        995                 1000                1005

Thr Leu Cys Ser Tyr Gly Phe Lys Gln Asp Ala Gly Ala Lys Leu Val
    1010                1015                1020

Leu Ala Ala Gly Ala Lys Leu Lys Ile Leu Asp Ser Gly Thr Pro Val
1025                1030                1035                1040

Gln Gln Gly His Ala Ile Ser Lys Pro Glu Ala Glu Ile Glu Ser Ser
                1045                1050                1055

Ser Glu Pro Glu Gly Ala His Ser Leu Trp Ile Ala Lys Asn Ala Gln
            1060                1065                1070

Thr Thr Val Pro Met Val Asp Ile His Thr Ile Ser Val Asp Leu Ala
        1075                1080                1085

Ser Phe Ser Ser Ser Gln Gln Glu Gly Thr Val Glu Ala Pro Gln Val
    1090                1095                1100

Ile Val Pro Gly Gly Ser Tyr Val Arg Ser Gly Glu Leu Asn Leu Glu
1105                1110                1115                1120

Leu Val Asn Thr Thr Gly Thr Gly Tyr Glu Asn His Ala Leu Leu Lys
                1125                1130                1135

Asn Glu Ala Lys Val Pro Leu Met Ser Phe Val Ala Ser Gly Asp Glu
            1140                1145                1150

Ala Ser Ala Glu Ile Ser Asn Leu Ser Val Ser Asp Leu Gln Ile His
        1155                1160                1165

Val Val Thr Pro Glu Ile Glu Glu Asp Thr Tyr Gly His Met Gly Asp
    1170                1175                1180

Trp Ser Glu Ala Lys Ile Gln Asp Gly Thr Leu Val Ile Ser Trp Asn
1185                1190                1195                1200

Pro Thr Gly Tyr Arg Leu Asp Pro Gln Lys Ala Gly Ala Leu Val Phe
                1205                1210                1215

Asn Ala Leu Trp Glu Glu Gly Ala Val Leu Ser Ala Leu Lys Asn Ala
            1220                1225                1230

Arg Phe Ala His Asn Leu Thr Ala Gln Arg Met Glu Phe Asp Tyr Ser
        1235                1240                1245

Thr Asn Val Trp Gly Phe Ala Phe Gly Gly Phe Arg Thr Leu Ser Ala
    1250                1255                1260

Glu Asn Leu Val Ala Ile Asp Gly Tyr Lys Gly Ala Tyr Gly Gly Ala
1265                1270                1275                1280

Ser Ala Gly Val Asp Ile Gln Leu Met Glu Asp Phe Val Leu Gly Val
                1285                1290                1295

Ser Gly Ala Ala Phe Leu Gly Lys Met Asp Ser Gln Lys Phe Asp Ala
            1300                1305                1310

Glu Val Ser Arg Lys Gly Val Val Gly Ser Val Tyr Thr Gly Phe Leu
        1315                1320                1325

Ala Gly Ser Trp Phe Phe Lys Gly Gln Tyr Ser Leu Gly Glu Thr Gln
    1330                1335                1340

Asn Asp Met Lys Thr Arg Tyr Gly Val Leu Gly Glu Ser Ser Ala Ser
1345                1350                1355                1360
```

-continued

```
Trp Thr Ser Arg Gly Val Leu Ala Asp Ala Leu Val Glu Tyr Arg Ser
                1365                1370                1375

Leu Val Gly Pro Val Arg Pro Thr Phe Tyr Ala Leu His Phe Asn Pro
            1380                1385                1390

Tyr Val Glu Val Ser Tyr Ala Ser Met Lys Phe Pro Gly Phe Thr Glu
        1395                1400                1405

Gln Gly Arg Glu Ala Arg Ser Phe Glu Asp Ala Ser Leu Thr Asn Ile
    1410                1415                1420

Thr Ile Pro Leu Gly Met Lys Phe Glu Leu Ala Phe Ile Lys Gly Gln
1425                1430                1435                1440

Phe Ser Glu Val Asn Ser Leu Gly Ile Ser Tyr Ala Trp Glu Ala Tyr
                1445                1450                1455

Arg Lys Val Glu Gly Gly Ala Val Gln Leu Leu Glu Ala Gly Phe Asp
            1460                1465                1470

Trp Glu Gly Ala Pro Met Asp Leu Pro Arg Gln Glu Leu Arg Val Ala
        1475                1480                1485

Leu Glu Asn Asn Thr Glu Trp Ser Ser Tyr Phe Ser Thr Val Leu Gly
    1490                1495                1500

Leu Thr Ala Phe Cys Gly Gly Phe Thr Ser Thr Asp Ser Lys Leu Gly
1505                1510                1515                1520

Tyr Glu Ala Asn Thr Gly Leu Arg Leu Ile Phe
                1525                1530


<210> SEQ ID NO 99
<211> LENGTH: 474
<212> TYPE: PRT
<213> ORGANISM: Chlamydia trachomatis serovar D

<400> SEQUENCE: 99

Met Lys Ile Ile His Thr Ala Ile Glu Phe Ala Pro Val Ile Lys Ala
                  5                  10                  15

Gly Gly Leu Gly Asp Ala Leu Tyr Gly Leu Ala Lys Ala Leu Ala Ala
             20                  25                  30

Asn His Thr Thr Glu Val Val Ile Pro Leu Tyr Pro Lys Leu Phe Thr
         35                  40                  45

Leu Pro Lys Glu Gln Asp Leu Cys Ser Ile Gln Lys Leu Ser Tyr Phe
     50                  55                  60

Phe Ala Gly Glu Gln Glu Ala Thr Ala Phe Ser Tyr Phe Tyr Glu Gly
 65                  70                  75                  80

Ile Lys Val Thr Leu Phe Lys Leu Asp Thr Gln Pro Glu Leu Phe Glu
                 85                  90                  95

Asn Ala Glu Thr Ile Tyr Thr Ser Asp Asp Ala Phe Arg Phe Cys Ala
            100                 105                 110

Phe Ser Ala Ala Ala Ala Ser Tyr Ile Gln Lys Glu Gly Ala Asn Ile
        115                 120                 125

Val His Leu His Asp Trp His Thr Gly Leu Val Ala Gly Leu Leu Lys
    130                 135                 140

Gln Gln Pro Cys Ser Gln Leu Gln Lys Ile Val Leu Thr Leu His Asn
145                 150                 155                 160

Phe Gly Tyr Arg Gly Tyr Thr Thr Arg Glu Ile Leu Glu Ala Ser Ser
                165                 170                 175

Leu Asn Glu Phe Tyr Ile Ser Gln Tyr Gln Leu Phe Arg Asp Pro Gln
            180                 185                 190

Thr Cys Val Leu Leu Lys Gly Ala Leu Tyr Cys Ser Asp Phe Val Thr
```

```
        195                 200                 205

Thr Val Ser Pro Thr Tyr Ala Lys Glu Ile Leu Glu Asp Tyr Ser Asp
    210                 215                 220

Tyr Glu Ile His Asp Ala Ile Thr Ala Arg Gln His His Leu Arg Gly
225                 230                 235                 240

Ile Leu Asn Gly Ile Asp Thr Thr Ile Trp Gly Pro Glu Thr Asp Pro
                245                 250                 255

Asn Leu Ala Lys Asn Tyr Thr Lys Glu Leu Phe Glu Thr Pro Ser Ile
            260                 265                 270

Phe Phe Glu Ala Lys Ala Glu Asn Lys Lys Ala Leu Tyr Glu Arg Leu
        275                 280                 285

Gly Leu Ser Leu Glu His Ser Pro Cys Val Cys Ile Ile Ser Arg Ile
    290                 295                 300

Ala Glu Gln Lys Gly Pro His Phe Met Lys Gln Ala Ile Leu His Ala
305                 310                 315                 320

Leu Glu Asn Ala Tyr Thr Leu Ile Ile Ile Gly Thr Cys Tyr Gly Asn
                325                 330                 335

Gln Leu His Glu Glu Phe Ala Asn Leu Gln Glu Ser Leu Ala Asn Ser
            340                 345                 350

Pro Asp Val Arg Ile Leu Leu Thr Tyr Ser Asp Val Leu Ala Arg Gln
        355                 360                 365

Ile Phe Ala Ala Ala Asp Met Ile Cys Ile Pro Ser Met Phe Glu Pro
    370                 375                 380

Cys Gly Leu Thr Gln Met Ile Gly Met Arg Tyr Gly Thr Val Pro Leu
385                 390                 395                 400

Val Arg Ala Thr Gly Gly Leu Ala Asp Thr Val Ala Asn Gly Ile Asn
                405                 410                 415

Gly Phe Ser Phe Phe Asn Pro His Asp Phe Tyr Glu Phe Arg Asn Met
            420                 425                 430

Leu Ser Glu Ala Val Thr Thr Tyr Arg Thr Asn His Asp Lys Trp Gln
        435                 440                 445

His Ile Val Arg Ala Cys Leu Asp Phe Ser Ser Asp Leu Glu Thr Ala
    450                 455                 460

Ala Asn Lys Tyr Leu Glu Ile Tyr Lys Gln
465                 470


<210> SEQ ID NO 100
<211> LENGTH: 393
<212> TYPE: PRT
<213> ORGANISM: Chlamydia trachomatis serovar D

<400> SEQUENCE: 100

Met Lys Lys Leu Leu Lys Ser Val Leu Val Phe Ala Ala Leu Ser Ser
                  5                  10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
         35                  40                  45

Asp Pro Cys Ala Thr Trp Cys Asp Ala Ile Ser Met Arg Val Gly Tyr
     50                  55                  60

Tyr Gly Asp Phe Val Phe Asp Arg Val Leu Lys Thr Asp Val Asn Lys
 65                  70                  75                  80

Glu Phe Gln Met Gly Ala Lys Pro Thr Thr Asp Thr Gly Asn Ser Ala
                 85                  90                  95
```

```
Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125

Ile Trp Asp Arg Phe Asp Val Phe Cys Thr Leu Gly Ala Thr Ser Gly
    130                 135                 140

Tyr Leu Lys Gly Asn Ser Ala Ser Phe Asn Leu Val Gly Leu Phe Gly
145                 150                 155                 160

Asp Asn Glu Asn Gln Lys Thr Val Lys Ala Glu Ser Val Pro Asn Met
                165                 170                 175

Ser Phe Asp Gln Ser Val Val Glu Leu Tyr Thr Asp Thr Thr Phe Ala
            180                 185                 190

Trp Ser Val Gly Ala Arg Ala Ala Leu Trp Glu Cys Gly Cys Ala Thr
        195                 200                 205

Leu Gly Ala Ser Phe Gln Tyr Ala Gln Ser Lys Pro Lys Val Glu Glu
    210                 215                 220

Leu Asn Val Leu Cys Asn Ala Ala Glu Phe Thr Ile Asn Lys Pro Lys
225                 230                 235                 240

Gly Tyr Val Gly Lys Glu Phe Pro Leu Asp Leu Thr Ala Gly Thr Asp
                245                 250                 255

Ala Ala Thr Gly Thr Lys Asp Ala Ser Ile Asp Tyr His Glu Trp Gln
            260                 265                 270

Ala Ser Leu Ala Leu Ser Tyr Arg Leu Asn Met Phe Thr Pro Tyr Ile
        275                 280                 285

Gly Val Lys Trp Ser Arg Ala Ser Phe Asp Ala Asp Thr Ile Arg Ile
    290                 295                 300

Ala Gln Pro Lys Ser Ala Thr Ala Ile Phe Asp Thr Thr Thr Leu Asn
305                 310                 315                 320

Pro Thr Ile Ala Gly Ala Gly Asp Val Lys Thr Gly Ala Glu Gly Gln
                325                 330                 335

Leu Gly Asp Thr Met Gln Ile Val Ser Leu Gln Leu Asn Lys Met Lys
            340                 345                 350

Ser Arg Lys Ser Cys Gly Ile Ala Val Gly Thr Thr Ile Val Asp Ala
        355                 360                 365

Asp Lys Tyr Ala Val Thr Val Glu Thr Arg Leu Ile Asp Glu Arg Ala
    370                 375                 380

Ala His Val Asn Ala Gln Phe Arg Phe
385                 390


<210> SEQ ID NO 101
<211> LENGTH: 195
<212> TYPE: PRT
<213> ORGANISM: Chlamydia trachomatis serovar D

<400> SEQUENCE: 101

Met Gly Ser Leu Val Gly Arg Gln Ala Pro Asp Phe Ser Gly Lys Ala
                  5                  10                  15

Val Val Cys Gly Glu Glu Lys Glu Ile Ser Leu Ala Asp Phe Arg Gly
             20                  25                  30

Lys Tyr Val Val Leu Phe Phe Tyr Pro Lys Asp Phe Thr Tyr Val Cys
         35                  40                  45

Pro Thr Glu Leu His Ala Phe Gln Asp Arg Leu Val Asp Phe Glu Glu
     50                  55                  60

Arg Gly Ala Val Val Leu Gly Cys Ser Val Asp Asp Ile Glu Thr His
 65                  70                  75                  80
```

```
Ser Arg Trp Leu Ala Val Ala Arg Asn Ala Gly Gly Ile Glu Gly Thr
                 85                  90                  95

Glu Tyr Pro Leu Leu Ala Asp Pro Ser Phe Lys Ile Ser Glu Ala Phe
            100                 105                 110

Gly Val Leu Asn Pro Glu Gly Ser Leu Ala Leu Arg Ala Thr Phe Leu
        115                 120                 125

Ile Asp Lys Tyr Gly Val Val Arg His Ala Val Ile Asn Asp Leu Pro
    130                 135                 140

Leu Gly Arg Ser Ile Asp Glu Glu Leu Arg Ile Leu Asp Ser Leu Ile
145                 150                 155                 160

Phe Phe Glu Asn His Gly Met Val Cys Pro Ala Asn Trp Arg Ser Gly
                165                 170                 175

Glu Arg Gly Met Val Pro Ser Glu Glu Gly Leu Lys Glu Tyr Phe Gln
            180                 185                 190

Thr Met Asp
        195
```

<210> SEQ ID NO 102
<211> LENGTH: 86
<212> TYPE: PRT
<213> ORGANISM: Chlamydia trachomatis serovar D

<400> SEQUENCE: 102

```
Met Ser Gln Asn Lys Asn Ser Ala Phe Met Gln Pro Val Asn Val Ser
                  5                  10                  15

Ala Asp Leu Ala Ala Ile Val Gly Ala Gly Pro Met Pro Arg Thr Glu
             20                  25                  30

Ile Ile Lys Lys Met Trp Asp Tyr Ile Lys Lys Asn Gly Leu Gln Asp
         35                  40                  45

Pro Thr Asn Lys Arg Asn Ile Asn Pro Asp Asp Lys Leu Ala Lys Val
     50                  55                  60

Phe Gly Thr Glu Lys Pro Ile Asp Met Phe Gln Met Thr Lys Met Val
 65                  70                  75                  80

Ser Gln His Ile Ile Lys
                 85
```

<210> SEQ ID NO 103
<211> LENGTH: 394
<212> TYPE: PRT
<213> ORGANISM: Chlamydia trachomatis serovar D

<400> SEQUENCE: 103

```
Met Ser Lys Glu Thr Phe Gln Arg Asn Lys Pro His Ile Asn Ile Gly
                  5                  10                  15

Thr Ile Gly His Val Asp His Gly Lys Thr Thr Leu Thr Ala Ala Ile
             20                  25                  30

Thr Arg Ala Leu Ser Gly Asp Gly Leu Ala Asp Phe Arg Asp Tyr Ser
         35                  40                  45

Ser Ile Asp Asn Thr Pro Glu Glu Lys Ala Arg Gly Ile Thr Ile Asn
     50                  55                  60

Ala Ser His Val Glu Tyr Glu Thr Ala Asn Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Val Ser Ala Thr Asp Gly Ala
            100                 105                 110
```

```
Met Pro Gln Thr Lys Glu His Ile Leu Leu Ala Arg Gln Val Gly Val
        115                 120                 125

Pro Tyr Ile Val Val Phe Leu Asn Lys Ile Asp Met Ile Ser Glu Glu
    130                 135                 140

Asp Ala Glu Leu Val Asp Leu Val Glu Met Glu Leu Val Glu Leu Leu
145                 150                 155                 160

Glu Glu Lys Gly Tyr Lys Gly Cys Pro Ile Ile Arg Gly Ser Ala Leu
                165                 170                 175

Lys Ala Leu Glu Gly Asp Ala Ala Tyr Ile Glu Lys Val Arg Glu Leu
            180                 185                 190

Met Gln Ala Val Asp Asp Asn Ile Pro Thr Pro Glu Arg Glu Ile Asp
        195                 200                 205

Lys Pro Phe Leu Met Pro Ile Glu Asp Val Phe Ser Ile Ser Gly Arg
    210                 215                 220

Gly Thr Val Val Thr Gly Arg Ile Glu Arg Gly Ile Val Lys Val Ser
225                 230                 235                 240

Asp Lys Val Gln Leu Val Gly Leu Arg Asp Thr Lys Glu Thr Ile Val
                245                 250                 255

Thr Gly Val Glu Met Phe Arg Lys Glu Leu Pro Glu Gly Arg Ala Gly
            260                 265                 270

Glu Asn Val Gly Leu Leu Leu Arg Gly Ile Gly Lys Asn Asp Val Glu
        275                 280                 285

Arg Gly Met Val Val Cys Leu Pro Asn Ser Val Lys Pro His Thr Gln
    290                 295                 300

Phe Lys Cys Ala Val Tyr Val Leu Gln Lys Glu Glu Gly Gly Arg His
305                 310                 315                 320

Lys Pro Phe Phe Thr Gly Tyr Arg Pro Gln Phe Phe Phe Arg Thr Thr
                325                 330                 335

Asp Val Thr Gly Val Val Thr Leu Pro Glu Gly Ile Glu Met Val Met
            340                 345                 350

Pro Gly Asp Asn Val Glu Phe Glu Val Gln Leu Ile Ser Pro Val Ala
        355                 360                 365

Leu Glu Glu Gly Met Arg Phe Ala Ile Arg Glu Gly Gly Arg Thr Ile
    370                 375                 380

Gly Ala Gly Thr Ile Ser Lys Ile Ile Ala
385                 390


<210> SEQ ID NO 104
<211> LENGTH: 82
<212> TYPE: PRT
<213> ORGANISM: Chlamydia trachomatis serovar D

<400> SEQUENCE: 104

Met Gly Gln Asp His Arg Arg Lys Phe Leu Lys Lys Val Ser Phe Val
                  5                  10                  15

Lys Lys Gln Ala Ala Phe Ala Gly Asn Phe Ile Glu Glu Ile Lys Lys
             20                  25                  30

Ile Glu Trp Val Asn Lys Arg Asp Leu Lys Arg Tyr Val Lys Ile Val
         35                  40                  45

Leu Met Asn Ile Phe Gly Phe Gly Phe Ser Ile Tyr Cys Val Asp Leu
     50                  55                  60

Ala Leu Arg Lys Ser Leu Ser Leu Phe Gly Lys Val Thr Ser Phe Phe
 65                  70                  75                  80

Phe Gly
```

<210> SEQ ID NO 105
<211> LENGTH: 379
<212> TYPE: PRT
<213> ORGANISM: Chlamydia trachomatis serovar D

<400> SEQUENCE: 105

```
Met Val Ile Pro Lys Val Asp Leu Gly Glu Ser Ala Val Met Met Gly
                  5                  10                  15

Tyr Lys Leu Thr Ser Gln Leu Ala Met Leu Ser Ile Leu Leu Thr Phe
             20                  25                  30

Thr His Thr Met Gly His Ala Ser Gln Met Ser Gln Thr Leu Pro Thr
         35                  40                  45

Ile Ile Glu Ala Gln Ala Glu Glu Ala Leu Gln Ala Asp Arg Gly Val
     50                  55                  60

Ala Gly Gln Ala Leu Lys Lys Leu Arg Lys Lys Arg Cys Ala Ser Arg
 65                  70                  75                  80

Lys Ser Ala Cys Lys Ala Ser Phe Lys Lys Lys Asp Phe Phe Ser Cys
                 85                  90                  95

Ile Thr Asn Gly Leu Phe Ser Gly Asn His Glu Gln Arg Leu Thr Ala
            100                 105                 110

Lys Lys Glu Asn Lys Ala Arg Gly Lys Glu Pro Arg Val Val Val Gln
        115                 120                 125

Thr Thr Lys Lys Arg Gln Ile Thr Gln Ser Glu Lys Glu Phe Phe Asp
    130                 135                 140

Trp Leu Cys Asn Ser Lys Arg Glu Arg Lys Leu Leu Lys Lys Lys Pro
145                 150                 155                 160

Val Asn Thr Ser Leu Ala Lys Ser Glu Glu Leu Ser Pro Lys Glu Ala
                165                 170                 175

Ala Ile Ala Ala Ala Arg Ala Ser Leu Ser Pro Glu Glu Lys Arg Gln
            180                 185                 190

Leu Ile Arg Glu Trp Leu Ala Glu Glu Lys Thr Ala Arg Lys Ser Gly
        195                 200                 205

Arg Ala Ala Cys Ala Val Ser Glu Asn Leu Lys Arg Asp Gly Ser Ile
    210                 215                 220

Thr Ser Thr Leu Arg Tyr Asp Ala Glu Lys Ala Leu Thr Thr Arg Val
225                 230                 235                 240

Lys Arg Asn Glu Asn Ser Val Asn Ala Arg Ala Arg Gln Arg Ala Ala
                245                 250                 255

Leu Gln Lys Ala Lys Lys Ala Lys Thr Glu Lys Pro Glu Ala Asp Glu
            260                 265                 270

Lys Ala Ala Glu Ala Val Ala Ala Ala Pro Thr Lys Gln Ala His Lys
        275                 280                 285

Glu Pro Glu Asn Tyr Phe Ala Ala Thr Ala Ser Thr Asn Asn Thr Asn
    290                 295                 300

Val Met Ser Tyr Leu Asn Ala His Gln Tyr Arg Cys Asp Ser Ser Glu
305                 310                 315                 320

Thr Asp Trp Pro Cys Ser Ser Cys Val Thr Lys Arg Arg Ala Asn Phe
                325                 330                 335

Gly Ile Ser Val Cys Thr Met Val Val Thr Val Ile Ala Met Ile Val
            340                 345                 350

Gly Ala Val Ile Ile Ser Asn Ala Thr Asp Ser Thr Val Ala Gly Ser
        355                 360                 365

Ser Gly Thr Gly Gly Gly Gly Ser Thr Gln Pro
```

-continued

```
    370                 375

<210> SEQ ID NO 106
<211> LENGTH: 563
<212> TYPE: PRT
<213> ORGANISM: Chlamydia trachomatis serovar D

<400> SEQUENCE: 106

Met Val Tyr Phe Arg Ala His Gln Pro Arg His Thr Pro Lys Thr Phe
                  5                  10                  15

Pro Leu Glu Val His His Ser Phe Ser Asp Lys His Pro Gln Ile Ala
             20                  25                  30

Lys Ala Met Arg Ile Thr Gly Ile Ala Leu Ala Ala Leu Ser Leu Leu
         35                  40                  45

Ala Val Val Ala Cys Val Ile Ala Val Ser Ala Gly Gly Ala Ala Ile
     50                  55                  60

Pro Leu Ala Val Ile Ser Gly Ile Ala Val Met Ser Gly Leu Leu Ser
 65                  70                  75                  80

Ala Ala Thr Ile Ile Cys Ser Ala Lys Lys Ala Leu Ala Gln Arg Lys
                 85                  90                  95

Gln Lys Gln Leu Glu Glu Ser Leu Pro Leu Asp Asn Ala Thr Glu His
            100                 105                 110

Val Ser Tyr Leu Thr Ser Asp Thr Ser Tyr Phe Asn Gln Trp Glu Ser
        115                 120                 125

Leu Gly Ala Leu Asn Lys Gln Leu Ser Gln Ile Asp Leu Thr Ile Gln
    130                 135                 140

Ala Pro Glu Lys Lys Leu Leu Lys Glu Val Leu Gly Ser Arg Tyr Asp
145                 150                 155                 160

Ser Ile Asn His Ser Ile Glu Glu Ile Ser Asp Arg Phe Thr Lys Met
                165                 170                 175

Leu Ser Leu Leu Arg Leu Arg Glu His Phe Tyr Arg Gly Glu Glu Arg
            180                 185                 190

Tyr Ala Pro Tyr Leu Ser Pro Pro Leu Leu Asn Lys Asn Arg Leu Leu
        195                 200                 205

Thr Gln Ile Thr Ser Asn Met Ile Arg Met Leu Pro Lys Ser Gly Gly
    210                 215                 220

Val Phe Ser Leu Lys Ala Asn Thr Leu Ser His Ala Ser Arg Thr Leu
225                 230                 235                 240

Tyr Thr Val Leu Lys Val Ala Leu Ser Leu Gly Val Leu Ala Gly Val
                245                 250                 255

Ala Ala Leu Ile Ile Phe Leu Pro Pro Ser Leu Pro Phe Ile Ala Val
            260                 265                 270

Ile Gly Val Ser Ser Leu Ala Leu Gly Met Ala Ser Phe Leu Met Ile
        275                 280                 285

Arg Gly Ile Lys Tyr Leu Leu Glu His Ser Pro Leu Asn Arg Lys Gln
    290                 295                 300

Leu Ala Lys Asp Ile Gln Lys Thr Ile Gly Pro Asp Val Leu Ala Ser
305                 310                 315                 320

Met Val His Tyr Gln His Gln Leu Leu Ser His Leu His Glu Thr Leu
                325                 330                 335

Leu Asp Glu Ala Ile Thr Ala Arg Trp Ser Glu Pro Phe Phe Ile Glu
            340                 345                 350

His Ala Asn Leu Lys Ala Lys Ile Glu Asp Leu Thr Lys Gln Tyr Asp
        355                 360                 365
```

-continued

```
Ile Leu Asn Ala Ala Phe Asn Lys Ser Leu Gln Gln Asp Glu Ala Leu
    370                 375                 380

Arg Ser Gln Leu Glu Lys Arg Ala Tyr Leu Phe Pro Ile Pro Asn Asn
385                 390                 395                 400

Asp Glu Asn Ala Lys Thr Lys Glu Ser Gln Leu Leu Asp Ser Glu Asn
                405                 410                 415

Asp Ser Asn Ser Glu Phe Gln Glu Ile Ile Asn Lys Gly Leu Glu Ala
            420                 425                 430

Ala Asn Lys Arg Arg Ala Asp Ala Lys Ser Lys Phe Tyr Thr Glu Asp
        435                 440                 445

Glu Thr Ser Asp Lys Ile Phe Ser Ile Trp Lys Pro Thr Lys Asn Leu
    450                 455                 460

Ala Leu Glu Asp Leu Trp Arg Val His Glu Ala Cys Asn Glu Glu Gln
465                 470                 475                 480

Gln Ala Leu Leu Leu Glu Asp Tyr Met Ser Tyr Lys Thr Ser Glu Cys
                485                 490                 495

Gln Ala Ala Leu Gln Lys Val Ser Gln Glu Leu Lys Ala Ala Gln Lys
            500                 505                 510

Ser Phe Ala Val Leu Glu Lys His Ala Leu Asp Arg Ser Tyr Glu Ser
        515                 520                 525

Ser Val Ala Thr Met Asp Leu Ala Arg Ala Asn Gln Glu Thr His Arg
    530                 535                 540

Leu Leu Asn Ile Leu Ser Glu Leu Gln Gln Leu Ala Gln Tyr Leu Leu
545                 550                 555                 560

Asp Asn His


<210> SEQ ID NO 107
<211> LENGTH: 358
<212> TYPE: PRT
<213> ORGANISM: Chlamydia trachomatis serovar D

<400> SEQUENCE: 107

Met Arg Lys Thr Val Ile Val Ala Met Ser Gly Gly Val Asp Ser Ser
                5                   10                  15

Val Val Ala Tyr Leu Leu Lys Lys Gln Gly Glu Tyr Asn Val Val Gly
            20                  25                  30

Leu Phe Met Lys Asn Trp Gly Glu Gln Asp Glu Asn Gly Glu Cys Thr
        35                  40                  45

Ala Thr Lys Asp Phe Arg Asp Val Glu Arg Ile Ala Glu Gln Leu Ser
    50                  55                  60

Ile Pro Tyr Tyr Thr Val Ser Phe Ser Lys Glu Tyr Lys Glu Arg Val
65                  70                  75                  80

Phe Ser Arg Phe Leu Arg Glu Tyr Ala Asn Gly Tyr Thr Pro Asn Pro
                85                  90                  95

Asp Val Leu Cys Asn Arg Glu Ile Lys Phe Asp Leu Leu Gln Lys Lys
            100                 105                 110

Val Arg Glu Leu Lys Gly Asp Phe Leu Ala Thr Gly His Tyr Cys Arg
        115                 120                 125

Gly Gly Ala Asp Gly Thr Gly Leu Ser Arg Gly Ile Asp Pro Asn Lys
    130                 135                 140

Asp Gln Ser Tyr Phe Leu Cys Gly Thr Pro Lys Asp Ala Leu Ser Asn
145                 150                 155                 160

Val Leu Phe Pro Leu Gly Gly Met Tyr Lys Thr Glu Val Arg Arg Ile
                165                 170                 175
```

-continued

```
Ala Gln Glu Ala Gly Leu Ala Thr Ala Thr Lys Lys Asp Ser Thr Gly
            180                 185                 190

Ile Cys Phe Ile Gly Lys Arg Pro Phe Lys Ser Phe Leu Glu Gln Phe
        195                 200                 205

Val Ala Asp Ser Pro Gly Asp Ile Ile Asp Phe Asp Thr Gln Gln Val
    210                 215                 220

Val Gly Arg His Glu Gly Ala His Tyr Tyr Thr Ile Gly Gln Arg Arg
225                 230                 235                 240

Gly Leu Asn Ile Gly Gly Met Glu Lys Pro Cys Tyr Val Leu Ser Lys
                245                 250                 255

Asn Met Glu Lys Asn Ile Val Tyr Ile Val Arg Gly Glu Asp His Pro
            260                 265                 270

Leu Leu Tyr Arg Gln Glu Leu Leu Ala Lys Glu Leu Asn Trp Phe Val
        275                 280                 285

Pro Leu Gln Glu Pro Met Ile Cys Ser Ala Lys Val Arg Tyr Arg Ser
    290                 295                 300

Pro Asp Glu Lys Cys Ser Val Tyr Pro Leu Glu Asp Gly Thr Val Lys
305                 310                 315                 320

Val Ile Phe Asp Val Pro Val Lys Ala Val Thr Pro Gly Gln Thr Val
                325                 330                 335

Ala Phe Tyr Gln Gly Asp Ile Cys Leu Gly Gly Gly Val Ile Glu Val
            340                 345                 350

Pro Met Ile His Gln Leu
        355


<210> SEQ ID NO 108
<211> LENGTH: 267
<212> TYPE: PRT
<213> ORGANISM: Chlamydia trachomatis serovar D

<400> SEQUENCE: 108

Met Ser Arg Lys Pro Ala Ser Asn Ser Ser Arg Asn Thr Lys Arg Ser
                  5                  10                  15

Ser Asp Thr Ser Trp Glu Val Ile Ala Gln Asp Tyr Asn Lys Ala Val
             20                  25                  30

Asp Arg Asp Gly His Phe Tyr His Lys Glu Val Ile Leu Pro Asn Leu
         35                  40                  45

Leu Ser Lys Leu His Ile Ser Arg Ser Ser Ser Leu Val Asp Val Gly
     50                  55                  60

Cys Gly Gln Gly Ile Leu Glu Lys His Leu Pro Lys His Leu Pro Tyr
 65                  70                  75                  80

Leu Gly Ile Asp Leu Ser Pro Ser Leu Leu Arg Phe Ala Lys Lys Ser
                 85                  90                  95

Ala Ser Ser Lys Ser Arg Arg Phe Leu His His Asp Met Thr Gln Pro
            100                 105                 110

Val Pro Ala Asp His His Glu Gln Phe Ser His Ala Thr Ala Ile Leu
        115                 120                 125

Ser Leu Gln Asn Met Glu Ser Pro Glu Gln Ala Ile Ala His Thr Ala
    130                 135                 140

Asn Leu Leu Ala Pro Gln Gly Arg Leu Phe Ile Val Leu Asn His Pro
145                 150                 155                 160

Cys Phe Arg Ile Pro Arg Leu Ser Ser Trp Leu Tyr Asp Glu Pro Lys
                165                 170                 175

Lys Leu Leu Ser Arg Lys Ile Asp Arg Tyr Leu Ser Pro Val Ala Val
            180                 185                 190
```

```
Pro Ile Val Val His Pro Gly Glu Lys His Ser Glu Thr Thr Tyr Ser
        195                 200                 205

Phe His Phe Pro Leu Ser Tyr Trp Val Gln Ala Leu Ser Asn His Asn
    210                 215                 220

Leu Leu Ile Asp Ser Met Glu Glu Trp Ile Ser Pro Lys Lys Ser Ser
225                 230                 235                 240

Gly Lys Arg Ala Arg Ala Glu Asn Leu Cys Arg Lys Glu Phe Pro Leu
                245                 250                 255

Phe Leu Phe Ile Ser Ala Leu Lys Ile Ser Lys
            260                 265


<210> SEQ ID NO 109
<211> LENGTH: 867
<212> TYPE: PRT
<213> ORGANISM: Chlamydia trachomatis serovar D

<400> SEQUENCE: 109

Met Glu Lys Phe Ser Asp Ala Val Ser Glu Ala Leu Glu Lys Ala Phe
                  5                  10                  15

Glu Leu Ala Lys Asn Ser Lys His Ser Tyr Val Thr Glu Asn His Leu
             20                  25                  30

Leu Lys Ser Leu Leu Gln Asn Pro Gly Ser Leu Phe Cys Leu Val Ile
         35                  40                  45

Lys Asp Val His Gly Asn Leu Gly Leu Leu Thr Ser Ala Val Asp Asp
     50                  55                  60

Ala Leu Arg Arg Glu Pro Thr Val Val Glu Gly Thr Ala Val Ala Ser
 65                  70                  75                  80

Pro Ser Pro Ser Leu Gln Gln Leu Leu Leu Asn Ala His Gln Glu Ala
                 85                  90                  95

Arg Ser Met Gly Asp Glu Tyr Leu Ser Gly Asp His Leu Leu Leu Ala
            100                 105                 110

Phe Trp Arg Ser Thr Lys Glu Pro Phe Ala Ser Trp Arg Lys Thr Val
        115                 120                 125

Lys Thr Thr Ser Glu Ala Leu Lys Glu Leu Ile Thr Lys Leu Arg Gln
    130                 135                 140

Gly Ser Arg Met Asp Ser Pro Ser Ala Glu Glu Asn Leu Lys Gly Leu
145                 150                 155                 160

Glu Lys Tyr Cys Lys Asn Leu Thr Val Leu Ala Arg Glu Gly Lys Leu
                165                 170                 175

Asp Pro Val Ile Gly Arg Asp Glu Glu Ile Arg Arg Thr Ile Gln Val
            180                 185                 190

Leu Ser Arg Arg Thr Lys Asn Asn Pro Met Leu Ile Gly Glu Pro Gly
        195                 200                 205

Val Gly Lys Thr Ala Ile Ala Glu Gly Leu Ala Leu Arg Ile Val Gln
    210                 215                 220

Gly Asp Val Pro Glu Ser Leu Lys Glu Lys His Leu Tyr Val Leu Asp
225                 230                 235                 240

Met Gly Ala Leu Ile Ala Gly Ala Lys Tyr Arg Gly Glu Phe Glu Glu
                245                 250                 255

Arg Leu Lys Ser Val Leu Lys Gly Val Glu Ala Ser Glu Gly Glu Cys
            260                 265                 270

Ile Leu Phe Ile Asp Glu Val His Thr Leu Val Gly Ala Gly Ala Thr
        275                 280                 285

Asp Gly Ala Met Asp Ala Ala Asn Leu Leu Lys Pro Ala Leu Ala Arg
```

-continued

```
    290                 295                 300

Gly Thr Leu His Cys Ile Gly Ala Thr Thr Leu Asn Glu Tyr Gln Lys
305                 310                 315                 320

Tyr Ile Glu Lys Asp Ala Ala Leu Glu Arg Arg Phe Gln Pro Ile Phe
                325                 330                 335

Val Thr Glu Pro Ser Leu Glu Asp Ala Val Phe Ile Leu Arg Gly Leu
            340                 345                 350

Arg Glu Lys Tyr Glu Ile Phe His Gly Val Arg Ile Thr Glu Gly Ala
        355                 360                 365

Leu Asn Ala Ala Val Val Leu Ser Tyr Arg Tyr Ile Thr Asp Arg Phe
    370                 375                 380

Leu Pro Asp Lys Ala Ile Asp Leu Ile Asp Glu Ala Ala Ser Leu Ile
385                 390                 395                 400

Arg Met Gln Ile Gly Ser Leu Pro Leu Pro Ile Asp Glu Lys Glu Arg
                405                 410                 415

Glu Leu Ser Ala Leu Ile Val Lys Gln Glu Ala Ile Lys Arg Glu Gln
            420                 425                 430

Ala Pro Ala Tyr Gln Glu Glu Ala Glu Asp Met Gln Lys Ala Ile Asp
        435                 440                 445

Arg Val Lys Glu Glu Leu Ala Ala Leu Arg Leu Arg Trp Asp Glu Glu
    450                 455                 460

Lys Gly Leu Ile Thr Gly Leu Lys Glu Lys Lys Asn Ala Leu Glu Asn
465                 470                 475                 480

Leu Lys Phe Ala Glu Glu Glu Ala Glu Arg Thr Ala Asp Tyr Asn Arg
                485                 490                 495

Val Ala Glu Leu Arg Tyr Ser Leu Ile Pro Ser Leu Glu Glu Glu Ile
            500                 505                 510

His Leu Ala Glu Glu Ala Leu Asn Gln Arg Asp Gly Arg Leu Leu Gln
        515                 520                 525

Glu Glu Val Asp Glu Arg Leu Ile Ala Gln Val Val Ala Asn Trp Thr
    530                 535                 540

Gly Ile Pro Val Gln Lys Met Leu Glu Gly Glu Ser Glu Lys Leu Leu
545                 550                 555                 560

Val Leu Glu Glu Ser Leu Glu Glu Arg Val Val Gly Gln Pro Phe Ala
                565                 570                 575

Ile Ala Ala Val Ser Asp Ser Ile Arg Ala Ala Arg Val Gly Leu Ser
            580                 585                 590

Asp Pro Gln Arg Pro Leu Gly Val Phe Leu Phe Leu Gly Pro Thr Gly
        595                 600                 605

Val Gly Lys Thr Glu Leu Ala Lys Ala Leu Ala Glu Leu Leu Phe Asn
    610                 615                 620

Lys Glu Glu Ala Met Ile Arg Phe Asp Met Thr Glu Tyr Met Glu Lys
625                 630                 635                 640

His Ser Val Ser Lys Leu Ile Gly Ser Pro Pro Gly Tyr Val Gly Tyr
                645                 650                 655

Glu Glu Gly Gly Ser Leu Ser Glu Ala Leu Arg Arg Arg Pro Tyr Ser
            660                 665                 670

Val Val Leu Phe Asp Glu Ile Glu Lys Ala Asp Lys Glu Val Phe Asn
        675                 680                 685

Ile Leu Leu Gln Ile Phe Asp Asp Gly Ile Leu Thr Asp Ser Lys Lys
    690                 695                 700

Arg Lys Val Asn Cys Lys Asn Ala Leu Phe Ile Met Thr Ser Asn Ile
705                 710                 715                 720
```

```
Gly Ser Gln Glu Leu Ala Asp Tyr Cys Thr Lys Lys Gly Thr Ile Val
                725                 730                 735

Asp Lys Glu Ala Val Leu Ser Val Val Ala Pro Ala Leu Lys Asn Tyr
            740                 745                 750

Phe Ser Pro Glu Phe Ile Asn Arg Ile Asp Asp Ile Leu Pro Phe Val
        755                 760                 765

Pro Leu Thr Thr Glu Asp Ile Val Lys Ile Val Gly Ile Gln Met Asn
    770                 775                 780

Arg Val Ala Leu Arg Leu Leu Glu Arg Lys Ile Ser Leu Thr Trp Asp
785                 790                 795                 800

Asp Ser Leu Val Leu Phe Leu Ser Glu Gln Gly Tyr Asp Ser Ala Phe
                805                 810                 815

Gly Ala Arg Pro Leu Lys Arg Leu Ile Gln Gln Lys Val Val Thr Met
            820                 825                 830

Leu Ser Lys Ala Leu Leu Lys Gly Asp Ile Lys Pro Gly Met Ala Val
        835                 840                 845

Glu Leu Thr Met Ala Lys Asp Val Val Val Phe Lys Ile Lys Thr Asn
    850                 855                 860

Pro Ala Val
865
```

<210> SEQ ID NO 110
<211> LENGTH: 1170
<212> TYPE: DNA
<213> ORGANISM: Chlamydia pneumoniae

<400> SEQUENCE: 110

```
atgaaaaaac tcttaaagtc ggcgttatta tccgccgcat ttgctggttc tgttggctcc      60

ttacaagcct tgcctgtagg gaacccttct gatccaagct tattaattga tggtacaata     120

tgggaaggtg ctgcaggaga tccttgcgat ccttgcgcta cttggtgcga cgctattagc     180

ttacgtgctg gattttacgg agactatgtt ttcgaccgta tcttaaaagt agatgcacct     240

aaaacatttt ctatgggagc caagcctact ggatccgctg ctgcaaacta tactactgcc     300

gtagatagac ctaacccggc ctacaataag catttacacg atgcagagtg gttcactaat     360

gcaggcttca ttgccttaaa catttgggat cgctttgatg ttttctgtac tttaggagct     420

tctaatggtt acattagagg aaactctaca gcgttcaatc tcgttggttt attcggagtt     480

aaaggtacta ctgtaaatgc aaatgaacta ccaaacgttt ctttaagtaa cggagttgtt     540

gaactttaca cagacacctc tttctcttgg agcgtaggcg ctcgtggagc cttatgggaa     600

tgcggttgtg caactttggg agctgaattc caatatgcac agtccaaacc taaagttgaa     660

gaacttaatg tgatctgtaa cgtatcgcaa ttctctgtaa acaaacccaa gggctataaa     720

ggcgttgctt tccccttgcc aacagacgct ggcgtagcaa cagctactgg aacaaagtct     780

gcgaccatca attatcatga atggcaagta ggagcctctc tatcttacag actaaactct     840

ttagtgccat acattggagt acaatggtct cgagcaactt ttgatgctga taacatccgc     900

attgctcagc caaaactacc tacagctgtt ttaaacttaa ctgcatggaa cccttcttta     960

ctaggaaatg ccacagcatt gtctactact gattcgttct cagacttcat gcaaattgtt    1020

tcctgtcaga tcaacaagtt taaatctaga aaagcttgtg gagttactgt aggagctact    1080

ttagttgatg ctgataaatg gtcacttact gcagaagctc gtttaattaa cgagagagct    1140

gctcacgtat ctggtcagtt cagattctaa                                     1170
```

<210> SEQ ID NO 111
<211> LENGTH: 2601
<212> TYPE: DNA
<213> ORGANISM: Chlamydia pneumoniae

<400> SEQUENCE: 111

```
atggagaaat tttccgatgc tgtctctgaa gctttagaga aggctttcga acttgctaaa     60
tcttcgaaac atacctatgt cacagaaaat cacctattac tggctttatt agaaaataca    120
gagtctctct tttatttggt aattaaggac attcatggga accctggttt gctcaatacg    180
gcagttaaag atgcgctctc acgagagccg actgtagttg aaggagaggt ggatcctaaa    240
ccttctccgg gtttacaaac ccttcttagg gatgccaaac aagaggcaaa gacattagga    300
gatgaataca tttctggaga tcatctgctg cttgcttttt ggagttcaaa caaagagcct    360
tttaattctt ggaagcaaac aacaaaagtt agttttaaag atcttaagaa tctgattact    420
aaaatacgac gaggaaatcg tatggattcg ccaagcgctg aaagtaattt tcagggttta    480
gaaaagtatt gtaaaaattt aacagcatta gctcgtgaag gtaaactgga tcctgtgatc    540
ggtagagatg aagaaattcg tagaaccatc caagtgcttt cccgtagaac taaaaataac    600
cctatgctta ttggtgagcc gggtgtaggg aaaactgcta tagcagaagg attagctctt    660
aggcttatcc agggtgatgt tcctgaatct ctcaaaggta aacagcttta tgtcttagat    720
atgggagctt tgattgcagg agctaagtat cgaggtgagt ttgaagaaag actaaagagt    780
gttttaaaag atgtagaatc tggagatggc gagcacatta tctttattga tgaggtgcat    840
actcttgttg gagcaggagc tactgatgga gctatggatg ctgcgaatct tttaaagcct    900
gcattagcaa gagggacgct acactgtatt ggcgcgacga ctttgaatga gtatcagaag    960
tatattgaaa aagatgctgc tttggaacgt cgatttcagc ctatttttgt gacagagcct   1020
tctttggagg atgctgtctt tattcttcgt ggactaagag aaaaatatga aattttccat   1080
ggagtcagga ttacagaggg ggctttgaat gccgcagtcc tactttccta tcgttatatc   1140
ccagatcgct ttcttccaga taaggctatc gatttgatag atgaagcggc aagtttaatt   1200
cgcatgcaaa ttggtagtct tcctcttcct attgatgaaa aggagagaga gcttgctgct   1260
ttgatcgtta agcaagaggc tataaaacgc gagcaatctc cttcctatca agaagaggcg   1320
gatgctatgc agaagtctat agatgctttg agagaggaat tagcatctct acgtttgggt   1380
tgggatgaag agaagaagtt gatttcgggg ctcaaggaaa aaaagaattc cttggaaagt   1440
atgaaatttt ctgaagagga ggcggagcgt gttgcagact ataatcgtgt agctgagctt   1500
cggtatagtt taattcccca acttgaagaa gaaatcaaac aggatgaagc ctctttaaat   1560
caaagagata accgtctcct tcaagaagaa gttgacgagc gattgattgc gcaagtggta   1620
gctaattgga cagggattcc tgtgcaaaaa atgctagaag gggaagctga gaaactgtta   1680
attcttgaag aatccttaga agaacgtgtg gtaggacagc cttttgcagt ctctgcggtt   1740
agtgattcta ttcgtgctgc acgtgtaggt ttaaatgatc ctcaacgtcc cttaggagtc   1800
tttttatttt tagggccaac aggggtagga aaaaccgagc ttgcaaaagc tcttgcagat   1860
cttcttttca ataaagagga agctatggtc cgcttcgata tgtcagagta tatggaaaag   1920
cattccattt ccaagcttat aggatcttct ccagggtatg tgggttatga ggaaggtggg   1980
agtctttctg aggctcttcg acgacgtccc tattcagtag ttctctttga tgagatagag   2040
aaagcagata aggaagttct aaatatcctt ttacaggttt ttgatgatgg gattcttacg   2100
gatgggaaaa aacgcaaagt aaattgtaaa aatgccttgt ttatcatgac atcaaatata   2160
```

-continued

```
ggttctccag aacttgcaga ttattgttca aaaaaaggaa gtgagcttac gaaagaagcg   2220

attctttctg tagtctctcc agtattgaaa agatacttga gccctgaatt tatgaaccga   2280

attgatgaga tacttccttt tgttccatta acgaaagaag atatcgtgaa aatagttggc   2340

attcaaatgc gaaggattgc ccagagatta aaggcacggc ggatcaattt atcttgggat   2400

gattctgtaa tattatttct tagtgaacag ggttatgaca gtgctttcgg agcccgccct   2460

ttaaaacgtt tgatccaaca aaaagttgtg atcttgcttt ctaaggcttt gcttaaagga   2520

gatattaaac ctgatacatc gattgagttg acgatggcaa aagaggtgct cgtatttaaa   2580

aaagtggaaa ctccttctta g                                              2601


<210> SEQ ID NO 112
<211> LENGTH: 389
<212> TYPE: PRT
<213> ORGANISM: Chlamydia pneumoniae

<400> SEQUENCE: 112

Met Lys Lys Leu Leu Lys Ser Ala Leu Leu Ser Ala Ala Phe Ala Gly
1               5                   10                  15

Ser Val Gly Ser Leu Gln Ala Leu Pro Val Gly Asn Pro Ser Asp Pro
            20                  25                  30

Ser Leu Leu Ile Asp Gly Thr Ile Trp Glu Gly Ala Ala Gly Asp Pro
        35                  40                  45

Cys Asp Pro Cys Ala Thr Trp Cys Asp Ala Ile Ser Leu Arg Ala Gly
    50                  55                  60

Phe Tyr Gly Asp Tyr Val Phe Asp Arg Ile Leu Lys Val Asp Ala Pro
65                  70                  75                  80

Lys Thr Phe Ser Met Gly Ala Lys Pro Thr Gly Ser Ala Ala Ala Asn
                85                  90                  95

Tyr Thr Thr Ala Val Asp Arg Pro Asn Pro Ala Tyr Asn Lys His Leu
            100                 105                 110

His Asp Ala Glu Trp Phe Thr Asn Ala Gly Phe Ile Ala Leu Asn Ile
        115                 120                 125

Trp Asp Arg Phe Asp Val Phe Cys Thr Leu Gly Ala Ser Asn Gly Tyr
    130                 135                 140

Ile Arg Gly Asn Ser Thr Ala Phe Asn Leu Val Gly Leu Phe Gly Val
145                 150                 155                 160

Lys Gly Thr Thr Val Asn Ala Asn Glu Leu Pro Asn Val Ser Leu Ser
                165                 170                 175

Asn Gly Val Val Glu Leu Tyr Thr Asp Thr Ser Phe Ser Trp Ser Val
            180                 185                 190

Gly Ala Arg Gly Ala Leu Trp Glu Cys Gly Cys Ala Thr Leu Gly Ala
        195                 200                 205

Glu Phe Gln Tyr Ala Gln Ser Lys Pro Lys Val Glu Glu Leu Asn Val
    210                 215                 220

Ile Cys Asn Val Ser Gln Phe Ser Val Asn Lys Pro Lys Gly Tyr Lys
225                 230                 235                 240

Gly Val Ala Phe Pro Leu Pro Thr Asp Ala Gly Val Ala Thr Ala Thr
                245                 250                 255

Gly Thr Lys Ser Ala Thr Ile Asn Tyr His Glu Trp Gln Val Gly Ala
            260                 265                 270

Ser Leu Ser Tyr Arg Leu Asn Ser Leu Val Pro Tyr Ile Gly Val Gln
        275                 280                 285
```

-continued

```
Trp Ser Arg Ala Thr Phe Asp Ala Asp Asn Ile Arg Ile Ala Gln Pro
    290                 295                 300

Lys Leu Pro Thr Ala Val Leu Asn Leu Thr Ala Trp Asn Pro Ser Leu
305                 310                 315                 320

Leu Gly Asn Ala Thr Ala Leu Ser Thr Thr Asp Ser Phe Ser Asp Phe
                325                 330                 335

Met Gln Ile Val Ser Cys Gln Ile Asn Lys Phe Lys Ser Arg Lys Ala
            340                 345                 350

Cys Gly Val Thr Val Gly Ala Thr Leu Val Asp Ala Asp Lys Trp Ser
        355                 360                 365

Leu Thr Ala Glu Ala Arg Leu Ile Asn Glu Arg Ala Ala His Val Ser
    370                 375                 380

Gly Gln Phe Arg Phe
385


<210> SEQ ID NO 113
<211> LENGTH: 866
<212> TYPE: PRT
<213> ORGANISM: Chlamydia pneumoniae

<400> SEQUENCE: 113

Met Glu Lys Phe Ser Asp Ala Val Ser Glu Ala Leu Glu Lys Ala Phe
                  5                  10                  15

Glu Leu Ala Lys Ser Ser Lys His Thr Tyr Val Thr Glu Asn His Leu
            20                  25                  30

Leu Leu Ala Leu Leu Glu Asn Thr Glu Ser Leu Phe Tyr Leu Val Ile
        35                  40                  45

Lys Asp Ile His Gly Asn Pro Gly Leu Leu Asn Thr Ala Val Lys Asp
     50                  55                  60

Ala Leu Ser Arg Glu Pro Thr Val Val Glu Gly Glu Val Asp Pro Lys
 65                  70                  75                  80

Pro Ser Pro Gly Leu Gln Thr Leu Leu Arg Asp Ala Lys Gln Glu Ala
                 85                  90                  95

Lys Thr Leu Gly Asp Glu Tyr Ile Ser Gly Asp His Leu Leu Leu Ala
            100                 105                 110

Phe Trp Ser Ser Asn Lys Glu Pro Phe Asn Ser Trp Lys Gln Thr Thr
        115                 120                 125

Lys Val Ser Phe Lys Asp Leu Lys Asn Leu Ile Thr Lys Ile Arg Arg
    130                 135                 140

Gly Asn Arg Met Asp Ser Pro Ser Ala Glu Ser Asn Phe Gln Gly Leu
145                 150                 155                 160

Glu Lys Tyr Cys Lys Asn Leu Thr Ala Leu Ala Arg Glu Gly Lys Leu
                165                 170                 175

Asp Pro Val Ile Gly Arg Asp Glu Glu Ile Arg Arg Thr Ile Gln Val
            180                 185                 190

Leu Ser Arg Arg Thr Lys Asn Asn Pro Met Leu Ile Gly Glu Pro Gly
        195                 200                 205

Val Gly Lys Thr Ala Ile Ala Glu Gly Leu Ala Leu Arg Leu Ile Gln
    210                 215                 220

Gly Asp Val Pro Glu Ser Leu Lys Gly Lys Gln Leu Tyr Val Leu Asp
225                 230                 235                 240

Met Gly Ala Leu Ile Ala Gly Ala Lys Tyr Arg Gly Glu Phe Glu Glu
                245                 250                 255

Arg Leu Lys Ser Val Leu Lys Asp Val Glu Ser Gly Asp Gly Glu His
            260                 265                 270
```

```
Ile Ile Phe Ile Asp Glu Val His Thr Leu Val Gly Ala Gly Ala Thr
        275                 280                 285

Asp Gly Ala Met Asp Ala Ala Asn Leu Leu Lys Pro Ala Leu Ala Arg
    290                 295                 300

Gly Thr Leu His Cys Ile Gly Ala Thr Thr Leu Asn Glu Tyr Gln Lys
305                 310                 315                 320

Tyr Ile Glu Lys Asp Ala Ala Leu Glu Arg Arg Phe Gln Pro Ile Phe
                325                 330                 335

Val Thr Glu Pro Ser Leu Glu Asp Ala Val Phe Ile Leu Arg Gly Leu
            340                 345                 350

Arg Glu Lys Tyr Glu Ile Phe His Gly Val Arg Ile Thr Glu Gly Ala
        355                 360                 365

Leu Asn Ala Ala Val Leu Leu Ser Tyr Arg Tyr Ile Pro Asp Arg Phe
    370                 375                 380

Leu Pro Asp Lys Ala Ile Asp Leu Ile Asp Glu Ala Ala Ser Leu Ile
385                 390                 395                 400

Arg Met Gln Ile Gly Ser Leu Pro Leu Pro Ile Asp Glu Lys Glu Arg
                405                 410                 415

Glu Leu Ala Ala Leu Ile Val Lys Gln Glu Ala Ile Lys Arg Glu Gln
            420                 425                 430

Ser Pro Ser Tyr Gln Glu Glu Ala Asp Ala Met Gln Lys Ser Ile Asp
        435                 440                 445

Ala Leu Arg Glu Glu Leu Ala Ser Leu Arg Leu Gly Trp Asp Glu Glu
    450                 455                 460

Lys Lys Leu Ile Ser Gly Leu Lys Glu Lys Lys Asn Ser Leu Glu Ser
465                 470                 475                 480

Met Lys Phe Ser Glu Glu Glu Ala Glu Arg Val Ala Asp Tyr Asn Arg
                485                 490                 495

Val Ala Glu Leu Arg Tyr Ser Leu Ile Pro Gln Leu Glu Glu Glu Ile
            500                 505                 510

Lys Gln Asp Glu Ala Ser Leu Asn Gln Arg Asp Asn Arg Leu Leu Gln
        515                 520                 525

Glu Glu Val Asp Glu Arg Leu Ile Ala Gln Val Val Ala Asn Trp Thr
    530                 535                 540

Gly Ile Pro Val Gln Lys Met Leu Glu Gly Glu Ala Glu Lys Leu Leu
545                 550                 555                 560

Ile Leu Glu Glu Ser Leu Glu Glu Arg Val Val Gly Gln Pro Phe Ala
                565                 570                 575

Val Ser Ala Val Ser Asp Ser Ile Arg Ala Ala Arg Val Gly Leu Asn
            580                 585                 590

Asp Pro Gln Arg Pro Leu Gly Val Phe Leu Phe Leu Gly Pro Thr Gly
        595                 600                 605

Val Gly Lys Thr Glu Leu Ala Lys Ala Leu Ala Asp Leu Leu Phe Asn
    610                 615                 620

Lys Glu Glu Ala Met Val Arg Phe Asp Met Ser Glu Tyr Met Glu Lys
625                 630                 635                 640

His Ser Ile Ser Lys Leu Ile Gly Ser Ser Pro Gly Tyr Val Gly Tyr
                645                 650                 655

Glu Glu Gly Gly Ser Leu Ser Glu Ala Leu Arg Arg Arg Pro Tyr Ser
            660                 665                 670

Val Val Leu Phe Asp Glu Ile Glu Lys Ala Asp Lys Glu Val Leu Asn
        675                 680                 685
```

-continued

```
Ile Leu Leu Gln Val Phe Asp Asp Gly Ile Leu Thr Asp Gly Lys Lys
    690                 695                 700

Arg Lys Val Asn Cys Lys Asn Ala Leu Phe Ile Met Thr Ser Asn Ile
705                 710                 715                 720

Gly Ser Pro Glu Leu Ala Asp Tyr Cys Ser Lys Lys Gly Ser Glu Leu
                725                 730                 735

Thr Lys Glu Ala Ile Leu Ser Val Val Ser Pro Val Leu Lys Arg Tyr
            740                 745                 750

Leu Ser Pro Glu Phe Met Asn Arg Ile Asp Glu Ile Leu Pro Phe Val
        755                 760                 765

Pro Leu Thr Lys Glu Asp Ile Val Lys Ile Val Gly Ile Gln Met Arg
    770                 775                 780

Arg Ile Ala Gln Arg Leu Lys Ala Arg Arg Ile Asn Leu Ser Trp Asp
785                 790                 795                 800

Asp Ser Val Ile Leu Phe Leu Ser Glu Gln Gly Tyr Asp Ser Ala Phe
                805                 810                 815

Gly Ala Arg Pro Leu Lys Arg Leu Ile Gln Gln Lys Val Val Ile Leu
            820                 825                 830

Leu Ser Lys Ala Leu Leu Lys Gly Asp Ile Lys Pro Asp Thr Ser Ile
        835                 840                 845

Glu Leu Thr Met Ala Lys Glu Val Leu Val Phe Lys Lys Val Glu Thr
    850                 855                 860

Pro Ser
865
```

<210> SEQ ID NO 114
<211> LENGTH: 1179
<212> TYPE: DNA
<213> ORGANISM: Homo sapiens

<400> SEQUENCE: 114

```
taactctccc ctctcttctt aaaaaagagg ggagcctttt ttccttacaa agatacgcta      60

gctttttcct gaagaatctc atcaagagat atttgcattt tcccacggat aaaggcatcc     120

caaggaagcc ctggaatcac ttcatattct cccgttgcta gcattcgaca agggaaacca     180

aagattaaat cttccggtaa tccataggga ttgtggtccg aacacactcc ggaagaaaac     240

cattctcctt cttttggctg atatattgat cgagcagcct ctgctaaagc tcgtgctgca     300

gaagctgccg aagacttccc tcgtgcttcg attactgcac taccacgact ctgtacagaa     360

ggcaccataa tattctctaa ccaatcacga tccgctatcg tctctgcgat aggacggtca     420

ttaatcagag cttgcgtaaa atcaggcact tgtttggcgg agtgatttcc ccaaaccaca     480

acttgtgata cagccgataa aggtacttct gctctatgcg ataacatgct atgcatacga     540

ttctggtcca atcgtagcat cgcatgaaag ttctttctca ataatctggg agcatgattc     600

attgctatcc agcaattggt attcacaggg ttcccaacaa caaaaatctt tgcatcccgc     660

ttggctgttg tgttcaaagc ttttccttgc gtagcaaaaa tctccccatt tttctttaga     720

agatcccttc tctccattcc tgggcctcta ggaactgacc ctataaggaa tgccgcatca     780

atgccatcaa aagcatcatg caatgatgtc gttacctgca cacgctgtaa taaagggaaa     840

gcaccatcat ctagctccat gcgcacacca gataaagccc tttctgttcc aggaatatcg     900

tagatacgca gatcgatgcc acaatcaagg ccaaaaacat ctccatgagc cagagaaaat     960

agaaagctat aggctatttg ccctgttcct cctgttactg ctacactcac tgtttgagaa    1020

accataagcc accctctctt tacttttaca aaacgcacat actctcaaca ctacgtttgc    1080
```

```
aactaactaa ttttggtccc aacatacgtt tggatgataa aagaatcaag tacctagatt   1140

ccttagtaaa agcttttggc aaaaaaaagc tcatctatt                          1179


<210> SEQ ID NO 115
<211> LENGTH: 772
<212> TYPE: DNA
<213> ORGANISM: Homo sapiens

<400> SEQUENCE: 115

gcaaaactgc tgacaaagct ggagacggaa ctacaacagc tactgttctt gctgaagcta     60

tctatacaga aggattacgc aatgtaacag ctggagcaaa tccaatggac ctcaaacgag    120

gtattgataa agctgttaag gttgttgttg atcaaatcag aaaaatcagc aaacctgttc    180

agcatcataa agaaattgct caagttgcaa caatttctgc taataatgat gcagaaatcg    240

ggaatctgat tgctgaagca atggagaaag ttggtaaaaa cggctctatc actgttgaag    300

aagcaaaagg atttgaaacc gttttggatg ttgttgaagg aatgaatttc aatagaggtt    360

acctctctag ctacttcgca acaaatccag aaactcaaga atgtgtatta gaagacgctt    420

tggttctaat ctacgataag aaaatttctg ggatcaaaga tttccttcct gttttacaac    480

aagttgctga atccggccgt cctcttctta ttatagcaga agacattgaa ggcgaagctt    540

tagctacttt ggtcgtgaac agaattcgtg gaggattccg ggtttgcgca gttaaagctc    600

caggctttgg agatagaaga aaagctatgt tggaagacat cgctatctta actggcggtc    660

aactcattag cgaagagttg ggcatgaaat tagaaaacgc taacttagct atgttaggta    720

aagctaaaaa agttatcgtt tctaaggaag acacgaccat cgtcgaagga at            772


<210> SEQ ID NO 116
<211> LENGTH: 487
<212> TYPE: DNA
<213> ORGANISM: Homo sapiens

<400> SEQUENCE: 116

gcagctcctg caaagccaca agctcctgtc gcacaaacac ggcattttaa aaagagccat     60

cagattttct ctcctaattt tacgcagtct tcccaacagg tgaataaacc tgaggaaaga    120

agacgtcctt tggagtctcg atacttacaa ggcgcggcta agcaggcagc tgctgcaaag    180

gaaaaaaagg ctcttgaaca ggaagtatcc aaacaagaag aagaagcttc taaactctgg    240

gaagagaaac agagttatgc tcgtcgtgct gtgaatgcca tcaatttcag tgtaagaaag    300

caaatagaag agcaacagaa aaccatttcc aatccaggaa atgaccagac tcttcctggg    360

aagaaagatc cacatacatc cggagaacct gttatccaaa cggtacaaga ctgttctcag    420

gatcaagaag aagagaaaaa agttctagag cgattaaaca aacgttctct gacgtgtcag    480

gatctta                                                              487


<210> SEQ ID NO 117
<211> LENGTH: 1014
<212> TYPE: DNA
<213> ORGANISM: Homo sapiens

<400> SEQUENCE: 117

ctcgtgccga atcttctaac aagagaacaa gctcctttct ttcttttcta aacaaggttc     60

agcgctttct attaaaagaa accctattca gaccctatgc agcacatagt tttataaaaa    120

atttttctat taacagagga aaaataacct attgataaac agagcggtac aaggagatgc    180
```

-continued

```
aaataaagct gctttaggat ccttacctag attctagaaa atggttgcat gaatttgaac    240

aaacaaacta attaaaaatt aaaactgaaa aaaatagttt aaaacaacaa ctagaggata    300

tttttcatg gcgctaaaag atacggcaaa aaaaatgact gacttgttgg aaagtatcca    360

acaaaatttg cttaaagcag aaaaaggaaa taaagccgca gcacaaagag ttcgtacaga    420

atctatcaaa ttagaaaaga tcgcgaaggt atatcgtaaa gagtccatta aagcagaaaa    480

aatgggctta atgaaaaaaa gcaaagccgc tgctaaaaaa gctaaagctg ctgctaagaa    540

gcctgttcgc gctacaaaaa cagtggctaa aaaagcttgt acaaaaaagaa cttgtgctac    600

taaagcaaag gtcaaaccaa caaaaaaagc cgctcctaaa acaaaagtta aaacagcgaa    660

aaaaactcgc tcaacaaaaa aataatattt tagcgctttc tctttttat agagggcact    720

tttatcaaca gggccctctt tcctcttctc attgatccct tctcttttt ttgttatcct    780

ttccgttctc gcaaaggcaa gtccttgcaa ataaaagtac aacctcacac ctcctttgga    840

ggaaaaacct ttcactttct ttaggattca agttgctctc ctgctatcgt aactgtaaac    900

attttggcgt ctgtggaggc tgttcatctc ctcaaatgga atatgcatcc tctttaaaaa    960

caaaagagct tgcgctccat aatttatttg cacctcttat cccatcccaa aata         1014
```

<210> SEQ ID NO 118
<211> LENGTH: 287
<212> TYPE: DNA
<213> ORGANISM: Homo sapiens

<400> SEQUENCE: 118

```
atgcaaataa agctgcttta ggatccttac ctagattcta gaaaatggtt gcatgaattt     60

gaacaaacaa actaattaaa aattaaaact gaaaaaaata gtttaaaaca acaactagag    120

gatatttttt catggcgcta aaagatacgg caaaaaaaat gactgacttg ttggaaagta    180

tccaacaaaa tttgcttaaa gcagaaaaag gaaataaagc cgcagcacaa agagttcgta    240

cagaatctat caaattagaa aagatcgcga aggtatatcg taaagag                  287
```

<210> SEQ ID NO 119
<211> LENGTH: 1002
<212> TYPE: DNA
<213> ORGANISM: Homo sapiens

<400> SEQUENCE: 119

```
catatgcatc accatcacca tcacatgagt attcgaccta ctaatgggag tggaaatgga     60

tacccgtcta ttaatccttc taacgataat caatacggtc ttgtgcaatc gacctctggg    120

cctaattacg gaggccatac ggtatcttct cgaggaggat ttcaagggat atgcgtacga    180

atagccgatt tattccgtaa ctgtttctct cgtaatagag gcactactac tacgccatct    240

cgaactgtta tcactcaggc agatatttat catccgacta tttctggaca aggagctcaa    300

cctattgtct ctacaggaga taagaaatta gatagcgcaa ttattcaagc agatttgcgt    360

gcgcagaata aacagacttt ggctacacat attcaaagta agctaggttc tatggaggga    420

caatctcctc aagattataa agctggtgcg tatagtgcgc taagattgat gctgtttact    480

ccaggcgaaa ctactgtgag tagcgagcgg gaacgtcaag cgtgcgttac gggtcgggat    540

ctctgggaac aggctgcagg agatcttgct accaatggga atacagatgg gcttatgtta    600

atggctaacc tatctgtggg agggaagcat gtgcctgcgg ggcatttaag agaatacatg    660

gatactgtaa agggtacgtt tactgatgag aacgaggcta cagatcctac ggtagatgcc    720

attttagatt tagcagcaaa aatcgatgcg acggaattct ctagtcctgg ttcagggcaa    780
```

```
gtcattctta attatatagg aaattatgga caagtcgttt tagaaaacga ggagatgaac    840

cttcttgttt tagaagatca aaatgggcaa gatcctcaac gtgttcaaga taactcaaaa    900

gagttacaaa aactgttaga aaatgctcga aaaacagatc ctgagttata tttccaaaca    960

ctaactgtca taacttcttc tgttttctta gactaaggat cc                      1002
```

<210> SEQ ID NO 120
<211> LENGTH: 1218
<212> TYPE: DNA
<213> ORGANISM: Homo sapiens

<400> SEQUENCE: 120

```
atgcatcacc atcaccatca cgtgagtagc ataagcccta tagggggggaa ttctgggcca    60

gagggatttt ctagtgcatc tcgaggcgat gagattgatg atgtaccaga tagtgaagag    120

ggagagctag aagagcgcgt ttcggatcat gcagagtcta tcattaccga gagctcggaa    180

acgctgtttc gtactacttc ttcatcaggg gtcagtgaag atcttcagca acacgttagc    240

ttggaggaat ctccacgaca acgaggtttc cttggacgga tccgtgatgc agtagcttct    300

atttggaagc gtcgtgttgc acgaaggaat gaaaactatg atgtgaaaaa agcagaagag    360

cagcaaggga ttgtgcaata tctgcaggat tcgaaaatgc ctgctttaac gcgtgcctat    420

cgccatctcc gtgctttcaa ttctgcatgc ttacgtacga ttcgtgagtt tttcgctacc    480

atttttcgtg ctttaaggga tgcgtattat cgacattgta cacgttctgg gatcaacttt    540

tgtggagctg ataaagactc tttagaagtt cttgttgcgg tgggtttgct tttgcgtatg    600

gctaccttac gctcttttga acatgtcggt gggaattacg aagatcgatt agtaaataat    660

gatgctccgg tgacaggtgc ggggagaact cttgttgatg atgctgtaga cgatattgaa    720

tcgattttaa atacgagaac caactggcct caacatgtca tgatagggtt ttctcgtggt    780

ctcgttcaat tatgtgcgac tccttataat gcgacttctc aagaatgttt caagtcgatt    840

gttcgtttag aaaaagaaga cccttcttca gattattctc aagctttatt attagcaggg    900

ataaatagatc gcttggcgga gaaagcccct atggctgcaa agtatgtttt ggatgcattg    960

cgtgttcgaa cttcggagct cataggagaa ctcattattc tcgatttgct tcctcctgta   1020

tggaaggttg gccgcggagg cgtattccct cctgtgaatg agcagctcgt tgtgcaaatt   1080

gttaatgcaa acgtagaacg attgcattcc actttcgctc atgagccaca agcttatttg   1140

cgtatgatcg aaggtttggt aaccaatttc tttttcttac ctagcgagga agatccttct   1200

tcggttggga atatctaa                                                 1218
```

<210> SEQ ID NO 121
<211> LENGTH: 726
<212> TYPE: DNA
<213> ORGANISM: Homo sapiens

<400> SEQUENCE: 121

```
catatgcatc accatcacca tcacacaaag catggaaaac gcattcgtgg tatccaagag    60

acttacgatt tagctaagtc gtattctttg ggtgaagcga tagatatttt aaaacagtgt    120

cctactgtgc gtttcgatca aacggttgat gtgtctgtta aattagggat cgatccaaga    180

aagagtgatc agcaaattcg tggttcggtt tctttacctc acggtacagg taaagttttg    240

cgaattttag tttttgctgc tggagataag gctgcagagg ctattgaagc aggagcggac    300

tttgttggta gcgacgactt ggtagaaaaa atcaaaggtg gatgggttga cttcgatgtt    360
```

```
gcggttgcca ctcccgatat gatgagagag gtcggaaagc taggaaaagt tttaggtcca    420

agaaacctta tgcctacgcc taaagccgga actgtaacaa cagatgtggt taaaactatt    480

gcggaactgc gaaaaggtaa aattgaattt aaagctgatc gagctggtgt atgcaacgtc    540

ggagttgcga agctttcttt cgatagtgcg caaatcaaag aaaatgttga agcgttgtgt    600

gcagccttag ttaaagctaa gcccgcaact gctaaaggac aatatttagt taatttcact    660

atttcctcga ccatggggcc aggggttacc gtggatacta gggagttgat tgcgttataa    720

gaattc                                                               726
```

```
<210> SEQ ID NO 122
<211> LENGTH: 330
<212> TYPE: PRT
<213> ORGANISM: Homo sapiens

<400> SEQUENCE: 122

Met His His His His His His Met Ser Ile Arg Pro Thr Asn Gly Ser
                    5                   10                  15

Gly Asn Gly Tyr Pro Ser Ile Asn Pro Ser Asn Asp Asn Gln Tyr Gly
            20                  25                  30

Leu Val Gln Ser Thr Ser Gly Pro Asn Tyr Gly Gly His Thr Val Ser
        35                  40                  45

Ser Arg Gly Gly Phe Gln Gly Ile Cys Val Arg Ile Ala Asp Leu Phe
    50                  55                  60

Arg Asn Cys Phe Ser Arg Asn Arg Gly Thr Thr Thr Thr Pro Ser Arg
65                  70                  75                  80

Thr Val Ile Thr Gln Ala Asp Ile Tyr His Pro Thr Ile Ser Gly Gln
                85                  90                  95

Gly Ala Gln Pro Ile Val Ser Thr Gly Asp Lys Lys Leu Asp Ser Ala
            100                 105                 110

Ile Ile Gln Ala Asp Leu Arg Ala Gln Asn Lys Gln Thr Leu Ala Thr
        115                 120                 125

His Ile Gln Ser Lys Leu Gly Ser Met Glu Gly Gln Ser Pro Gln Asp
    130                 135                 140

Tyr Lys Ala Gly Ala Tyr Ser Ala Leu Arg Leu Met Leu Phe Thr Pro
145                 150                 155                 160

Gly Glu Thr Thr Val Ser Ser Glu Arg Glu Arg Gln Ala Cys Val Thr
                165                 170                 175

Gly Arg Asp Leu Trp Glu Gln Ala Ala Gly Asp Leu Ala Thr Asn Gly
            180                 185                 190

Asn Thr Asp Gly Leu Met Leu Met Ala Asn Leu Ser Val Gly Gly Lys
        195                 200                 205

His Val Pro Ala Gly His Leu Arg Glu Tyr Met Asp Thr Val Lys Gly
    210                 215                 220

Thr Phe Thr Asp Glu Asn Glu Ala Thr Asp Pro Thr Val Asp Ala Ile
225                 230                 235                 240

Leu Asp Leu Ala Ala Lys Ile Asp Ala Thr Glu Phe Ser Ser Pro Gly
                245                 250                 255

Ser Gly Gln Val Ile Leu Asn Tyr Ile Gly Asn Tyr Gly Gln Val Val
            260                 265                 270

Leu Glu Asn Glu Glu Met Asn Leu Leu Val Leu Glu Asp Gln Asn Gly
        275                 280                 285

Gln Asp Pro Gln Arg Val Gln Asp Asn Ser Lys Glu Leu Gln Lys Leu
    290                 295                 300
```

```
Leu Glu Asn Ala Arg Lys Thr Asp Pro Glu Leu Tyr Phe Gln Thr Leu
305                 310                 315                 320

Thr Val Ile Thr Ser Ser Val Phe Leu Asp
                325                 330


<210> SEQ ID NO 123
<211> LENGTH: 405
<212> TYPE: PRT
<213> ORGANISM: Homo sapiens

<400> SEQUENCE: 123

Met His His His His His His Val Ser Ser Ile Ser Pro Ile Gly Gly
                  5                  10                  15

Asn Ser Gly Pro Glu Gly Phe Ser Ser Ala Ser Arg Gly Asp Glu Ile
             20                  25                  30

Asp Asp Val Pro Asp Ser Glu Glu Gly Glu Leu Glu Glu Arg Val Ser
         35                  40                  45

Asp His Ala Glu Ser Ile Ile Thr Glu Ser Ser Glu Thr Leu Phe Arg
     50                  55                  60

Thr Thr Ser Ser Ser Gly Val Ser Glu Asp Leu Gln Gln His Val Ser
 65                  70                  75                  80

Leu Glu Glu Ser Pro Arg Gln Arg Gly Phe Leu Gly Arg Ile Arg Asp
                 85                  90                  95

Ala Val Ala Ser Ile Trp Lys Arg Arg Val Ala Arg Arg Asn Glu Asn
            100                 105                 110

Tyr Asp Val Lys Lys Ala Glu Glu Gln Gln Gly Ile Val Gln Tyr Leu
        115                 120                 125

Gln Asp Ser Lys Met Pro Ala Leu Thr Arg Ala Tyr Arg His Leu Arg
    130                 135                 140

Ala Phe Asn Ser Ala Cys Leu Arg Thr Ile Arg Glu Phe Phe Ala Thr
145                 150                 155                 160

Ile Phe Arg Ala Leu Arg Asp Ala Tyr Tyr Arg His Cys Thr Arg Ser
                165                 170                 175

Gly Ile Asn Phe Cys Gly Ala Asp Lys Asp Ser Leu Glu Val Leu Val
            180                 185                 190

Ala Val Gly Leu Leu Leu Arg Met Ala Thr Leu Arg Ser Phe Glu His
        195                 200                 205

Val Gly Gly Asn Tyr Glu Asp Arg Leu Val Asn Asn Asp Ala Pro Val
    210                 215                 220

Thr Gly Ala Gly Arg Thr Leu Val Asp Asp Ala Val Asp Asp Ile Glu
225                 230                 235                 240

Ser Ile Leu Asn Thr Arg Thr Asn Trp Pro Gln His Val Met Ile Gly
                245                 250                 255

Phe Ser Arg Gly Leu Val Gln Leu Cys Ala Thr Pro Tyr Asn Ala Thr
            260                 265                 270

Ser Gln Glu Cys Phe Lys Ser Ile Val Arg Leu Glu Lys Glu Asp Pro
        275                 280                 285

Ser Ser Asp Tyr Ser Gln Ala Leu Leu Leu Ala Gly Ile Ile Asp Arg
    290                 295                 300

Leu Ala Glu Lys Ala Pro Met Ala Ala Lys Tyr Val Leu Asp Ala Leu
305                 310                 315                 320

Arg Val Arg Thr Ser Glu Leu Ile Gly Glu Leu Ile Ile Leu Asp Leu
                325                 330                 335

Leu Pro Pro Val Trp Lys Val Gly Arg Gly Gly Val Phe Pro Pro Val
            340                 345                 350
```

-continued

```
Asn Glu Gln Leu Val Val Gln Ile Val Asn Ala Asn Val Glu Arg Leu
        355                 360                 365

His Ser Thr Phe Ala His Glu Pro Gln Ala Tyr Leu Arg Met Ile Glu
    370                 375                 380

Gly Leu Val Thr Asn Phe Phe Phe Leu Pro Ser Glu Glu Asp Pro Ser
385                 390                 395                 400

Ser Val Gly Asn Ile
                405
```

<210> SEQ ID NO 124
<211> LENGTH: 238
<212> TYPE: PRT
<213> ORGANISM: Homo sapiens

<400> SEQUENCE: 124

```
Met His His His His His His Thr Lys His Gly Lys Arg Ile Arg Gly
                  5                  10                  15

Ile Gln Glu Thr Tyr Asp Leu Ala Lys Ser Tyr Ser Leu Gly Glu Ala
             20                  25                  30

Ile Asp Ile Leu Lys Gln Cys Pro Thr Val Arg Phe Asp Gln Thr Val
         35                  40                  45

Asp Val Ser Val Lys Leu Gly Ile Asp Pro Arg Lys Ser Asp Gln Gln
     50                  55                  60

Ile Arg Gly Ser Val Ser Leu Pro His Gly Thr Gly Lys Val Leu Arg
 65                  70                  75                  80

Ile Leu Val Phe Ala Ala Gly Asp Lys Ala Ala Glu Ala Ile Glu Ala
                 85                  90                  95

Gly Ala Asp Phe Val Gly Ser Asp Asp Leu Val Glu Lys Ile Lys Gly
            100                 105                 110

Gly Trp Val Asp Phe Asp Val Ala Val Ala Thr Pro Asp Met Met Arg
        115                 120                 125

Glu Val Gly Lys Leu Gly Lys Val Leu Gly Pro Arg Asn Leu Met Pro
    130                 135                 140

Thr Pro Lys Ala Gly Thr Val Thr Thr Asp Val Val Lys Thr Ile Ala
145                 150                 155                 160

Glu Leu Arg Lys Gly Lys Ile Glu Phe Lys Ala Asp Arg Ala Gly Val
                165                 170                 175

Cys Asn Val Gly Val Ala Lys Leu Ser Phe Asp Ser Ala Gln Ile Lys
            180                 185                 190

Glu Asn Val Glu Ala Leu Cys Ala Ala Leu Val Lys Ala Lys Pro Ala
        195                 200                 205

Thr Ala Lys Gly Gln Tyr Leu Val Asn Phe Thr Ile Ser Ser Thr Met
    210                 215                 220

Gly Pro Gly Val Thr Val Asp Thr Arg Glu Leu Ile Ala Leu
225                 230                 235
```

<210> SEQ ID NO 125
<211> LENGTH: 713
<212> TYPE: DNA
<213> ORGANISM: Chlamydia trachomatis

<400> SEQUENCE: 125

```
ataacaatcc ctcccaatca tcgttgaacg tacaaggagg agccatctat gccaaaacct      60

ctttgtctat tggatcttcc gatgctggaa cctcctatat tttctcgggg aacagtgtct     120

ccactgggaa atctcaaaca acagggcaaa tagcgggagg agcgatctac tcccctactg     180
```

```
ttacattgaa ttgtcctgcg acattctcta acaatacagc ctctatagct acaccgaaga    240

cttcttctga agatggatcc tcaggaaatt ctattaaaga taccattgga ggagccattg    300

cagggacagc cattacccta tctggagtct ctcgattttc agggaatacg gctgatttag    360

gagctgcaat aggaactcta gctaatgcaa atacacccag tgcaactagc ggatctcaaa    420

atagcattac agaaaaaatt actttagaaa acggttcttt tatttttgaa agaaaccaag    480

ctaataaacg tggagcgatt tactctccta gcgtttccat taaagggaat aatattacct    540

tcaatcaaaa tacatccact catgatggaa gcgctatcta ctttacaaaa gatgctacga    600

ttgagtcttt aggatctgtt ctttttacag gaaataacgt tacagctaca caagctagtt    660

ctgcaacatc tggacaaaat acaaatactg ccaactatgg ggcagccatc ttt           713
```

<210> SEQ ID NO 126
<211> LENGTH: 780
<212> TYPE: DNA
<213> ORGANISM: Chlamydia trachomatis

<400> SEQUENCE: 126

```
ccttctcctt actcaggagt tttaaaagaa aacgcaccgt ttttacgttt cctcacacaa     60

ttaactaaca agcatactca ttctggattt cattgcctcc taaaattctt agtcaaatcc    120

gaaagaagcc gacactcgag cgctcttctc ctaaaaatct tgttttttct ctgcttccga    180

gttataacgc ggctgtctca taacccacac taacatgatg aaacctctac gtttcggtta    240

tttcttttgc acaatctatt ttactttgtt acaggcagcg tttgctaaag aaccgaattc    300

ttgtcccgac tgccagaata attggaaaga agtcacccac acggatcaac tccctgaaaa    360

catcattcat gctgatgatg cttgttatca ctctggttat gtacaggctc tcattgatat    420

gcatttctta gatagctgct gccaggtcat cgttgaaaac caaactgctt acttattttc    480

tcttcctaca gatgatgtta cgcgcaacgc cattatcaac ctaattaaag accttccatt    540

cattcactcc gtagaaatct gccaagcatc ctatcaaacc tgtcatcatc aaggccctca    600

tggaaagact tctcttccag aacaacgttc tttctgtaca aaggtctgtg gaaaagaagc    660

tatttggtta ccacagaata ccatcctatt ctcgcctctt gtagcagata ctatccaagc    720

aactaatagt gcaggtatcc gttttaacga cgaagtcgta ggaaaacgtg ttggctctgc    780
```

<210> SEQ ID NO 127
<211> LENGTH: 433
<212> TYPE: DNA
<213> ORGANISM: Chlamydia trachomatis

<400> SEQUENCE: 127

```
ctttaaagat tcgtcgtcct tttggtacta cgagagaagt tcgtgtgaaa tggcgttatg     60

ttcctgaagg tgtaggagat ttggctacca tagctccttc tatcagggct ccacagttac    120

agaaatcgat gagaagcttt ttccctaaga aagatgatgc gtttcatcgg tctagttcgc    180

tattctactc tccaatggtt ccgcattttt gggcagagct tcgcaatcat tatgcaacga    240

gtggtttgaa aagcgggtac aatattggga gtaccgatgg gtttctccct gtcattgggc    300

ctgttatatg ggagtcggag ggtcttttcc gcgcttatat ttcttcggtg actgatgggg    360

atggtaagag ccataaagta ggatttctaa gaattcctac atatagttgg caggacatgg    420

aagatttga tcc                                                        433
```

<210> SEQ ID NO 128

-continued

```
<211> LENGTH: 803
<212> TYPE: DNA
<213> ORGANISM: Chlamydia trachomatis

<400> SEQUENCE: 128

atctattaat taatagcaag cttgaaacta aaaacctaat ttatttaaag ctcaaaataa     60

aaaagagttt taaaatggga aattctggtt tttatttgta taacactgaa aactgcgtct    120

ttgctgataa tatcaaagtt gggcaaatga cagagccgct caaggaccag caaataatcc    180

ttgggacaac atcaacacct gtcgcagcca aaatgacagc ttctgatgga atatctttaa    240

cagtctccaa taattcatca accaatgctt ctattacaat tggtttggat gcggaaaaag    300

cttaccagct tattctagaa aagttgggag atcaaattct tgatggaatt gctgatacta    360

ttgttgatag tacagtccaa gatattttag acaaaatcaa aacagaccct tctctaggtt    420

tgttgaaagc ttttaacaac tttccaatca ctaataaaat tcaatgcaac gggttattca    480

ctcccagtaa cattgaaact ttattaggag gaactgaaat aggaaaattc acagtcacac    540

ccaaaagctc tgggagcatg ttcttagtct cagcagatat tattgcatca agaatggaag    600

gcggcgttgt tctagctttg gtacgagaag gtgattctaa gccctgcgcg attagttatg    660

gatactcatc aggcattcct aatttatgta gtctaagaac cagtattact aatacaggat    720

tgactccgac aacgtattca ttacgtgtag gcggtttaga aagcggtgtg gtatgggtta    780

atgccctttc taatctcgtg ccg                                            803


<210> SEQ ID NO 129
<211> LENGTH: 842
<212> TYPE: DNA
<213> ORGANISM: Chlamydia trachomatis

<400> SEQUENCE: 129

tgggaatgtc gaagaatacg attacgttct cgtatctata ggacgccgtt tgaatacaga     60

aaatattggc ttggataaag ctggtgttat ttgtgatgaa cgcggagtca tccctaccga    120

tgccacaatg cgcacaaacg tacctaacat ttatgctatt ggagatatca caggaaaatg    180

gcaacttgcc catgtagctt ctcatcaagg aatcattgca gcacggaata tagctggcca    240

taaagaggaa atcgattact ctgccgtccc ttctgtgatc tttaccttcc ctgaagtcgc    300

ttcagtaggc ctctccccaa cagcagctca acaacaaaaa atccccgtca aagtaacaaa    360

attcccattt cgagctattg gaaaagcggt cgcaatgggc gaggccgatg gatttgcagc    420

cattatcagc catgagacta ctcagcagat cctaggagct tatgtgattg gccctcatgc    480

ctcatcactg atttccgaaa ttaccctagc agttcgtaat gaactgactc ttccttgtat    540

ttacgaaact atccacgcac atccaacctt agcagaagtt tgggctgaaa gtgcgttgtt    600

agctgctgat accccattac atatgccccc tgctaaaaaa tgaccgattc agaatctcct    660

actcctaaaa aatctatacc cgccagattc cctaagtggc tacgccagaa actcccttta    720

gggcgggtat ttgctcaaac tgataatact atcaaaaata aagggcttcc tacagtctgt    780

gaggaagcct cttgtccgaa tcgcacccat tgttggtcta gacatacagc tacctatcta    840

gc                                                                   842


<210> SEQ ID NO 130
<211> LENGTH: 813
<212> TYPE: DNA
<213> ORGANISM: Chlamydia trachomatis

<400> SEQUENCE: 130
```

```
aaaatacttt gagctgcaca agctcccccc tgttctagag aagaacatga tgcaaattcc     60
aatccaccct taatcttttc aaagataaga tcttctgtag aatataaagc cgctccagac    120
aaagaagctt tcacgtcagt taatgtgatt ccagccttac tactatcccc aacaaaagca    180
atacctaaaa aagattctcc gtcacgagga gaatcaaggt tgctgctcgt aaaactacaa    240
attaaccctt gggaagagac ttgatcctgt tggtccacac cttggaaaac tacgggattg    300
gttactgaga acaaagtact ttgctctacc ttaccgggaa gagtatccgc atctttctct    360
tggaaagaac ttggatctcc tacaattaac ctatactgtc cttcagcctg actatcttta    420
gacccaacga atagatctcg aatttggtct aacaataaaa ccgcttgagg gcctacatat    480
accagctcat ttacagactg tcctccagca tgaagatcta cgcaactagc taacccgcta    540
acagaggcaa ggatagctgc tactacagac aaagaaaact tagaacaggt gctttttata    600
tctttctcgg aactcatttc aaacctgcga aatagcactt ttttgacaaa ctagcgtacc    660
gaaacaatcg gtccaacaac gcgttctgcc tatgatttca caaagacaaa acgacccata    720
gacaagctcc agagacgaca ttagagcttt agaccgtgga atgtacaatg ctgactgctt    780
tttgagaaag atttttata aagaacaggc cct                                  813
```

```
<210> SEQ ID NO 131
<211> LENGTH: 1947
<212> TYPE: DNA
<213> ORGANISM: Chlamydia trachomatis

<400> SEQUENCE: 131
```

```
tcttttgcct atagagcaat ctcttatcat tgggtctgat ccaccagact atttcttcta     60
gatagagatt ctactacccc atccatggca ttcaacctct catcagtaaa cactttatta    120
gagttgttta tctgcccatc atcgatgata tcttctgaag tctttaatac cttcttacat    180
aagatccatc tctccggaga acagtgtcct tctatggata aaattcctac gcagatattc    240
acgcatccca aaatagcagg aatacctaga tagatggcat ttacaaacga agctgccgaa    300
actaggaata tcaaagcagt aatcactaaa agtagtccta tcaccactaa tcccacctta    360
aatgcagtgg aagatagaag attcgatata cgctctttca gtgttaatgg tgcagaacta    420
gtggaaatat cctgtgccga attggaagat ccagctcctt gaacaacggg tacagtgctc    480
atattttaca ttcctttttt ggttgtgagc agggagtcta cacaaacact tattttttc     540
aaaaacccgt ctagaatatg ctctgagacc gaaaatgaac tcttttattt tcatatagat    600
aacaaaaaaa agccgcccag gaatccctgg acggcaccta cacatcgata aaatcaaaga    660
ttaatagatg tgtgtattct ctgtatcaga aactggaaca gtcaatgtat cggaagaaag    720
aatcgcttcc ccacgagcat ctccagctga tactgctttc aatgttacag aaaactctac    780
agtttcttta gaacctaatc taggtaacga atcgaatact actgtattgc ctgtaatcgt    840
tcctttagtt ggtccagaga aggatacagg ttgcagttct ttagagaatt taagcattaa    900
agaaacattt gtatcttctg cagaacctct gttggtgaca caaatacggt aaacagtatt    960
ttctcctaca caaacagggt cacaagtatc tactacgcac atatgagtag cagcaactcc   1020
tttccagtaa gttgtcgctt ctgcgcaaga agtacaagta ccacagtcag agcagctctt   1080
cacaacaaca ttatttgtga attgtccagg agtttgtgct cttactagaa ctttatactg   1140
tagagactct ccaggattca gttctttcac agtccaaact actttattac aagaaatttg   1200
agctcctgca gcttcaagaa ctgtgactcc gggagaaaga gtgtcttcaa cgacgacatc   1260
```

-continued

```
tcgcaacaca agatctccag gattggaaac ggagatcaca tattctacag gcttacaaac   1320

ataagaccaa tctgctcctg caatacttac ttgtacgcaa ggctcattga tcacagttgt   1380

tacgcttgct gtatttttat gtcctccaca gtaagaaacc gttgctatat tggtagcacg   1440

accacgttta agcggacaaa actctacagt aattgttctg tgctctccag gttgcatatc   1500

tccaagagta aacgtcagta cacgctgtcc agaagagtga gcgtaaccat ctggaacagg   1560

attttcaaca acaacgttac gagctattgc tgttccttgg ttcactacat taattttgta   1620

aactactggg caacgcaaac aagcattctc tgggccttct tgtttaacac agatagcagg   1680

ttgtccacat tttgtaaccg aacggatctc tggacaagcg catactgttg cagctgtaaa   1740

gcagcaacct tctttaagag gttttaccca tacagtaatt ttactctttt cgccttgtcc   1800

taagcggtca attttccaaa ctagcttacc atcagcagta ggagttgtcg ctggatcact   1860

gcgtacgaac tctgcttcac atggtaattg ctgagtaatg ataacatcaa cacaatccct   1920

tttacctgta gcagtaattt caatagg                                       1947
```

<210> SEQ ID NO 132
<211> LENGTH: 1278
<212> TYPE: DNA
<213> ORGANISM: Chlamydia trachomatis

<400> SEQUENCE: 132

```
gataacaaaa aaaagccgcc caggaatccc tggacggcac ctacacatcg ataaaatcaa     60

agattaatag atgtgtgtat tctctgtatc agaaactgga acagtcaatg tatcggaaga    120

aagaatcgct tccccacgag catctccagc tgatactgct ttcaatgtta cagaaaactc    180

tacagtttct ttagaaccta atctaggtaa cgaatcgaat actactgtat tgcctgtaat    240

cgttccttta gttggtccag agaaggatac aggttgcagt tctttagaga atttaagcat    300

taaagaaaca tttgtatctt ctgcagaacc tctgttggtg acacaaatac ggtaaacagt    360

attttctcct acacaaacag ggtcacaagt atctactacg cacatatgag tagcagcaac    420

tcctttccag taagttgtcg cttctgcgca agaagtacaa gtaccacagt cagagcagct    480

cttcacaaca acattatttg tgaattgtcc aggagtttgt gctcttacta gaactttata    540

ctgtagagac tctccaggat tcagttcttt cacagtccaa actactttat tacaagaaat    600

ttgagctcct gcagcttcaa gaactgtgac tccgggagaa agagtgtctt caacgacgac    660

atctcgcaac acaagatctc caggattgga aacggagatc acatattcta caggcttaca    720

aacataagac caatctgctc ctgcaatact tacttgtacg caaggctcat tgatcacagt    780

tgttacgctt gctgtatttt tatgtcctcc acagtaagaa accgttgcta tattggtagc    840

acgaccacgt ttaagcggac aaaactctac agtaattgtt ctgtgctctc caggttgcat    900

atctccaaga gtaaacgtca gtacacgctg tccagaagag tgagcgtaac catctggaac    960

aggattttca acaacaacgt tacgagctat tgctgttcct tggttcacta cattaatttt   1020

gtaaactact gggcaacgca aacaagcatt ctctgggcct tcttgtttaa cacagatagc   1080

aggttgtcca cattttgtaa ccgaacggat ctctggacaa gcgcatactg ttgcagctgt   1140

aaagcagcaa ccttctttaa gaggttttac ccatacagta attttactct tttcgccttg   1200

tcctaagcgg tcaattttcc aaactagctt accatcagca gtaggagttg tcgctggatc   1260

actgcgtacg aactctgc                                                 1278
```

<210> SEQ ID NO 133
<211> LENGTH: 916

```
<212> TYPE: DNA
<213> ORGANISM: Chlamydia trachomatis

<400> SEQUENCE: 133

atggcgacaa tttaacgatt accggacaaa accatacatt atcatttaca gattctcaag     60

ggccagttct tcaaaattat gccttcattt cagcaggaga gacacttact ctgaaagatt    120

tttcgagttt gatgttctcg aaaaatgttt cttgcggaga aaagggaatg atctcaggga    180

aaaccgtgag tatttccgga gcaggcgaag tgattttttg ggataactct gtggggtatt    240

ctcctttgtc tattgtgcca gcatcgactc caactcctcc agcaccagca ccagctcctg    300

ctgcttcaag ctctttatct ccaacagtta gtgatgctcg gaaagggtct atttttctg     360

tagagactag tttggagatc tcaggcgtca aaaaaggggt catgttcgat aataatgccg    420

ggaattttgg aacagttttt cgaggtaata gtaataataa tgctggtagt gggggtagtg    480

ggtctgctac aacaccaagt tttacagtta aaaactgtaa agggaaagtt tctttcacag    540

ataacgtagc ctcctgtgga ggcggagtag tctacaaagg aactgtgctt ttcaaagaca    600

atgaaggagg catattcttc cgagggaaca cagcatacga tgatttaggg attcttgctg    660

ctactagtcg ggatcagaat acggagacag gaggcggtgg aggagttatt tgctctccag    720

atgattctgt aaagtttgaa ggcaataaag gttctattgt ttttgattac aactttgcaa    780

aaggcagagg cggaagcatc ctaacgaaag aattctctct tgtagcagat gattcggttg    840

tctttagtaa caatacagca gaaaaaggcg gtggagctat ttatgctcct acgtatcgat    900

ataagcacga atggag                                                    916


<210> SEQ ID NO 134
<211> LENGTH: 751
<212> TYPE: DNA
<213> ORGANISM: Chlamydia trachomatis
<220> FEATURE:
<221> NAME/KEY: misc_feature
<222> LOCATION: (1)...(751)
<223> OTHER INFORMATION: n = A,T,C or G

<400> SEQUENCE: 134

agcctctggc gaaggagagc cataaaaagt gcctaccagc ggagaaacaa taaaatctcc     60

ctgagcaggc acctcacttt ctttcttctc gatactctct ttaacaatag gattcccaag    120

gttttgatct gaggataagt tttgaaatcc agcaaacagt ctgttatcat aaaagactgg    180

ctcctgaata cttgggactg tatccctttc taactctaac tccaaacctt cacgcttgat    240

aacaatgcgc ttcacgtgcc gaattcggca cgaggctctt tcttacgagg atctcgagtc    300

aagaagcctt gagccttcaa ttcttgcttc atgtcttctt tctcttgcag aacagctcta    360

gctaaaccca atcgagtagc aataacctga ccttgaaccc ctcctccact tactcggata    420

atcaaatcga aactgttgac atcaccgagc attctgagcg gagctaagat ggttgctctt    480

tgaacttcaa gagggaaata ttgctctaaa gtctttccat ttacgtcaat ttttccattc    540

ccagaacgaa gacgaacgca cacctgcttt cttctgcctg ttgcaacaga ctcttgtatc    600

atattctttg tcacaaatta ccccaaatta cgcgtctaaa acaattggtt tgatagcttc    660

atactgtgcg taagaactac ctttcaaaac tcttaaagat ttcatttgac gtcttccaag    720

ttttgtttta ggcaacattc nttaacagca t                                   751


<210> SEQ ID NO 135
<211> LENGTH: 410
<212> TYPE: DNA
```

-continued

<213> ORGANISM: Chlamydia trachomatis

<400> SEQUENCE: 135
ataatccaga ctcttcctca tctggagata gcgctggaga ctctgaagaa ctgactgaga 60
cagaagctgg ttctacaaca gaaactccta ctttaatagg aggaggtgct atctatggag 120
aaactgttaa gattgagaac ttctctggcc aaggaatatt ttctggaaac aaagctatcg 180
ataacaccac agaaggctcc tcttccaaat ctgacgtcct cggaggtgcg gtctatgcta 240
aaacattgtt taatctcgat agcgggagct ctagacgaac tgtcaccttc tccgggaata 300
ctgtctcttc tcaatctaca acaggtcagg ttgctggagg agctatctac tctcctactg 360
taaccattgc tactcctgta gtattttcta aaaactctgc aacaaacaat 410

<210> SEQ ID NO 136
<211> LENGTH: 2719
<212> TYPE: DNA
<213> ORGANISM: Chlamydia trachomatis

<400> SEQUENCE: 136
ctcgtgccga aaagctttct gctctaccaa agagattcgt tttttaaatt cttcattctc 60
tctaagagat ttagtttctt tcgcagaaca attgatagat actccgtacg tttggggtgg 120
ccggtgcatt cataaacagc ttcctcgtaa tggtgtagat tgttcggggt atattcaact 180
actttaccaa gtcacaggaa gaaatatccc tcgcaatgct agagatcaat acagagactg 240
ttctccagta aaagatttct cgtctctacc tataggagga cttatcttcc tcaagaaagc 300
aagcacggga caaatcaacc atgttatgat gaaaatctcg gagcatgaat tcattcatgc 360
tgcggaaaaa atagggaaag tagaaaaagt aatcctagga aatagggctt tctttaaagg 420
gaatctattc tgctcattag gtgaaccgcc tatagaagct gtttttggcg ttcctaaaaa 480
tagaaaagcc ttcttttgaa agaaggcttt tctgaaacgc actccaatat atggacaagc 540
aatagcttat cgtttggaga attggaaact cttacgagct ttcttacgac cgtatttttt 600
acgctctttc ttacgaggat ctcgagtcaa gaagccttga gccttcaatt cttgcttcat 660
gtcttctttc tcttgcagaa cagctctagc taaacccaat cgagtagcaa taacctgacc 720
ttgaacccct cctccactta ctcggataat caaatcgaaa ctgttgacat caccgagcat 780
tctgagcgga gctaagatgg ttgctctttg aacttcaaga gggaaatatt gctctaaagt 840
ctttccattt acgtcaattt ttccattccc agaacgaaga cgaacgctag aaacagcctg 900
ctttcttctg cctgttgcaa cagactcttg tatcatattc tttgtcacaa attaccccaa 960
attacgcgtc taaaacaatt ggtttgatag cttcatactg tgcgtaagaa ctacctttca 1020
aaactcttaa agatttcatt tgacgtcttc caagttttgt tttaggcaac attcctttaa 1080
cagcatgctc gataacataa gcaggctttc gcgcaatcat gttttcaaaa ggaacttctc 1140
gcatcccaga aataaagcct gtgtaatagt gatacacttt ctgagttcct tttgcgccag 1200
tcaaacgcac tttctcagca ttgatcacaa tgacaccatc tcccatcgct acgtgaggag 1260
taaaagtcac cttatgctta cctctcagga tcttcgcaac ttctgaagat aatctcccta 1320
aggtcttccc ttcagcatta actacatacc aggctttgtt tcgatcgtcc gaagccttag 1380
ctagggtcgt tttcgtatct tttcttttt ccataactta aatcacctta tcagagggaa 1440
tgattataat tttgatgatt attttttcca aacaaaaagc agctgtattt gccttctaaa 1500
gaatttagaa aagaaaaaat ttcaaaaaga tctcttttct ttttgccttc aaaaacagcc 1560
ttacacttct atacttcttt cgaaaaaata ttttagggaa gttcttgaat catgatttac 1620

-continued

```
ataataaaaa aaatagttag ctgccatcag ctaaatttaa aaaggtgcta ccagacgcta   1680

aaagctggtc cacgtaatta atatcataat cagaaagaag aaacttcgga ttatccaaca   1740

tgaactgatg aaaaggaatt gtagaatgca ccccaccaat atggaactct tttaaagctc   1800

ttttcataat ggctatcgct tcctctcgat tctttccttt tgtgattacc ttagcaatca   1860

tggaatcata ataaggaggt atcgcataac cactgtagca agccccgtct actcgcacag   1920

caggacctgc aggagggaga taataatcta atctaccagg ggaaggagta aagttattaa   1980

ttggatcctc tgcattgatt cggcattgaa tcacgtgccc tttaaactct atattctttt   2040

gcttccaagg cagtttttct cccttagcga cactaatctg agcctttaac aaatcgatcc   2100

ctgtcacttc ttccgtaata gtatgttcca cttggatacg cgtattcatc tccatgaaat   2160

aaaaacgctt ctccttatct aacagaaatt ctactgttcc aacagagaaa tacccggcac   2220

tccgagctaa atccactgct acttttccaa ctttagctcg catttctgga gttaaaatag   2280

gacttggagt ctcttctatt aatttttgcc gacgcctttg tactgacaat ctcgttctcc   2340

aagatacacg taatttccgt gcttatctcc aattacttga acttctaaat gtcttggatt   2400

ttcaataaat ttttcaatat acacgtcagg attattaaat cccgcttctg cttcagcccg   2460

agcggcagta aaagccctat agaattcgtc tttttctcta acaatccgta ttcctcgtcc   2520

accgcctcca gcaacagctt tgatgacgat ggggaatccg atcttttctg caattctaat   2580

cccttccacc tcatccttca ctacaccttc agatccaggg attacagggc acttaatctt   2640

tttagccaac tgcttagctg cgactttatc tcccatagtc gctatcgact cagcactagg   2700

accgataaat ctcgtgccg                                                2719
```

<210> SEQ ID NO 137
<211> LENGTH: 2354
<212> TYPE: DNA
<213> ORGANISM: Chlamydia trachomatis

<400> SEQUENCE: 137

```
gtgcaagatg ggacgagttt gaagtttaat actagcacat aacttccctt ctggaggttt     60

aggagagagc ccttttatta gggctctctt tttttgtgtg tgaggaaagc tagcgtctaa    120

ctaaatgtct ctaagtaagg atgtttttag gggaaatagc gattttcagt gttgagaagc    180

ttagttacaa gacaataaac aaggctaaga aaaacctttc ttagccttgt ttctcaacga    240

atcgcctata gaagactaat cttccagcgt tgccctatgg ctcagcttca actggccttt    300

ttcgttaatg ctaaggagtt taacagcaag cttgtctcct tctttgacaa agccagagat    360

attgtctact ttttgtttag acaattcaga aatatgacag agcccttctt ttcctgggag    420

gacttctacg aatactccaa atgttgcgat agatgtaaca cggccattat aaactttacc    480

gacttcaact tctccagtta atccttcgat aagttcttta gctttgttaa tcgattcttg    540

ggtgcttgca gctatgttaa tgacgccgtc atcattgatg tcaacttgcg caccagaacg    600

ctcgataatt tgacggattt gttttcctcc gggaccaatg accgttgcga tttttgaggt    660

attgatctgc atagtttcaa tgcgcggagc atatttagaa acagttccct taggggaggc    720

cagaacctgt gtcataagat taaggatatg actacgccct tgtttagctt gcgctagagc    780

ttgctccata atcttatgag tgattccctc tatcttgata tccatttgga aagctgtaat    840

acctttagct gttccggcta ctttaaagtc catatctcct agatgatctt ctataccgga    900

aatatcagac aagatgatgg cttgatctcg atctaagatt aagcccatag caatacctgc    960
```

-continued

```
cacgggagct ttgataggaa ctccagcatc catgagtgca agacagcctc cacatacgga   1020

tgccatggag gaagatccat tagactcagt aatattagat tctaggcgaa tgatataagg   1080

gaatcgcgat gtctcaggaa gaacatgact taaagctttc tcagctaatt tcccatgtcc   1140

aatttcacgt cttcctgggg aaccaattct gccaacttct cctacggaga aaggagggaa   1200

gaaatactgt agatagaagc gagcggctcc atctccattc agatcttcga atcgctgtgc   1260

catattttcg cctccaagcg tacatacggc catgctttgc gtctctccgc gagtaaataa   1320

gcaacttccg tgtgttcttg gaagaaaagg agtctctatg gaaatggggc gaatctctgt   1380

ggtggttcgt ccatctacac gaataccaag atcttggata agagctcgca tttgattgga   1440

ttttgctgtc ttaaatgcag ccttaacgtt caacaaagaa aaatcactgt tttcttcttg   1500

aaccaagtta gcaataacgg attcctctaa ttctttcgag gcttgctcta gagcttcttt   1560

atctctaaaa gacaatgctt tttcgaattt ttctctaata aaatctgaaa ctacattttg   1620

tacgtcttct ggcatatcaa gaacggcaga gaaattcttt tgtttgccga tagctttctg   1680

ccatgcttca atagcatcgc atattttagc tatataggtt tgcccaaaaa caatagcttc   1740

tagaacttgc tcttctgtta aaaagtcgca atgtccttca atcattaaaa ctgcagaagc   1800

tgttcctgcc atgacgagat ccagcctgga ggcacttaac tcatctctgg ttgggttaat   1860

gacccacttt cctccgacga gcccaacgcg tacacccgca acgatacaat tttgaggaac   1920

ctctgagata gctaaagcgg cagaagctcc gcaaatagct agaggatcag gtaaagtttt   1980

cccgtcgtaa gaccaaacgt aggacaagac ttgaatatct tgcatgagtc tattaggaaa   2040

cgacggacgc aaagagcgat ccattagccg agaaacaaga atttctctct cggaaggccg   2100

tccttcacgt tttagaaatc ctccagaggt tcttcctgcg gaggaaaact tctcttgata   2160

gtctactctg aaaggcagaa aatcgacagc ctctgacaag gaggctgcac acgctgaaga   2220

aaaaacccaa gtctcgttca ttttgacgag aacagcccca ctggcctggc gagctatttt   2280

ccctgtctcg aaaattaatg ttttattttt gtctaacgca acagaaaaag tctcaaaagc   2340

catggagttg tcct                                                     2354
```

<210> SEQ ID NO 138
<211> LENGTH: 898
<212> TYPE: DNA
<213> ORGANISM: Chlamydia trachomatis

<400> SEQUENCE: 138

```
tcatcttgtc tgatatttcc ggtatagaag atcatctagg agatatggac tttaaagtag     60

ccggaacagc taaaggtatt acagctttcc aaatggatat caagatagag ggaatcactc    120

ataagattat ggagcaagct ctagcgcaag ctaaacaagg gcgtagtcat atccttaatc    180

ttatgacaca ggttctggcc tcccctaagg gaactgtttc taaatatgct ccgcgcattg    240

aaactatgca gatcaatacc tcaaaaatcg caacggtcat tggtcccgga ggaaaacaaa    300

tccgtcaaat tatcgagcgt tctggtgcgc aagttgacat caatgatgac ggcgtcatta    360

acatagctgc aagcacccaa gaatcgatta acaaagctaa agaacttatc gaaggattaa    420

ctggagaagt tgaagtcggt aaagtttata atggccgtgt tacatctatc gcaacatttg    480

gagtattcgt agaagtcctc ccaggaaaag aagggctctg tcatatttct gaattgtcta    540

aacaaaaagt agacaatatc tctggctttg tcaaagaagg agacaagctt gctgttaaac    600

tccttagcat taacgaaaaa ggccagttga agctgagcca tagggcaacg ctggaagatt    660

agtcttctat aggcgattcg ttgagaaaca aggctaagaa aggtttttct tagccttgtt    720
```

-continued

```
tattgtcttg taactaagct tctcaacact gaaaatcgct atttcccta aaaacatcct    780

tacttagaga catttagtta gacgctagct ttcctcacac acaaaaaaag agagccctaa    840

taaaagggct ctctcctaaa cctccagaag ggaagttatg tgctagtatt aaacttca      898


<210> SEQ ID NO 139
<211> LENGTH: 660
<212> TYPE: PRT
<213> ORGANISM: Chlamydia trachomatis

<400> SEQUENCE: 139

Met His His His His His His Met Glu Ser Gly Pro Glu Ser Val Ser
                  5                  10                  15

Ser Asn Gln Ser Ser Met Asn Pro Ile Ile Asn Gly Gln Ile Ala Ser
             20                  25                  30

Asn Ser Glu Thr Lys Glu Ser Thr Lys Ala Ser Glu Ala Ser Pro Ser
         35                  40                  45

Ala Ser Ser Ser Val Ser Ser Trp Ser Phe Leu Ser Ser Ala Lys Asn
     50                  55                  60

Ala Leu Ile Ser Leu Arg Asp Ala Ile Leu Asn Lys Asn Ser Ser Pro
 65                  70                  75                  80

Thr Asp Ser Leu Ser Gln Leu Glu Ala Ser Thr Ser Thr Ser Thr Val
                 85                  90                  95

Thr Arg Val Ala Ala Lys Asp Tyr Asp Glu Ala Lys Ser Asn Phe Asp
            100                 105                 110

Thr Ala Lys Ser Gly Leu Glu Asn Ala Lys Thr Leu Ala Glu Tyr Glu
        115                 120                 125

Thr Lys Met Ala Asp Leu Met Ala Ala Leu Gln Asp Met Glu Arg Leu
    130                 135                 140

Ala Asn Ser Asp Pro Ser Asn Asn His Thr Glu Glu Val Asn Asn Ile
145                 150                 155                 160

Lys Lys Ala Leu Glu Ala Gln Lys Asp Thr Ile Asp Lys Leu Asn Lys
                165                 170                 175

Leu Val Thr Leu Gln Asn Gln Asn Lys Ser Leu Thr Glu Val Leu Lys
            180                 185                 190

Thr Thr Asp Ser Ala Asp Gln Ile Pro Ala Ile Asn Ser Gln Leu Glu
        195                 200                 205

Ile Asn Lys Asn Ser Ala Asp Gln Ile Ile Lys Asp Leu Glu Arg Gln
    210                 215                 220

Asn Ile Ser Tyr Glu Ala Val Leu Thr Asn Ala Gly Glu Val Ile Lys
225                 230                 235                 240

Ala Ser Ser Glu Ala Gly Ile Lys Leu Gly Gln Ala Leu Gln Ser Ile
                245                 250                 255

Val Asp Ala Gly Asp Gln Ser Gln Ala Ala Val Leu Gln Ala Gln Gln
            260                 265                 270

Asn Asn Ser Pro Asp Asn Ile Ala Ala Thr Lys Glu Leu Ile Asp Ala
        275                 280                 285

Ala Glu Thr Lys Val Asn Glu Leu Lys Gln Glu His Thr Gly Leu Thr
    290                 295                 300

Asp Ser Pro Leu Val Lys Lys Ala Glu Glu Gln Ile Ser Gln Ala Gln
305                 310                 315                 320

Lys Asp Ile Gln Glu Ile Lys Pro Ser Gly Ser Asp Ile Pro Ile Val
                325                 330                 335

Gly Pro Ser Gly Ser Ala Ala Ser Ala Gly Ser Ala Ala Gly Ala Leu
```

-continued

```
            340                 345                 350

Lys Ser Ser Asn Asn Ser Gly Arg Ile Ser Leu Leu Leu Asp Asp Val
        355                 360                 365

Asp Asn Glu Met Ala Ala Ile Ala Leu Gln Gly Phe Arg Ser Met Ile
    370                 375                 380

Glu Gln Phe Asn Val Asn Asn Pro Ala Thr Ala Lys Glu Leu Gln Ala
385                 390                 395                 400

Met Glu Ala Gln Leu Thr Ala Met Ser Asp Gln Leu Val Gly Ala Asp
                405                 410                 415

Gly Glu Leu Pro Ala Glu Ile Gln Ala Ile Lys Asp Ala Leu Ala Gln
            420                 425                 430

Ala Leu Lys Gln Pro Ser Ala Asp Gly Leu Ala Thr Ala Met Gly Gln
        435                 440                 445

Val Ala Phe Ala Ala Ala Lys Val Gly Gly Gly Ser Ala Gly Thr Ala
    450                 455                 460

Gly Thr Val Gln Met Asn Val Lys Gln Leu Tyr Lys Thr Ala Phe Ser
465                 470                 475                 480

Ser Thr Ser Ser Ser Ser Tyr Ala Ala Ala Leu Ser Asp Gly Tyr Ser
                485                 490                 495

Ala Tyr Lys Thr Leu Asn Ser Leu Tyr Ser Glu Ser Arg Ser Gly Val
            500                 505                 510

Gln Ser Ala Ile Ser Gln Thr Ala Asn Pro Ala Leu Ser Arg Ser Val
        515                 520                 525

Ser Arg Ser Gly Ile Glu Ser Gln Gly Arg Ser Ala Asp Ala Ser Gln
    530                 535                 540

Arg Ala Ala Glu Thr Ile Val Arg Asp Ser Gln Thr Leu Gly Asp Val
545                 550                 555                 560

Tyr Ser Arg Leu Gln Val Leu Asp Ser Leu Met Ser Thr Ile Val Ser
                565                 570                 575

Asn Pro Gln Ala Asn Gln Glu Glu Ile Met Gln Lys Leu Thr Ala Ser
            580                 585                 590

Ile Ser Lys Ala Pro Gln Phe Gly Tyr Pro Ala Val Gln Asn Ser Ala
        595                 600                 605

Asp Ser Leu Gln Lys Phe Ala Ala Gln Leu Glu Arg Glu Phe Val Asp
    610                 615                 620

Gly Glu Arg Ser Leu Ala Glu Ser Gln Glu Asn Ala Phe Arg Lys Gln
625                 630                 635                 640

Pro Ala Phe Ile Gln Gln Val Leu Val Asn Ile Ala Ser Leu Phe Ser
                645                 650                 655

Gly Tyr Leu Ser
            660


<210> SEQ ID NO 140
<211> LENGTH: 598
<212> TYPE: PRT
<213> ORGANISM: Chlamydia trachomatis

<400> SEQUENCE: 140

Met His His His His His His Met Ser Ile Arg Gly Val Gly Gly Asn
                  5                  10                  15

Gly Asn Ser Arg Ile Pro Ser His Asn Gly Asp Gly Ser Asn Arg Arg
             20                  25                  30

Ser Gln Asn Thr Lys Gly Asn Asn Lys Val Glu Asp Arg Val Cys Ser
         35                  40                  45
```

-continued

```
Leu Tyr Ser Ser Arg Ser Asn Glu Asn Arg Glu Ser Pro Tyr Ala Val
     50                  55                  60

Val Asp Val Ser Ser Met Ile Glu Ser Thr Pro Thr Ser Gly Glu Thr
 65                  70                  75                  80

Thr Arg Ala Ser Arg Gly Val Leu Ser Arg Phe Gln Arg Gly Leu Val
                 85                  90                  95

Arg Ile Ala Asp Lys Val Arg Arg Ala Val Gln Cys Ala Trp Ser Ser
            100                 105                 110

Val Ser Thr Ser Arg Ser Ser Ala Thr Arg Ala Ala Glu Ser Gly Ser
        115                 120                 125

Ser Ser Arg Thr Ala Arg Gly Ala Ser Ser Gly Tyr Arg Glu Tyr Ser
    130                 135                 140

Pro Ser Ala Ala Arg Gly Leu Arg Leu Met Phe Thr Asp Phe Trp Arg
145                 150                 155                 160

Thr Arg Val Leu Arg Gln Thr Ser Pro Met Ala Gly Val Phe Gly Asn
                165                 170                 175

Leu Asp Val Asn Glu Ala Arg Leu Met Ala Ala Tyr Thr Ser Glu Cys
            180                 185                 190

Ala Asp His Leu Glu Ala Lys Glu Leu Ala Gly Pro Asp Gly Val Ala
        195                 200                 205

Ala Ala Arg Glu Ile Ala Lys Arg Trp Glu Lys Arg Val Arg Asp Leu
    210                 215                 220

Gln Asp Lys Gly Ala Ala Arg Lys Leu Leu Asn Asp Pro Leu Gly Arg
225                 230                 235                 240

Arg Thr Pro Asn Tyr Gln Ser Lys Asn Pro Gly Glu Tyr Thr Val Gly
                245                 250                 255

Asn Ser Met Phe Tyr Asp Gly Pro Gln Val Ala Asn Leu Gln Asn Val
            260                 265                 270

Asp Thr Gly Phe Trp Leu Asp Met Ser Asn Leu Ser Asp Val Val Leu
        275                 280                 285

Ser Arg Glu Ile Gln Thr Gly Leu Arg Ala Arg Ala Thr Leu Glu Glu
    290                 295                 300

Ser Met Pro Met Leu Glu Asn Leu Glu Glu Arg Phe Arg Arg Leu Gln
305                 310                 315                 320

Glu Thr Cys Asp Ala Ala Arg Thr Glu Ile Glu Glu Ser Gly Trp Thr
                325                 330                 335

Arg Glu Ser Ala Ser Arg Met Glu Gly Asp Glu Ala Gln Gly Pro Ser
            340                 345                 350

Arg Val Gln Gln Ala Phe Gln Ser Phe Val Asn Glu Cys Asn Ser Ile
        355                 360                 365

Glu Phe Ser Phe Gly Ser Phe Gly Glu His Val Arg Val Leu Cys Ala
    370                 375                 380

Arg Val Ser Arg Gly Leu Ala Ala Ala Gly Glu Ala Ile Arg Arg Cys
385                 390                 395                 400

Phe Ser Cys Cys Lys Gly Ser Thr His Arg Tyr Ala Pro Arg Asp Asp
                405                 410                 415

Leu Ser Pro Glu Gly Ala Ser Leu Ala Glu Thr Leu Ala Arg Phe Ala
            420                 425                 430

Asp Asp Met Gly Ile Glu Arg Gly Ala Asp Gly Thr Tyr Asp Ile Pro
        435                 440                 445

Leu Val Asp Asp Trp Arg Arg Gly Val Pro Ser Ile Glu Gly Glu Gly
    450                 455                 460

Ser Asp Ser Ile Tyr Glu Ile Met Met Pro Ile Tyr Glu Val Met Asn
```

-continued

```
465                 470                 475                 480

Met Asp Leu Glu Thr Arg Arg Ser Phe Ala Val Gln Gln Gly His Tyr
                485                 490                 495

Gln Asp Pro Arg Ala Ser Asp Tyr Asp Leu Pro Arg Ala Ser Asp Tyr
            500                 505                 510

Asp Leu Pro Arg Ser Pro Tyr Pro Thr Pro Pro Leu Pro Pro Arg Tyr
        515                 520                 525

Gln Leu Gln Asn Met Asp Val Glu Ala Gly Phe Arg Glu Ala Val Tyr
    530                 535                 540

Ala Ser Phe Val Ala Gly Met Tyr Asn Tyr Val Val Thr Gln Pro Gln
545                 550                 555                 560

Glu Arg Ile Pro Asn Ser Gln Gln Val Glu Gly Ile Leu Arg Asp Met
                565                 570                 575

Leu Thr Asn Gly Ser Gln Thr Phe Arg Asp Leu Met Lys Arg Trp Asn
            580                 585                 590

Arg Glu Val Asp Arg Glu
        595
```

COMPOUNDS AND METHODS FOR TREATMENT AND DIAGNOSIS OF CHLAMYDIAL INFECTION

CROSS REFERENCE TO RELATED APPLICATIONS

This application is a divisional of U.S. Utility Application No. 09/841,260, filed Apr. 23, 2001, now abandoned, which is related to U.S. Provisional Application No. 60/198,853, filed Apr. 21, 2000, and U.S. Provisional Application No. 60/219,752, filed Jul. 20, 2000, which are incorporated by reference in their entireties.

TECHNICAL FIELD

The present invention relates generally to the detection and treatment of Chlamydial infection. In particular, the invention is related to polypeptides comprising a *Chlamydia* antigen and the use of such polypeptides for the serodiagnosis and treatment of Chlamydial infection.

BACKGROUND OF THE INVENTION

Chlamydiae are intracellular bacterial pathogens that are responsible for a wide variety of important human and animal infections. *Chlamydia trachomatis* is one of the most common causes of sexually transmitted diseases and can lead to pelvic inflammatory disease (PID), resulting in tubal obstruction and infertility. *Chlamydia trachomatis* may also play a role in male infertility. In 1990, the cost of treating PID in the US was estimated to be $4 billion. Trachoma, due to ocular infection with *Chlamydia trachomatis*, is the leading cause of preventable blindness worldwide. *Chlamydia* pneumonia is a major cause of acute respiratory tract infections in humans and is also believed to play a role in the pathogenesis of atherosclerosis and, in particular, coronary heart disease. Individuals with a high titer of antibodies to *Chlamydia* pneumonia have been shown to be at least twice as likely to suffer from coronary heart disease as seronegative individuals. Chlamydial infections thus constitute a significant health problem both in the US and worldwide.

Chlamydial infection is often asymptomatic. For example, by the time a woman seeks medical attention for PID, irreversible damage may have already occurred resulting in infertility. There thus remains a need in the art for improved vaccines and pharmaceutical compositions for the prevention and treatment of *Chlamydia* infections. The present invention fulfills this need and further provides other related advantages.

SUMMARY OF THE INVENTION

The present invention provides compositions and methods for the diagnosis and therapy of *Chlamydia* infection. In one aspect, the present invention provides polypeptides comprising an immunogenic portion of a *Chlamydia* antigen, or a variant of such an antigen. Certain portions and other variants are immunogenic, such that the ability of the variant to react with antigen-specific antisera is not substantially diminished. Within certain embodiments, the polypeptide comprises an amino acid sequence encoded by a polynucleotide sequence selected from the group consisting of (a) a sequence of SEQ ID NO: 1-48, 114-121, and 125-138; (b) the complements of said sequences; and (c) sequences that hybridize to a sequence of (a) or (b) under moderately stringent conditions. In specific embodiments, the polypeptides of the present invention comprise at least a portion of a Chlamydial protein that includes an amino acid sequence selected from the group consisting of sequences recited in SEQ ID NO:122-124 and 139-140 and variants thereof.

The present invention further provides polynucleotides that encode a polypeptide as described above, or a portion thereof (such as a portion encoding at least 15 amino acid residues of a Chlamydial protein), expression vectors comprising such polynucleotides and host cells transformed or transfected with such expression vectors.

In a related aspect, polynucleotide sequences encoding the above polypeptides, recombinant expression vectors comprising one or more of these polynucleotide sequences and host cells transformed or transfected with such expression vectors are also provided.

In another aspect, the present invention provides fusion proteins comprising an inventive polypeptide, or, alternatively, an inventive polypeptide and a known *Chlamydia* antigen, as well as polynucleotides encoding such fusion proteins, in combination with a physiologically acceptable carrier or immunostimulant for use as pharmaceutical compositions and vaccines thereof.

The present invention further provides pharmaceutical compositions that comprise: (a) an antibody, both polyclonal and monoclonal, or antigen-binding fragment thereof that specifically binds to a Chlamydial protein; and (b) a physiologically acceptable carrier. Within other aspects, the present invention provides pharmaceutical compositions that comprise one or more *Chlamydia* polypeptides disclosed herein, for example, a polypeptide of SEQ ID NO: 95-109, 122-124 and 139-140, or a polynucleotide molecule encoding such a polypeptide, such as a polynucleotide sequence of SEQ ID NO: 1-48, 80-94, 114-121 and 125-138, and a physiologically acceptable carrier. The invention also provides compositions for prophylactic and therapeutic purposes comprising one or more of the disclosed polynucleotides and/or polypeptides and an immunostimulant, e.g., an adjuvant.

In yet another aspect, methods are provided for stimulating an immune response in a patient, e.g., for inducing protective immunity in a patient, comprising administering to a patient an effective amount of one or more of the above pharmaceutical compositions or vaccines.

In yet a further aspect, methods for the treatment of *Chlamydia* infection in a patient are provided, the methods comprising obtaining peripheral blood mononuclear cells (PBMC) from the patient, incubating the PBMC with a polypeptide of the present invention (or a polynucleotide that encodes such a polypeptide) to provide incubated T cells and administering the incubated T cells to the patient. The present invention additionally provides methods for the treatment of *Chlamydia* infection that comprise incubating antigen presenting cells with a polypeptide of the present invention (or a polynucleotide that encodes such a polypeptide) to provide incubated antigen presenting cells and administering the incubated antigen presenting cells to the patient. Proliferated cells may, but need not, be cloned prior to administration to the patient. In certain embodiments, the antigen presenting cells are selected from the group consisting of dendritic cells, macrophages, monocytes, B-cells, and fibroblasts. Compositions for the treatment of *Chlamydia* infection comprising T cells or antigen presenting cells that have been incubated with a polypeptide or polynucleotide of the present invention are also provided. Within related aspects, vaccines are provided that comprise: (a) an antigen presenting cell that expresses a polypeptide as described above and (b) an immunostimulant.

The present invention further provides, within other aspects, methods for removing Chlamydial-infected cells from a biological sample, comprising contacting a biological sample with T cells that specifically react with a Chlamydial protein, wherein the step of contacting is performed under conditions and for a time sufficient to permit the removal of cells expressing the protein from the sample.

Within related aspects, methods are provided for inhibiting the development of Chlamydial infection in a patient, comprising administering to a patient a biological sample treated as described above. In further aspects of the subject invention, methods and diagnostic kits are provided for detecting *Chlamydia* infection in a patient. In one embodiment, the method comprises: (a) contacting a biological sample with at least one of the polypeptides or fusion proteins disclosed herein; and (b) detecting in the sample the presence of binding agents that bind to the polypeptide or fusion protein, thereby detecting *Chlamydia* infection in the biological sample. Suitable biological samples include whole blood, sputum, serum, plasma, saliva, cerebrospinal fluid and urine. In one embodiment, the diagnostic kits comprise one or more of the polypeptides or fusion proteins disclosed herein in combination with a detection reagent. In yet another embodiment, the diagnostic kits comprise either a monoclonal antibody or a polyclonal antibody that binds with a polypeptide of the present invention.

The present invention also provides methods for detecting *Chlamydia* infection comprising: (a) obtaining a biological sample from a patient; (b) contacting the sample with at least two oligonucleotide primers in a polymerase chain reaction, at least one of the oligonucleotide primers being specific for a polynucleotide sequence disclosed herein; and (c) detecting in the sample a polynucleotide sequence that amplifies in the presence of the oligonucleotide primers. In one embodiment, the oligonucleotide primer comprises at least about 10 contiguous nucleotides of a polynucleotide sequence peptide disclosed herein, or of a sequence that hybridizes thereto.

In a further aspect, the present invention provides a method for detecting *Chlamydia* infection in a patient comprising: (a) obtaining a biological sample from the patient; (b) contacting the sample with an oligonucleotide probe specific for a polynucleotide sequence disclosed herein; and (c) detecting in the sample a polynucleotide sequence that hybridizes to the oligonucleotide probe. In one embodiment, the oligonucleotide probe comprises at least about 15 contiguous nucleotides of a polynucleotide sequence disclosed herein, or a sequence that hybridizes thereto.

These and other aspects of the present invention will become apparent upon reference to the following detailed description. All references disclosed herein are hereby incorporated by reference in their entirety as if each was incorporated individually.

Sequence Identifiers

SEQ ID NO:1 sets forth a DNA sequence identified for clone E4-A2-39 (CT10 positive) that is 1311 bp and contains the entire ORF for CT460 (SWIB) and a partial ORF for CT461 (yaeI).

SEQ ID NO:2 sets forth a DNA sequence for clone E2-B10-52 (CT10 positive) that has a 1516 bp insert that contains partial ORFs for genes CT827 (nrdA-ribonucleoside reductase large chain) and CT828 (ndrB-ribonucleoside reductase small chain). These genes as were not identified in a Ct L2 library screening.

SEQ ID NO:3 sets forth a DNA sequence for clone E1-B1-80 (CT10 positive) (2397 bp) that contains partial ORFs for several genes, CT812 (pmpD), CT015 (phoH ATPase), CT016 (hypothetical protein) and pGp1-D (*C. trachomatis* plasmid gene).

SEQ ID NO:4 sets forth a DNA sequence for clone E4-F9-4 (CT10, CL8, CT1, CT5, CT13, and CHH037 positive) that contains a 1094 bp insert that has a partial ORF for the gene CT316 (L7/L12 ribosomal protein) as well as a partial ORF for gene CT315 (RNA polymerase beta).

SEQ ID NO:5 sets forth a DNA sequence for clone E2-H6-40 (CT3 positive) that has a 2129 bp insert that contains the entire ORF for the gene CT288 and very small fragments of genes CT287 and CT289. Genes in this clone have not been identified in screening with a Ct L2 library.

SEQ ID NO:6 sets forth a DNA sequence for clone E5-D4-2 (CT3, CT10, CT1, CT5, CT12, and CHH037 positive) that has a 1828 bp insert that contains a partial ORF for gene CT378 (pgi), complete ORF for gene CT377 (ltuA) and a complete ORF for the gene CT376 (malate dehydrogenase). In addition, the patient lines CT10, CT11, CT5, CT12, and CHH037 also identified this clone.

SEQ ID NO:7 sets forth a DNA sequence for clone E6-C1-31 (CT3 positive) that has a 861 bp insert that contains a partial ORF for gene CT858.

SEQ ID NO:8 sets forth a DNA sequence for clone E9-E11-76 (CT3 positive) that contains a 763 bp insert that is an amino terminal region of the gene for CT798 (Glycogen synthase). This gene was not identified in a previous screening with a Ct L2 library.

SEQ ID NO:9 sets forth a DNA sequence for clone E2-A9-26 (CT1-positive) that contains part of the gene for ORF-3 which is found on the plasmid in *Chlamydia trachomatis.*

SEQ ID NO:10 sets forth a DNA sequence for clone E2-G8-94 (CT1-positive) that has the carboxy terminal end of Lpda gene as well as a partial ORF for CT556.

SEQ ID NO: 11 sets forth a DNA sequence for clone E1-H1-14 (CT1 positive) that has a 1474 bp insert that contains the amino terminal part of an Lpda ORF on the complementary strand.

SEQ ID NO: 12 sets forth a DNA sequence for clone E1-A5-53 (CT1 positive) that contains a 2017 bp insert that has an amino terminal portion of the ORF for dnaK gene on the complementary strand, a partial ORF for the grpE gene (CT395) and a partial ORF for CT166.

SEQ ID NO: 13 sets forth a DNA sequence for clone E3-A1-50 (positive on CT1 line) that is 1199 bp and contains a carboxy terminal portion of the ORF for CT622.

SEQ ID NO: 14 sets forth a DNA sequence for clone E3-E2-22 that has 877 bp, containing a complete ORF for CT610 on the complementary strand, and was positive on both CT3 and CT10 lines.

SEQ ID NO: 15 sets forth the DNA sequence for clone E5-E2-10 (CT10 positive) which is 427 bp and contains a partial ORF for the major outer membrane protein omp1. SEQ ID NO: 16 sets forth the DNA sequence for clone E2-D5-89 (516 bp) which is a CT10 positive clone that contains a partial ORF for pmpD gene (CT812).

SEQ ID NO: 17 sets forth the DNA sequence for clone E4-G9-75 (CT10 positive) which is 723 bp and contains a partial ORF for the amino terminal region of the pmpH gene (CT872).

SEQ ID NO: 18 sets forth the DNA sequence for clone E3-F2-37 (CT10, CT3, CT11, and CT13 positive-1377 bp insert) which contains a partial ORF for the tRNA-Trp (CT322) gene and a complete ORF for the gene secE (CT321).

SEQ ID NO: 19 sets forth the DNA sequence for clone E5-A11-8 (CT10 positive-736 bp) which contains the complete ORF for groES (CT111) and a majority of the ORF for groEL (CT110).

SEQ ID NO: 20 sets forth the DNA sequence for clone E7-H11-61 (CT3 positive-1135 bp) which has partial inserts for fliA (CT061), tyrS (CT062), TSA (CT603) and a hypothetical protein (CT602).

SEQ ID NO: 21 sets forth a DNA sequence for clone E6-C8-95 which contains a 731 bp insert that was identified using the donor lines CT3, CT1, and CT12 line. This insert has a carboxy terminal half for the gene for the 60 kDa ORF.

SEQ ID NO: 22 sets forth the DNA sequence for clone E4-D2-79 (CT3 positive) which contains a 1181 bp insert that is a partial ORF for nrdA gene. The ORF for this gene was also identified from clone E2-B10-52 (CT10 positive).

SEQ ID NO: 23 sets forth the DNA sequence for clone E1-F9-79 (167 bp; CT11 positive) which contains a partial ORF for the gene CT133 on the complementary strand. CT133 is a predicted rRNA methylase.

SEQ ID NO: 24 sets forth the DNA sequence for clone E2-G12-52 (1265 bp; CT11 positive) which contains a partial ORF for clpB, a protease ATPase.

SEQ ID NO: 25 sets forth the DNA sequence for clone E4-H3-56 (463 bp insert; CT1 positive) which contains a partial ORF for the TSA gene (CT603) on the complementary strand.

SEQ ID NO: 26 sets forth the DNA sequence for clone E5-E9-3 (CT1 positive) that contains a 636 bp insert partially encoding the ORF for dnaK like gene. Part of this sequence was also identified in clone E1-A5-53.

SEQ ID NO:27 sets forth the full-length serovar E DNA sequence of CT875.

SEQ ID NO:28 sets for the full-length serovar E DNA sequence of CT622.

SEQ ID NO:29 sets forth the DNA sequence for clone E3-B4-18 (CT1 positive) that contains a 1224 bp insert containing 4 ORFs. The complete ORF for CT772, and the partial ORFs of CT771, CT191, and CT190.

SEQ ID NO:30 sets forth the DNA sequence for the clone E9-E10-51 (CT10 positive) that contains an 883 bp insert containing two partial ORF, CT680 and CT679.

SEQ ID NO:31 sets forth the DNA sequence of the clone E9-D5-8 (CT10, CTCT1, CT4, and CT11 positive) that contains a393 bp insert containing the partial ORF for CT680.

SEQ ID NO:32 sets forth the DNA sequence of the clone E7-B1-16 (CT10, CT3, CT5, CT11, CT13, and CHH037 positive) that contains a 2577 bp insert containing three ORFs, two full length ORFs for CT694 and CT695 and the third containing the N-terminal portion of CT969.

SEQ ID NO:33 sets forth the DNA sequence of the clone E9-G2-93 (CT10 positive) that contains a 554 bp insert containing a partial ORF for CT178.

SEQ ID NO:34 sets forth the DNA sequence of the clone E5-A8-85 (CT1 positive) that contains a 1433 bp insert containing two partial ORFs for CT875 and CT001.

SEQ ID NO:35 sets forth the DNA sequence of the clone E10-C6-45 (CT3 positive) that contains a 196 bp insert containing a partial ORF for CT827.

SEQ ID NO:36 sets forth the DNA sequence of the clone E7-H11-10 (CT3 positive) that contains a 1990 bp insert containing the partial ORFs of CT610 and CT613 and the complete ORFs of CT611 and CT612.

SEQ ID NO:37 sets forth the DNA sequence of the clone E2-F7-11 (CT3 and CT10 positive) that contains a 2093 bp insert. It contains a large region of CT609, a complete ORF for CT610 and a partial ORF for CT611.

SEQ ID NO:38 sets forth the DNA sequence of the clone E3-A3-31 (CT1 positive) that contains an 1834 bp insert containing a large region of CT622.

SEQ ID NO:39 sets forth the DNA sequence of the clone E1-G9-23 (CT3 positive) that contains an 1180 bp insert containing almost the entire ORF for CT798.

SEQ ID NO:40 sets forth the DNA sequence of the clone E4-D6-21 (CT 3 positive) that contains a 1297 bp insert containing the partial ORFs of CT329 and CT327 and the complete ORF of CT328.

SEQ ID NO:41 sets forth the DNA sequence of the clone E3-F3-18 (CT1 positive) that contains an 1141 bp insert containing the partial ORF of CT871.

SEQ ID NO:42 sets forth the DNA sequence of the clone E10-B2-57 (CT10 positive) that contains an 822 bp insert containing the complete ORF of CT066.

SEQ ID NO:43 sets forth the DNA sequence of the clone E3-F3-7 (CT1 positive) that contains a 1643 bp insert containing the partial ORFs of CT869 and CT870.

SEQ ID NO:44 sets forth the DNA sequence of the clone E10-H8-1 (CT3 and CT10 positive) that contains an 1862 bp insert containing the partial ORFs of CT871 and CT872.

SEQ ID NO:45 sets forth the DNA sequence of the clone E3-D10-46 (CT1, CT3, CT4, CT11, and CT12 positive) that contains a 1666 bp insert containing the partial ORFs for CT770 and CT773 and the complete ORFs for CT771 and CT722.

SEQ ID NO:46 sets forth the DNA sequence of the clone E2-D8-19 (CT1 positive) that contains a 2010 bp insert containing partial ORFs, ORF3 and ORF6, and complete ORFs, ORF4 and ORF5.

SEQ ID NO:47 sets forth the DNA sequence of the clone E4-C3-40 (CT10 positive) that contains a 2044 bp insert containing the partial ORF for CT827 and a complete ORF for CT828.

SEQ ID NO:48 sets forth the DNA sequence of the clone E3-H6-10 (CT12 positive) that contains a 3743 bp insert containing the partial ORFs for CT223 and CT229 and the complete ORFs for CT224 and CT224, CT225, CT226, CT227, and CT228.

SEQ ID NO:49 sets forth the DNA sequence for the *Chlamydia pneumoniae* homologue, CPn0454 of the *Chlamydia trachomatis* gene CT872.

SEQ ID NO:50 sets forth the DNA sequence for the *Chlamydia pneumoniae* homologue, CPn0187, of the *Chlamydia trachomatis* gene CT133.

SEQ ID NO:51 sets forth the DNA sequence for the *Chlamydia pneumoniae* homologue, CPn0075 of the *Chlamydia trachomatis* gene CT321.

SEQ ID NO:52 sets forth the DNA sequence for the *Chlamydia pneumoniae* homologue, CPn0074, of the *Chlamydia trachomatis* gene CT322.

SEQ ID NO:53 sets forth the DNA sequence for the *Chlamydia pneumoniae* homologue, CPn0948, of the *Chlamydia trachomatis* gene CT798.

SEQ ID NO:54 sets forth the DNA sequence for the *Chlamydia pneumoniae* homologue, CPn0985, of the *Chlamydia trachomatis* gene CT828.

SEQ ID NO:55 sets forth the DNA sequence for the *Chlamydia pneumoniae* homologue, CPn0984, of the *Chlamydia trachomatis* gene CT827.

SEQ ID NO:56 sets forth the DNA sequence for the *Chlamydia pneumoniae* homologue, CPn0062, of the *Chlamydia trachomatis* gene CT289.

SEQ ID NO:57 sets forth the DNA sequence for the *Chlamydia pneumoniae* homologue, CPn00065, of the *Chlamydia trachomatis* gene CT288.

SEQ ID NO:58 sets forth the DNA sequence for the *Chlamydia pneumoniae* homologue, CPn0438, of the *Chlamydia trachomatis* gene CT287.

SEQ ID NO:59 sets forth the DNA sequence for the *Chlamydia pneumoniae* homologue, CPn0963, of the *Chlamydia trachomatis* gene CT812.

SEQ ID NO:60 sets forth the DNA sequence for the *Chlamydia pneumoniae* homologue, CPn0778, of the *Chlamydia trachomatis* gene CT603.

SEQ ID NO:61 sets forth the DNA sequence for the *Chlamydia pneumoniae* homologue, CPn0503, of the *Chlamydia trachomatis* gene CT396.

SEQ ID NO:62 sets forth the DNA sequence for the *Chlamydia pneumoniae* homologue, CPn1016, of the *Chlamydia trachomatis* gene CT858.

SEQ ID NO:63 sets forth the DNA sequence for the *Chlamydia pneumoniae* homologue, CPn0728, of the *Chlamydia trachomatis* gene CT622.

SEQ ID NO:64 sets forth the DNA sequence for the *Chlamydia pneumoniae* homologue, CPn0557, of the *Chlamydia trachomatis* gene CT460.

SEQ ID NO:65 sets forth the amino acid sequence for the *Chlamydia pneumoniae* homologue, CPn0454, of the *Chlamydia trachomatis* gene CT872.

SEQ ID NO:66 sets forth the amino acid sequence for the *Chlamydia pneumoniae* homologue, CPn0187, of the *Chlamydia trachomatis* gene CT133.

SEQ ID NO:67 sets forth the amino acid sequence for the *Chlamydia pneumoniae* homologue, CPn0075, of the *Chlamydia trachomatis* gene CT321.

SEQ ID NO:68 sets forth the amino acid sequence for the *Chlamydia pneumoniae* homologue, CPn0074, of the *Chlamydia trachomatis* gene CT322.

SEQ ID NO:69 sets forth the amino acid sequence for the *Chlamydia pneumoniae* homologue, CPn0948, of the *Chlamydia trachomatis* gene CT798.

SEQ ID NO:70 sets forth the amino acid sequence for the *Chlamydia pneumoniae* homologue, CPn0985, of the *Chlamydia trachomatis* gene CT828.

SEQ ID NO:71 sets forth the amino acid sequence for the *Chlamydia pneumoniae* homologue, CPn0984, of the *Chlamydia trachomatis* gene CT827.

SEQ ID NO:72 sets forth the amino acid sequence for the *Chlamydia pneumoniae* homologue, CPn0062, of the *Chlamydia trachomatis* gene CT289.

SEQ ID NO:73 sets forth the amino acid sequence for the *Chlamydia pneumoniae* homologue, CPn0065, of the *Chlamydia trachomatis* gene CT288.

SEQ ID NO:74 sets forth the amino acid sequence for the *Chlamydia pneumoniae* homologue, CPn0438, of the *Chlamydia trachomatis* gene CT287.

SEQ ID NO:75 sets forth the amino acid sequence for the *Chlamydia pneumoniae* homologue, CPn0963, of the *Chlamydia trachomatis* gene CT812.

SEQ ID NO:76 sets forth the amino acid sequence for the *Chlamydia pneumoniae* homologue, CPn0778, of the *Chlamydia trachomatis* gene CT603.

SEQ ID NO:77 sets forth the amino acid sequence for the *Chlamydia pneumoniae* homologue, CPn1016, of the *Chlamydia trachomatis* gene CT858.

SEQ ID NO:78 sets forth the amino acid sequence for the *Chlamydia pneumoniae* homologue, CPn0728, of the *Chlamydia trachomatis* gene CT622.

SEQ ID NO:79 sets forth the amino acid sequence for the *Chlamydia pneumoniae* homologue, CPn0557, of the *Chlamydia trachomatis* gene CT460.

SEQ ID NO:80 sets forth the full-length serovar D DNA sequence of the *Chlamydia trachomatis* gene CT872.

SEQ ID NO:81 sets forth the full-length serovar D DNA sequence of the *Chlamydia trachomatis* gene CT828.

SEQ ID NO:82 sets forth the full-length serovar D DNA sequence of the *Chlamydia trachomatis* gene CT827.

SEQ ID NO:83 sets forth the full-length serovar D DNA sequence of the *Chlamydia trachomatis* gene CT812.

SEQ ID NO:84 sets forth the full-length serovar D DNA sequence of the *Chlamydia trachomatis* gene CT798.

SEQ ID NO:85 sets forth the full-length serovar D DNA sequence of the *Chlamydia trachomatis* gene CT681 (MompF).

SEQ ID NO:86 sets forth the full-length serovar D DNA sequence of the *Chlamydia trachomatis* gene CT603.

SEQ ID NO:87 sets forth the full-length serovar D DNA sequence of the *Chlamydia trachomatis* gene CT460.

SEQ ID NO:88 sets forth the full-length serovar D DNA sequence of the *Chlamydia trachomatis* gene CT322.

SEQ ID NO:89 sets forth the full-length serovar D DNA sequence of the *Chlamydia trachomatis* gene CT321.

SEQ ID NO:90 sets forth the full-length serovar D DNA sequence of the *Chlamydia trachomatis* gene CT289.

SEQ ID NO:91 sets forth the full-length serovar D DNA sequence of the *Chlamydia trachomatis* gene CT288.

SEQ ID NO:92 sets forth the full-length serovar D DNA sequence of the *Chlamydia trachomatis* gene CT287.

SEQ ID NO:93 sets forth the full-length serovar D DNA sequence of the *Chlamydia trachomatis* gene CT133.

SEQ ID NO:94 sets forth the full-length serovar D DNA sequence of the *Chlamydia trachomatis* gene CT113.

SEQ ID NO:95 sets forth the full-length serovar D amino acid sequence of the *Chlamydia trachomatis* gene CT872.

SEQ ID NO:96 sets forth the full-length serovar D amino acid sequence of the *Chlamydia trachomatis* gene CT828.

SEQ ID NO:97 sets forth the full-length serovar D amino acid sequence of the *Chlamydia trachomatis* gene CT827.

SEQ ID NO:98 sets forth the full-length serovar D amino acid sequence of the *Chlamydia trachomatis* gene CT812.

SEQ ID NO:99 sets forth the full-length serovar D amino acid sequence of the *Chlamydia trachomatis* gene CT798.

SEQ ID NO:100 sets forth the full-length serovar D amino acid sequence of the *Chlamydia trachomatis* gene CT681.

SEQ ID NO:101 sets forth the full-length serovar D amino acid sequence of the *Chlamydia trachomatis* gene CT603.

SEQ ID NO:102 sets forth the full-length serovar D amino acid sequence of the *Chlamydia trachomatis* gene CT460.

SEQ ID NO:103 sets forth the full-length serovar D amino acid sequence of the *Chlamydia trachomatis* gene CT322.

SEQ ID NO:104 sets forth the full-length serovar D amino acid sequence of the *Chlamydia trachomatis* gene CT321.

SEQ ID NO:105 sets forth the full-length serovar D amino acid sequence of the *Chlamydia trachomatis* gene CT289.

SEQ ID NO:106 sets forth the full-length serovar D amino acid sequence of the *Chlamydia trachomatis* gene CT288.

SEQ ID NO:107 sets forth the full-length serovar D amino acid sequence of the *Chlamydia trachomatis* gene CT287.

SEQ ID NO:108 sets forth the full-length serovar D amino acid sequence of the *Chlamydia trachomatis* gene CT133.

SEQ ID NO:109 sets forth the full-length serovar D amino acid sequence of the *Chlamydia trachomatis* gene CT113.

SEQ ID NO:110 sets forth the DNA sequence for the *Chlamydia pneumoniae* homologue, CPn0695, of the *Chlamydia trachomatis* gene CT681.

SEQ ID NO:111 sets forth the DNA sequence for the *Chlamydia pneumoniae* homologue, CPn0144, of the *Chlamydia trachomatis* gene CT113.

SEQ ID NO:112 sets forth the amino acid sequence for the *Chlamydia pneumoniae* homologue, CPn0695, of the *Chlamydia trachomatis* gene CT681.

SEQ ID NO:113 sets forth the amino acid sequence for the *Chlamydia pneumoniae* homologue, CPn0144, of the *Chlamydia trachomatis* gene CT113.

SEQ ID NO:114 sets forth the DNA sequence of the clone E7-B12-65 (CHH037 positive) that contains a 1179 bp insert containing complete ORF for 376.

SEQ ID NO:115 sets forth the DNA sequence of the clone E4-H9-83 (CHH037 positive) that contains the partial ORF for the heat shock protein GroEL (CT110).

SEQ ID NO:116 sets forth the DNA sequence of the clone E9-B10-52 (CHH037 positive) that contains the partial ORF for the the gene yscC (CT674).

SEQ ID NO:117 sets forth the DNA sequence of the clone E7-A7-79 (CHH037 positive) that contains the complete ORF for the histone like development gene hctA (CT743) and a partial ORF for the rRNA methyltransferase gene ygcA (CT742).

SEQ ID NO:118 sets forth the DNA sequence of the clone E2-D11-18 (CHH037 positive) that contains the partial ORF for hctA (CT743).

SEQ ID NO:119 sets forth the DNA sequence for the *Chlamydia trachomatis* serovar E hypothetical protein CT694.

SEQ ID NO:120 sets forth the DNA sequence for the *Chlamydia trachomatis* serovar E hypothetical protein CT695.

SEQ ID NO:121 sets forth the DNA sequence for the *Chlamydia trachomatis* serovar E L1 ribosomal protein.

SEQ ID NO:122 sets forth the amino acid sequence for the *Chlamydia trachomatis* serovar E hypothetical protein CT694.

SEQ ID NO:123 sets forth the amino acid sequence for the *Chlamydia trachomatis* serovar E hypothetical protein CT695.

SEQ ID NO:124 sets forth the amino acid sequence for the *Chlamydia trachomatis* serovar E L1 ribosomal protein.

SEQ ID NO:125 sets forth the DNA sequence of the clone E9-H6-15 (CT3 positive) that contains the partial ORF for the pmpB gene (CT413).

SEQ ID NO:126 sets forth the DNA sequence of the clone E3-D10-87 (CT1 positive) that contains the partial ORFs for the hypothetical genes CT388 and CT389.

SEQ ID NO:127 sets forth the DNA sequence of the clone E9-D6-43 (CT3 positive) that contains the partial ORF for the CT858.

SEQ ID NO:128 sets forth the DNA sequence of the clone E3-D10-4 (CT1 positive) that contains the partial ORF for pGP3-D, an ORF encoded on the plasmid pCHL1.

SEQ ID NO:129 sets forth the DNA sequence of the clone E3-G8-7 (CT1 positive) that contains the partial ORFs for the CT557 (LpdA) and CT558 (LipA).

SEQ ID NO:130 sets forth the DNA sequence of the clone E3-F11-32 (CT1 positive) that contains the partial ORF for pmpD (CT812).

SEQ ID NO:131 sets forth the DNA sequence of the clone E2-F8-5 (CT12 positive) that contains the complete ORF for the 15 kDa ORF (CT442) and a partial ORF for the 60 kDa ORF (CT443).

SEQ ID NO:132 sets forth the DNA sequence of the clone E2-G4-39 (CT12 positive) that contains the partial ORF for the 60 kDa ORF (CT443).

SEQ ID NO:133 sets forth the DNA sequence of the clone E9-D1-16 (CT10 positive) that contains the partial ORF for pmpH (CT872).

SEQ ID NO:134 sets forth the DNA sequence of the clone E3-F3-6 (CT1 positive) that contains the partial ORFs for the genes accB (CT123), L1 ribosomal (CT125) and S9 ribosomal (CT126).

SEQ ID NO:135 sets forth the DNA sequence of the clone E2-D4-70 (CT12 positive) that contains the partial ORF for the pmpC gene (CT414).

SEQ ID NO:136 sets forth the DNA sequence of the clone E5-A1-79 (CT1 positive) that contains the partial ORF for ydhO (CT127), a complete ORF for S9 ribosomal gene (CT126), a complete ORF for the L1 ribosomal gene (CT125) and a partial ORF for accC (CT124).

SEQ ID NO:137 sets forth the DNA sequence of the clone E1-F7-16 (CT12, CT3, and CT11 positive) that contains the partial ORF for the ftsH gene (CT841) and the entire ORF for the pnp gene (CT842).

SEQ ID NO:138 sets forth the DNA sequence of the clone E1-D8-62 (CT12 positive) that contains the partial ORFs for the ftsH gene (CT841) and for the pnp gene (CT842).

SEQ ID NO: 139 sets forth the amino acid sequence for the serovar E protein CT622.

SEQ ID NO:140 sets forth the amino acid sequence for the serovar E protein CT875.

DESCRIPTION OF ILLUSTRATIVE EMBODIMENTS

As noted above, the present invention is generally directed to compositions and methods for the diagnosis and treatment of Chlamydial infection. In one aspect, the compositions of the subject invention include polypeptides that comprise at least one immunogenic portion of a *Chlamydia* antigen, or a variant thereof.

In specific embodiments, the subject invention discloses polypeptides comprising an immunogenic portion of a *Chlamydia* antigen, wherein the Chlamydia antigen comprises an amino acid sequence encoded by a polynucleotide molecule including a sequence selected from the group consisting of (a) nucleotide sequences recited in SEQ ID NO:1-48, 114-121, and 125-138 (b) the complements of said nucleotide sequences, and (c) variants of such sequences.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

"Isolated," as used herein, means that a polynucleotide is substantially away from other coding sequences, and that the DNA segment does not contain large portions of unrelated coding DNA, such as large chromosomal fragments or other functional genes or polypeptide coding regions. Of course, this refers to the DNA segment as originally isolated, and does not exclude genes or coding regions later added to the segment by the hand of man.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native Chlamydia sequence or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native Chlamydia protein. The effect on the immunogenicity of the encoded polypeptide may generally be assessed as described herein. The term "variants" also encompasses homologous genes of xenogenic origin.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626-645 *Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) *J. Mol. Biol.* 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, the present invention encompasses polynucleotide and polypeptide sequences having substantial identity to the sequences disclosed herein, for example those comprising at least 50% sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

In other embodiments, the present invention is directed to polynucleotides that are capable of hybridizing under moderately stringent conditions to a polynucleotide sequence provided herein, or a fragment thereof, or a complementary sequence thereof. Hybridization techniques are well known in the art of molecular biology. For purposes of illustration, suitable moderately stringent conditions for testing the hybridization of a polynucleotide of this invention with other polynucleotides include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Probes and Primers

In other embodiments of the present invention, the polynucleotide sequences provided herein can be advantageously used as probes or primers for nucleic acid hybridization. As such, it is contemplated that nucleic acid segments that comprise a sequence region of at least about 15 nucleotide long contiguous sequence that has the same sequence as, or is complementary to, a 15 nucleotide long contiguous sequence disclosed herein will find particular utility. Longer contiguous identical or complementary sequences, e.g., those of about 20, 30, 40, 50, 100, 200, 500, 1000 (including all intermediate lengths) and even up to full length sequences will also be of use in certain embodiments.

The ability of such nucleic acid probes to specifically hybridize to a sequence of interest will enable them to be of use in detecting the presence of complementary sequences in a given sample. However, other uses are also envisioned, such as the use of the sequence information for the preparation of mutant species primers, or primers for use in preparing other genetic constructions.

Polynucleotide molecules having sequence regions consisting of contiguous nucleotide stretches of 10-14, 15-20, 30, 50, or even of 100-200 nucleotides or so (including intermediate lengths as well), identical or complementary to a polynucleotide sequence disclosed herein, are particularly contemplated as hybridization probes for use in, e.g., Southern and Northern blotting. This would allow a gene product, or fragment thereof, to be analyzed, both in diverse cell types and also in various bacterial cells. The total size of fragment, as well as the size of the complementary stretch(es), will ultimately depend on the intended use or application of the particular nucleic acid segment. Smaller fragments will generally find use in hybridization embodiments, wherein the length of the contiguous complementary region may be varied, such as between about 15 and about 100 nucleotides, but larger contiguous complementarity stretches may be used, according to the length complementary sequences one wishes to detect.

The use of a hybridization probe of about 15-25 nucleotides in length allows the formation of a duplex molecule that is both stable and selective. Molecules having contiguous complementary sequences over stretches greater than 15 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 25 contiguous nucleotides, or even longer where desired.

Hybridization probes may be selected from any portion of any of the sequences disclosed herein. All that is required is to review the sequence set forth in SEQ ID NO:1-48, 114-121, and 125-138, or to any continuous portion of the sequence, from about 15-25 nucleotides in length up to and including the full length sequence, that one wishes to utilize as a probe or primer. The choice of probe and primer sequences may be governed by various factors. For example, one may wish to employ primers from towards the termini of the total sequence.

Small polynucleotide segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. No. 4,683,202 (incorporated herein by reference), by introducing selected sequences into recombinant vectors for recombinant production, and by other recombinant DNA techniques generally known to those of skill in the art of molecular biology.

The nucleotide sequences of the invention may be used for their ability to selectively form duplex molecules with complementary stretches of the entire gene or gene fragments of interest. Depending on the application envisioned, one will typically desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by a salt concentration of from about 0.02 M to about 0.15 M salt at temperatures of from about 50° C. to about 70° C. Such selective conditions tolerate little, if any, mismatch between the probe and the template or target strand, and would be particularly suitable for isolating related sequences.

Of course, for some applications, for example, where one desires to prepare mutants employing a mutant primer strand hybridized to an underlying template, less stringent (reduced stringency) hybridization conditions will typically be needed in order to allow formation of the heteroduplex. In these circumstances, one may desire to employ salt conditions such as those of from about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

Polynucleotide Identification and Characterization

Polynucleotides may be identified, prepared and/or manipulated using any of a variety of well established techniques. For example, a polynucleotide may be identified, by screening a microarray of cDNAs for *Chlamydia* expression. Such screens may be performed, for example, using a Synteni microarray (Palo Alto, Calif.) according to the manufacturer's instructions (and essentially as described by Schena et al., *Proc. Natl. Acad. Sci. USA* 93:10614-10619, 1996 and Heller et al., *Proc. Natl. Acad. Sci. USA* 94:2150-2155, 1997). Alternatively, polynucleotides may be amplified from cDNA prepared from cells expressing the proteins described herein. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., *Chlamydia* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19, 1991) and walking PCR (Parker et al., *Nucl. Acids. Res.* 19:3055-60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al. (1980) *Nucl. Acids Res. Symp. Ser.* 215-223, Horn, T. et al. (1980) *Nucl. Acids Res. Symp. Ser.* 225-232). Alternatively, the protein itself may be produced using chemical methods to synthesize the amino acid sequence of a polypeptide, or a portion thereof. For example, peptide synthesis can be performed using various solid-phase techniques (Roberge, J. Y. et al. (1995) *Science* 269:202-204) and automated synthesis may be achieved, for example, using the ABI 431 A Peptide Synthesizer (Perkin Elmer, Palo Alto, Calif.).

A newly synthesized peptide may be substantially purified by preparative high performance liquid chromatography (e.g., Creighton, T. (1983) Proteins, Structures and Molecular Principles, WH Freeman and Co., New York, N.Y.) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook, J. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York. N.Y.

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of .beta.-galactosidase so that a hybrid protein is produced; pIN vectors (Van Heeke, G. and S. M. Schuster (1989) *J. Biol. Chem.* 264:5503-5509); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) *Methods Enzymol.* 153:516-544.

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, N. (1987) *EMBO J.* 6:307-311. Alternatively, plant promoters such as the small subunit of RUBISCO or heat shock promoters may be used (Coruzzi, G. et al. (1984) *EMBO J.* 3:1671-1680; Broglie, R. et al. (1984) *Science* 224:838-843; and Winter, J. et al. (1991) *Results Probl. Cell Differ.* 17:85-105). These constructs can be introduced into plant cells by direct DNA transformation or pathogen-mediated transfection. Such techniques are described in a number of generally available reviews (see, for example, Hobbs, S. or Murry, L. E. in McGraw Hill Yearbook of Science and Technology (1992) McGraw Hill, New York, N.Y.; pp. 191-196).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard, E. K. et al. (1994) *Proc. Natl. Acad. Sci.* 91:3224-3227).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan, J. and Shenk, T. (1984) *Proc. Natl. Acad. Sci.* 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) *Results Probl. Cell Differ.* 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) *Cell* 11:223-32) and adenine phosphoribosyltransferase (Lowy, I. et al. (1990) *Cell* 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) *Proc. Natl. Acad. Sci.* 77:3567-70); npt, which confers resistance to the aminoglycosides, neomycin and G-418 (Colbere-Garapin, F. et al (1981) *J. Mol. Biol.* 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) *Proc. Natl. Acad. Sci.* 85:8047-51). Recently, the use of visible markers has gained popularity with such markers as anthocyanins, beta-glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) *Methods Mol. Biol.* 55:121-131).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton, R. et al. (1990; Serological Methods, a Laboratory Manual, APS Press, St Paul. Minn.) and Maddox, D. E. et al. (1983; *J. Exp. Med.* 158:1211-1216).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, *Prot. Exp. Purif* 3:263-281) while the enterokinase cleavage site provides a means for purifying the desired polypeptide from the fusion protein. A discussion of vectors which contain fusion proteins is provided in Kroll, D. J. et al. (1993; *DNA Cell Biol.* 12:441-453).

In addition to recombinant production methods, polypeptides of the invention, and fragments thereof, may be produced by direct peptide synthesis using solid-phase techniques (Merrifield J. (1963) *J. Am. Chem. Soc.* 85:2149-2154). Protein synthesis may be performed using manual techniques or by automation. Automated synthesis may be achieved, for example, using Applied Biosystems 431 A Peptide Synthesizer (Perkin Elmer). Alternatively, various fragments may be chemically synthesized separately and combined using chemical methods to produce the full length molecule.

Site-Specific Mutagenesis

Site-specific mutagenesis is a technique useful in the preparation of individual peptides, or biologically functional equivalent polypeptides, through specific mutagenesis of the underlying polynucleotides that encode them. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

In certain embodiments of the present invention, the inventors contemplate the mutagenesis of the disclosed polynucleotide sequences to alter one or more properties of the encoded polypeptide, such as the antigenicity of a polypeptide vaccine. The techniques of site-specific mutagenesis are well-known in the art, and are widely used to create variants of both polypeptides and polynucleotides. For example, site-specific mutagenesis is often used to alter a specific portion of a DNA molecule. In such embodiments, a primer comprising typically about 14 to about 25 nucleotides or so in length is employed, with about 5 to about 10 residues on both sides of the junction of the sequence being altered.

As will be appreciated by those of skill in the art, site-specific mutagenesis techniques have often employed a phage vector that exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis that eliminates the step of transferring the gene of interest from a plasmid to a phage.

In general, site-directed mutagenesis in accordance herewith is performed by first obtaining a single-stranded vector or melting apart of two strands of a double-stranded vector that includes within its sequence a DNA sequence that encodes the desired peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis provides a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy et al., 1994; Segal, 1976; Prokop and Bajpai, 1991; Kuby, 1994; and Maniatis et al., 1982, each incorporated herein by reference, for that purpose.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" is intended to refer to a process that involves the template-dependent extension of a primer molecule. The term template dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237, 224, specifically incorporated herein by reference in its entirety.

Polynucleotide Amplification Techniques

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates is added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction product and the process is repeated. Preferably reverse transcription and PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308 (specifically incorporated herein by reference in its entirety). In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[$\alpha$-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, i.e. nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Sequences can also be detected using a cyclic probe reaction (CPR). In CPR, a probe having a 3' and 5' sequences of non-target DNA and an internal or "middle" sequence of the target protein specific RNA is hybridized to DNA which is present in a sample. Upon hybridization, the reaction is treated with RNaseH, and the products of the probe are identified as distinctive products by generating a signal that is released after digestion. The original template is annealed to another cycling probe and the reaction is repeated. Thus, CPR involves amplifying a signal generated by hybridization of a probe to a target gene specific expressed nucleic acid.

Still other amplification methods described in Great Britain Pat. Appl. No. 2 202 328, and in PCT Intl. Pat. Appl. Publ. No. PCT/US89/01025, each of which is incorporated herein by reference in its entirety, may be used in accordance with the present invention. In the former application, "modified" primers are used in a PCR-like, template and enzyme dependent synthesis. The primers may be modified by labeling with a capture moiety (e.g., biotin) and/or a detector moiety (e.g., enzyme). In the latter application, an excess of labeled probes is added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer that has sequences specific to the target sequence. Following polymerization, DNA/RNA hybrids are digested with RNase H while double stranded DNA molecules are heat-denatured again. In either case the single stranded DNA is made fully double stranded by addition of second target-specific primer, followed by polymerization. The double stranded DNA molecules are then multiply transcribed by a polymerase such as T7 or SP6. In an isothermal cyclic reaction, the RNAs are reverse transcribed into DNA, and transcribed once again with a polymerase such as T7 or SP6. The resulting products, whether truncated or complete, indicate target-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H(RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

Biological Functional Equivalents

Modification and changes may be made in the structure of the polynucleotides and polypeptides of the present invention and still obtain a functional molecule that encodes a polypeptide with desirable characteristics. As mentioned above, it is often desirable to introduce one or more mutations into a specific polynucleotide sequence. In certain circumstances, the resulting encoded polypeptide sequence is altered by this mutation, or in other cases, the sequence of the polypeptide is unchanged by one or more mutations in the encoding polynucleotide.

When it is desirable to alter the amino acid sequence of a polypeptide to create an equivalent, or even an improved, second-generation molecule, the amino acid changes may be achieved by changing one or more of the codons of the encoding DNA sequence, according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenyl-alanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |

TABLE 1-continued

| Amino Acids | | | Codons | | | | | |
|---|---|---|---|---|---|---|---|---|
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

In addition, any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

In Vivo Polynucleotide Delivery Techniques

In additional embodiments, genetic constructs comprising one or more of the polynucleotides of the invention are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. "Adenovirus expression vector" is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

2. Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

3. Adeno-Associated Viruses

AAV (Ridgeway, 1988; Hermonat and Muzycska, 1984) is a parovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka and McLaughlin, 1988).

The AAV DNA is approximately 4.7 kilobases long. It contains two open reading frames and is flanked by two ITRs (FIG. 2). There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat and Muzyczka, 1984).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, 1988; Coupar et al., 1988), lentiviruses, polio viruses and herpes viruses may be employed. They offer several attractive features for various mammalian cells (Friedmann, 1989; Ridgeway, 1988; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. (1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Reshef (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e. ex vivo treatment. Again, DNA encoding a particular gene may be delivered via this method and still be incorporated by the present invention.

Antisense Oligonucleotides

The end result of the flow of genetic information is the synthesis of protein. DNA is transcribed by polymerases into messenger RNA and translated on the ribosome to yield a folded, functional protein. Thus there are several steps along the route where protein synthesis can be inhibited. The native DNA segment coding for a polypeptide described herein, as all such mammalian DNA strands, has two strands: a sense strand and an antisense strand held together by hydrogen bonding. The messenger RNA coding for polypeptide has the same nucleotide sequence as the sense DNA strand except that the DNA thymidine is replaced by uridine. Thus, synthetic antisense nucleotide sequences will bind to a mRNA and inhibit expression of the protein encoded by that mRNA.

The targeting of antisense oligonucleotides to mRNA is thus one mechanism to shut down protein synthesis, and, consequently, represents a powerful and targeted therapeutic approach. For example, the synthesis of polygalactauronase and the muscarine type 2 acetylcholine receptor are inhibited by antisense oligonucleotides directed to their respective mRNA sequences (U.S. Pat. No. 5,739,119 and U.S. Pat. No. 5,759,829, each specifically incorporated herein by reference in its entirety). Further, examples of antisense inhibition have been demonstrated with the nuclear protein cyclin, the multiple drug resistance gene (MDG1), ICAM-1, E-selectin, STK-1, striatal $GABA_A$ receptor and human EGF (Jaskulski et al., 1988; Vasanthakumar and Ahmed, 1989; Peris et al., 1998; U.S. Pat. No. 5,801,154; U.S. Pat. No. 5,789,573; U.S. Pat. No. 5,718,709 and U.S. Pat. No. 5,610,288, each specifically incorporated herein by reference in its entirety). Antisense constructs have also been described that inhibit and can be used to treat a variety of abnormal cellular proliferations, e.g. cancer (U.S. Pat. No. 5,747,470; U.S. Pat. No. 5,591,317 and U.S. Pat. No. 5,783,683, each specifically incorporated herein by reference in its entirety).

Therefore, in exemplary embodiments, the invention provides oligonucleotide sequences that comprise all, or a portion of, any sequence that is capable of specifically binding to polynucleotide sequence described herein, or a complement thereof. In one embodiment, the antisense oligonucleotides comprise DNA or derivatives thereof. In another embodiment, the oligonucleotides comprise RNA or derivatives thereof. In a third embodiment, the oligonucleotides are modified DNAs comprising a phosphorothioated modified backbone. In a fourth embodiment, the oligonucleotide sequences comprise peptide nucleic acids or derivatives thereof. In each case, preferred compositions comprise a sequence region that is complementary, and more preferably substantially-complementary, and even more preferably, completely complementary to one or more portions of polynucleotides disclosed herein.

Selection of antisense compositions specific for a given gene sequence is based upon analysis of the chosen target sequence (i.e. in these illustrative examples the rat and human sequences) and determination of secondary structure, $T_m$, binding energy, relative stability, and antisense compositions were selected based upon their relative inability to form dimers, hairpins, or other secondary structures that would reduce or prohibit specific binding to the target mRNA in a host cell.

Highly preferred target regions of the mRNA, are those which are at or near the AUG translation initiation codon, and those sequences which were substantially complementary to 5' regions of the mRNA. These secondary structure analyses and target site selection considerations were performed using v.4 of the OLIGO primer analysis software (Rychlik, 1997) and the BLASTN 2.0.5 algorithm software (Altschul et al., 1997).

The use of an antisense delivery method employing a short peptide vector, termed MPG (27 residues), is also contemplated. The MPG peptide contains a hydrophobic domain derived from the fusion sequence of HIV gp41 and a hydrophilic domain from the nuclear localization sequence of SV40 T-antigen (Morris et al., 1997). It has been demonstrated that several molecules of the MPG peptide coat the antisense oligonucleotides and can be delivered into cultured mammalian cells in less than 1 hour with relatively high efficiency (90%). Further, the interaction with MPG strongly increases both the stability of the oligonucleotide to nuclease and the ability to cross the plasma membrane (Morris et al., 1997).

Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or Neurospora VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis 6 virus motif is described by Perrotta and Been (1992); an example of the RNaseP motif is described by Guerrier-Takada et al. (1983); Neurospora VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes are well known in the art, and include detection of the presence of mRNA associated with an IL-5 related condition. Such RNA is detected by determining the presence of a cleavage product after treatment with a ribozyme using standard methodology.

Peptide Nucleic Acids

In certain embodiments, the inventors contemplate the use of peptide nucleic acids (PNAs) in the practice of the methods of the invention. PNA is a DNA mimic in which the nucleobases are attached to a pseudopeptide backbone (Good and Nielsen, 1997). PNA is able to be utilized in a number methods that traditionally have used RNA or DNA. Often PNA sequences perform better in techniques than the corresponding RNA or DNA sequences and have utilities that are not inherent to RNA or DNA. A review of PNA including methods of making, characteristics of, and methods of using, is provided by Corey (1997) and is incorporated herein by reference. As such, in certain embodiments, one may prepare PNA sequences that are complementary to one or more portions of the ACE mRNA sequence, and such PNA compositions may be used to regulate, alter, decrease, or reduce the translation of ACE-specific mRNA, and thereby alter the level of ACE activity in a host cell to which such PNA compositions have been administered.

PNAs have 2-aminoethyl-glycine linkages replacing the normal phosphodiester backbone of DNA (Nielsen et al., 1991; Hanvey et al., 1992; Hyrup and Nielsen, 1996; Neilsen, 1996). This chemistry has three important consequences: firstly, in contrast to DNA or phosphorothioate oligonucleotides, PNAs are neutral molecules; secondly, PNAs are achiral, which avoids the need to develop a stereoselective synthesis; and thirdly, PNA synthesis uses standard Boc (Dueholm et al., 1994) or Fmoc (Thomson et al., 1995) protocols for solid-phase peptide synthesis, although other methods, including a modified Merrifield method, have been used (Christensen et al., 1995).

PNA monomers or ready-made oligomers are commercially available from PerSeptive Biosystems (Framingham, Mass.). PNA syntheses by either Boc or Fmoc protocols are straightforward using manual or automated protocols (Norton et al., 1995). The manual protocol lends itself to the production of chemically modified PNAs or the simultaneous synthesis of families of closely related PNAs.

As with peptide synthesis, the success of a particular PNA synthesis will depend on the properties of the chosen sequence. For example, while in theory PNAs can incorporate any combination of nucleotide bases, the presence of adjacent purines can lead to deletions of one or more residues in the product. In expectation of this difficulty, it is suggested that, in producing PNAs with adjacent purines, one should repeat the coupling of residues likely to be added inefficiently. This should be followed by the purification of PNAs by reverse-phase high-pressure liquid chromatography (Norton et al., 1995) providing yields and purity of product similar to those observed during the synthesis of peptides.

Modifications of PNAs for a given application may be accomplished by coupling amino acids during solid-phase synthesis or by attaching compounds that contain a carboxylic acid group to the exposed N-terminal amine. Alternatively, PNAs can be modified after synthesis by coupling to an introduced lysine or cysteine. The ease with which PNAs can be modified facilitates optimization for better solubility or for specific functional requirements. Once synthesized, the identity of PNAs and their derivatives can be confirmed by mass spectrometry. Several studies have made and utilized modifications of PNAs (Norton et al., 1995; Haaima et al., 1996; Stetsenko et al., 1996; Petersen et al., 1995; Ulmann et al., 1996; Koch et al., 1995; Orum et al., 1995; Footer et al., 1996; Griffith et al., 1995; Kremsky et al., 1996; Pardridge et al., 1995; Boffa et al., 1995; Landsdorp et al., 1996; Gambacorti-Passerini et al., 1996; Armitage et al., 1997; Seeger et al., 1997; Ruskowski et al., 1997). U.S. Pat. No. 5,700,922 discusses PNA-DNA-PNA chimeric molecules and their uses in diagnostics, modulating protein in organisms, and treatment of conditions susceptible to therapeutics.

In contrast to DNA and RNA, which contain negatively charged linkages, the PNA backbone is neutral. In spite of this dramatic alteration, PNAs recognize complementary DNA and RNA by Watson-Crick pairing (Egholm et al., 1993), validating the initial modeling by Nielsen et al. (1991). PNAs lack 3' to 5' polarity and can bind in either parallel or antiparallel fashion, with the antiparallel mode being preferred (Egholm et al., 1993).

Hybridization of DNA oligonucleotides to DNA and RNA is destabilized by electrostatic repulsion between the negatively charged phosphate backbones of the complementary strands. By contrast, the absence of charge repulsion in PNA-DNA or PNA-RNA duplexes increases the melting temperature ($T_m$) and reduces the dependence of $T_m$ on the concentration of mono- or divalent cations (Nielsen et al., 1991). The enhanced rate and affinity of hybridization are significant because they are responsible for the surprising ability of PNAs to perform strand invasion of complementary sequences within relaxed double-stranded DNA. In addition, the efficient hybridization at inverted repeats suggests that PNAs can recognize secondary structure effectively within double-stranded DNA. Enhanced recognition also occurs with PNAs immobilized on surfaces, and Wang et al. have shown that support-bound PNAs can be used to detect hybridization events (Wang et al., 1996).

One might expect that tight binding of PNAs to complementary sequences would also increase binding to similar (but not identical) sequences, reducing the sequence specificity of PNA recognition. As with DNA hybridization, however, selective recognition can be achieved by balancing oligomer length and incubation temperature. Moreover, selective hybridization of PNAs is encouraged by PNA-DNA hybridization being less tolerant of base mismatches than DNA-DNA hybridization. For example, a single mismatch within a 16 bp PNA-DNA duplex can reduce the $T_m$ by up to 15° C. (Egholm et al., 1993). This high level of discrimination has allowed the development of several PNA-based strategies for the analysis of point mutations (Wang et al., 1996; Carlsson et al., 1996; Thiede et al., 1996; Webb and Hurskainen, 1996; Perry-O'Keefe et al., 1996).

High-affinity binding provides clear advantages for molecular recognition and the development of new applications for PNAs. For example, 11-13 nucleotide PNAs inhibit the activity of telomerase, a ribonucleo-protein that extends telomere ends using an essential RNA template, while the analogous DNA oligomers do not (Norton et al., 1996).

Neutral PNAs are more hydrophobic than analogous DNA oligomers, and this can lead to difficulty solubilizing them at neutral pH, especially if the PNAs have a high purine content or if they have the potential to form secondary structures. Their solubility can be enhanced by attaching one or more positive charges to the PNA termini (Nielsen et al., 1991).

Findings by Allfrey and colleagues suggest that strand invasion will occur spontaneously at sequences within chromosomal DNA (Boffa et al., 1995; Boffa et al., 1996). These studies targeted PNAs to triplet repeats of the nucleotides CAG and used this recognition to purify transcriptionally active DNA (Boffa et al., 1995) and to inhibit transcription (Boffa et al., 1996). This result suggests that if PNAs can be delivered within cells then they will have the potential to be general sequence-specific regulators of gene expression. Studies and reviews concerning the use of PNAs as antisense and anti-gene agents include Nielsen et al. (1993b), Hanvey et al. (1992), and Good and Nielsen (1997). Koppelhus et al. (1997) have used PNAs to inhibit HIV-1 inverse transcription, showing that PNAs may be used for antiviral therapies.

Methods of characterizing the antisense binding properties of PNAs are discussed in Rose (1993) and Jensen et al. (1997). Rose uses capillary gel electrophoresis to determine binding of PNAs to their complementary oligonucleotide, measuring the relative binding kinetics and stoichiometry. Similar types of measurements were made by Jensen et al. using BIAcore™ technology.

Other applications of PNAs include use in DNA strand invasion (Nielsen et al., 1991), antisense inhibition (Hanvey et al., 1992), mutational analysis (Orum et al., 1993), enhancers of transcription (Mollegaard et al., 1994), nucleic acid purification (Orum et al., 1995), isolation of transcriptionally active genes (Boffa et al., 1995), blocking of transcription factor binding (Vickers et al., 1995), genome cleavage (Veselkov et al., 1996), biosensors (Wang et al., 1996), in situ hybridization (Thisted et al., 1996), and in a alternative to Southern blotting (Perry-O'Keefe, 1996).

Polypeptide Compositions and Uses

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

Likewise, a polypeptide composition of the present invention is understood to comprise one or more polypeptides that are capable of eliciting antibodies that are immunologically reactive with one or more polypeptides encoded by one or more contiguous nucleic acid sequences contained in SEQ ID NO:1-48, 114-121, and 125-138, or to active fragments, or to variants thereof, or to one or more nucleic acid sequences which hybridize to one or more of these sequences under conditions of moderate to high stringency.

As used herein, an active fragment of a polypeptide includes a whole or a portion of a polypeptide which is modified by conventional techniques, e.g., mutagenesis, or by addition, deletion, or substitution, but which active fragment exhibits substantially the same structure function, antigenicity, etc., as a polypeptide as described herein.

In certain illustrative embodiments, the polypeptides of the invention will comprise at least an immunogenic portion of a *Chlamydia* protein or a variant thereof, as described herein. Proteins that are *Chlamydia* proteins generally also react detectably within an immunoassay (such as an ELISA) with antisera from a patient with a Chlamydial infection. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a *Chlamydia* protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1-30 amino acids, preferably 5-15 amino acids), relative to the mature protein.

Immunogenic portions may generally be identified using well known techniques, such as those summarized in Paul, Fundamental Immunology, 3rd ed., 243-247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native *Chlamydia* protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native *Chlamydia* protein. A polypeptide "variant," as used herein, is a polypeptide that differs from a native *Chlamydia* protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the N- and/or C-terminal of the mature protein.

Polypeptide variants encompassed by the present invention include those exhibiting at least about 70%, 75%, 80%, 85%, 90%, 91%, 92%, 93%, 94%, 95%, 96%, 97%, 98%, or 99% or more identity (determined as described above) to the polypeptides disclosed herein.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known Chlamydia protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86-91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798, 1992). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Illustrative Therapeutic Compositions and Uses

In another aspect, the present invention provides methods for using one or more of the above polypeptides or fusion proteins (or polynucleotides encoding such polypeptides or fusion proteins) to induce protective immunity against Chlamydial infection in a patient. As used herein, a "patient" refers to any warm-blooded animal, preferably a human. A patient may be afflicted with a disease, or may be free of detectable disease and/or infection. In other words, protective immunity may be induced to prevent or treat Chlamydial infection.

In this aspect, the polypeptide, fusion protein or polynucleotide molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and an immunostimulant, such as an adjuvant or a liposome (into which the polypeptide is incorporated). Such pharmaceutical compositions and vaccines may also contain other Chlamydia antigens, either incorporated into a combination polypeptide or present within a separate polypeptide.

Alternatively, a vaccine may contain polynucleotides encoding one or more polypeptides or fusion proteins as described above, such that the polypeptide is generated in situ. In such vaccines, the polynucleotides may be present within any of a variety of delivery systems known to those of ordinary skill in the art, including nucleic acid expression systems, bacterial and viral expression systems. Appropriate nucleic acid expression systems contain the necessary polynucleotide sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective) virus. Techniques for incorporating polynucleotides into such expression systems are well known to those of ordinary skill in the art. The polynucleotides may also be administered as "naked" plasmid vectors as described, for example, in Ulmer et al., *Science* 259:1745-1749, 1993 and reviewed by Cohen, *Science* 259:1691-1692, 1993. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The uptake of naked polynucleotides may be increased by incorporating the polynucleotides into and/or onto biodegradable beads, which are efficiently transported into the cells. The preparation and use of such systems is well known in the art.

In a related aspect, a polynucleotide vaccine as described above may be administered simultaneously with or sequentially to either a polypeptide of the present invention or a known *Chlamydia* antigen. For example, administration of polynucleotides encoding a polypeptide of the present invention, either "naked" or in a delivery system as described above, may be followed by administration of an antigen in order to enhance the protective immune effect of the vaccine.

Polypeptides and polynucleotides disclosed herein may also be employed in adoptive immunotherapy for the treatment of Chlamydial infection. Adoptive immunotherapy may be broadly classified into either active or passive immunotherapy. In active immunotherapy, treatment relies on the in vivo stimulation of the endogenous host immune system with the administration of immune response-modifying agents (for example, vaccines, bacterial adjuvants, and/or cytokines).

In passive immunotherapy, treatment involves the delivery of biologic reagents with established immune reactivity (such as effector cells or antibodies) that can directly or indirectly mediate anti-*Chlamydia* effects and does not necessarily depend on an intact host immune system. Examples of effector cells include T lymphocytes (for example, CD8+ cytotoxic T-lymphocyte, CD4+ T-helper), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particlate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews,* 157: 177, 1997).

The polypeptides disclosed herein may also be employed to generate and/or isolate chlamydial-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ or CD4+ T-cell clones may be isolated from the patient, expanded using standard tissue culture techniques, and returned to the patient.

Alternatively, peptides corresponding to immunogenic portions of the polypeptides may be employed to generate *Chlamydia* reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.,* 22(3), 213, 1996). Cells of the immune system, such as T cells, may be isolated from the peripheral blood of a patient, using a commercially available cell separation system, such as Isolex™ System, available from Nexell Therapeutics, Inc. Irvine, Calif. The separated cells are stimulated with one or more of the immunoreactive polypeptides contained within a delivery vehicle, such as a microsphere, to provide antigen-specific T cells. The population of antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from chlamydia specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother,* 45(3-4):131-6, 1997 and Hwu, P., et al, *Cancer Res,* 55(15):3369-73, 1995. Another embodiment may include the transfection of *chlamydia* antigen specific alpha and beta T cell receptor chains into alternate T cells, as in Cole, D J, et al, *Cancer Res,* 55(4):748-52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate disease in a murine model has been demonstrated by Cheever et al, *Immunological Reviews,* 157:177, 1997). Additionally, vectors expressing the disclosed polynucleotides may be introduced into stem cells taken from the patient and clonally propagated in vitro for autologous transplant back into the same patient.

Within certain aspects, polypeptides, polynucleotides, T cells and/or binding agents disclosed herein may be incorporated into pharmaceutical compositions or immunogenic compositions (i.e., vaccines). Alternatively, a pharmaceutical composition may comprise an antigen-presenting cell (e.g. a dendritic cell) transfected with a Chlamydial polynucleotide such that the antigen presenting cell expresses a Chlamydial polypeptide. Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other Chlamydial antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface or secretes such an epitope.

In a preferred embodiment, the DNA may be introduced using a viral expression system (e.g., vaccinia or other pox virus, retrovirus, adenovirus, baculovirus, togavirus, bacteriophage, and the like), which often involves the use of a non-pathogenic (defective), replication competent virus.

For example, many viral expression vectors are derived from viruses of the retroviridae family. This family includes the murine leukemia viruses, the mouse mammary tumor viruses, the human foamy viruses, Rous sarcoma virus, and the immunodeficiency viruses, including human, simian, and feline. Considerations when designing retroviral expression vectors are discussed in Comstock et al. (1997).

Excellent murine leukemia virus (MLV)-based viral expression vectors have been developed by Kim et al. (1998). In creating the MLV vectors, Kim et al. found that the entire gag sequence, together with the immediate upstream region, could be deleted without significantly affecting viral packaging or gene expression. Further, it was found that nearly the entire U3 region could be replaced with the immediately-early promoter of human cytomegalovirus without deleterious effects. Additionally, MCR and internal ribosome entry sites (IRES) could be added without adverse effects. Based on their observations, Kim et al. have designed a series of MLV-based expression vectors comprising one or more of the features described above.

As more has been learned about human foamy virus (HFV), characteristics of HFV that are favorable for its use as an expression vector have been discovered. These characteristics include the expression of pol by splicing and start of translation at a defined initiation codon. Other aspects of HFV viral expression vectors are reviewed in Bodem et al. (1997).

Murakami et al. (1997) describe a Rous sarcoma virus (RSV)-based replication-competent avian retrovirus vectors, IR1 and IR2 to express a heterologous gene at a high level. In these vectors, the IRES derived from encephalomyocarditis virus (EMCV) was inserted between the env gene and the heterologous gene. The IR1 vector retains the splice-acceptor site that is present downstream of the env gene while the IR2 vector lacks it. Murakami et al. have shown high level expression of several different heterologous genes by these vectors.

Recently, a number of lentivirus-based retroviral expression vectors have been developed. Kafri et al. (1997) have shown sustained expression of genes delivered directly into liver and muscle by a human immunodeficiency virus (HIV)-based expression vector. One benefit of the system is the inherent ability of HIV to transduce non-dividing cells. Because the viruses of Kafri et al. are pseudotyped with vesicular stomatitis virus G glycoprotein (VSVG), they can transduce a broad range of tissues and cell types.

A large number of adenovirus-based expression vectors have been developed, primarily due to the advantages offered by these vectors in gene therapy applications. Adenovirus expression vectors and methods of using such vectors are the subject of a number of United States patents, including U.S. Pat. No. 5,698,202, U.S. Pat. No. 5,616,326, U.S. Pat. No. 5,585,362, and U.S. Pat. No. 5,518,913, all incorporated herein by reference.

Additional adenoviral constructs are described in Khatri et al. (1997) and Tomanin et al. (1997). Khatri et al. describe novel ovine adenovirus expression vectors and their ability to infect bovine nasal turbinate and rabbit kidney cells as well as a range of human cell type, including lung and foreskin fibroblasts as well as liver, prostate, breast, colon and retinal lines. Tomanin et al. describe adenoviral expression vectors containing the T7 RNA polymerase gene. When introduced into cells containing a heterologous gene operably linked to a T7 promoter, the vectors were able to drive gene expression from the T7 promoter. The authors suggest that this system may be useful for the cloning and expression of genes encoding cytotoxic proteins.

Poxviruses are widely used for the expression of heterologous genes in mammalian cells. Over the years, the vectors have been improved to allow high expression of the heterologous gene and simplify the integration of multiple heterologous genes into a single molecule. In an effort to diminish cytopathic effects and to increase safety, vaccinia virus mutant and other poxviruses that undergo abortive infection in mammalian cells are receiving special attention (Oertli et al., 1997). The use of poxviruses as expression vectors is reviewed in Carroll and Moss (1997).

Togaviral expression vectors, which includes alphaviral expression vectors have been used to study the structure and function of proteins and for protein production purposes. Attractive features of togaviral expression vectors are rapid and efficient gene expression, wide host range, and RNA genomes (Huang, 1996). Also, recombinant vaccines based on alphaviral expression vectors have been shown to induce a strong humoral and cellular immune response with good immunological memory and protective effects (Tubulekas et al., 1997). Alphaviral expression vectors and their use are discussed, for example, in Lundstrom (1997).

In one study, Li and Garoff (1996) used Semliki Forest virus (SFV) expression vectors to express retroviral genes and to produce retroviral particles in BHK-21 cells. The particles produced by this method had protease and reverse transcriptase activity and were infectious. Furthermore, no helper virus could be detected in the virus stocks. Therefore, this system has features that are attractive for its use in gene therapy protocols.

Baculoviral expression vectors have traditionally been used to express heterologous proteins in insect cells. Examples of proteins include mammalian chemokine receptors (Wang et al., 1997), reporter proteins such as green fluorescent protein (Wu et al., 1997), and FLAG fusion proteins (Wu et al., 1997; Koh et al., 1997). Recent advances in baculoviral expression vector technology, including their use in virion display vectors and expression in mammalian cells is reviewed by Possee (1997). Other reviews on baculoviral expression vectors include Jones and Morikawa (1996) and O'Reilly (1997).

Other suitable viral expression systems are disclosed, for example, in Fisher-Hoch et al., *Proc. Natl. Acad. Sci. USA* 86:317-321, 1989; Flexner et al., *Ann. N.Y. Acad. Sci.* 569:86-103, 1989; Flexner et al., *Vaccine* 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627, 1988; Rosenfeld et al., *Science* 252:431-434, 1991; Kolls et al., *Proc. Natl. Acad. Sci. USA* 91:215-219, 1994; Kass-Eisler et al., *Proc. Natl. Acad. Sci. USA* 90:11498-11502, 1993; Guzman et al., *Circulation* 88:2838-2848, 1993; and Guzman et al., *Cir. Res.* 73:1202-1207, 1993. Techniques for incorporating DNA into such expression systems are well known to those of ordinary skill in the art. In other systems, the DNA may be introduced as "naked" DNA, as described, for example, in Ulmer et al., *Science* 259:1745-1749, 1993 and reviewed by Cohen, *Science* 259:1691-1692, 1993. The uptake of naked DNA may be increased by coating the DNA onto biodegradable beads, which are efficiently transported into the cells.

It will be apparent that a vaccine may comprise a polynucleotide and/or a polypeptide component, as desired. It will also be apparent that a vaccine may contain pharmaceutically acceptable salts of the polynucleotides and/or polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts). While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, under select circumstances, the adjuvant composition may be designed to induce an immune response predominantly of the Th1 type or Th2 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145-173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WO 99/33488. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa Corporation; Seattle, Wash.), RC-529 (Corixa Corporation; Seattle, Wash.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any vaccine provided herein may be prepared using well known methods that result in a combination of antigen, immunostimulant and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly (lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets *Chlamydia*-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-Chlamydia effects per se and/or to be immunologically compatible with the receiver (i.e., matched HLA haplotype). APCs may generally be isolated from any of a variety of biological fluids and organs, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245-251, 1998) and have been shown to be effective as a physiological adjuvant for eliciting prophylactic or therapeutic immunity (see Timmerman and Levy, *Ann. Rev. Med.* 50:507-529, 1999). In general, dendritic cells may be identified based on their typical shape (stellate in situ, with marked cytoplasmic processes (dendrites) visible in vitro), their ability to take up, process and present antigens with high efficiency, and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600, 1998).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a Chlamydial protein (or portion or other variant thereof) such that the Chlamydial polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456-460, 1997. Antigen loading of dendritic cells may be achieved by incubating dendritic cells or progenitor cells with the Chlamydial polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Routes and frequency of administration of pharmaceutical compositions and vaccines, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1-36 week period. Preferably, 3 doses are administered, at intervals of 3-4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from Chlamydial infection for at least 1-2 years. In general, the amount of polypeptide present in a dose (or produced in situ by the DNA in a dose) ranges from about 1 μg to about 100 mg per kg of host, typically from about 10 μg to about 1 mg, and preferably from about 100 μg to about 1 μg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In general, an appropriate dosage and treatment regimen provides the active compound(s) in an amount sufficient to provide therapeutic and/or prophylactic benefit. Such a response can be monitored by establishing an improved clinical outcome in treated patients as compared to non-treated patients. Increases in preexisting immune responses to a Chlamydial protein generally correlate with an improved clinical outcome. Such immune responses may generally be evaluated using standard proliferation, cytotoxicity or cytokine assays, which may be performed using samples obtained from a patient before and after treatment.

Detection and Diagnosis

In another aspect, the present invention provides methods for using the polypeptides described above to diagnose Chlamydial infection. In this aspect, methods are provided for detecting Chlamydial infection in a biological sample, using one or more of the above polypeptides, either alone or in combination. For clarity, the term "polypeptide" will be used when describing specific embodiments of the inventive diagnostic methods. However, it will be clear to one of skill in the art that the fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Chlamydia antigens which may be indicative of *Chlamydia*-infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with *Chlamydia*. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 μg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12-A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable dilutent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Chlamydia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for *Chlamydia*-infection. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, pp. 106-107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for Chlamydial infection.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-*Chlamydia* antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 11 g, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only. One example of an alternative assay protocol which may be usefully employed in such methods is a Western blot, wherein the proteins present in a biological sample are separated on a gel, prior to exposure to a binding agent. Such techniques are well known to those of skill in the art.

Binding Agents and Their Uses

The present invention further provides agents, such as antibodies and antigen-binding fragments thereof, that specifically bind to a Chlamydial protein. As used herein, an antibody, or antigen-binding fragment thereof, is said to "specifically bind" to a Chlamydial protein if it reacts at a detectable level (within, for example, an ELISA) with a Chlamydial protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a Chlamydial infection using the representative assays provided herein. In other words, antibodies or other binding agents that bind to a Chlamydial protein will generate a signal indicating the presence of a Chlamydial infection in at least about 20% of patients with the disease, and will generate a negative signal indicating the absence of the disease in at least about 90% of individuals without infection. To determine whether a binding agent satisfies this requirement, biological samples (e.g., blood, sera, sputum urine and/or tissue biopsies) from patients with and without Chlamydial infection (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in site-specific regions by appropriate methods. It will be evident that the precise dose of the antibody/immunoconjugate will vary depending upon the antibody used, the antigen density, and the rate of clearance of the antibody.

Antibodies may be used in diagnostic tests to detect the presence of *Chlamydia* antigens using assays similar to those detailed above and other techniques well known to those of skill in the art, thereby providing a method for detecting Chlamydial infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify *Chlamydia*-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

The following Examples are offered by way of illustration and not by way of limitation.

EXAMPLE 1

CD4 T Cell Expression Cloning for the Identification of T Cell Stimulating Antigens from *Chlamydia Trachomatis* Serovar E In this example, a CD4+ T cell expression cloning strategy was used to identify *Chlamydia trachomatis* antigens recognized by patients enrolled in Corixa Corporation's blood donor program. A genomic library of *Chlamydia trachomatis* serovar E was constructed and screened with *Chlamydia* specific T cell lines generated by stimulating PBMCs from these donors. Donor CT1 is a 27 yr. old male whose clinical manifestation was non-gonococcal urethritis and his urine was tested positive for *Chlamydia* by ligase chain reaction. Donor CT3 is a 43 yr. old male who is asymptomatic and infected with serovar J. Donor CT10 is a 24 yr. old female who is asymptomatic and was exposed to Chlamydia through her partner but did not develop the disease. Donor CT11 is a 24 yr. old female with multiple infections (serovar J, F and E).

*Chlamydia* specific T-cell lines were generated from donors with chlamydial genital tract infection or donors exposed to *chlamydia* who did not develop the disease. T cell lines from donor CT-1, CT-3 and CT-10 were generated by stimulating PBMC's with reticulate bodies of *C. trachomatis* serovar E. T-cell lines from donor CT-11 were generated by stimulating PBMC's with either reticulate bodies or elementary bodies of *C. trachomatis* serovar E. A randomly sheared genomic library of *C. trachomatis* serovar E was constructed in lambda Zap II vector and an amplified library plated out in 96 well microtiter plates at a density of 25 clones/well. Bacteria were induced to express the recombinant protein in the presence of 2 mM IPTG for 2 hr, then pelleted and resuspended in 200 ul RPMI/10% FBS. 10 ul of the induced bacterial suspension was transferred to 96 well plates containing autologous monocyte-derived dendritic cells. After a 2 hour incubation, dendritic cells were washed to remove *E. coli* and the T cells were added. Positive *E. coli* pools were identified by determining IFN gamma production and proliferation of T cells in the pools. The number of pools identified by each T-cell line is as follows: CT1 line: 30/480 pools; CT3 line: 91/960 pools; CT10 line: 40/480 pools; CT11 line: 51/480 pools. The clones identified using this approach are set forth in SEQ ID NO:1-14.

In another example using substantially the same approach described above, we identified 12 additional T-cell reactive clones from *Chlamydia trachomatis* serovar E expression screening. Clone E5-E9-3 (CT1 positive) contains a 636 bp insert that encodes partially the ORF for dnaK like gene. Part of this sequence was also identified in clone E1-A5-53. Clone E4-H3-56 (CT1 positive, 463 bp insert) contains a partial ORF for the TSA gene (CT603) on the complementary strand. The insert for clone E2-G12-52 (1265 bp) was identified with the CT11 line. It contains a partial ORF for clpB, a protease ATPase. Another clone identified with the CT11 line, E1-F9-79 (167 bp), contains a partial ORF for the gene CT133 on the complementary strand. CT133 is a predicted rRNA methylase. Clone E4-D2-79 (CT3 positive) contains a 1181 bp insert that is a partial ORF for nrdA gene. The ORF for this gene was also identified in clone E2-B10-52 (CT10 positive). Clone E6-C8-95 contains a 731 bp insert that was identified using the donor lines CT3, CT1, and CT12. This insert has a carboxy terminal half for the gene for the 60 kDa ORF. Clone E7-H11-61 (CT3 positive-1135 bp) has partial inserts for fliA (CT061), tyrS (CT062), TSA (CT603) and a hypothetical protein (CT602). The insert for clone E5-A11-8 (CT10 positive-1736 bp) contains the complete ORF for groES (CT111) and a majority of the ORF for groEL (CT110). Clone E3-F2-37 (CT10, CT3, CT11, and CT12 positive-1377 bp insert) contains a partial ORF for gene tRNA-Trp (CT322) and a complete ORF for the gene secE (CT321). E4-G9-75 is another CT10 clone that contains a partial ORF (723 bp insert) for the amino terminal region of the pmpH gene (CT872). Clone E2-D5-89 (516 bp) is also a CT10 positive clone that contains a partial ORF for pmpD gene (12). The insert for clone E5-E2-10 (CT10 positive) is 427 bp and contains a partial ORF for the major outer membrane protein omp1.

EXAMPLE 2

Additional CD4 T Cell Expression Cloning for the Identification of T Cell Stimulating Antigens from *Chlamydia Trachomatis* Serovar E Twenty sequences were isolated from single clones using a *Chlamydia trachomatis* serovar E (Ct E) library expression screening method. Descriptions of how the clones and lines were generated are provided in Example 1.

Clone E5-A8-85 (identified using the CT1 patient line) was found to contain a 1433 bp insert. This insert contains a large region of the C-terminal half of the CT875, a *Chlamydia trachomatis* hypothetical specific gene that is disclosed in SEQ ID NO:34. Also present in the clone is a partial open reading frame (ORF) of a hypothetical protein CT001 which is on the complementary strand.

The clone E9-G2-93 (identified using the C10 patient line) was shown to contain a 554 bp insert, the sequence of which is disclosed in SEQ ID NO:33. This sequence encodes a partial ORF for CT178, a hypothetical CT protein.

Clone E7-B1-16 (identified using the patient lines CT10, CT3, CT5, CT11, CT13, and CHH037) has a 2577 bp insert, the sequence of which is disclosed in SEQ ID NO:32. This clone was found to contain three ORFs. The first ORF contains almost the entire ORF for CT694, a *Chlamydia trachomatis* (CT) specific hypothetical protein. The second ORF is a full length ORF for CT695, another hypothetical CT protein. The third ORF is the N-terminal portion of CT696.

Clone E9-D5-8 (identified using the patient lines CT10, CT1, CT4, and CT11) contains a 393 bp insert, which is disclosed in SEQ ID NO:31. It was found to encode a partial ORF for CT680, the S2 ribosomal protein.

Clone E9-E10-51 (identified using the patient line CT10) contains an 883 bp insert, the sequence of which is disclosed in SEQ ID NO:30. This clone contains two partial ORF. The first of these is for the C-terminal half of CT680, which may show some overlap with the insert present in clone E9-D5-8. The second ORF is the N-terminal partial ORF for CT679, which is the elongation factor TS.

Clone E3-B4-18 (identified using the CT1 patient line) contains a 1224 bp insert, the sequence of which is disclosed in SEQ ID NO:29. This clone contains 4 ORFs. At the N-terminal end of the clone is the complete ORF for CT772, coding for inorganic pyrophosphatase. The second ORF is a small portion of the C-terminal end of CT771, on the complementary frame. The third is a partial ORF of the hypothetical protein, CT191 and the fourth is a partial ORF for CT190, DNA gyrase-B.

Clone E10-B2-57 (identified using the CT10 patient line) contains an 822 bp insert, the sequence of which is disclosed in SEQ ID NO:42. This clone contains the complete ORF for CT066, a hypothetical protein, on the complementary strand.

Clone E3-F3-18 (identified using the CT1 patient line) contains an 1141 bp insert, the sequence of which is disclosed in SEQ ID NO:41. It contains a partial ORF for pmpG (CT871) in frame with the β-gal gene.

Clone E4-D6-21 (identified using the CT3 patient line) contains a 1297 bp insert, the sequence of which is disclosed in SEQ ID NO:40. This clone contains a very small portion of xseA (CT329), the entire ORF for tpiS (CT328) on the complementary strand, and a partial amino terminal ORF for trpC (CT327) on the top frame.

Clone E1-G9-23 (identified using the CT3 patient line) contains an 1180 bp insert, the sequence of which is disclosed in SEQ ID NO:39. This clone contains almost the entire ORF for glycogen synthase (CT798).

Clone E3-A3-31 (identified using the CT1 patient line) contains an 1834 bp insert, the sequence of which is disclosed in SEQ ID NO:38. This clone contains a large region of the hypothetical gene CT622.

Clone E2-F7-11 (identified using both the CT3 and CT10 patient lines) contains a 2093 bp insert, the sequence of which is disclosed in SEQ ID NO:37. This clone contains a large region of the rpoN gene (CT609) in frame with β-gal and the complete ORF for the hypothetical gene CT610 on the complementary strand. In addition, it also contains the carboxy-terminal end of CT611, another hypothetical gene.

Clone E7-H11-10 (identified using the CT3 patient line) contains a 1990 bp insert, the sequence of which is disclosed in SEQ ID NO:36. This clone contains the amino terminal partial ORF for CT610, a complete ORF for CT611, another complete ORF for CT612, and a carboxy-terminal portion of CT613. All of these genes are hypothetical and all are present on the complementary strand.

Clone E10-C6-45 (identified using the CT3 patient line) contains a 196 bp insert, the sequence of which is disclosed in SEQ ID NO:35. This clone contains a partial ORF for nrdA (CT827) in frame with β-gal. This clone contains a relatively small insert and has particular utility in determining the epitope of this gene that contributes to the immunogenicity of Serovar E.

Clone E3-H6-10 (identified using the CT12 patient line) contains a 3734 bp insert, the sequence of which is disclosed in SEQ ID NO:48. This clone contains ORFs for a series of hypothetical proteins. It contains the partial ORFs for CT223 and CT229 and the complete ORFs for CT224, CT225, CT226, CT227, and CT228.

Clone E4-C3-40 (identified using the CT10 patient line) contains a 2044 bp insert, the sequence of which is disclosed in SEQ ID NO:47. This clone contains a partial ORF for nrdA (CT827) and the complete ORF for nrdB (CT828).

Clone E2-D8-19 (identified using the CT1 patient line) contains a 2010 bp insert, the sequence of which is disclosed in SEQ ID NO:46. This clone contains ORF from the *Chlamydia trachomatis* plasmid as well as containing partial ORFs for ORF3 and ORF6, and complete ORFs for ORF4 and ORF5.

Clone E3-D10-46 (identified using the patient lines CT1, CT3, CT4, CT11, and CT12) contains a 1666 bp insert, the sequence of which is identified in SEQ ID NO: 45. This clone contains a partial ORF for CT770 (fab F), a complete ORF for CT771 (hydrolase/phosphatase homologue), a complete ORF for CT772 (ppa, inorganic phosphatase), and a partial ORF for CT773 (Idh, Leucine dehydrogenase).

Clone E10-H8-1 (identified using both the CT3 and CT10 patient lines) contains an 1862 bp insert, the sequence of which is disclosed in SEQ ID NO:44. It contains the partial ORFs for CT871 (pmpG) as well as CT872 (pmpH).

Clone E3-F3-7 (identified using the CT1 patient line) contains a 1643 bp insert, the sequence of which is identified in SEQ ID NO:43. It contains the partial ORFs for both CT869 (pmpE) and CT870 (pmpF).

EXAMPLE 3

Additional CD4 T Cell Expression Cloning for the Identification of T Cell Stimulating Antigens from *Chlamydia Trachomatis* Serovar E The T cell line CHH037 was generated from a 22 year-old healthy female sero-negative for Chlamydia. This line was used to screen the *Chlamydia trachomatis* serovar E library. Nineteen clones were identified from this screen, as described below.

Clone E7-B12-65, contains an 1179 bp insert, the sequence of which is disclosed in SEQ ID NO:114. It contains the complete ORF of the gene for Malate dehydrogenase (CT376) on the complementary strand.

Clone E4-H9-83 contains a 772 bp insert, the sequence of which is identified in SEQ ID NO:115. It contains the partial ORF for the heat shock protein GroEL (CT110).

Clone E9-B10-52 contains a 487 bp insert, the sequence of which is identified in SEQ ID NO:116. It contains a partial ORF for the gene yscC (CT674), a general secretion pathway protein.

Clone E7-A7-79 contains a 1014 bp insert, the sequence of which is disclosed in SEQ ID NO:117. It contains the complete ORF for the histone like development gene, hctA (CT743) and a partial ORF for the rRNA methyltransferase gene ygcA (CT742).

Clone E2-D11-18 contains a 287 bp insert, the sequence of which is disclosed in SEQ ID NO:118. It contains the partial ORF for hctA (CT743).

Clone E9-H6-15, identified using the CT3 line, contains a 713 bp insert the sequence of which is disclosed in SEQ ID NO:125. It contains the partial ORF of the pmpB gene (CT413).

Clone E3-D10-87, identified using the CT1 line, contains a 780 bp insert, the sequence of which is disclosed in SEQ ID NO:126. It contains the partial ORF for CT388, a hypothetical gene, on the complementary strand, and a partial ORF for CT389, another hypothetical protein.

Clone E9-D6-43, identified using the CT3 line, contains a 433 bp insert, the sequence of which is disclosed in SEQ ID NO:127. It contains a partial ORF for CT858.

Clone E3-D10-4, identified using the CT1 line, contains an 803 bp insert, the sequence of which is disclosed in SEQ ID NO:128. It contains a partial ORF for pGP3-D, an ORF encoded on the plasmid pCHL1.

Clone E3-G8-7, identified using the CT1 line, contains an 842 bp insert, the sequence of which is disclosed in SEQ ID NO:129. It contains partial ORFs for CT557 (Lpda) and CT558 (LipA).

Clone E3-F11-32, identified using the CT1 line, contains an 813 bp insert, the sequence of which is disclosed in SEQ ID NO:130. It contains a partial ORF for pmpD (CT812).

Clone E2-F8-5, identified using the CT12 line, contains a 1947 bp insert, the sequence of which is disclosed in SEQ ID NO:131. It contains a complete ORF for the 15 kDa ORF (CT442) and a partial ORF for the 60 kDa ORF (CT443).

Clone E2-G4-39, identified using the CT12 line, contains a 1278 bp insert, the sequence of which is disclosed in SEQ ID NO:132. It contains the partial ORF of the 60 kDa ORF (CT443).

Clone E9-D1-16, identified using the CT10 line, contains a 916 bp insert, the sequence of which is disclosed in SEQ ID NO:133. It contains the partial ORF for the pmpH (CT872).

Clone E3-F3-6, identified using the CT1 line, contains a 751 bp insert, the sequence of which is disclosed in SEQ ID NO:134. It contains the partial ORFs, all on he complementary strand, for genes accB (CT123), L13 ribosomal (CT125), and S9 ribosomal (CT126).

Clone E2-D4-70, identified using the CT12 line, contains a 410 bp insert, the sequence of which is disclosed in SEQ ID NO:135. It contains the partial ORF for the pmpC gene (CT414).

Clone E5-A1-79, identified using the CT1 line, contains a 2719 bp insert, the sequence of which is disclosed in SEQ ID NO:136. It contains a partial ORF for ydhO (CT127), a complete ORF for S9 ribosomal gene (CT126 on the complementary strand), a complete ORF for the L13 ribosomal gene (CT125 on the complementary strand) and a partial ORF for accC (CT124 on the complementary strand).

Clone E1-F7-16, identified using the lines CT12, CT3, and CT11, contains a 2354 bp insert, the sequence of which is disclosed in SEQ ID NO:137. It contains a partial ORF of the ftsH gene (CT841) and the entire ORF for the pnp gene (CT842) on the complementary strand.

Clone E1-D8-62, identified using the CT12 line, contains an 898 bp insert, the sequence of which is disclosed in SEQ ID NO:138. It contains partial ORFs for the ftsH gene (CT841) and for the pnp gene (CT842).

EXAMPLE 4

Expression of *Chlamydia Tracomatis* Recombinant Proteins

Several *Chlamydia trachomatis* serovar E specific genes were cloned into pET17b. This plasmid incorporates a 6× histidine tag at the N-terminal to allow for expression and purification of recombinant protein.

Two full-length recombinant proteins, CT622 and CT875, were expressed in *E. coli*. Both of these genes were identified using CtLG VII expression screening, but the serovar E homologues were expressed. The primers used to amplify these genes were based on serovar D sequences. The genes were amplified using serovar E genomic DNA as the template. Once amplified, the fragments were cloned in pET-17 b with a N-terminal 6×-His Tag. After transforming the recombinant plasmid in XL-I blue cells, the DNA was prepared and the clones fully sequenced. The DNA was then transformed into the expression host BL21-pLysS cells (Novagen) for production of the recombinant proteins. The proteins were induced with IPTG and purified on Ni-NTA agarose using standard methods. The DNA sequences for CTE622 and CTE875 are disclosed in SEQ ID NO:28 and 27, respectively, and their amino acid sequences are disclosed in SEQ ID NO:139 and 140. i.e. respectively.

Five additional *Chlamydia trachomatis* genes were cloned. The *Chlamydia trachomatis* specific protein CT694, the protein CT695, and the L1 ribosomal protein, the DNA sequences of which are disclosed in SEQ ID NO:119, 120 and 121 respectively. The protein sequences of these 6×-histidine recombinant proteins are disclosed in SEQ ID NO: 122 (CT694), 123 (CT695), and 124 (L1 ribosomal protein). The genes CT875 and CT622, from serovar E were also cloned using pET17b as 6×-His fusion proteins. These recombinant proteins were expressed and purified and their the amino acid sequences disclosed in SEQ ID NO:140 and 139, respectively.

EXAMPLE 5

Recombinant Chlamydial Antigens Recognized by T Cell Lines

Patient T cell lines were generated from the following donors: CT1, CT2, CT3, CT4, CT5, CT6, CT7, CT8, CT9, CT10, CT11, CT12, CT13, CT14, CT15, and CT16. A summary of their details is included in Table II.

TABLE II

| *C. trachomatis* patients | | | | | | |
|---|---|---|---|---|---|---|
| Patients | Gender | Age | Clinical Manifestation | Serovar | IgG titer | Multiple Infections |
| CT1 | M | 27 | NGU | LCR | Negative | No |
| CT2 | M | 24 | NGU | D | Negative | E |
| CT3 | M | 43 | Asymptomatic Shed Eb Dx was HPV | J | Ct 1:512 Cp 1:1024 Cps 1:256 | No |
| CT4 | F | 25 | Asymptomatic Shed Eb | J | Ct 1:1024 | Y |

TABLE II-continued

| C. trachomatis patients | | | | | | |
|---|---|---|---|---|---|---|
| Patients | Gen-der | Age | Clinical Manifestation | Serovar | IgG titer | Multiple Infections |
| CT5 | F | 27 | BV | LCR | Ct 1:256 Cp 1:256 | F/F |
| CT6 | M | 26 | Perinial rash Discharge, dysuria | G | Cp 1:1024 | N |
| CT7 | F | 29 | BV Genital ulcer | E | Ct 1:512 Cp 1:1024 | N |
| CT8 | F | 24 | Not Known | LCR | Not tested | NA |
| CT9 | M | 24 | asymptomatic | LCR | Ct 1:128 Cp 1:128 | N |
| CT10 | F | 20 | Mild itch vulvar | negative | negative | 12/1/98 |
| CT11 | F | 21 | BV Abnormal pap smear | J | Ct 1:512 | F/F/J/E/E PID 6/96 |
| CT12 | M | 20 | asymptomatic | LCR | Cp 1:512 | N |
| CT13 | F | 18 | BV, gonorrhea, Ct vaginal discharge, dysuria | G | Ct 1:1024 | N |
| CT14 | M | 24 | NGU | LCR | Ct 1:256 Cp 1:256 | N |
| CT15 | F | 21 | Muco-purulint cervicitis Vaginal discharge | culture | Ct 1:256 Ct IgM 1:320 Cp 1:64 | N |
| CT16 | M | 26 | Asymptomatic/ contact | LCR | NA | N |
| CL8 | M | 38 | No clinical history of disease | negative | negative | No |

NGU=Non-Gonococcal Urethritis; BV=Bacterial Vaginosis; CT=*Chlamydia trachomatis*; Cp=*Chlamydia pneumoniae*; Eb=*Chlamydia* elementary bodies; HPV=human papiloma virus; Dx=diagnosis; PID=pelvic inflammatory disease; LCR=Ligase change reaction.

PBMC were collected from a second series of donors and T cell lines have been generated from a sub-set of these. A summary of the details for three such T cell lines is listed in the table below.

TABLE III

| Normal Donors | | | | |
|---|---|---|---|---|
| Donor | Gender | Age | CT IgG Titer | CP IgG Titer |
| CHH011 | F | 49 | 1:64 | 1:16 |
| CHH037 | F | 22 | 0 | 0 |
| CHH042 | F | 25 | 0 | 1:16 |

Donor CHH011 is a healthy 49 year old female donor sero-negaitve for *C. trachomatis*. PBMC produced higher quantities of IFN-gamma in response to *C. trachomatis* elementary bodies as compared to *C. pneumoniae* elementary bodies, indicating a *C. trachomatis*-specific response. Donor CHH037 is a 22 year old healthy female donor sero-negative for *C. trachomatis*. PBMC poruced higher quantities of IFN-gamma in response to *C. trachomatis* elementary bodies as compared to *C. pneumoniae* elementary bodies, indicating a *C. trachomatis*-specific response. CHH042 is a 25 year old healthy female donor with an IgG titer of 1:16 to *C. pneumoniae*. PBMC produced higher quantities of IFN-gamma in response to *C. trachomatis* elementary bodies as compared to *C. pneumoniae* elementary bodies, indicating a *C. trachomatis*-specific response.

Recombinant proteins for several *Chlamydia trachomatis* genes were generated as described above. Sequences for MOMP was derived from serovar F. The genes CT875, CT622, pmp-B-2, pmpA, and CT529 were derived from serovar E and sequences for the genes gro-EL, Swib, pmpD, pmpG, TSA, CT610, pmpC, pmpE, S13, lpdA, pmpI, and pmpH-C were derived from LII.

Several of the patient and donor lines described above were tested against the recombinant *Chlamydia* proteins. Table IV summarizes the results of the T cell responses to the recombinant *Chlamydia* proteins.

TABLE IV

| Recombinant Chlamydia Antigens Recognized By T Cell Lines | | | | | | | | | | | | | |
|---|---|---|---|---|---|---|---|---|---|---|---|---|---|
| Antigen | Serovar | #of hits | CL8 L2 | CT10 E | CT1 E | CT3 E | CT4 L2 | CT5 E | CT11 E | CT12 E | CT13 E | CHH-011 E | CHH-037 E |
| gro-EL (CT110) | L2 | 10 | − | + | + | + | + | + | + | + | + | + | + |
| MompF (CT681) | F | 10 | − | + | + | + | + | + | + | + | + | + | + |
| CT875 | E | 8 | − | + | + | − | + | + | + | + | + | − | + |
| SWIB (CT460) | L2 | 8 | + | + | − | + | − | + | − | + | + | + | + |
| pmpD (CT812) | L2 | 5 | − | + | + | + | + | − | − | + | + | − | − |
| pmpG (CT871) | L2 | 6 | − | + | + | − | + | + | nt | − | + | + | − |
| TSA (CT603) | L2 | 6 | − | − | + | + | + | + | − | − | + | − | + |
| CT622 | E | 3 | − | − | + | − | + | − | − | − | + | − | − |
| CT610 | L2 | 3 | − | + | − | + | − | − | − | + | − | − | − |
| pmpB-2 (CT413) | E | 3 | − | − | + | + | + | − | − | − | − | − | − |
| pmpC (CT414) | L2 | 4 | − | − | − | + | − | + | − | + | − | − | + |

TABLE IV-continued

Recombinant Chlamydia Antigens Recognized By T Cell Lines

| Antigen | Serovar | #of hits | CL8 L2 | CT10 E | CT1 E | CT3 E | CT4 L2 | CT5 E | CT11 E | CT12 E | CT13 E | CHH-011 E | CHH-037 E |
|---|---|---|---|---|---|---|---|---|---|---|---|---|---|
| pmpE (CT869) | L2 | 3 | – | + | + | – | – | – | – | – | + | – | – |
| S13 (CT509) | L2 | 2 | + | – | – | – | + | – | – | – | – | – | – |
| lpdA (CT557) | L2 | 3 | – | – | + | + | – | – | – | – | – | + | – |
| pmpI (CT874) | L2 | 2 | – | – | + | – | – | – | – | – | – | + | – |
| pmpH-C (CT872) | L2 | 1 | – | – | – | – | – | – | – | + | – | – | – |
| pmpA (CT412) | E | 0 | – | – | – | – | – | – | – | – | – | – | – |
| CT529 | E | 0 | – | – | – | – | – | – | – | – | – | – | – |

Although the present invention has been described in some detail by way of illustration and example for purposes of clarity of understanding, changes and modifications can be carried out without departing from the scope of the invention which is intended to be limited only by the scope of the appended claims.

What is claimed:

1. A method of stimulating an immune response, said method comprising administering a composition comprising an isolated polypeptide having at least 98% identity to the entirety of SEQ ID NO: 140, and thereby stimulating an immune response specific for the polypeptide of SEQ ID NO: 140.

2. The method of claim 1, wherein the composition further comprises a physiologically acceptable carrier.

3. The method of claim 1, wherein the composition further comprises an adjuvant.

4. The method of claim 3, wherein the adjuvant induces an immune response predominantly of the Th1 type.

5. The method of claim 4, wherein the adjuvant is selected from the group consisting of monophosphoryl lipid A, 3-de-O-acylated monophosphoryl lipid A, CpG-containing oligonucleotides, saponins, QS21, and combinations thereof.

6. The method of claim 3, wherein the adjuvant is an aminoalkyl glucosaminide 4-phosphate.

7. The method of claim 6, wherein the aminoalkyl glucosaminide 4-phosphate is RC-529.

8. The method of claim 1, wherein the composition comprises the polypeptide of SEQ ID NO: 140.

* * * * *